US011124792B2

(12) United States Patent
Crawford et al.

(10) Patent No.: US 11,124,792 B2
(45) Date of Patent: Sep. 21, 2021

(54) COMPOSITIONS AND METHODS FOR CONTROLLING INSECT PESTS

(71) Applicant: MONSANTO TECHNOLOGY LLC, St. Louis, MO (US)

(72) Inventors: Michael John Crawford, St. Louis, MO (US); Brian Donovan Eads, St. Louis, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

(21) Appl. No.: 16/455,171

(22) Filed: Jun. 27, 2019

(65) Prior Publication Data
US 2019/0316130 A1 Oct. 17, 2019

Related U.S. Application Data

(63) Continuation of application No. 15/329,808, filed as application No. PCT/US2015/042415 on Jul. 28, 2015, now Pat. No. 10,378,012.

(60) Provisional application No. 62/030,430, filed on Jul. 29, 2014.

(51) Int. Cl.
C12N 15/82 (2006.01)
C12N 15/113 (2010.01)
C12N 15/11 (2006.01)
A01N 57/16 (2006.01)
A01N 63/60 (2020.01)

(52) U.S. Cl.
CPC ............ C12N 15/113 (2013.01); A01N 57/16 (2013.01); A01N 63/60 (2020.01); C12N 15/111 (2013.01); C12N 15/8286 (2013.01); C12N 2310/14 (2013.01); Y02A 40/146 (2018.01)

(58) Field of Classification Search
CPC .................................................. C12N 15/113
USPC ....................................................... 800/279
See application file for complete search history.

(56) References Cited

U.S. PATENT DOCUMENTS

| | | | |
|---|---|---|---|
| 3,687,808 A | 8/1972 | Merigan et al. |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,469,863 A | 9/1984 | Ts'o et al. |
| 4,476,301 A | 10/1984 | Imbach et al. |
| 4,535,060 A | 8/1985 | Comai |
| 4,581,847 A | 4/1986 | Hibberd et al. |
| 4,666,828 A | 5/1987 | Gusella |
| 4,683,202 A | 7/1987 | Mullis |
| 4,732,250 A | 3/1988 | Maucher et al. |
| 4,761,373 A | 8/1988 | Anderson et al. |
| 4,769,061 A | 9/1988 | Comai |
| 4,801,531 A | 1/1989 | Frossard |
| 4,810,648 A | 3/1989 | Stalker |
| 4,879,219 A | 11/1989 | Wands et al. |
| 4,940,835 A | 7/1990 | Shah et al. |
| 4,971,908 A | 11/1990 | Kishore et al. |
| 5,004,863 A | 4/1991 | Umbeck |
| 5,011,771 A | 4/1991 | Bellet et al. |
| 5,013,659 A | 5/1991 | Bedbrook et al. |
| 5,015,580 A | 5/1991 | Christou et al. |
| 5,023,243 A | 6/1991 | Tullis |
| 5,034,506 A | 7/1991 | Summerton et al. |
| 5,094,945 A | 3/1992 | Comai |
| 5,141,870 A | 8/1992 | Bedbrook et al. |
| 5,145,783 A | 9/1992 | Kishore et al. |
| 5,159,135 A | 10/1992 | Umbeck |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,642 A | 2/1993 | Shah et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. |
| 5,276,019 A | 1/1994 | Cohen et al. |
| 5,278,302 A | 1/1994 | Caruthers et al. |
| 5,281,521 A | 1/1994 | Trojanowski et al. |
| 5,286,634 A | 2/1994 | Stadler et al. |
| 5,286,717 A | 2/1994 | Cohen et al. |
| 5,304,732 A | 4/1994 | Anderson et al. |
| 5,310,667 A | 5/1994 | Eichholtz et al. |
| 5,312,910 A | 5/1994 | Kishore et al. |

(Continued)

FOREIGN PATENT DOCUMENTS

| | | |
|---|---|---|
| AU | 2008325989 A1 | 5/2009 |
| AU | 2008258254 B2 | 7/2014 |

(Continued)

OTHER PUBLICATIONS

Thomas et al. The Plant Journal 25(4):417-425 (Year: 2001).*

(Continued)

Primary Examiner — Li Zheng
(74) Attorney, Agent, or Firm — Arnold & Porter Kaye Scholer LLP; Amanda Carmany-Rampey; David R. Marsh

(57) ABSTRACT

Disclosed herein are polynucleotides, compositions, and methods for controlling insect pests, especially flea beetles, such as *Phyllotreta* spp. and *Psylliodes* spp., particularly in plants. More specifically, polynucleotides such as double-stranded RNA triggers and methods of use thereof for modifying the expression of genes in flea beetles.

8 Claims, No Drawings

Specification includes a Sequence Listing.

(56) References Cited

U.S. PATENT DOCUMENTS

| | | |
|---|---|---|
| 5,321,131 A | 6/1994 | Agrawal et al. |
| 5,331,107 A | 7/1994 | Anderson et al. |
| 5,339,107 A | 8/1994 | Henry et al. |
| 5,346,107 A | 9/1994 | Bouix et al. |
| 5,378,824 A | 1/1995 | Bedbrook et al. |
| 5,384,253 A | 1/1995 | Krzyzek et al. |
| 5,390,667 A | 2/1995 | Kumakura et al. |
| 5,392,910 A | 2/1995 | Bell et al. |
| 5,393,175 A | 2/1995 | Courville |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,459,127 A | 10/1995 | Felgner et al. |
| 5,460,667 A | 10/1995 | Moriyuki et al. |
| 5,462,910 A | 10/1995 | Ito et al. |
| 5,463,174 A | 10/1995 | Moloney et al. |
| 5,463,175 A | 10/1995 | Barry et al. |
| 5,466,677 A | 11/1995 | Baxter et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,518,908 A | 5/1996 | Corbin et al. |
| 5,519,126 A | 5/1996 | Hecht |
| 5,536,821 A | 7/1996 | Agrawal et al. |
| 5,538,880 A | 7/1996 | Lundquist et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,550,398 A | 8/1996 | Kocian et al. |
| 5,550,468 A | 8/1996 | Häberlein et al. |
| 5,558,071 A | 9/1996 | Ward et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,597,717 A | 1/1997 | Guerineau et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,714,331 A | 2/1998 | Buchardt et al. |
| 5,719,046 A | 2/1998 | Guerineau et al. |
| 5,719,262 A | 2/1998 | Buchardt et al. |
| 5,721,138 A | 2/1998 | Lawn |
| 5,731,180 A | 3/1998 | Dietrich |
| 5,739,180 A | 4/1998 | Taylor-Smith |
| 5,746,180 A | 5/1998 | Jefferson et al. |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,837,848 A | 11/1998 | Ely et al. |
| 5,859,347 A | 1/1999 | Brown et al. |
| 5,866,775 A | 2/1999 | Eichholtz et al. |
| 5,874,265 A | 2/1999 | Adams et al. |
| 5,879,903 A | 3/1999 | Strauch et al. |
| 5,898,031 A | 4/1999 | Crooke |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,089 A | 7/2000 | Mine et al. |
| 6,084,155 A | 7/2000 | Volrath et al. |
| 6,107,094 A | 8/2000 | Crooke |
| 6,118,047 A | 9/2000 | Anderson et al. |
| 6,121,513 A | 9/2000 | Zhang et al. |
| 6,130,366 A | 10/2000 | Herrera-Estrella et al. |
| 6,140,078 A | 10/2000 | Sanders et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,194,636 B1 | 2/2001 | McElroy et al. |
| 6,225,105 B1 | 5/2001 | Sathasivan et al. |
| 6,225,114 B1 | 5/2001 | Eichholtz et al. |
| 6,232,526 B1 | 5/2001 | McElroy et al. |
| 6,232,536 B1 | 5/2001 | McElroy et al. |
| 6,245,968 B1 | 6/2001 | Boudec et al. |
| 6,248,876 B1 | 6/2001 | Barry et al. |
| 6,252,138 B1 | 6/2001 | Karimi et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,303,374 B1 | 10/2001 | Zhang et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,426,446 B1 | 7/2002 | McElroy et al. |
| 6,433,252 B1 | 8/2002 | Kriz et al. |
| 6,437,217 B1 | 8/2002 | McElroy et al. |
| 6,453,609 B1 | 9/2002 | Soll et al. |
| 6,479,291 B2 | 11/2002 | Kumagai et al. |
| 6,506,559 B1 | 1/2003 | Fire et al. |
| 6,642,435 B1 | 11/2003 | Rafalski et al. |
| 6,644,341 B1 | 11/2003 | Chemo et al. |
| 6,645,914 B1 | 11/2003 | Woznica et al. |
| 6,768,044 B1 | 7/2004 | Boudec et al. |
| 6,843,985 B2 | 1/2005 | Erickson, Jr. et al. |
| 6,992,237 B1 | 1/2006 | Habben et al. |
| 7,022,896 B1 | 4/2006 | Weeks et al. |
| 7,026,528 B2 | 4/2006 | Cheng et al. |
| 7,056,704 B2 | 6/2006 | Tuschl et al. |
| 7,078,196 B2 | 7/2006 | Tuschl et al. |
| RE39,247 E | 8/2006 | Barry et al. |
| 7,105,724 B2 | 9/2006 | Weeks et al. |
| 7,119,256 B2 | 10/2006 | Shimizu et al. |
| 7,138,564 B2 | 11/2006 | Tian et al. |
| 7,297,541 B2 | 11/2007 | Moshiri et al. |
| 7,304,209 B2 | 12/2007 | Zink et al. |
| 7,312,379 B2 | 12/2007 | Andrews et al. |

(56) References Cited

U.S. PATENT DOCUMENTS

| | | |
|---|---|---|
| 7,323,310 B2 | 1/2008 | Peters et al. |
| 7,371,927 B2 | 5/2008 | Yao et al. |
| 7,392,379 B2 | 6/2008 | Le Pennec et al. |
| 7,405,347 B2 | 7/2008 | Hammer et al. |
| 7,406,981 B2 | 8/2008 | Hemo et al. |
| 7,462,379 B2 | 12/2008 | Fukuda et al. |
| 7,485,777 B2 | 2/2009 | Nakajima et al. |
| 7,525,013 B2 | 4/2009 | Hildebrand et al. |
| 7,550,578 B2 | 6/2009 | Budworth et al. |
| 7,622,301 B2 | 11/2009 | Ren et al. |
| 7,657,299 B2 | 2/2010 | Huizenga et al. |
| 7,671,254 B2 | 3/2010 | Tranel et al. |
| 7,714,188 B2 | 5/2010 | Castle et al. |
| 7,738,626 B2 | 6/2010 | Weese et al. |
| 7,807,791 B2 | 10/2010 | Sekar et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,855,323 B2 | 12/2010 | Huang et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,090,164 B2 | 1/2012 | Bullitt et al. |
| 8,097,712 B2 | 1/2012 | Paldi et al. |
| 8,143,480 B2 | 3/2012 | Axtell et al. |
| 8,158,414 B2 | 4/2012 | Rommens et al. |
| 8,226,938 B1 | 7/2012 | Meikle et al. |
| 8,507,457 B2 | 8/2013 | Paldi et al. |
| 8,548,778 B1 | 10/2013 | Hart et al. |
| 8,554,490 B2 | 10/2013 | Tang et al. |
| 8,598,332 B1 | 12/2013 | Waterhouse et al. |
| 9,006,414 B2 | 4/2015 | Huang et al. |
| 9,121,022 B2 | 9/2015 | Sammons et al. |
| 9,422,557 B2 | 8/2016 | Ader |
| 9,445,603 B2 | 9/2016 | Baum et al. |
| 2001/0006797 A1 | 7/2001 | Kumagai et al. |
| 2001/0042257 A1 | 11/2001 | Connor-Ward et al. |
| 2002/0069430 A1 | 6/2002 | Kiaska et al. |
| 2002/0086356 A1 | 7/2002 | Tuschl et al. |
| 2002/0114784 A1 | 8/2002 | Li et al. |
| 2002/0123476 A1 | 9/2002 | Emanuele et al. |
| 2003/0017068 A1 | 1/2003 | Larrain et al. |
| 2003/0044443 A1 | 3/2003 | Erickson, Jr. et al. |
| 2003/0092651 A1 | 5/2003 | Norris et al. |
| 2003/0096980 A1 | 5/2003 | Froehler et al. |
| 2003/0140371 A1 | 7/2003 | Stevens et al. |
| 2003/0150017 A1 | 8/2003 | Mesa et al. |
| 2003/0154508 A1 | 8/2003 | Stevens et al. |
| 2003/0167537 A1 | 9/2003 | Jiang |
| 2003/0180945 A1 | 9/2003 | Wang et al. |
| 2003/0221211 A1 | 11/2003 | Rottmann et al. |
| 2004/0029275 A1 | 2/2004 | Brown et al. |
| 2004/0053289 A1 | 3/2004 | Allen et al. |
| 2004/0055041 A1 | 3/2004 | Labate et al. |
| 2004/0072692 A1 | 4/2004 | Hoffman et al. |
| 2004/0082475 A1 | 4/2004 | Hoffman et al. |
| 2004/0123347 A1 | 6/2004 | Hinchey et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0216189 A1 | 10/2004 | Houmard et al. |
| 2004/0244075 A1 | 12/2004 | Cai et al. |
| 2004/0250310 A1 | 12/2004 | Shukla et al. |
| 2004/0259247 A1 | 12/2004 | Tuschl et al. |
| 2005/0005319 A1 | 1/2005 | Della-Cioppa et al. |
| 2005/0044591 A1 | 2/2005 | Yao et al. |
| 2005/0080032 A1 | 4/2005 | Gross et al. |
| 2005/0095199 A1 | 5/2005 | Whyard et al. |
| 2005/0215435 A1 | 9/2005 | Menges et al. |
| 2005/0223425 A1 | 10/2005 | Clinton et al. |
| 2005/0246784 A1 | 11/2005 | Plesch et al. |
| 2005/0250647 A1 | 11/2005 | Hills et al. |
| 2006/0009358 A1 | 1/2006 | Kibler et al. |
| 2006/0021087 A1 | 1/2006 | Baum et al. |
| 2006/0040826 A1 | 2/2006 | Eaton et al. |
| 2006/0111241 A1 | 5/2006 | Gerwick, III et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0223708 A1 | 10/2006 | Hoffman et al. |
| 2006/0223709 A1 | 10/2006 | Helmke et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011448 A1 | 1/2007 | Chhabra et al. |
| 2007/0011775 A1 | 1/2007 | Allen et al. |
| 2007/0021360 A1 | 1/2007 | Nyce et al. |
| 2007/0050860 A1 | 3/2007 | Andersen et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0219151 A1 | 9/2007 | Satishchandran et al. |
| 2007/0232188 A1 | 10/2007 | Probasco |
| 2007/0250947 A1 | 10/2007 | Boukharov et al. |
| 2007/0259785 A1 | 11/2007 | Heck et al. |
| 2007/0269815 A1 | 11/2007 | Rivory et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0113351 A1 | 5/2008 | Naito et al. |
| 2008/0155716 A1 | 6/2008 | Sonnewald et al. |
| 2008/0194512 A1 | 8/2008 | John et al. |
| 2008/0214443 A1 | 9/2008 | Baum et al. |
| 2008/0261303 A1 | 10/2008 | Kreutzer et al. |
| 2009/0011934 A1 | 1/2009 | Zawierucha et al. |
| 2009/0018016 A1 | 1/2009 | Duck et al. |
| 2009/0036311 A1 | 2/2009 | Witschel et al. |
| 2009/0054240 A1 | 2/2009 | Witschel et al. |
| 2009/0075921 A1 | 3/2009 | Ikegawa et al. |
| 2009/0098614 A1 | 4/2009 | Zamore et al. |
| 2009/0118214 A1 | 5/2009 | Paldi et al. |
| 2009/0137395 A1 | 5/2009 | Chicoine et al. |
| 2009/0165153 A1 | 6/2009 | Wang et al. |
| 2009/0165166 A1 | 6/2009 | Feng et al. |
| 2009/0172838 A1 | 7/2009 | Axtell et al. |
| 2009/0188005 A1 | 7/2009 | Boukharov et al. |
| 2009/0205079 A1 | 8/2009 | Kumar et al. |
| 2009/0215628 A1 | 8/2009 | Witschel et al. |
| 2009/0285784 A1 | 11/2009 | Raemaekers et al. |
| 2009/0293148 A1 | 11/2009 | Ren et al. |
| 2009/0298787 A1 | 12/2009 | Raemaekers et al. |
| 2009/0306189 A1 | 12/2009 | Raemaekers et al. |
| 2009/0307803 A1 | 12/2009 | Baum et al. |
| 2010/0005551 A1 | 1/2010 | Roberts et al. |
| 2010/0048670 A1 | 2/2010 | Biard et al. |
| 2010/0068172 A1 | 3/2010 | Van De Craen |
| 2010/0071088 A1 | 3/2010 | Sela et al. |
| 2010/0099561 A1 | 4/2010 | Selby et al. |
| 2010/0100988 A1 | 4/2010 | Tranel et al. |
| 2010/0152443 A1 | 6/2010 | Hirai et al. |
| 2010/0154083 A1 | 6/2010 | Ross et al. |
| 2010/0192237 A1 | 7/2010 | Ren et al. |
| 2010/0247578 A1 | 9/2010 | Salama |
| 2010/0248373 A1 | 9/2010 | Baba et al. |
| 2011/0015084 A1 | 1/2011 | Christian et al. |
| 2011/0015284 A1 | 1/2011 | Dees et al. |
| 2011/0028412 A1 | 2/2011 | Cappello et al. |
| 2011/0035836 A1 | 2/2011 | Eudes et al. |
| 2011/0041400 A1 | 2/2011 | Trias Vila et al. |
| 2011/0053226 A1 | 3/2011 | Rohayem |
| 2011/0098180 A1 | 4/2011 | Michel et al. |
| 2011/0105327 A1 | 5/2011 | Nelson |
| 2011/0105329 A1 | 5/2011 | Song et al. |
| 2011/0112570 A1 | 5/2011 | Mannava et al. |
| 2011/0126310 A1 | 5/2011 | Feng et al. |
| 2011/0126311 A1 | 5/2011 | Velcheva et al. |
| 2011/0152339 A1 | 6/2011 | Brown et al. |
| 2011/0152346 A1 | 6/2011 | Karleson et al. |
| 2011/0152353 A1 | 6/2011 | Koizumi et al. |

(56) References Cited

U.S. PATENT DOCUMENTS

| | | |
|---|---|---|
| 2011/0160082 A1 | 6/2011 | Woo et al. |
| 2011/0166022 A1 | 7/2011 | Israels et al. |
| 2011/0166023 A1 | 7/2011 | Nettleton-Hammond et al. |
| 2011/0171176 A1 | 7/2011 | Baas et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |
| 2011/0191897 A1 | 8/2011 | Poree et al. |
| 2011/0201501 A1 | 8/2011 | Song et al. |
| 2011/0203013 A1 | 8/2011 | Peterson et al. |
| 2011/0296555 A1 | 12/2011 | Ivashuta et al. |
| 2011/0296556 A1 | 12/2011 | Sammons et al. |
| 2012/0036594 A1 | 2/2012 | Cardoza et al. |
| 2012/0053231 A1 | 3/2012 | Paldi et al. |
| 2012/0107355 A1 | 5/2012 | Harris et al. |
| 2012/0108497 A1 | 5/2012 | Paldi et al. |
| 2012/0128218 A1 | 5/2012 | Amyot et al. |
| 2012/0137387 A1 | 5/2012 | Baum et al. |
| 2012/0150048 A1 | 6/2012 | Kang et al. |
| 2012/0156784 A1 | 6/2012 | Adams, Jr. et al. |
| 2012/0157512 A1 | 6/2012 | Ben-Chanoch et al. |
| 2012/0164205 A1 | 6/2012 | Baum et al. |
| 2012/0174262 A1 | 7/2012 | Azhakanandam et al. |
| 2012/0185967 A1 | 7/2012 | Sela et al. |
| 2012/0198586 A1 | 8/2012 | Narva et al. |
| 2012/0230565 A1 | 9/2012 | Steinberg et al. |
| 2012/0258646 A1 | 10/2012 | Sela et al. |
| 2012/0316220 A1 | 12/2012 | Ward et al. |
| 2013/0003213 A1 | 1/2013 | Kabelac et al. |
| 2013/0041004 A1 | 2/2013 | Drager et al. |
| 2013/0047297 A1 | 2/2013 | Sammons et al. |
| 2013/0047298 A1 | 2/2013 | Tang |
| 2013/0058890 A1 | 3/2013 | Raemaekers et al. |
| 2013/0060133 A1 | 3/2013 | Kassab et al. |
| 2013/0067618 A1 | 3/2013 | Ader et al. |
| 2013/0084243 A1 | 4/2013 | Goetsch et al. |
| 2013/0096073 A1 | 4/2013 | Sidelman |
| 2013/0097726 A1 | 4/2013 | Ader et al. |
| 2013/0212739 A1 | 8/2013 | Giritch et al. |
| 2013/0226003 A1 | 8/2013 | Edic et al. |
| 2013/0232646 A1 | 9/2013 | Baum et al. |
| 2013/0247247 A1 | 9/2013 | Ader et al. |
| 2013/0254940 A1 | 9/2013 | Ader et al. |
| 2013/0254941 A1 | 9/2013 | Ader et al. |
| 2013/0288895 A1 | 10/2013 | Ader et al. |
| 2013/0289097 A1 | 10/2013 | Paldi et al. |
| 2013/0318657 A1 | 11/2013 | Avniel et al. |
| 2013/0318658 A1 | 11/2013 | Ader et al. |
| 2013/0324842 A1 | 12/2013 | Mittal et al. |
| 2013/0326731 A1 | 12/2013 | Ader et al. |
| 2014/0018241 A1 | 1/2014 | Sammons et al. |
| 2014/0057789 A1 | 2/2014 | Sammons et al. |
| 2014/0109258 A1 | 4/2014 | Van De Craen et al. |
| 2014/0230090 A1 | 8/2014 | Avniel et al. |
| 2014/0274712 A1 | 9/2014 | Finnessy et al. |
| 2014/0275208 A1 | 9/2014 | Hu et al. |
| 2014/0296503 A1 | 10/2014 | Avniel et al. |
| 2014/0371298 A1 | 12/2014 | Paldi et al. |
| 2015/0096079 A1 | 4/2015 | Avniel et al. |
| 2015/0143580 A1 | 5/2015 | Beattie et al. |
| 2015/0159156 A1 | 6/2015 | Inberg et al. |
| 2015/0203867 A1 | 7/2015 | Beattie et al. |
| 2015/0240258 A1 | 8/2015 | Beattie et al. |
| 2016/0015035 A1 | 1/2016 | Tao |
| 2016/0029644 A1 | 2/2016 | Tao |
| 2017/0037407 A1 | 2/2017 | Gleit-Kielmanowicz et al. |
| 2017/0088838 A1 | 3/2017 | Inberg et al. |
| 2017/0183683 A1 | 6/2017 | Zheng et al. |

FOREIGN PATENT DOCUMENTS

| | | |
|---|---|---|
| CA | 2806295 A1 | 2/2011 |
| CN | 1505504 A | 6/2004 |
| CN | 101139607 A | 3/2008 |
| CN | 101279950 A | 10/2008 |
| CN | 101279951 A | 10/2008 |
| CN | 101892247 A | 11/2010 |
| CN | 101914540 A | 12/2010 |
| CN | 102154364 A | 8/2011 |
| CN | 102481311 A | 5/2012 |
| CN | 102822350 A | 12/2012 |
| CN | 102906263 A | 1/2013 |
| DE | 288618 A5 | 4/1991 |
| DE | 10000600 A1 | 7/2001 |
| DE | 10116399 A1 | 10/2002 |
| DE | 10256353 A1 | 6/2003 |
| DE | 10256354 A1 | 6/2003 |
| DE | 10256367 A1 | 6/2003 |
| DE | 10204951 A1 | 8/2003 |
| DE | 10234875 A1 | 2/2004 |
| DE | 10234876 A1 | 2/2004 |
| DE | 102004054666 A1 | 5/2006 |
| DE | 102005014638 A1 | 10/2006 |
| DE | 102005014906 A1 | 10/2006 |
| DE | 102007012168 A1 | 9/2008 |
| DE | 102010042866 A1 | 5/2011 |
| EP | 0 375 408 A1 | 6/1990 |
| EP | 0 804 600 A1 | 11/1997 |
| EP | 1 155 615 A1 | 11/2001 |
| EP | 1 157 991 A2 | 11/2001 |
| EP | 1 238 586 A1 | 9/2002 |
| EP | 1 416 049 A1 | 5/2004 |
| EP | 1 496 123 A1 | 1/2005 |
| EP | 1 889 902 A1 | 2/2008 |
| EP | 1 964 919 A1 | 9/2008 |
| EP | 2 147 919 A1 | 1/2010 |
| EP | 2 160 098 B1 | 11/2010 |
| EP | 2 530 159 A1 | 3/2011 |
| EP | 2 305 813 A2 | 4/2011 |
| EP | 2 545 182 A1 | 1/2013 |
| EP | 2 703 489 A1 | 3/2014 |
| EP | 2 703 490 A1 | 3/2014 |
| EP | 2 706 114 A1 | 3/2014 |
| JP | 2001253874 A | 9/2001 |
| JP | 2002080454 A | 3/2002 |
| JP | 2002138075 A | 5/2002 |
| JP | 2002145707 A | 5/2002 |
| JP | 2002220389 A | 8/2002 |
| JP | 2003064059 A | 3/2003 |
| JP | 2003096059 A | 4/2003 |
| JP | 2004051628 A | 2/2004 |
| JP | 2004107228 A | 4/2004 |
| JP | 2005008583 A | 1/2005 |
| JP | 2005239675 A | 9/2005 |
| JP | 2005314407 A | 11/2005 |
| JP | 2006232824 A | 9/2006 |
| JP | 2006282552 A | 10/2006 |
| JP | 2007153847 A | 6/2007 |
| JP | 2007161701 A | 6/2007 |
| JP | 2007182404 A | 7/2007 |
| JP | 2008074840 A | 4/2008 |
| JP | 2008074841 A | 4/2008 |
| JP | 2008133207 A | 6/2008 |
| JP | 2008133218 A | 6/2008 |
| JP | 2008169121 A | 7/2008 |
| JP | 2009-508481 A | 3/2009 |
| JP | 2009067739 A | 4/2009 |
| JP | 2009114128 A | 5/2009 |
| JP | 2009126792 A | 6/2009 |
| JP | 2009137851 A | 6/2009 |
| RU | 2 293 613 C1 | 1/2007 |
| RU | 2 337 529 C1 | 11/2008 |
| WO | WO 89/11789 A1 | 12/1989 |
| WO | WO 95/34659 A1 | 12/1995 |
| WO | WO 95/34668 A2 | 12/1995 |
| WO | WO 96/005721 A1 | 2/1996 |
| WO | WO 96/033270 A1 | 10/1996 |
| WO | WO 96/038567 A2 | 12/1996 |
| WO | WO 96/040964 A2 | 12/1996 |
| WO | WO 97/47193 | 12/1997 |
| WO | WO 97/49816 A1 | 12/1997 |
| WO | WO 99/024585 A1 | 5/1999 |
| WO | WO 99/26467 A1 | 6/1999 |

(56) References Cited

FOREIGN PATENT DOCUMENTS

| | | |
|---|---|---|
| WO | WO 99/27116 A2 | 6/1999 |
| WO | WO 99/32619 A1 | 7/1999 |
| WO | WO 99/61631 A1 | 12/1999 |
| WO | WO 99/67367 A1 | 12/1999 |
| WO | WO 00/04176 A1 | 1/2000 |
| WO | WO 00/32757 A2 | 6/2000 |
| WO | WO 00/044914 A1 | 8/2000 |
| WO | WO 01/07601 A2 | 2/2001 |
| WO | WO 01/34815 A1 | 5/2001 |
| WO | WO 2001/085970 A2 | 11/2001 |
| WO | WO 02/14472 A2 | 2/2002 |
| WO | WO 02/066660 A2 | 8/2002 |
| WO | WO 03/000679 A2 | 1/2003 |
| WO | WO 03/004649 | 1/2003 |
| WO | WO 03/006422 A1 | 1/2003 |
| WO | WO 03/012052 A2 | 2/2003 |
| WO | WO 03/013247 A1 | 2/2003 |
| WO | WO 03/016308 A1 | 2/2003 |
| WO | WO 2003/014357 A1 | 2/2003 |
| WO | WO 03/020704 A1 | 3/2003 |
| WO | WO 03/022051 A1 | 3/2003 |
| WO | WO 03/022831 A1 | 3/2003 |
| WO | WO 03/022843 A1 | 3/2003 |
| WO | WO 03/029243 A2 | 4/2003 |
| WO | WO 03/037085 A1 | 5/2003 |
| WO | WO 03/037878 A1 | 5/2003 |
| WO | WO 03/045878 A2 | 6/2003 |
| WO | WO 03/050087 A2 | 6/2003 |
| WO | WO 03/051823 A1 | 6/2003 |
| WO | WO 03/051824 A1 | 6/2003 |
| WO | WO 03/051846 A2 | 6/2003 |
| WO | WO 03/064625 A2 | 8/2003 |
| WO | WO 03/076409 A1 | 9/2003 |
| WO | WO 03/077648 A2 | 9/2003 |
| WO | WO 03/087067 A1 | 10/2003 |
| WO | WO 03/090539 A1 | 11/2003 |
| WO | WO 03/091217 A1 | 11/2003 |
| WO | WO 03/093269 A2 | 11/2003 |
| WO | WO 03/104206 A2 | 12/2003 |
| WO | WO 2004/002947 A1 | 1/2004 |
| WO | WO 2004/002981 A2 | 1/2004 |
| WO | WO 2004/005485 A2 | 1/2004 |
| WO | WO 2004/009761 A2 | 1/2004 |
| WO | WO 2004/011429 A1 | 2/2004 |
| WO | WO 2004/022771 A2 | 3/2004 |
| WO | WO 2004/029060 A1 | 4/2004 |
| WO | WO 2004/035545 A2 | 4/2004 |
| WO | WO 2004/035563 A1 | 4/2004 |
| WO | WO 2004/035564 A1 | 4/2004 |
| WO | WO 2004/037787 A1 | 5/2004 |
| WO | WO 2004/049806 A1 | 6/2004 |
| WO | WO 2004/062351 A2 | 7/2004 |
| WO | WO 2004/067518 A1 | 8/2004 |
| WO | WO 2004/067527 A1 | 8/2004 |
| WO | WO 2004/074443 A2 | 9/2004 |
| WO | WO 2004/077950 A1 | 9/2004 |
| WO | WO 2005/000824 A1 | 1/2005 |
| WO | WO 2005/003362 A2 | 1/2005 |
| WO | WO 2005/007627 A1 | 1/2005 |
| WO | WO 2005/007860 A1 | 1/2005 |
| WO | WO 2005/040152 A1 | 5/2005 |
| WO | WO 2005/047233 A1 | 5/2005 |
| WO | WO 2005/047281 A1 | 5/2005 |
| WO | WO 2005/061443 A2 | 7/2005 |
| WO | WO 2005/061464 A1 | 7/2005 |
| WO | WO 2005/068434 A1 | 7/2005 |
| WO | WO 2005/070889 A1 | 8/2005 |
| WO | WO 2005/089551 A1 | 9/2005 |
| WO | WO 2005/095335 A1 | 10/2005 |
| WO | WO 2005/107437 A2 | 11/2005 |
| WO | WO 2005/110068 A2 | 11/2005 |
| WO | WO 2006/006569 A1 | 1/2006 |
| WO | WO 2006/024820 A1 | 3/2006 |
| WO | WO 2006/029828 A1 | 3/2006 |
| WO | WO 2006/029829 A1 | 3/2006 |
| WO | WO 2006/037945 A1 | 4/2006 |
| WO | WO 2006/050803 A1 | 5/2006 |
| WO | WO 2006/074400 A2 | 7/2006 |
| WO | WO 2006/090792 A1 | 8/2006 |
| WO | WO 2006/123088 A2 | 11/2006 |
| WO | WO 2006/125687 A1 | 11/2006 |
| WO | WO 2006/125688 A1 | 11/2006 |
| WO | WO 2006/138638 A1 | 12/2006 |
| WO | WO 2007/003294 A1 | 1/2007 |
| WO | WO 2007/007316 A1 | 1/2007 |
| WO | WO 2007/024783 | 3/2007 |
| WO | WO 2007/026834 A1 | 3/2007 |
| WO | WO 2007/035650 A2 | 3/2007 |
| WO | WO 2007/038788 A2 | 4/2007 |
| WO | WO 2007/039454 A1 | 4/2007 |
| WO | WO 2007/050715 A2 | 5/2007 |
| WO | WO 2007/051462 A2 | 5/2007 |
| WO | WO 2007/070389 A2 | 6/2007 |
| WO | WO 2007/071900 A1 | 6/2007 |
| WO | WO 2007/074405 A2 | 7/2007 |
| WO | WO 2007/074976 A1 | 7/2007 |
| WO | WO 2007/077201 A1 | 7/2007 |
| WO | WO 2007/077247 A1 | 7/2007 |
| WO | WO 2007/080126 A2 | 7/2007 |
| WO | WO 2007/080127 A2 | 7/2007 |
| WO | WO 2007/083193 A2 | 7/2007 |
| WO | WO 2007/096576 A1 | 8/2007 |
| WO | WO 2007/051462 A3 | 10/2007 |
| WO | WO 2007/119434 A1 | 10/2007 |
| WO | WO 2007/134984 A1 | 11/2007 |
| WO | WO 2008/007100 A2 | 1/2008 |
| WO | WO 2008/009908 A1 | 1/2008 |
| WO | WO 2008/029084 A1 | 3/2008 |
| WO | WO 2008/042231 A2 | 4/2008 |
| WO | WO 2008/059948 A1 | 5/2008 |
| WO | WO 2008/063203 A2 | 5/2008 |
| WO | WO 2008/071918 A1 | 6/2008 |
| WO | WO 2008/074991 A1 | 6/2008 |
| WO | WO 2008/084073 A1 | 7/2008 |
| WO | WO 2008/100426 A2 | 8/2008 |
| WO | WO 2008/102908 A1 | 8/2008 |
| WO | WO 2008/148223 A1 | 12/2008 |
| WO | WO 2008/152072 A2 | 12/2008 |
| WO | WO 2008/152073 A2 | 12/2008 |
| WO | WO 2009/000757 A1 | 12/2008 |
| WO | WO 2009/005297 A2 | 1/2009 |
| WO | WO 2009/029690 A1 | 3/2009 |
| WO | WO 2009/035150 A2 | 3/2009 |
| WO | WO 2009/037329 A2 | 3/2009 |
| WO | WO 2009/046384 A1 | 4/2009 |
| WO | WO 2009/060429 A2 | 5/2009 |
| WO | WO 2009/063180 A1 | 5/2009 |
| WO | WO 2009/068170 A2 | 6/2009 |
| WO | WO 2009/068171 A2 | 6/2009 |
| WO | WO 2009/086041 A1 | 7/2009 |
| WO | WO 2009/090402 A2 | 7/2009 |
| WO | WO 2009/091862 A2 | 7/2009 |
| WO | WO 2009/091863 A1 | 7/2009 |
| WO | WO 2009/115788 A1 | 9/2009 |
| WO | WO 2009/116558 A1 | 9/2009 |
| WO | WO 2009/125401 A2 | 10/2009 |
| WO | WO 2009/152995 A1 | 12/2009 |
| WO | WO 2009/158258 A1 | 12/2009 |
| WO | WO 2010/012649 A1 | 2/2010 |
| WO | WO 2010/026989 A1 | 3/2010 |
| WO | WO 2010/034153 A1 | 4/2010 |
| WO | WO 2010/049270 A1 | 5/2010 |
| WO | WO 2010/049369 A1 | 5/2010 |
| WO | WO 2010/049405 A1 | 5/2010 |
| WO | WO 2010/049414 A1 | 5/2010 |
| WO | WO 2010/056519 A1 | 5/2010 |
| WO | WO 2010/063422 A1 | 6/2010 |
| WO | WO 2010/069802 A1 | 6/2010 |
| WO | WO 2010/078906 A2 | 7/2010 |
| WO | WO 2010/078912 A1 | 7/2010 |
| WO | WO 2010/093788 A2 | 8/2010 |
| WO | WO 2010/104217 A1 | 9/2010 |
| WO | WO 2010/108611 A1 | 9/2010 |
| WO | WO 2010/112826 A2 | 10/2010 |

(56) References Cited

FOREIGN PATENT DOCUMENTS

| | | |
|---|---|---|
| WO | WO 2010/116122 A2 | 10/2010 |
| WO | WO 2010/119906 A1 | 10/2010 |
| WO | WO 2010/128465 A1 | 11/2010 |
| WO | WO 2010/130970 A1 | 11/2010 |
| WO | WO 2011/001434 A1 | 1/2011 |
| WO | WO 2011/003776 A2 | 1/2011 |
| WO | WO 2011/021171 A1 | 2/2011 |
| WO | WO 2011/035874 A1 | 3/2011 |
| WO | WO 2011/045796 A1 | 4/2011 |
| WO | WO 2011/065451 A1 | 6/2011 |
| WO | WO 2011/067745 A2 | 6/2011 |
| WO | WO 2011/075188 A1 | 6/2011 |
| WO | WO 2011/080674 A2 | 7/2011 |
| WO | WO 2011/112570 A1 | 9/2011 |
| WO | WO 2011/132127 A1 | 10/2011 |
| WO | WO 2012/001626 A1 | 1/2012 |
| WO | WO 2012/056401 A1 | 5/2012 |
| WO | WO 2012/092580 A2 | 7/2012 |
| WO | WO 2012/164100 A2 | 12/2012 |
| WO | WO 2013/010691 A1 | 1/2013 |
| WO | WO 2013/025670 A1 | 2/2013 |
| WO | WO 2013/039990 A1 | 3/2013 |
| WO | WO 2013/040005 A1 | 3/2013 |
| WO | WO 2013/040021 A1 | 3/2013 |
| WO | WO 2013/040033 A1 | 3/2013 |
| WO | WO 2013/040049 A1 | 3/2013 |
| WO | WO 2013/040057 A1 | 3/2013 |
| WO | WO 2013/040116 A9 | 3/2013 |
| WO | WO 2013/040117 A9 | 3/2013 |
| WO | WO 2013/153553 A2 | 10/2013 |
| WO | WO 2013/175480 A1 | 11/2013 |
| WO | WO 2014/022739 A2 | 2/2014 |
| WO | WO 2014/106837 A2 | 7/2014 |
| WO | WO 2014/106838 A2 | 7/2014 |
| WO | WO 2014/151255 A1 | 9/2014 |
| WO | WO 2014/164761 A1 | 10/2014 |
| WO | WO 2014/164797 A2 | 10/2014 |
| WO | WO 2015/010026 A2 | 1/2015 |
| WO | WO 2016/018887 A1 | 2/2016 |

OTHER PUBLICATIONS

Advisory Action dated Feb. 22, 2013, in U.S. Appl. No. 13/332,430.
Agricultural Chemical Usage 2006 Vegetables Summary, Agricultural Statistics Board, NASS, USDA, pp. 1-372 (2007).
Agrios, Plant Pathology (Second Edition), 2:466-470 (1978).
Alarcón-Reverte et al., "Resistance to ACCase-inhibiting herbicides in the weed Lolium multiflorum," Comm. Appl. Biol. Sci., 73(4):899-902 (2008).
Al-Kaff et al., "Plants rendered herbicide-susceptible by cauliflower mosaic virus-elicited suppression of a 35S promoter-regulated transgene," Nature Biotechnology, 18:995-999 (2000).
Ambrus et al., "The Diverse Roles of RNA Helicases in RNAi," Cell Cycle, 8(21):3500-3505 (2009).
Amarzguioui et al., "An algorithm for selection of functional siRNA sequences," Biochemical and Biophysical Research Communications, 316:1050-1058 (2004).
Amdam et al., Disruption of vitellogenin gene function in adult honeybees by intra-abdominal injection of double-stranded RNA, BMC Biotechnology, 3(1):1-8 (2003).
An et al., "Transient RNAi Induction against Endogenous Genes in Arabidopsis Protoplasts Using in Vitro-Prepared Double-Stranded RNA," Biosci Biotechnol Biochem, 69(2):415-418 (2005).
Andersen et al., "Delivery of siRNA from lyophilized polymeric surfaces," Biomaterials, 29:506-512 (2008).
Andersson et al., "A novel selection system for potato transformation using a mutated AHAS gene," Plant Cell Reports, 22(4):261-267 (2003).
Anonymous, "Agronomy Facts 37: Adjuvants for enhancing herbicide performance," n.p., 1-8, (Jan. 26, 2000), Web, (Jan. 21, 2014).
Anonymous, "A handbook for high-level expression and purification of 6xHis-tagged proteins," The QiaExpressionist, (2003).
Anonymous, "Devgen, The mini-Monsanto," KBC Securities (2006).
Anonymous, "Do Monsanto have the next big thing?," Austalian Herbicide Resistance Initiative (AHRI), (Apr. 23, 2013) Web. (Jan. 19, 2015).
Anonymous, "Resistant Weeds Spur Research Into New Technologies," Grains Research & Development Corporation, 2013.
Aoki et al., "In Vivo Transfer Efficiency of Antisense Oligonucleotides into the Myocardium Using HVJ-Liposome Method," Biochem Biophys Res Commun, 231:540-545 (1997).
Arpaia et al., "Production of transgenic eggplant (Solanum melongena L.) resistant to Colorado Potato Beetle (Leptinotarsa decemlineata Say)," (1997) Theor. Appl. Genet., 95:329-334 (1997).
Artymovich, "Using RNA interference to increase crop yield and decrease pest damage," MMG 445 Basic Biotech., 5(1):7-12 (2009).
Asad et al., "Silicon Carbide Whisker-mediated Plant Transformation," Properties and Applications of Silicon Carbide, pp. 345-358 (2011).
Ascencio-Ibanez et al., "DNA abrasion onto plants is an effective method for geminivirus infection and virus-induced gene silencing," Journal of Virological Methods, 142:198-203 (2007).
Axtell et al., "A Two-Hit Trigger for siRNA Biogenesis in Plants," Cell, 127:565-577 (2006).
Bachman et al., "Characterization of the spectrum of insecticidal activity of a double-stranded RNA with targeted activity against Western Corn Rootworm (Diabrotica virgifera virgifera LeConte)," Transgenic Res., 22(6):1207-22 (2013).
Baerson et al., "Glyphosate-Resistant Goosegrass. Identification of a Mutation in the Target Enzyme 5-Enolpyruvylshikimate-3-Phosphate Synthase," Plant Physiol., 129(3):1265-1275 (2002).
Bai et al., "Naturally Occurring Broad-Spectrum Powdery Mildew Resistance in a Central American Tomato Accession Is Caused by Loss of Mlo Function," MPMI, 21(1):30-39 (2008).
Baker, "Chlorophyll Fluorescence: A Probe of Photosynthesis In Vivo," Annu. Rev. Plant Biol., 59:89-113 (2008).
Balibrea et al., "Extracellular Invertase is an Essential Component of Cytokinin-Mediated Delay of Senescence," The Plant Cell, 16(5):1276-1287 (2004).
Bannerjee et al., "Efficient production of transgenic potato (S. tuberosum L. ssp. andigena) plants via Agrobacterium tumefaciens-mediated transformation," Plant Sci., 170:732 738 (2006).
Bart et al., "A novel system for gene silencing using siRNAs in rice leaf and stem-derived protoplasts," Plant Methods, 2(13):1-9 (2006).
Basu et al., "Weed genomics: new tools to understand weed biology," TRENDS in Plant Science, 9(8):391-398 (2004).
Bauer et al., "The major protein import receptor of plastids is essential for chloroplast biogenesis," Nature, 403:203-207 (2000).
Baulcombe, "RNA silencing in plants," Nature, 431:356-363 (2004).
Baulcombe, "RNA silencing and heritable epigenetic effects in tomato and Arabidopsis," Abstract 13th Annual Fall Symposium, Plant Genomes to Phenomes, Donald Danforth Plant Science Center, 28-30 (2011).
Baum et al., "Control of coleopteran insect pests through RNA interference," Nature Biotechnology, 25(11):1322-1326 (2007).
Baum et al., "Progress Towards RNAi-Mediated Insect Pest Management," Advances in Insect Physiology, 47:249-295 (2014).
Bayer et al., "Programmable ligand-controlled riboregulators of eukaryotic gene expression," Nature Biotechnol., 23(3):337-343 (2005).
Beal, et al., "Second Structural Motif for Recognition of DNA by Oligonucleotide-Directed Triple-Helix Formation," Science, 251:1360-1363 (1992).
Becker et al., "Fertile transgenic wheat from microprojectile bombardment of scutellar tissue," The Plant Journal, 5(2):299-307 (1994).
Bedell et al., "Sorghum Genome Sequencing by Methylation Filtration," PLOS Biology, 3(1):E13/104-115 (2005).
Belhadj et al., "Methyl Jasmonate Induces Defense Responses in Grapevine and Triggers Protection against Erysiphe necator," J. Agric Food Chem., 54:9119-9125 (2006).
Bhargava et al., "Long double-stranded RNA-mediated RNA interference as a tool to achieve site-specific silencing of hypothalamic neuropeptides," Brain Research Protocols, 13:115-125 (2004).

(56) References Cited

OTHER PUBLICATIONS

Bhatia et al., "Aphid resistance in *Brassica* crops: Challenges, biotechnological progress and emerging possibilities," *Biotechnology Advances* 29:879-955 (2011).
Boletta et al., "High Efficient Non-Viral Gene Delivery to the Rat Kidney by Novel Polycationic Vectors," J. Am Soc. Nephrol., 7:1728 (1996).
Bolognesi et al., "Characterizing the Mechanism of Action of Double-Stranded RNA Activity against Western Corn Rootworm(*Diabrotica virgifera virgifera* LeConte)," PLoS ONE 7(10):e47534 (2012).
Bolter et al., "A chloroplastic inner envelope membrane protease is essential for plant development," FEBS Letters, 580:789-794 (2006).
Bourgeois et al., "Field and producer survey of ACCase resistant wild oat in Manitoba," Canadian Journal of Plant Science, 709-715 (1997).
Breaker et al., "A DNA enzyme with Mg2+-dependent RNA phosphoesterase activity," Chemistry and Biology, 2:655-660 (1995).
Brodersen et al., "The diversity of RNA silencing pathways in plants," Trends in Genetics, 22(5):268-280 (2006).
Brugière et al., "Glutamine Synthetase in the Phloem Plays a Major Role in Controlling Proline Production," The Plant Cell, 11:1995-2011 (1999).
Busch et al., "RNAi for discovery of novel crop protection products," Pflanzenschutz-Nachrichten Bayer, 58(1):34-50 (2005).
Busi et al., "Gene flow increases the initial frequency of herbicide resistance alleles in unselectedpopulations," Agriculture, Ecosystems and Environments, Elsevier, Amsterdam, NL, 142(3):403-409 (2011).
Butler et al., "Priming and re-drying improve the survival of mature seeds of Digitalis purpurea during storage," Annals of Botany, 103:1261-1270 (2009).
Burgos et al., "Review: Confirmation of Resistance to Herbicides and Evaluation of Resistance Levels," Weed Science, 61 (1):4-20 (2013).
Burleigh, "Relative quantitative RT-PCR to study the expression of plant nutrient transporters in arbuscular mycorrhizas," Plant Science, 160:899-904 (2001).
Bytebier et al., "T-DNA organization in tumor cultures and transgenic plants of the monocotyledon Asparagus officinalis," Proc. Natl. Acad. Sci. U.S.A., 84:5345-5349 (1987).
Campbell et al., "Gene-knockdown in the honey bee mite Varroa destructor by a non-invasive approach: studies on a glutathione S-transferase," Parasites & Vectors, 3(1):73, pp. 1-10 (2010).
Carthew, "Gene silencing by double-stranded RNA," *Curr Opin Cell Biol.*, 13(2):244-248 (2001).
Chabannes et al., "In situ analysis of lignins in transgenic tobacco reveals a differential impact of individual transformations on the spatial patterns of lignin deposition at the cellular and subcellular levels," The Plant Journal, 28(3):271-282 (2001).
Chabbouh et al., "Cucumber mosaic virus in artichoke," FAO Plant Protection Bulletin, 38:52-53 (1990).
Chakravarty et al., "Genetic Transformation in Potato: Approaches and Strategies," Amer J Potato Res, 84:301 311 (2007).
Chang et al., "Dual-target gene silencing by using long, sythetic siRNA duplexes without triggering antiviral responses," Molecules and Cells, 27(6)689-695 (2009).
Chang et al., "Cellular Internalization of Fluorescent Proteins via Arginine-rich Intracellular Delivery Peptide in Plant Cells," Plant Cell Physiol., 46(3):482-488 (2005).
Chee et al., "Transformation of Soybean (Glycine max) by Infecting Germinating Seeds with Agrobacterium tumefaciens," Plant Physiol., 91:1212-1218 (1989).
Chen et al., "In Vivo Analysis of the Role of atTic20 in Protein Import into Chloroplasts," The Plant Cell, 14:641-654 (2002).
Chen et al., "Transfection and Expression of Plasmid DNA in Plant Cells by an Arginine-Rich Intracellular Delivery Peptide without Protoplast Preparation," FEBS Letters 581, pp. 1891-1897 (2007).

Chen et al., "Exploring MicroRNA-Like Small RNAs in the Filamentous Fungus Fusarium oxysporum," PLOS One, 9(8):e104956:1-10 (2014).
Cheng et al., "Production of fertile transgenic peanut (*Arachis hypogaea* L.) plants using Agrobacterium tumefaciens," Plant Cell Reports, 15:653-657 (1996).
Cheng et al., "Transient Expression of Minimum Linear Gene Cassettes in Onion Epidermal Cells Via Direct Transformation," Appl Biochem Biotechnol, 159:739-749 (2009).
Chi et al., "The Function of RH22, a DEAD RNA Helicase, in the Biogenesis of the 50S Ribosomal Subunits of *Arabidopsis* Chloroplasts," Plant Physiology, 158:693-707 (2012).
Christiaens et al., "The challenge of RNAi-mediated control of hemipterans," Current Opinion in Insect Science, 6:15-21 (2014).
Chupp et al., "Chapter 8: White Rust," Vegetable Diseases and Their Control, The Ronald Press Company, New York, pp. 267-269 (1960).
Clough et al., "Floral dip: a simplified method for Agrobacterium-mediated transformation of *Arabidopsis thaliana*," The Plant Journal, 16(6):735-743 (1998).
CN101914540 Patent Diclosure, "Introduction of RNA into plant by interference," (2010).
Colbourne et al., "The Ecoresponsive Genome of Daphnia pulex," Science, 331(6017):555-561 (2011).
Colliver et al., "Differential modification of flavonoid and isoflavonoid biosynthesis with an antisense chalcone synthase construct in transgenic Lotus corniculatus," Plant Molecular Biology, 35:509-522 (1997).
Colorado Potato Beetle, *Leptinotarsa decemlineata*,Transcriptome, PLoS One, 9(1):e86012 (2014).
Communication pursuant to Article 94(3) EPC dated Jan. 14, 2016, in European Patent Application No. 12 832 415.9.
Communication pursuant to Article 94(3) EPC dated Jun. 26, 2015, in European Patent Application No. 11 753 916.3.
Communication pursuant to Article 94(3) EPC dated Mar. 18, 2016, in European Patent Application No. 12 832 160.1.
Communication pursuant to Article 94(3) EPC dated Mar. 24, 2016, in European Patent Application No. 12 831 684.1.
Communication pursuant to Article 94(3) EPC dated Mar. 4, 2016, in European Patent Application No. 12 830 932.5.
Communication pursuant to Article 94(3) EPC dated Mar. 9, 2016, in European Patent Application No. 12 831 166.9.
Communication pursuant to Article 94(3) EPC dated Oct. 23, 2015, in European Patent Application No. 12 831 945.6.
Communication Pursuant to Article 94(3) EPC dated Sep. 5, 2018, in European Patent Application No. 17152830.0.
Concise Descriptions of Relevance filed by a third party on Nov. 29, 2012, in U.S. Appl. No. 13/042,856.
Cong et al., "Multiplex Genome Engineering Using CRISPR/Cas Systems," Science, 339:819-823 (2013)
Constan et al., "An outer envelope membrane component of the plastid protein import apparatus plays an essential role in *Arabidopsis*," The Plant Journal, 38:93-106 (2004).
Cooney et al., "Site-Specific Oligonueleotide Binding Represses Transcription of the Human c-myc Gene in Vitro," Science ,241:456-459 (1988).
COST Action FA0806 progress report "Plant Virus control employing RNA-based vaccines: A novel non-transgenic strategy" (2010).
Coticchia et al., "Calmodulin modulates Akt activity in human breast cancer cell lines," Breast Cancer Res. Treat, 115:545-560 (2009).
Cox-Foster et al., "A Metagenomic Survey of Microbes in Honey Bee Colony Collapse Disorder," *Science*, 318(5848):283-287 (2007).
Dalakouras et al., "Induction of Silencing in Plants by High-Pressure Spraying of In vitro-Synthesized Small RNAs," Frontiers in Plant Science, 7(1327):1-5 (2016).
Dalmay et al., "An RNA-Depenedent RNA Polymerase Gene in *Arabidopsis* Is Required for Posttranscriptional Gene Silencing Mediated by a Transgene but Not by a Virus," Cell, 101:543-553 (2000).

(56) References Cited

OTHER PUBLICATIONS

Danka et al., "Field Test of Resistance to Acarapis woodi (*Acari: Tarsonemidae*) and of Colony Production by Four Stocks of Honey Bees (*Hymenoptera: Apidae*)" Journal of Economic Entomology, 88(3):584-591 (1995).
Database EMBL XP-002781749(BG442539) dated Mar. 20, 2001.
Davidson et al., "Engineering regulatory RNAs," TRENDS in Biotechnology, 23(3):109-112 (2005).
Dawson et al., "cDNA cloning of the complete genome of tobacco mosaic virus and production of infectious transcripts," Proc. Natl. Acad. Sci. USA, 83:1832-1836 (1986).
De Block, et al. "Engineering herbicide resistance in plants by expression of a detoxifying enzyme," EMBO J. 6(9):2513-2519 (1987).
Declaration of Jerzy Zabkiewicz executed Nov. 28, 2017, as filed by Opponent in Australian Patent Application No. 2014262189, pp. 1-73.
Declaration of Jerzy Zabkiewicz executed Nov. 28, 2017, as filed by Opponent in Australian Patent Application No. 2014262189, pp. 1-4.
Declaration of Neena Mitter executed Nov. 30, 2017, as filed by Opponent in Australian Patent Application No. 2014262189, pp. 1-114.
Declaration of Neena Mitter executed Nov. 30, 2017, as filed by Opponent in Australian Patent Application No. 2014262189, pp. 1-25.
De Framond, "MINI-Ti: A New Vector Strategy for Plant Genetic Engineering," Nature Biotechnology, 1:262-269 (1983).
Della-Cioppa et al., "Import of a precursor protein into chloroplasts is inhibited by the herbicide glyphosate," The EMBO Journal, 7(5):1299-1305 (1988).
Delye et al., "PCR-based detection of resistance to acetyl-CoA carboxylase-inhibiting herbicides in black-grass (*Alopecurus myosuroides* Huds) and ryegrass (*Lolium rigidum* Gaud)," Pest Management Science, 58:474-478 (2002).
Delye et al., "Variation in the gene encoding acetolactate-synthase in Lolium species and proactive detection of mutant, herbicide-resistant alleles," Weed Research, 49:326-336 (2009).
Desai et al., "Reduction in deformed wing virus infection in larval and adult honey bees (*Apis mellifera* L.) by double-stranded RNA ingestion," Insect Molecular Biology, 21(4):446-455 (2012).
Desveaux et al., "PBF-2 Is a Novel Single-Stranded DNA Binding Factor Implicated in Pr-10a Gene Activation in Potato," The Plant Cell, 12:1477-1489 (2000).
Di Prisco et al. "Varroa Destructor Is an Effective Vector of Israeli Acute Paralysis Virus in the Honeybee, *Apis mellifera*", Journal of General Virology, 92: 151-155, 2011.
Di Stilio et al., "Virus-Induced Gene Silencing as a Tool for Comparative Functional Studies in Thalictrum," PLoS One, 5(8):e12064 (2010).
Diallo et al., "Long Endogenous dsRNAs Can Induce Complete Gene Silencing in Mammalian Cells and Primary Cultures," Oligonucleotides, 13:381-392 (2003).
Dietemann et al., "Varroa destructor: research avenues towards sustainable control," Journal of Apicultural Research, 51(1):125-132 (2012).
Dietzgen et al., "Transgenic gene silencing strategies for virus control," Australasian Plant Pathology, 35:605-618 (2006).
Dietzl et al., "A genome-wide transgenic RNAi library for conditional gene inactivation in *Drosophila,*" Nature, 448:151-157 (2007).
Dilpreet et al., "Glyphosate Rsistance in a Johnsongrass (*Sorghum halepense*) Biotype from Arkansas," Weed Science, 59(3):299-304 (2011).
Downey et al., "Single and dual parasitic mite infestations on the honey bee, *Apis mellifera* L.," Insectes Sociaux, 47(2):171-176 (2000).
Drobyazko R.V., "Reliable and environmentally friendly insecticide," Protection and quarantine of plants, 2012 (pp. 52, 53) (in Russian).

Du et al., "A systematic analysis of the silencing effects of an active siRNA at all single-nucleotide mismatched target sites," Nucleic Acids Research, 33(5):1671-1677 (2005).
Duhoux et al., "Reference Genes to Study Herbicide Stress Response in *Lolium* sp.: Up-Regulation of P3450 Genes in Plants Resistant to Acetolactate-Synthase Inhibitors," PLOS One, 8(5):e63576 (2013).
Dunoyer et al., "Small RNA Duplexes Function as Mobile Silencing Signals Between Plant Cells," Science, 328:912-916 (2010).
Eamens et al., "RNA Silencing in Plants: Yesterday, Today, and Tomorrow," Plant Physiology, 147(2):456-468 (2008).
Egli et al., "A Maize Acetyl-Coenzyme A Carboxylase cDNA Sequence," Plant Physiol., 108: 1299-1300 (1995).
Ellington et al., "In vitro selection of RNA molecules that bind specific ligands," Nature, 346:818-822 (1990).
Emery et al., "Radial Patterning of *Arabidopsis* Shoots by Class III HD-ZIP and KANADI Genes," Current Biology, 13:1768-1774 (2003).
Eudes et al., "Cell-penetrating peptides," Plant Signaling & Behavior, 3(8):549-5550 (2008).
European Cooperation in the field of Scientific and Technical Research—Memorandum of Understanding for COST Action FA0806 (2008).
European Search Report and the European Search Opinion dated Feb. 3, 2014, in European Patent Application No. 13156180.4.
European Search Report and the European Search Opinion dated Feb. 3, 2014, in European Patent Application No. 13156180.5.
European Search Report dated Feb. 3, 2014, in European Patent Application No. 13156180.4.
European Search Report dated Feb. 3, 2014, in European Patent Application No. 13156180.5.
European Search Report dated Feb. 6, 2014, in European Patent Application No. 13156183.9.
European Search Report dated Jun. 29, 2018, in European Patent Application No. 18157745.3.
European Search Report dated Sep. 7, 2017, in European Patent Application No. 17152830.0.
Examination Report dated Mar. 1, 2018, in Australian Patent Application No. 2013264742.
Extended European Search Report dated Feb. 2, 2015, in European Patent Application No. 12 830 932.5.
Extended European Search Report dated Feb. 27, 2015, in European Patent Application No. 12 832 160.1.
Extended European Search Report dated Feb. 3, 2015, in European Patent Application No. 12 831 945.6.
Extended European Search Report dated Feb. 6, 2014, in European Patent Application No. 13156183.9.
Extended European Search Report dated Jan. 20, 2016, in European Patent Application No. 13 794 339.5.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Jun. 29, 2015, in European Patent Application No. 12 831 494.5.
Extended European Search Report dated Mar. 17, 2015, in European Patent Application No. 12 831 684.1.
Extended European Search Report dated Mar. 3, 2015, in European Patent Application No. 12 831 166.9.
Extended European Search Report dated May 23, 2018, in European Patent Application No. 15826865.6.
Extended European Search Report dated Nov. 7, 2017, in European Patent Application No. 15811092.4.
Extended European Search Report dated Nov. 8, 2017, in European Patent Application No. 15737282.2.
Extended European Search Report dated Oct. 8, 2013, in European Patent Application No. 11753916.3.
Extended European Search Report dated Sep. 29, 2016, in European Patent Application No. 14778840.0.
Extended European Search Report dated Apr. 13, 2018, in European Patent Application No. 15812530.0.
Extended European Search Report dated Mar. 15, 2018, in European Patent Application No. 17181861.0.

(56) References Cited

OTHER PUBLICATIONS

Extended European Search Report dated Sep. 28, 2018, in European Patent Application No. 16740770.9.
Extended European Search Report dated Nov. 21, 2018, in European Patent Application No. 18175809.5.
Extended European Search Report dated Nov. 16, 2018, in European Patent Application No. 18182238.8.
Extended European Search Report dated Dec. 19, 2018, in European Patent Application No. 16804395.8.
Fairbairn et al. "Host-Delivered RNAi: An Effective Strategy to Silence Genes in Plant Parasitic Nematodes", Planta, 226(6):1525-1533 (2007) Abstract.
Fassler, BLAST Glossary, National Center for Biotechnology Information (2011).
Farooq et al., "Rice seed priming," IPRN, 30(2):45-48 (2005).
Fernandez et al., "Uptake of Hydrophilic Solutes Through Plant Leaves: Current State of Knowledge and Perspectives of Foliar Fertilization," Critical Reviews in Plant Sciences, 28:36-38 (2009).
Feuillet et al., "Crop genome sequencing: lessons and rationales," Trends Plant Sci., 16:77-88 (2011).
Fiala et al., "Reversible Downregulation of Protein Kinase A during Olfactory Learning Using Antisense Technique Impairs Long-Term Memory Formation in the Honeybee, *Apis mellifera*," J. Neuroscience, 19:10125-10134 (1999).
Final Office Action dated Apr. 7, 2016, in U.S. Appl. No. 13/619,980.
Final Office Action dated Aug. 1, 2013, in U.S. Appl. No. 13/318,636.
Final Office Action dated Dec. 17, 2015, in U.S. Appl. No. 14/335,135.
Final Office Action dated Feb. 17, 2016, in U.S. Appl. No. 13/612,929.
Final Office Action dated Feb. 4, 2016, in U.S. Appl. No. 13/612,936.
Final Office Action dated Jun. 30, 2016, in U.S. Appl. No. 13/901,326.
Final Office Action dated Mar. 18, 2011, in U.S. Appl. No. 12/222,949.
Final Office Action dated Mar. 2, 2016, in U.S. Appl. No. 13/612,995.
Final Office Action dated Mar. 21, 2016, in U.S. Appl. No. 13/612,925.
Final Office Action dated May 26, 2016, in U.S. Appl. No. 14/532,596.
Final Office Action dated Nov. 10, 2015, in U.S. Appl. No. 13/612,985.
Final Office Action dated Nov. 10, 2016, in U.S. Appl. No. 13/583,302.
Final Office Action dated Nov. 19, 2015, in U.S. Appl. No. 13/612,941.
Final Office Action dated Nov. 30, 2015, in U.S. Appl. No. 13/612,948.
Final Office Action dated Nov. 7, 2013, in U.S. Appl. No. 13/042,856.
Final Office Action dated Oct. 15, 2012, in U.S. Appl. No. 13/332,430.
Final Office Action dated Oct. 20, 2016, in U.S. Appl. No. 14/480,199.
Final Office Action dated Oct. 22, 2015, in U.S. Appl. No. 14/608,951.
Final Office Action dated Sep. 9, 2016, in U.S. Appl. No. 13/612,954.
Final Office Action dated Sep. 9, 2016, in U.S. Appl. No. 14/603,347.
Final Office Action dated Sep. 9, 2016, in U.S. Appl. No. 14/608,951.
Fire et al., "Potent and specific genetic interference by double-stranded RNA in Caenorhabditis elegans," Nature, 391:806-811 (1998).
First Examination Report dated Apr. 23, 2013, in New Zealand Patent Application No. 601784.
First Examination Report dated Jul. 28, 2014, in New Zealand Patent Application No. 627060.
First Office Action dated Aug. 31, 2015, in Chinese Patent Application No. 201280053985.3.
First Office Action dated Feb. 2, 2016, in Chinese Patent Application No. 201380039346.6.
First Office Action dated Jul. 7, 2015, in Chinese Patent Application No. 201280054820.8.
First Office Action dated Mar. 12, 2015, in Chinese Patent Application No. 201280053984.9.
First Office Action dated Mar. 2, 2015, in Chinese Patent Application No. 201280054819.5.
First Office Action dated May 27, 2015, in Chinese Patent Application No. 201280054179.8.
First Office Action dated Sep. 9, 2015, in Chinese Patent Application No. 201280055409.2.
Foley et al., "The distribution of *Aspergillus* spp. Opportunistic parasites in hives and their pathogenicity to honey bees," *Veterinary Microbiology*, 169:203-210 (2014).

Fraley et al., "Liposome-mediated delivery of tobacco mosaic virus RNA into tobacco protoplasts: A sensitive assay for monitoring liposome-protoplast interactions," Proc Natl Acad Sci U S A., 79(6):1859-1863 (1982).
Friedberg, "Automated protein function prediction—the genomic challenge," Briefings in Bioinformatics, 7(3):225-242 (2006).
Fukuhara et al., "Enigmatic Double-Stranded RNA in Japonica Rice," Plant Molecular Biology, 21:1121-1130 (1993).
Fukuhara et al., "The Unusual Structure of a Novel RNA Replicon in Rice," The Journal of Biological Chemistry, 270(30):18147-18149 (1995).
Fukuhara et al., "The wide distribution of endornaviruses, large double-stranded RNA replicons with plasmid-like properties," Archives of Virology, 151:995-1002 (2006).
Fukunaga et al., "dsRNA with 5' overhangs v contributes to endogenous and antiviral RNA silencing pathways in plants," The EMBO Journal, 28(5):545-555 (2009).
Funke et al., "Molecular basis for herbicide resistance in Roundup Ready crops," PNAS, 103:13010-13015 (2006).
Further Examination Report dated May 16, 2014, in New Zealand Patent Application No. 601784.
Gaines et al., "Gene amplification confers glyphosate resistance in Amaranthus palmeri," Proc. Natl. Acad. Sci. USA, 107(3):1029-1034 (2010).
Gan et al., "Inhibition of Leaf Senescence by Autoregulated Production of Cytokinin," Science, 270:1986-1988 (1995).
Gan et al., "Bacterially expressed dsRNA protects maize against SCMV infection," Plant Cell Rep, 29(11):1261-1268 (2010).
Gao et al., "Down-regulation of acetolactate synthase compromises 01-1-mediated resistance to powdery mildew in tomato," BMC Plant Biology, 14 (2014).
Gao et al., "Nonviral Methods for siRNA Delivery," Molecular Pharmaceutics, 6(3):651-658 (2008).
Gao et al., "DNA-guided genome editing using the Natronobacterium gregoryi Argonaute," Nature Biotechnology, 34(7):768-773 (2016).
Garbian et al., "Bidirectional Transfer of RNAi between Honey Bee and Varroa destructor: Varroa Gene Silencing Reduces Varroa Population," 8(12):1-9:e1003035 (2012).
Gaskin et al., "Novel organosillicone adjuvants to reduce agrochemical spray volumes on row crops," New Zealand Plant Protection, 53:350-354 (2000).
Gasser et al., "Structure, Expression, and Evolution of the 5-Enolpyravylshikimate-3-phosphate Synthase Genes of Petunia and Tomato," J. Biol. Chem., 263: 4280-4287 (1988).
Ge et al., "Rapid vacuolar sequestration: the horseweed glyphosate resistance mechanism," Pest Management Sci., 66:345-348 (2010).
GenBank Accession No. AY545657.1 (2004).
GenBank Accession No. CB377464, "CmaE1_37_J02_T3 Cowpea weevil larvae Lambda Zap Express Library Callosobruchus maculatus cDNA, mRNA sequence," (2007).
GenBank Accession No. DY640489, "PU2_plate27_F03 PU2 Prunus persica cDNA similar to expressed mRNA inferred from Prunus persica hypothetical domain/motif cont aining IPR011005:Dihydropteroate synthase-like, MRNA sequence" (2006).
GenBank Accession No. EU024568, "Amaranthus hypochondriacus acetolactate synthase (ALS) gene" (2007).
GenBank Accession No. EW765249, "ST020010B10C12 Normalized and subtracted western corn rootworm female head cDNA library Diabrotica virgifera virgifera cDNA clone STO20010B10C12 5-, mRNA sequence," (2007).
GenBank Accession No. EW771198, "ST020010B10C12 Normalized and subtracted western corn rootworm female head cDNA library Diabrotica virgifera virgifera cDNA clone STO20010B10C12 5-, mRNA sequence," (2007).
GenBank Accession No. FE348695, "CBIB7954.fwd CBIB_Daphnia_pulex_Chosen_One_Library_2 Daphnia pulex cDNA clone CBIB7954 5', mRNA sequence" (2011).
GenBank Accession No. FJ972198, "Solanum lycopersicum cultivar Ailsa Craig dihydropterin pyrophosphokinase-dihydropteroate synthase (HPPK-DHPS) gene, complete cds" (2010).
GenBank Accession No. GI:186478573 (2014).
GenBank Accession No. GU120406, "Chiysomela tremulae ribosomal protein L7 (RpL7) mRNA, complete cds" (2009).

(56) References Cited

OTHER PUBLICATIONS

GenBank Accession No. HD315444, "Sequence 192160 from Patent EP2213738" (2010).
GenBank Accession No. Q4GXM3_BIPLU, "Ribosomal protein L7e" (2006).
GenBank Accession No. U87257.1, "Daucus carota 4-hydroxyphenylpyruvate dioxygenase mRNA, complete cds" (1997).
GenBank Accession No. XM_014456745.1, Predicted: Myotis lucifugus ribonucleoprotein, PTB-binding 2 (RAVER2), transcript variant X3, mRNA,: (2015).
GenBank Accession No. Y08611.1, "P.sativum mRNA for dihydropterin pyrophosphokinase/dihydropteroate synthase." (2006).
GenBank Accession No. EF143582 (2007).
GenEmbl Accession No. FJ861243 (2010).
Gill et al. "Stripped-Down DNA Repair in a High Reduced Parasite", BMC Molecular Biology, 8(24): 1-14, Mar. 20, 2007.
Gilmer et al., "Latent Viruses of Apple I. Detection with Woody Indicators," Plant Pathology, 1(10):1-9 (1971).
Gomez-Zurita et al., "Recalibrated Tree of Leaf Beetles (*Chrysomelidae*) Indicates Independent Diversification of Angiosperms and Their Insect Herbivores," PLoS One, 4(e360):1-8 (2007).
Gong et al., "Silencing of Rieske iron-sulfur protein using chemically synthesised siRNA as a potential biopesticide against Plutella xylostella," Pest Manag Sci, 67:514-520 (2011).
Gossamer Threads, Compendium of Herbicide Adjuvants: Organo-Silicone Surfactant, p. 1-4 (1998).
Gressel et al., "A strategy to provide long-term control of weedy rice while mitigating herbicide resistance transgene flow, and its potential use for other crops with related weeds," Pest Manag Sci, 65(7):723-731 (2009).
Gudkov, "Minireview: The L7/L12 ribosomal domain of the ribosome: structural and functional studies," FEBS Letters, 407:253-256 (1997).
Gutensohn et al., "Functional analysis of the two *Arabidopsis* homologues of Toc34, a component of the chloroplast protein import apparatus," The Plant Journal, 23(6):771-783 (2000).
Guttieri et al., "DNA Sequence Variation in Domain A of the Acetolactate Synthase Genes of Herbicide-Resistant and -Susceptible Weed Biotypes," Weed Science, 40:670-679 (1992).
Hagio, "Chapter 25: Direct Gene Transfer into Plant Mature Seeds via Electroporation After Vacuum Treatment," Electroporation and Sonoporation in Developmental Biology, p. 285-293 (2009).
Haigh, "The Priming of Seeds: Investigation into a method of priming large quantities of seeds using salt solutions," Thesis submitted to Macquarie University (1983).
Hajirezaei et al., "Impact of elevated cytosolic and apoplastic invertase activity on carbon metabolism during potato tuber development," Journal of Experimental Botany, 51:439-445 (2000).
Hamilton et al., "Guidelines for the Identification and Characterization of Plant Viruses," J. gen. Virol., 54:223-241 (1981).
Hamilton et al., "Two classes of short interfering RNA in RNA silencing," EMBO J., 21(17):4671-4679 (2002).
Han et al., "Molecular Basis for the Recognition of Primary microRNAs by the Drosha-DGCR8 Complex," Cell, 125(5):887-901 (2006).
Hardegree, "Drying and storage effects on germination of primed grass seeds," Journal of Range Management, 47(3):196-199 (1994).
Harrison et al., "Does Lowering Glutamine Synthetase Activity in Nodules Modigy Nitrogen Metabolism and Growth of Lotus japonicus?," Plant Physiology, 133:253-262 (2003).
Hannon, "RNA interference," Nature,481:244-251 (2002).
Heffer et al., "Rapid isolation of gene homologs across taxa: Efficient identification and isolation of gene orthologs from non-model organism genomes, a technical report," EvoDevo Journal, 2(7):1-5 (2011).
Henderson et al., "U.S. National Bee Colony Loss Survey, www.beesurvey.com, Preliminary Findings With Respect to Colony Collapse Disorder (CCD)," Bee Alert Technology, Inc. (2007).

Heneberg et al., "Assemblage of filamentous fungi associated with aculeate hymenopteran brood in reed galls," *Journal of Invertebrate Pathology*, 133:95-106 (2016).
Herman et al., "A three-component dicamba O-demethylase from Pseudomonas maltophilia, strain DI-6: gene isolation, characterization, and heterologous expression," J. Biol. Chem., 280: 24759-24767 (2005).
Hess, "Surfactants and Additives," 1999 Proceedings of the California Weed Science Society, 51:156-172 (1999).
Hewezi et al., "Local infiltration of high- and low-molecular-weight RNA from silenced sunflower (*Helianthus annuus* L.) plants triggers post-transcriptional gene silencing in non-silenced plants," Plant Biotechnology Journal, 3:81-89 (2005).
Hidayat et al., "Enhanced Metabolism of Fluazifop Acid in a Biotype of Digitaria sanguinalis Resistant to the Herbicide Fluazifop-P-Butyl," Pesticide Biochem. Physiol., 57:137-146 (1997).
Himber et al., "Transitivity-dependant and -independent cell-to-cell movement of RNA silencing," The EMBO Journal, 22(17):4523-4533 (2003).
Hsieh et al., "A library of siRNA duplexes targeting the phosphoinositide 3-kinase pathway: determinants of gene silencing for use in cell-based screens," Nucleic Acids Res., 32(3):893-901 (2004).
Hirschberg et al., "Molecular Basis of Herbicide Resistance in Amaranthus hybridus," Science, 222:1346-1349 (1983).
Hoekema et al., "A binary plant vector strategy based on separation of vir- and T-region of the Agrobacterium tumefaciens Ti-plasmid," Nature, 303:179-180 (1983).
Hofgen et al., "Repression of Acetolactate Synthase Activity through Antisense Inhibition: Molecular and Biochemical Analysis of Transgenic Potato (*Solanum tuberosum* L. cv *Desiree*) Plants," Plant Physiol., 107(2):469-477 (1995).
Holtra et al., "Assessment of the Physiological Condition of *Salvinia Natans* L. Exposed to Copper(II) Ions," Environ. Protect. Eng., 41:147-158 (2015).
Hörmann et al., "Tic32, as Essential Component in Chloroplast Biogenesis," The Journal of Biological Chemistry, 279(33):34756-34762 (2004).
Horsch et al., "Inheritance of Functional Foreign Genes in Plants," Science, 223:496-498 (1984).
Hsu et al., "DNA targeting specificity of RNA-guided Cas9 nucleases," Nature Biotechnology, 31:827-832 (2013).
Hu et al., "High efficiency transport of quantum dots into plant roots with the aid of silwet L-77," Plant Physiology and Biochemistry, 48:703-709 (2010).
Huang et al., "Engineering broad root-know resistance in transgenic plants by RNAi silencing of a conserved and essential root-knot nematode parasitism gene," *Proc. Natl. Acad. Sci. USA*, 103(39):14302-14306 (2006).
Huang et al., "In Vivo Analyses of the Roles of Essential Omp85-Related Proteins in the Chloroplast Outer Envelope Membrane," Plant Physiol., 157:147-159 (2011).
Huesken et al., "Design of a genome-wide siRNA library using an artificial neural network," Nature Biotechnology, 23(8): 995-1001 (2005).
Huggett et al., "Real-time RT-PCR normalisation; strategies and considerations," Genes and Immunity, 6:279-284 (2005).
Hunter et al., "Large-Scale Field Application of RNAi Technology Reducing Israeli Acute Paralysis Virus Disease in Honey Bees (*Apis mellifera, Hymenoptera: Apidae*)," PLoS Pathogens, 6(12):e1001160-1-e1 001160-10 (2010).
Hunter et al., "RNA Interference Strategy to suppress Psyllids & Leafhoppers," International Plant and Animal Genome XIX, 15-19 (2011).
Huvenne et al., "Mechanisms of dsRNA uptake in insects and potential of RNAi for pest control: A review," *Journal of Insect Physiology*, 56:227-235 (2010).
Ichihara et al., "Thermodynamic instability of siRNA duplex is a prerequisite for dependable prediction of siRNA activities," Nucleic Acids Res., 35(18):e123 (2007).
Inaba et al., "*Arabidopsis* Tic110 Is Essential for the Assembly and Function of the Protein Import Machinery of Plastids," The Plant Cell, 17:1482-1496 (2005).

(56) References Cited

OTHER PUBLICATIONS

International Preliminary Report on Patentability (Chapter II) dated Jul. 24, 2015, in International Application No. PCT/US2014/047204.
International Preliminary Report on Patentability dated Apr. 26, 2012, in International Application No. PCT/IL2010/000844.
International Preliminary Report on Patentability dated Feb. 1, 2010, in International Application No. PCT/IL2008/001440.
International Preliminary Report on Patentability dated Feb. 21, 2012, in International Application No. PCT/IB2010/053776.
International Preliminary Report on Patentability dated Mar. 1, 2010, in International Application No. PCT/IB2010/053776.
International Preliminary Report on Patentability dated Nov. 17, 2011, in International Application No. PCT/IB2010/051980.
International Preliminary Report on Patentability dated Oct. 23, 2014, in International Application No. PCT/IL2013/050321.
International Preliminary Report on Patentability dated Sep. 11, 2012, in International Application No. PCT/US2011/027528.
International Preliminary Report on Patentability dated Sep. 11, 2014, in International Application No. PCT/IL2013/050447.
International Rice Genome Sequencing Project, The map-based sequence of the rice genome, Nature, 436(11):793-800 (2005).
International Search Report and the Written Opinion dated Feb. 25, 2013, in International Application No. PCT/US2012/054883.
International Search Report and the Written Opinion dated Feb. 27, 2013, in International Application No. PCT/US2012/054814.
International Search Report and the Written Opinion dated Feb. 27, 2013, in International Application No. PCT/US2012/054842.
International Search Report and the Written Opinion dated Feb. 27, 2013, in International Application No. PCT/US2012/054862.
International Search Report and the Written Opinion dated Feb. 27, 2013, in International Application No. PCT/US2012/054894.
International Search Report and the Written Opinion dated Feb. 27, 2013, in International Application No. PCT/US2012/054974.
International Search Report and the Written Opinion dated Feb. 27, 2013, in International Application No. PCT/US2012/054980.
International Search Report and the Written Opinion dated Jul. 15, 2014, in International Application No. PCT/US2014/025305.
International Search Report and the Written Opinion dated Jul. 22, 2014, in International Application No. PCT/IL2013/051083.
International Search Report and the Written Opinion dated Jul. 22, 2014, in International Application No. PCT/IL2013/051085.
International Search Report and the Written Opinion dated Jul. 24, 2014, in International Application No. PCT/US2014/026036.
International Search Report and the Written Opinion dated May 10, 2011, in International Application No. PCT/US2011/027528.
International Search Report and the Written Opinion dated Oct. 1, 2013, in International Application No. PCT/IL2013/050447.
International Search Report and Written Opinion dated Dec. 31, 2015, in International Application No. PCT/US2015/042415.
International Search Report and Written Opinion dated Feb. 24, 2011, in International Application No. PCT/IL2010/000844.
International Search Report and Written Opinion dated Jul. 19, 2010, in International Application No. PCT/IB2010/051980.
International Search Report and Written Opinion dated Mar. 26, 2015, in International Application No. PCT/US2014/069535.
International Search Report and Written Opinion dated May 23, 2017, in International Application No. PCT/US2017/015061.
International Search Report and Written Opinion dated Nov. 30, 2010, in International Application No. PCT/IB2010/053776.
International Search Report and Written Opinion dated Oct. 17, 2016, in International Application No. PCT/US2016/030579.
International Search Report and Written Opinion dated Oct. 28, 2013, in International Application No. PCT/IL2013/050321.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Feb. 23, 2015, in International Application No. PCT/US2014/063832.
International Search Report and Written Opinion dated Jul. 8, 2015, in International Application No. PCT/US2015/011408.
International Search Report and Written Opinion dated Mar. 26, 2015, in International Application No. PCT/US2014/069353.
International Search Report and Written Opinion dated May 26, 2016, in International Application No. PCT/US2016/014344.
International Search Report and Written Opinion dated Nov. 24, 2015, in International Application No. PCT/US2015/037522.
International Search Report and Written Opinion dated Nov. 27, 2015, in International Application No. PCT/US2015/037015.
International Search Report and Written Opinion dated Oct. 1, 2015 in International Application No. PCT/US2015/022985.
International Search Report dated Aug. 13, 2009, in International Application No. PCT/IL2008/001440.
International Search Report dated Mar. 12, 2013, in International Application No. PCT/US2012/054789.
International Search Report dated Oct. 13, 2016, in International Patent Application No. PCT/US2016/35500.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.
Isaacs et al., "Engineered riboregulators enable post-transcriptional control of gene expression," Nature Biotechnology, 22(7):841-847 (2004).
Ivanova et al., "Members of the Toc159 Import Receptor Family Represent Distinct Pathways for Protein Targeting to Plastids," Molecular Biology of the Cell, 15:3379-3392 (2004).
Jacque et al., "Modulation of HIV-1 replication by RNA interference," Nature, 418, 435-438 (2002).
Jang et al., "Resistance to herbicides caused by single amino acid mutations in acetyl-CoA carboxylase in resistant populations of grassy weeds," New Phytologist, 197(4):1110-1116 (2013).
Jarvis et al, "An *Arabidopsis* mutant defective in the plastid general protein import apparatus," Science, 282:100-103 (1998).
Ji et al., "Regulation of small RNA stability: methylation and beyond," Cell Research, 22:624-636 (2012).
Jiang et al., Chapter III Seeds and Seedlings, Botany, Northwest A&F University Press, pp. 87-92 (2009).
Jin et al., "Posttranslational Elevation of Cell Wall Invertase Activity by Silencing its Inhibitor in Tomato Delays Leaf Senescence and Increases Seed Weight and Fruit Hexose Level," The Plant Cell, 21:2072-2089 (2009).
Jofre-Garfias et al., "Agrobacterium-mediated transformation of Amaranthus hypochondriacus: light- and tissue-specific expression of a pea chlorophyll a/b-binding protein promoter," Plant Cell Reports, 16:847-852 (1997).
Jones-Rhoades et al., "MicroRNAs and Their Regulatory Roles in Plants," Annu. Rev. Plant Biol., 57:19-53 (2006).
Josse et al., "A DELLA in Disguise: SPATULA Restrains the Growth of the Developing *Arabidopsis* Seedling," Plant Cell, 23:1337-1351 (2011).
Kaloumenos et al., "Identification of a Johnsongrass (*Sorghum halepense*) Biotype Resistant to ACCase-Inhibiting Herbicides in Northern Greece," Weed Technol, 23:470-476 (2009).
Kam et al., "Nanotube Molecular Transporters: Internalization of Carbon Nanotube—Protein Conjugates into Mammalian Cells," J. Am. Chem. Soc., 126(22):6850-6851 (2004).
Kambiranda et al., "Relationship Between Acid Invertase Activity and Sugar Content in Grape Species," Journal of Food Biochemistry, 35:1646-1652 (2011).
Katoh et al., "Specific residues at every third position of siRNA shape its efficient RNAi activity," Nucleic Acids Res., 35(4): e27 (2007).
Kertbundit et al., "In vivo random β-glucuronidase gene fusions in *Arabidopsis thaliana*," Proc. Natl. Acad. Sci. U S A., 88:5212-5216 (1991).

(56) References Cited

OTHER PUBLICATIONS

Khachigian, "DNAzymes: Cutting a path to a new class of therapeutics," Curr Opin Mol Ther 4(2):119-121 (2002).
Khanbekova et al., The defeat of the honey bee apis melifera caucasica Gorb. By viruses and parasites, and condition of bee colonies in different ecogeographical conditions of Greater Caucasus, Agricultural Biology. 2013 (p. 43) (in Russian).
Khan et al., "Matriconditioning of Vegetable Seeds to Improve Stand Establishment in Early Field Plantings," J. Amer. Soc. Hort. Sci., 117(1):41-47 (1992).
Khodakovskaya et al., "Carbon Nanotubes Are Able to Penetrate Plant Seed Coat and Dramatically Affect Seed Germination and Plant Growth," ACS Nano, 3(10):3221-3227 (2009).
Khovorova et al., "Rational siRNA design for RNA interference," Nature Biotechnol., 22 :326-330 (2004).
Kikkert et al., "Stable Transformation of Plant Cells by Particle Bombardment/Biolistics," Methods in Molecular Biology, 286:61-78 (2005).
Kim et al., "Optimization of Conditions for Transient Agrobacterium-Mediated Gene Expression Assays in *Arabidopsis*," Plant Cell Reports, 28:1159-1167 (2009).
Kim et al., "Synthetic dsRNA Dicer substrates enhance RNAi potency and efficacy," Nature Biotechnology, 23(2):222-226 (2005).
Kim et al., "Synthesis and characterization of mannosylated pegylated polyethylenimine as a carrier for siRNA," International Journal of Pharmaceutics, 427:123-133 (2012).
Kirkwood, "Herbicides and Plants," Botanical Journal of Scotland, 46(3):447-462 (1993).
Kirkwood, "Use and Mode of Action of Adjuvants for Herbicides: A Review of some Current Work," Pestic Sci., 38:93-102 (1993).
Kirkwood, "Recent developments in our understanding of the plant cuticle as a barrier to the foliar uptake of pesticides," Pestic Sci, 55:69-77 (1999).
Klahre et al., "High molecular weight RNAs and small interfering RNAs induce systemic posttranscriptional gene silencing in plants," Proc. Natl. Acad. Sci. USA, PNAS, 99(18):11981-11986 (2002).
Kondylis et al., "The Golgi apparatus: Lessons from *Drosophila*," FEBS Letters 583:3827-3838 (2009).
Kovacheva et al., "In vivo studies on the roles of Tic100, Tic40 and Hsp93 during chloroplast protein import," The Plant Journal, 41:412-428 (2005).
Kovacheva et al., "Further in vivo studies on the role of the molecular chaperone, Hsp93, in plastid protein import," The Plant Journal, 50:364-379 (2007).
Knudsen, "Promoter2.0: for the recognition of PolI promoter sequences," Bioinformatics, 15(5):356-361 (1999).
Kronenwett et al., "Oligodeoxyribonucleotide Uptake in Primary Human Hematopoietic Cells Is Enhanced by Cationic Lipids and Depends on the Hematopoietic Cell Subset," Blood, 91(3):852-862 (1998).
Kumar et al., "Sequencing, De Novo Assembly and Annotation of the Colorado Potato Beetle, *Leptinotarsa decemlineata*, Transcriptome," PLoS One, 9(1):e86012 (2014).
Kusaba et al., "Low glutelin content1: A Dominant Mutation That Suppresses the Glutelin Multigene Family via RNA Silencing ni Rice," The Plant Cell, 15(6):1455-1467(2003).
Kusaba, "RNA interference in crop plants," Curr Opin Biotechnol, 15(2):139-143 (2004).
Lavigne et al., "Enhanced antisense inhibition of human immunodeficiency virus type 1 in cell cultures by DLS delivery system," Biochem Biophys Res Commun, 237:566-571 (1997).
Lee et al., "A systematic RNAi screen identifies a critical role for mitochondria in C. elegans longevity." Nature Genetics, 33:40-48 (2003).
Lee et al., "Aptamer Database," Nucleic Acids Research, 32:D95-D100 (2004).
Lein et al., "Target-based discovery of novel herbicides," Current Opinion in Plant Biology, 7:219-225 (2004).
Leopold et al., "Chapter 4: Moisture as a Regulator of Physiological Reaction in Seeds," Seed Moisture, CSSA Special Publication No. 14, pp. 51-69 (1989).
Lermontova et al., "Reduced activity of plastid protoporphyrinogen oxidase causes attenuated photodynamic damage during high-light compared to low-light exposure," The Plant Journal, 48(4):499-510 (2006).
Lesnik et al., "Prediction of rho-independent transcriptional terminators in *Escherichia coli*," Nucleic Acids Research, 29(17):3583-3594 (2001).
Li et al., "Establishment of a highly efficient transformation system for pepper (*Capsicum annuum* L.)," Plant Cell Reports, 21: 785-788 (2003).
Li et al., "The FAST technique: a simplified Agrobacterium-based transformation method for transient gene expression analysis in seedlings of *Arabidopsis* and other plant species," Plant Methods, 5(6):1-15 (2009).
Li et al., "A Simplified Seed Transformation Method for Obtaining Transgenic *Brassica napus* Plants," Agricultural Sciences in China, 8(6):658-663 (2009).
Li et al, "RNA interference in *Nilaparvata lugens* (Homoptera:Delphacidae) based on dsRNA ingestion," Pest Manag. Sci., 67:852-859 (2011).
Li et at., "Long dsRNA but not siRNA initiates RNAi in western corn rootworm larvae and adults," Journal of Applied Entomology, 139(6):432-445 (2015).
Liu et al., "Identification and Application of a Rice Senescence-Associated Promoter," Plant Physiology, 153:1239-1249 (2010).
Liu et al., "Prevention of Chinese Sacbrood Virus Infection in Apis Cerana Using RNA Interference," Current Microbiology, 61(5):422-428 (2010).
Liu, "Calmodulin and Cell Cycle," Foreign Medical Sciences Section of Pathophysiology and Clinical Medicine, 18(4):322-324 (1998).
Liu, "Confocal laser scanning microscopy—an attractive tool for studying the uptake of xenobiotics into plant foliage," Journal of Microscopy, 213(Pt 2): 87-93 (2004).
Liu et al., "Carbon Nanotubes as Molecular Transporters for Walled Plant Cells," Nano Letters, 9(3):1007-1010 (2009).
Liu et al., "Comparative study on the interaction of DNA with three different kinds of surfactants and the formation of multilayer films," Bioelectrochemistry, 70:301-307 (2007).
Liu et al., "DNAzyme-mediated recovery of small recombinant RNAs from a 5S rRNA-derived chimera expressed in *Escherichia coli*," BMC Biotechnology, 10:85 (2010).
Liu et al., "RNA interference in Nilaparvata lugens (Homoptera : Delphacidae) based on dsRNA ingestion," Pest Manag. Sci., 67:852-859 (2011).
Liu, "Influence of Sugars on the Foliar Uptake of Bentazone and Glyphosate," New Zealand Plant Protection, 55:159-162 (2002).
Liu, "The Transformation of Nucleic Acid Degradants in Plants," China Organic Fertilizers, Agriculture Press, ISBN: 7-1091634 (1991) (with English translation).
Liu et al, "The Helicase and RNaseIIIa Domains of *Arabidopsis* Dicer-Like1 Modulate Catalytic Parameters during MicroRNA Biogenesis," Plant Physiology, 159:748-758 (2012).
Llave et al., "Endogenous and Silencing-Associated Small RNAs in Plants," The Plant Cell, 14:1605-1619 (2002).
Lodish et al., Molecular Cell Biology, Fourth Edition, p. 210 (2000).
Lu et al., "OligoWalk: an online siRNA design tool utilizing hybridization thermodynamics," Nucleic Acids Research, 36:W104-W108 (2008).
Lu et al., "RNA silencing in plants by the expression of siRNA duplexes," Nucleic Acids Res., 32(21):e171 (2004).
Lucas et al., "Plasmodesmata—bridging the gap between neighboring plant cells," Trends in Cell Biology, 19:495-503 (2009).
Luft, "Making sense out of antisense oligodeoxynucleotide delivery: getting there is half the fun," J Mol Med, 76:75-76 (1998).
Luque et al., "Water Permeability of Isolated Cuticular Membranes: A Structural Analysis," Archives of Biochemistry and Biophysics, 317(2):417-422 (1995).

(56) References Cited

OTHER PUBLICATIONS

Maas et al., "Mechanism and optimized conditions for PEG mediated DNA transfection into plant protoplasts," Plant Cell Reports, 8:148-149 (1989).
MacKenzie et al., "Transgenic Nicotiana debneyii expressing viral coat protein are resistant to potato virus S infection," Journal of General Virology, 71:2167-2170 (1990).
Maggi et al., "Resistance Phenomena to Amitraz From Population of the Ectoparasitic Mite Varroa Destructor of Argentina," Parasitology Research, 107(5):1189-1192 (2010).
Maher III et al., "Inhibition of DNA binding proteins by oligonucleotide-directed triple helix formation," Science, 245(4919):725-730 (1989).
Makkouk et al., "Virus Diseases of Peas, Beans, and Faba Bean in the Mediterranean region," Adv Virus Res, 84:367-402 (2012).
Mandal et al., "Adenine riboswitches and gene activation by disruption of a transcription terminator," Nature Struct. Mol. Biol., 11(1):29-35 (2004).
Mandal et al., "Gene Regulation by Riboswitches," Nature Reviews | Molecular Cell Biology, 5:451-463 (2004).
Manoharan, "Oligonucleotide Conjugates as Potential Antisense Drugs with Improved Uptake, Biodistribution, Targeted Delivery, and Mechanism of Action," Antisense & Nucleic Acid Drug Development, 12:103-128 (2002).
Mao et al., "Silencing a cotton bollworm P450 monooxygenase gene by plant-mediated RNAi impairs larval tolerance of gossypol.," Nat Biotechnol., 25(11):1307-13 (2007).
Maori et al., "Isolation and characterization of Israeli acute paralysis virus, a dicistrovirus affecting honeybees in Israel: evidence for diversity due to intra- and inter-species recombination," *Journal of General Virology*, 88:3428-3438 (2007).
Maori et al., "Israel Acute Paralysis Virus of Bees, Complete Genome," GenBank EMBL, EBI Dbfetch, XP002533679, Accession No. EF219380, Nov. 21, 2007.
Maori et al., "Reciprocal sequence exchange between non-retro viruses and hosts leading to the appearance of new host phenotypes," *Virology*, 362(2):342-349 (2007).
Maori et al., "IAPV, a bee-affecting virus associated with Colony Collapse Disorder can be silenced by dsRNA ingestion," Insect Molecular Biology, 18(1):55-60 (2009).
Masoud, "Constitutive expression of an inducible β-1,3-glucanase in alfalfa reduces disease severity caused by the oomycete pathogen *Phytophthora megasperma* f. sp *medicaginis* . . . .," Trans Res, 5:313-323 (1996).
Matveeva et al., "Prediction of antisense oligonucleotide efficacy by in vitro methods," Nature Biotechnology, 16:1374-1375 (1998).
McGinnis, "RNAi for functional genomics in plants," Brief Funct Genomics, 9(2):111-7 (2010).
Meinke, et al., "Identifying essential genes in *Arabidopsis thaliana*," Trends. Plant Sci., 13(9):483-491 (2008).
Meins et al., "RNA Silencing Systems and Their Relevance to Plant Development," Annu. Rev. Cell Dev. Biol., 21:297-318 (2005).
Melnyk et al., "Intercellular and systemic movement of RNA silencing signals," The EMBO Journal, 30:3553-3563 (2011).
Migge et al., "Greenhouse-grown conditionally lethal tobacco plants obtained by expression of plastidic glutamine synthetase antisense RNA may contribute to biological safety," Plant Science 153:107-112 (2000).
Misawa, "Functional expression of the Erwinia uredovora carotenoid biosynthesis gene crtl in transgenic plants showing an increase of β-carotene biosynthesis activity and resistance . . . ," The Plant Jrnl, 4(5):833-840 (1993).
Misawa, "Expression of an Erwinia phytoene desaturase gene not only confers multiple resistance to herbicides interfering with carotenoid biosynthesis but also alters xanthophyll metabolism . . . ," The Plant Jrnl, 6(4):481-489 (1994).
Miura et al., "The Balance between Protein Synthesis and Degradation in Chloroplasts Determines Leaf Variegation in *Arabidopsis* yellow variegated Mutants," The Plant Cell, 19:1313-1328 (2007).

Molina et al., "Inhibition of protoporphyrinogen oxidase expression in *Arabidopsis* causes a lesion-mimic phenotype that induces systemic acquired resistance," The Plant Journal, 17(6):667-678 (1999).
Molnar et al., "Plant Virus-Derived Small Interfering RNAs Originate redominantly from Highly Structured Single-Stranded Viral RNAs," Journal of Virology, 79(12):7812-7818 (2005).
Molnar et al., "Small Silencing RNAs in Plants Are Mobile and Direct Epigenetic Modification in Recipient Cells," Science, 328:872-875 (2010).
Mora et al., "How Many Species Are There on Earth and in the Ocean?," PLOS Biol., 9(8):e100127, p. 1-8 (2011).
Moriyama et al., "Double-stranded RNA in rice: a novel RNA replicon in plants," Molecular & General Genetics, 248(3):364-369 (1995).
Moriyama et al., "Stringently and developmentally regulated levels of a cytoplasmic double-stranded RNA and its high-efficiency transmission via egg and pollen in rice," Plant Molecular Biology, 31:713-719 (1996).
Morrissey et al., "Potent and persistent in vivo anti-HBV activity of chemically modified siRNAs," Nat Biotechnol. 23(8):1002-1007 (2005).
Morozov et al., "Evaluation of Preemergence Herbicides for Control of Diclofop-resistant Italian Ryegrass (*Lolium multiflorum*) in Virginia," Virginia Polytechnic Institute and State University, pp. 43-71 (2004).
Moser et al., "Sequence-Specific Cleavage of Double Helical DNA by Triple Helix Formation," Science, 238:645-646 (1987).
Mount et al., "Gene and Metabolite Regulatory Network Analysis of Early Developing Fruit Tissues Highlights New Candidate Genes for the Control of Tomato Fruit Composition and Development," Plant Physiology, 149:1505-1528 (2009).
Nakayashiki et al. "Evolution and Diversification of RNA Silencing Proteins in Fungi", Journal of Molecular Evolution, 63(1):127-135 (2006).
Nemeth, "Virus, mycoplasma and rickettsia diseases of fruit trees," Martinus Nijhoff Publishers, 197-204 (1986).
Non-Final Office Action dated Apr. 11, 2013, in U.S. Appl. No. 13/042,856.
Non-Final Office Action dated Apr. 15, 2014, in U.S. Appl. No. 13/446,557.
Non-Final Office Action dated Apr. 29, 2016, in U.S. Appl. No. 13/583,302.
Non-Final Office Action dated Aug. 10, 2016, in U.S. Appl. No. 13/612,995.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Aug. 19, 2016, in U.S. Appl. No. 13/612,925.
Non-Final Office Action dated Aug. 19, 2016, in U.S. Appl. No. 13/612,929.
Non-Final Office Action dated Aug. 3, 2016, in U.S. Appl. No. 14/015,715.
Non-Final Office Action dated Aug. 5, 2016, in U.S. Appl. No. 14/015,785.
Non-Final Office Action dated Aug. 8, 2016, in U.S. Appl. No. 13/612,936.
Non-Final Office Action dated Dec. 17, 2015, in U.S. Appl. No. 14/532,596.
Non-Final Office Action dated Feb. 10, 2016, in U.S. Appl. No. 13/901,326.
Non-Final Office Action dated Feb. 23, 2016, in U.S. Appl. No. 14/603,347.
Non-Final Office Action dated Feb. 23, 2016, in U.S. Appl. No. 14/608,951.
Non-Final Office Action dated Feb. 5, 2014, in U.S. Appl. No. 13/446,557.
Non-Final Office Action dated Jan. 7, 2013, in U.S. Appl. No. 13/318,636.
Non-Final Office Action dated Jul. 23, 2015, in U.S. Appl. No. 14/335,135.

(56) References Cited

OTHER PUBLICATIONS

Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated Mar. 1, 2016, in U.S. Appl. No. 13/612,954.
Non-Final Office Action dated Mar. 21, 2018, in U.S. Appl. No. 13/619,980.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Non-Final Office Action dated May 30, 2012, in U.S. Appl. No. 13/332,430.
Non-Final Office Action dated May 4, 2015, in U.S. Appl. No. 13/932,051.
Non-Final Office Action dated Nov. 9, 2016, in U.S. Appl. No. 14/901,003.
Non-Final Office Action dated Oct. 3, 2016, in U.S. Appl. No. 14/403,491.
Non-Final Office Action dated Sep. 1, 2015, in U.S. Appl. No. 13/612,954.
Non-Final Office Action dated Sep. 11, 2015, in U.S. Appl. No. 13/612,925.
Non-Final Office Action dated Sep. 23, 2010, in U.S. Appl. No. 12/222,949.
Non-Final Office Action dated Sep. 4, 2015, in U.S. Appl. No. 13/612,995.
Non-Final Office Action dated Sep. 6, 2016, in U.S. Appl. No. 14/335,135.
Nookaraju et al., "Molecular approaches for enhancing sweetness in fruits and vegetables," Scientia Horticulture, 127:1-15 (2010).
Notice of Allowance dated Apr. 11, 2016, in U.S. Appl. No. 13/612,985.
Notice of Allowance dated Apr. 19, 2016, in U.S. Appl. No. 13/612,941.
Notice of Allowance dated Apr. 20, 2016, in U.S. Appl. No. 13/612,948.
Notice of Allowance dated Feb. 23, 2015, in U.S. Appl. No. 13/042,856.
Notice of Allowance dated Jun. 2, 2015, in U.S. Appl. No. 13/042,856.
Notice of Allowance dated Oct. 5, 2015, in U.S. Appl. No. 13/583,302.
N-TER Nanoparticle siRNA, Sigma Aldrich TM website, Web. Nov. 20, 2018.
Nord-Larsen et al., "Cloning, characterization and expression analysis of tonoplast intrinsic proteins and glutamine synthetase in ryegrass (*Lolium perenne* L.)," Plant Cell Reports, 28(10):1549-1562 (2009).
Nowak et al., "A new and efficient method for inhibition of RNA viruses by in DNA interference," The FEBS Journal, 276:4372-4380 (2009).
Nunes et al., "A non-invasive method for silencing gene transcriptoin in honeybees maintained under natural conditions," *Insect Biochemistry and Molecular Biology*, 39:157-160 (2009).
Office Action dated 2015, in Chinese Patent Application No. 201080056585.9.
Office Action dated Apr. 13, 2016, in Chinese Patent Application No. 201280053985.3.
Office Action dated Apr. 15, 2014, in U.S. Appl. No. 13/446,557.
Office Action dated Aug. 1, 2013, in U.S. Appl. No. 13/318,636.
Office Action dated Aug. 1, 2017, in European Patent Application No. 12 830 932.5.
Office Action dated Aug. 14, 2017, in Israeli Patent Application No. 235878.
Office Action dated Aug. 22, 2017, in Korean Patent Application No. 10-2012-7023415.
Office Action dated Aug. 25, 2015, in New Zealand Patent Application No. 700791.
Office Action dated Aug. 25, 2016, in Eurasian Patent Application No. 201201264.
Office Action dated Aug. 28, 2013, in Chinese Patent Application No. 201180012795.2.
Office Action dated Aug. 3, 2015, in Chinese Patent Application No. 201080056585.9 (English translation attached).
Office Action dated Aug. 3, 2017, in Chinese Patent Application No. 201480014392.5 (with English translation).
Office Action dated Aug. 3, 2017, in European Patent Application No. 12 831 684.1.
Office Action dated Aug. 8, 2017, in Chilean Patent Application No. 201501874.
Office Action dated Sep. 20, 2018, in Chilean Patent Application No. 201601440 (with English translation).
Office Action dated Dec. 13, 2016, in Ukrainian Patent Application No. a 2014 03843.
Office Action dated Dec. 14, 2016, in Ukrainian Patent Application No. a 2014 03850.
Office Action dated Dec. 15, 2016, in Ukrainian Patent Application No. a 2014 03845.
Office Action dated Dec. 15, 2016, in Ukrainian Patent Application No. a 2014 03849.
Office Action dated Dec. 15, 2016, in Ukrainian Patent Application No. a 2014 03852.
Office Action dated Dec. 18, 2014, in Israeli Patent Application No. 216154 (with English translation).
Office Action dated Dec. 21, 2015, in Israeli Patent Application No. 240416 (with English translation).
Office Action dated Dec. 27, 2016, in Ukrainian Patent Application No. a 2012 11548.
Office Action dated Dec. 31, 2014, in Israeli Patent Application No. 205594 (with English translation).
Office Action dated Dec. 5, 2017, in Japanese Patent Application No. 2016-502033.
Office Action dated Feb. 17, 2011, in European Patent Application No. 08847971.2.
Office Action dated Feb. 17, 2014, in European Patent Application No. 08847971.2.
Office Action dated Feb. 17, 2014, in Mexican Patent Application No. Mx/a/2012/010479.
Office Action dated Feb. 21, 2018, in Mexican Patent Application No. Mx/a/2015/012632 (with English translation).
Office Action dated Feb. 24, 2014, in Eurasian Patent Application No. 201201264.
Office Action dated Feb. 5, 2015, in European Patent Application No. 13156183.9.
Office Action dated Feb. 6, 2015, in European Patent Application No. 10719620.6.
Office Action dated Jan. 19, 2014, in Israeli Patent Application No. 205594 (with English translation).
Office Action dated Jan. 26, 2015, in Israeli Patent Application No. 205594 (with English translation).
Office Action dated Jan. 26, 2015, in Israeli Patent Application No. 219193 (with English translation).
Office Action dated Jan. 30, 2015, in Mexican Patent Application No. MX/a/2012/004378 (with English translation).
Office Action dated Jan. 7, 2013, in U.S. Appl. No. 13/318,636.
Office Action dated Jul. 11, 2017, in Mexican Patent Application No. MX/a/2015/013118 (with English translation).
Office Action dated Jul. 12, 2013, in European Patent Application No. 08847971.2.
Office Action dated Jul. 18, 2016, in Indonesian Patent Application No. W00201203610.
Office Action dated Jul. 2, 2013, in Chinese Patent Application No. 201080056585.9.
Office Action dated Jul. 23, 2015, in Ukrainian Patent Application No. 201211548.
Office Action dated Jul. 3, 2017, in Mexican Patent Application No. MX/a/2015/012632 (with English translation).

(56) References Cited

OTHER PUBLICATIONS

Office Action dated Jul. 6, 2017, in Mexican Patent Application No. MX/a/2015/013103 (with English translation).
Office Action dated Jun. 29, 2012, in European Patent Application No. 08847971.2.
Office Action dated Jun. 20, 2016, in Chinese Patent Application No. 201280054819.5.
Office Action dated Jun. 24, 2016, in Chinese Patent Application No. 201280053984.9.
Office Action dated Jun. 28, 2010, in U.S. Appl. No. 12/222,949.
Office Action dated Jun. 8, 2015, in European Patent Application No. 13156185.4.
Office Action dated Mar. 10, 2014, in European Patent Application No. 13156180.4.
Office Action dated Mar. 10, 2014, in European Patent Application No. 13156180.5.
Office Action dated Mar. 16, 2017, in Chinese Patent Application No. 201280054819.5.
Office Action dated Mar. 17, 2014, in European Patent Application No. 13156183.9.
Office Action dated Mar. 18, 2011, in U.S. Appl. No. 12/222,949.
Office Action dated Mar. 19, 2012, in Israeli Patent Application No. 205594 (English Translation attached).
Office Action dated Mar. 19, 2015, in Canadian Patent Application No. 2,704,858.
Office Action dated Mar. 20, 2015, in Indian Patent Application No. 1150/MUMNP/2010.
Office Action dated Mar. 8, 2018 (with English translation), in Chilean Patent Application No. 201403192.
Office Action dated May 12, 2014, in Chinese Patent Application No. 201080056585.9.
Office Action dated May 12, 2014, in Mexican Patent Application No. MX/a/2012/004378 (English Translation attached).
Office Action dated May 29, 2015, in European Patent Application No. 13156180.4.
Office Action dated May 29, 2015, in European Patent Application No. 13156180.5.
Office Action dated May 3, 2016, in Chilean Patent Application No. 201601057.
Office Action dated May 30, 2012, in U.S. Appl. No. 13/332,430.
Office Action dated Nov. 10, 2014, in European Patent Application No. 10779855.5.
Office Action dated Nov. 15, 2016, in Mexican Patent Application No. MX/a/2014/003068 (with English translation).
Office Action dated Nov. 21, 2012, in U.S. Appl. No. 13/318,636.
Office Action dated Nov. 6, 2014, in Australian Patent Application No. 2010244122.
Office Action dated Oct. 15, 2012, in U.S. Appl. No. 13/332,430.
Office Action dated Oct. 21, 2015, in European Patent Application No. 13723252.6.
Office Action dated Oct. 23, 2013, in Australian Patent Application No. 2008325989.
Office Action dated Oct. 31, 2013, in Mexican Patent Application No. MX/a/2012/004378 (English Translation attached).
Office Action dated Oct. 31, 2013, in Mexican Patent Application No. MX/a/2012/004378.
Office Action dated Oct. 8, 2013, in European Patent Application No. 10719620.6.
Office Action dated Sep. 29, 2014, European Patent Application No. 13156180.4.
Office Action dated Sep. 29, 2014, in European Patent Application No. 13156180.5.
Office Action dated Sep. 1, 2015, in European Patent Application No. 10779855.5.
Office Action dated Sep. 23, 2010, in U.S. Appl. No. 12/222,949.
Office Action dated Sep. 28, 2015, in U.S. Appl. No. 13/932,051.
Office Action dated Sep. 29, 2014, in European Patent Application No. 13156180.4.
Office Action dated Sep. 4, 2015, in European Patent Application No. 13156183.9.
Office Action dated Sep. 5, 2016, in Ukrainian Patent Application No. a 2014 03846.
Office Action dated Sep. 6, 2017, in Chinese Patent Application No. 2014800154012 (with English translation).
Office Action dated Nov. 3, 2014, in Chinese Patent Application No. 201180012795.2.
Office Action dated Jan. 6, 2015, in Japanese Patent Application No. 2012-557165.
Office Action dated Nov. 19, 2014, in Eurasian Patent Application No. 201201264/28.
Office Action dated Oct. 5, 2015, in Eurasian Patent Application No. 201201264/28.
Office Action dated Jul. 30, 2018, in Canadian Patent Application No. 2,848,576.
Office Action dated Aug. 9, 2018, in Canadian Patent Application No. 2,848,371.
Ongvarrasopone et al., "A Simple and Cost Effective Method to Generate dsRNA for RNAi Studies in Invertebrates," Science Asia, 33:35-39 (2007).
Orbović et al., "Foliar-Applied Surfactants and Urea Temporarily Reduce Carbon Assimilation of Grapefruit Leaves," J. Amer. Soc. Hort. Sci., 126(4):486-490 (2001).
Ouellet et al., "Members of the Acetohydroxyacid Synthase Muligene Family of *Brassica napus* Have Divergent Patterns of Expression," The Plant Journal, Blackwell Scientific Publications, Oxford, GB, 2(3):321-330 (1992).
Paddison et al., "Stable suppression of gene expression by RNAi in mammalian cells," Proc. Natl Acad. Sci. USA, 99(3):1443-1448 (2002).
Palacios et al., "Genetic Analysis of Israel Acute Paralysis Virus: Distinct Clusters Are Circulating in the United States," *Journal of Virology*, 82(13):6209-6217 (2008).
Palauqui et al., "Activation of systemic acquired silencing by localised introduction of DNA," Current Biology, 9:59-66 (1999).
Paldi et al. "Effective Gene Silencing in a Microsporidian Parasite Associated With Honeybee (*Apis mellifera*) Colony Declines", Applied and Environmental Microbiology, 760(17):5960-5964 (2010).
Parera et al., "Dehydration Rate after Solid Matrix Priming Alters Seed Performance of Shrunken-2 Corn," J. Amer. Soc. Hort. Sci., 119(3):629-635 (1994).
Partial European Search Report dated Dec. 6, 2017, in European Patent Application No. 17181861.0.
Partial International Search Report dated Jul. 24, 2013, International Application No. PCT/2013/050321.
Partial International Search Report dated May 13, 2009, in International Application No. PCT/IL2008/001440.
Partial Supplementary European Search Report dated Mar. 2, 2015, in European Patent Application No. 12 831 494.5.
Partial Supplementary European Search Report dated Jan. 11, 2018, in European Patent Application No. 15812530.0.
Partial European Search Report dated Jun. 29, 2018, in European Patent Application No. 18157745.3.
Patent Examination Report dated Nov. 6, 2014, in Australian Patent Application No. 2010244122.
Patent Examination Report dated Oct. 23, 2013, in Australian Patent Application No. 2008325989.
Patent Examination Report No. 1 dated Feb. 8, 2016, in Australian Patent Application No. 2014262189.
Patent Examination Report No. 1 dated Jun. 17, 2016, in Australian Patent Application No. 2012308659.
Patent Examination Report No. 1 dated Jun. 17, 2016, in Australian Patent Application No. 2012308660.
Patent Examination Report No. 1 dated Jun. 8, 2017, in Australian Patent Application No. 2012308686.
Patent Examination Report No. 1 dated Nov. 11, 2013, in Australian Patent Application No. 2011224570.
Paungfoo-Lonhienne et al., "DNA is Taken up by Root Hairs and Pollen, and Stimulates Root and Pollen Tube Growth," Plant Physiology, 153:799-805 (2010).
Paungfoo-Lonhienne et al., "DNA uptake by *Arabidopsis* induces changes in the expression of CLE peptides which control root morphology," Plant Signaling & Behavior, 5(9):1112-1114 (2010).

(56) References Cited

OTHER PUBLICATIONS

Pei et al., "On the art of identifying effective and specific siRNAs," Nature Methods, 3(9):670-676 (2006).
Peretz et al., "A Universal Expression/Silencing Vector in Plants," Plant Physiology, 145:1251-1263 (2007).
Pitino et al., "Silencing of Aphid Genes by dsRNA Feeding from Plants," PLos ONE, 6:e25709 (2011).
Pornprom et al., "Glutamine synthetase mutation conferring target-site-based resistance to glufosinate in soybean cell selections," Pest Manag Sci, 2009; 65(2):216-222 (2009).
Powles et al., "Evolution in Action: Plants Resistant to Herbicides," Annual Review of Plant Biology, 61(1):317-347 (2010).
Pratt et al., "Amaranthus rudis and A. tuberculatus, One Species or Two?," Journal of the Torrey Botanical Society, 128(3):282-296 (2001).
Pratt et al., "Sorghum Expressed Sequence Tags Identify Signature Genes for Drought, Pathogenesis, and Skotomorphogenesis from a Milestone Set of 16,801 Unique Transcripts," Plant Physiology, 139:869-884 (2005).
Preston et al., "Multiple effects of a naturally occurring proline to threonine substitution within acetolactate synthase in two herbicide-resistant populations of Lactuca serriola," Pesticide Biochem. Physiol., 84(3):227-235 (2006).
Price et al. "RNAi-Mediated Crop Protection Against Insects", Trends in Biotechnology, XP022757296, 26(7):393-400 (2008).
Pridgeon et al., "Topically Applied AaeIAP1 Double-Stranded RNA Kills Feman Adults of *Aedes aegypti,*" *J. Med. Entomol.*, 45(3):414-420 (2008).
Promoter Prediction for SEQ ID No. 1702 from 13/612929/MK/, Promoter 2.0 Prediction Results, pp. 1-4 (2016).
Promoter Prediction for SEQ ID No. 4 from 13/612995/MK/, Promoter 2.0 Prediction Results, pp. 1-3 (2016).
Promoter Prediction for SEQ ID No. 7 from 13/612936/MK/, Promoter 2.0 Prediction Results, pp. 1-2 (2016).
Promoter Prediction for SEQ ID No. 8 from 13/612,925/MK/, Promoter 2.0 Prediction Results, pp. 1-6 (2016).
Qi et al., "RNA processing enables predictable programming of gene expression," Nature Biotechnology, 30:1002-1007 (2012).
Qiwei,"Advance in DNA interference," Progress in Veterinary Medicine, 30(1):71-75 (2009).
Rajur et al., "Covalent Protein-Oligonucleotide Conjugates for Efficient Delivery of Antisense Molecules," Bioconjug Chem., 8:935-940 (1997).
Rakoczy-Trojanowska, "Alternative Methods of Plant Transformation—a short review," Cellular & Molecular Biology Letters, 7:849-858 (2002).
Reddy et al "Organosilicone Adjuvants Increased the Efficacy of Glyphosate for Control of Weeds in Citrus (*Citrus* spp.)" HortScience 27(9):1003-1005 (1992).
Reddy et al., "Aminomethylphosphonic Acid Accumulation in Plant Species Treated with Glyphosate," J. Agric. Food Chem., 56(6):2125-2130 (2008).
Regalado, "The Next Great GMO Debate," MIT Technology Review,pp. 1-19 (2015).
Reither et al., "Specificity of DNA triple helix formation analyzed by a FRET assay," BMC Biochemistry, 3:27 (2002).
Requisition by the Examiner and Examination Search Report dated Mar. 19, 2015, in Canadian Patent Application No. 2,704,858.
Restriction Requirement dated Apr. 21, 2015, in U.S. Appl. No. 13/612,954.
Restriction Requirement dated Feb. 12, 2015, in U.S. Appl. No. 13/612,985.
Restriction Requirement dated Jul. 15, 2016, in U.S. Appl. No. 14/143,748.
Restriction Requirement dated Jul. 18, 2016, in U.S. Appl. No. 14/143,836.
Restriction Requirement dated Mar. 12, 2015, in U.S. Appl. No. 13/612,948.
Restriction Requirement dated Mar. 4, 2015, in U.S. Appl. No. 13/612,941.
Restriction Requirement dated May 4, 2015, in U.S. Appl. No. 13/612,929.
Restriction Requirement dated May 5, 2015, in U.S. Appl. No. 13/612,936.
Restriction Requirement dated May 7, 2015, in U.S. Appl. No. 13/612,925.
Restriction Requirement dated May 7, 2015, in U.S. Appl. No. 13/612,995.
Restriction Requirement dated Oct. 2, 2012, in U.S. Appl. No. 13/042,856.
Restriction Requirement dated Oct. 13, 2016, in U.S. Appl. No. 14/206,707.
Restriction Requirement dated Oct. 21, 2014, in U.S. Appl. No. 13/583,302.
Restriction Requirement dated Oct. 28, 2015, in U.S. Appl. No. 14/603,347.
Restriction Requirement dated Sep. 2, 2015, in U.S. Appl. No. 14/532,596.
Reverdatto et al., "A Multisubunit Acetyl Coenzyme A Carboxylase from Soybean," Plant Physiol., 119: 961-978 (1999).
Rey et al., "Diversity of Dicotyledenous-Infecting Geminiviruses and Their Associated DNA Molecules in Southern Africa, Including the South-West Indian Ocean Islands," Viruses, 4:1753-1791 (2012).
Reynolds et al., "Rational siRNA design for RNA interference," Nature Biotechnology, 22:326-330 (2004).
Riar et al., "Glyphosate Resistance in a Johnsongrass (*Sorghum halepense*) Biotype from Arkansas," Weed Science, 59:299-304 (2011).
Richardson et al., "Targeting and assembly of components of the TOC protein import complex at the chloroplast outer envelope membrane," Frontiers in Plant Science, 5:1-14 (2014).
Riggins et al., "Characterization of de novo transcriptome for waterhemp (*Amaranthus tuberculatus*) using GS-FLX 454 pyrosequencing and its application for studies of herbicide target-site genes," Pest Manag. Sci., 66:1042-1052 (2010).
Robalino et al., "Double-Stranded RNA and Antiviral Immunity in Marine Shrimp: Inducible Host Mechanisms and Evidence for the Evolution of Viral Counter-Responses," Developmental & Comparative Immunology, 31: 539-547 (2007).
Roberts, "Fast-track applications: The potential for direct delivery of proteins and nucleic acids to plant cells for the discovery of gene function," Plant Methods, 1(12):1-3 (2005).
Robson et al., "Leaf senescence is delayed in maize expressing the Agrobacterium IPT gene under the control of a novel maize senescence-enhanced promoter," Plant Biotechnology Journal, 2:101-112 (2004).
Roitsch et al., "Extracellular invertase: key metabolic enzyme and PR protein," Journal of Experimental Botany, 54(382):513-524 (2003).
Roitsch et al., "Function and regulation of plant invertases: sweet sensations," Trades in Plant Science, 9(12):606-613 (2004).
Rose et al., "Functional polarity is introduced by Dicer processing of short substrate RNAs," Nucleic Acids Research, 33(13):4140-4156 (2005).
Rothnie et al., Pararetroviruses and Retroviruses: A Comparative Review of Viral Structure and Gene Expression Straiegies, Advances in Virus Research, 44:1-67 (1994).
Ruan et al., "Suppression of Sucrose Synthase Gene Expression Represses Herewith. Cotton Fiber Cell Initiation, Elongation, and Seed Development," The Plant Cell, 15:952-964 (2003).
Ryabov et al., "Cell-to-Cell, but Not Long-Distance, Spread of RNA Silencing That Is Induced in Individual Epidermal Cells," Journal of Virology, 78(6):3149-3154 (2004).
Ryan, "Human endogenous retroviruses in health and disease: a symbiotic perspective," Journal of the Royal Society of Medicine, 97:560-565 (2004).
Salanenka et al., "Seedcoat Permeability: Uptake and Post-germination Transport of Applied Model Tracer Compounds," HortScience, 46(4):622-626 (2011).
Sammataro et al., "Some Volatile Plant Oils as Potential Control Agents for Varroa Mites (*Acari: Varroidae*) in Honey Bee Colonies (*Hymenoptera: Apidae*)," American Bee Journal, 138(9):681-685 (1998).

(56) References Cited

OTHER PUBLICATIONS

Santoro et al., "A general purpose RNA-cleaving DNA enzyme," *Proc. Natl. Acad. Sci. USA*, 94:4262-4266 (1997).
Santosh et al., "RNA interference for the control of whiteflies (*Bemisia tabaci*) by oral route," Journal of Biosciences, 36(1):153-161 (2011).
Sathasivan et al., "Nucleotide sequence of a mutant acetolactate synthase gene from an imidazolinone-resistant *Arabidopsis thaliana* var. *Columbia*," Nucleic Acids Research, 18(8):2188-2193 (1990).
Schönherr, "Water Permeability of Isolated Cuticular Membranes: The Effect of pH and Cations on Diffusion, Hydrodynamic Permeability and Size of Polar Pores in the Cutin Matrix," Planta, 128:113-126 (1976).
Schönherr et al., "Size selectivity of aqueous pores in astomatous cuticular membranes isolated from Populus canescens (Aiton) Sm. Leaves," Planta, 219:405-411 (2004).
Schwab et al., "RNA silencing amplification in plants: Size matters," PNAS, 107(34):14945-14946 (2010).
Schweizer et al., "Double-stranded RNA interferes with gene function at the single-cell level in cereals," The Plant Journal, 24(6):895-903 (2000).
Schwember et al., "Drying Rates following Priming Affect Temperature Sensitivity of Germination and Longevity of Lettuce Seeds," HortScience, 40(3):778-781 (2005).
Scott et al., "Towards the elements of successful insect RNAi," Journal of Insect Physiology, 59(12):1212-1221 (2013).
Scott et al., Botanical Insecticides for Controlling Agricultural Pests: Piperamides and the Colorado Potato Beetle *Leptinotarsa decemlineata* Say (*Coleoptera: Chrysomelidae*), Archives of Insect Biochemistry and Physiology, 54:212-225 (2003).
Search Report dated Jul. 24, 2017, in Chinese Patent Application No. 201480014392.5 (with English translation).
Search Report dated Oct. 20, 2017, in Chinese Patent Application No. 201380039346.6.
Second Chinese Office Action dated Jun. 10, 2014, in Chinese Patent Application No. 201180012795.2.
Second Office Action dated Feb. 25, 2016, in Chinese Patent Application No. 201280054179.8.
Second Office Action dated Mar. 4, 2016, in Chinese Patent Application No. 201280054820.8.
Second Office Action dated May 12, 2014, in Chinese Patent Application No. 201080056585.9.
Seidman et al., "The potential for gene repair via triple helix formation," J Clin Invest., 112(4):487-494 (2003).
Selvarani et al., "Evaluation of seed priming methods to improve seed vigour of onion (*Allium cepa* cv. *Aggregatum*) and carrot (*Daucus carota*)," Journal of Agricultural Technology, 7(3):857-867 (2011).
Senthil-Kumar et al., "A systematic study to determine the extent of gene silencing in Nicotiana benthamiana and other *Solanaceae* species when heterologous gene sequences are used for virus-induced gene silencing," New Phytologist, 176:782-791 (2007).
Sharma et al., "A simple and efficient Agrobacterium-mediated procedure for transformation of tomato," J. Biosci., 34(3):423 433 (2009).
Shen et al., "The Role of Varroa Mites in Infections and Deformed Wing Virus (DWV) in Honey," Available Online Aug. 18, 2005.
Shintani et al., "Antisense Expression and Overexpression of Biotin Carboxylase in Tobacco Leaves," Plant Physiol., 114:881-886 (1997).
Showalter, "Structure and Function of Plant Cell Wall Proteins," The Plant Cell, 5:9-23 (1993).
Sijen et al., "On the Role of RNA Amplification in dsRNA-Triggered Gene Silencing," Cell, 107:465-476 (2001).
Silwet L-77 Spray Adjuvant for agricultural applications, product description from Momentive Performance Materials, Inc. (2003).
Simeoni et al., "Insight into the mechanism of the peptide-based gene delivery system MPG: implications for delivery of siRNA into mammalian cells," Nucleic Acids Research, 31(11):2717-2724 (2003).
Sindhu et al., "Effective and specific in planta RNAi in cyst nematodes: expression interference of four parasitism genes reduces parasitic success," *J. Exp. Botany*, 60:315-324 (2008).
Singh et al., "Absorption and translocation of glyphosate with conventional and organosilicone adjuvants," Weed Biology and Management, 8:104-111 (2008).
Siomi et al. "On the Road to Reading the RNA-Interference Code", Nature, 457(7228): 396-404, Jan. 22, 2009. Abstract.
Slamovits et al. "Genome Compaction and Stability in Microsporidian Intracellular Parasites", Current Biology, 14(10): 891-896, May 25, 2004.
Small, "RNAi for revealing and engineering plant gene functions," Current Opinion in Biotechnology, 18:148-153 (2007).
Snead et al., "Molecular basis for improved gene silencing by Dicer substrate interfering RNA compared with other siRNA variants," Nucleic Acids Research, 41(12):6209-6221 (2013).
Soares et al., "Capillary feeding of specific dsRNA induces silencing of the isac gene in nymphal Ixodes scapularis ticks," Insect Mol. Biol., 14(4):443-452 (2005).
Song et al., "Herbicide," New Heterocyclic Pesticide, Chemical Industry Press, 354-356 (2011).
Standifer et al., "Supplemental Feeding of Honey Bee Colonies," *Agriculture Information Bullentin No. 413*, USDA, pp. 1-8 (1977).
Statement of Grounds and Particulars dated Sep. 1, 2017, in Australian Patent No. 2014262189.
Steeves et al., "Transgenic soybeans expressing siRNAs specific to a major sperrn protein gene suppress Heterodera glycines reproduction," Funct. Plant Biol., 33:991-999 (2006).
Stevens et al., "New Formulation Technology—Silwet® Organosilicone Surfactants Have Physical and Physiological Properties Which Enhance the Performance of Sprays," Proceedings of the 9th Australian Weeds Conference, pp. 327-331 (1990).
Stevens, "Formulation of Sprays to Improve the Efficacy of Foliar Fertilisers," New Zealand Journal of Forestry Science, 24(1):27-34 (1994).
Stevens, "Organosilicone Sulfactants as Adjuvants for Agrochemicals," Journal of Pesticide Science, 38:103-122 (1993).
Stock et al., "Possible Mechanisms for Surfactant-Induced Foliar Uptake of Agrochemicals," Pestic. Sci., 38:165-177 (1993).
Strat et al., "Specific and nontoxic silencing in mammalian cells with expressed long dsRNAs," Nucleic Acids Research, 34(13):3803-3810 (2006).
Street, "Why is DNA (and not RNA) a stable storage form for genetic inforrnation?," Biochemistry Revisited, pp. 1-4 (2008).
Sudarsan et al., "Metabolite-binding RNA domains are present in the genes of eukaryotes," RNA, 9:644-647 (2003).
Summons to Attend Oral Proceedings Pursuant to Rule 115(1) EPC, dated Aug. 7, 2017, in European Patent Application No. 12832160.1.
Sun, "Characterization of Organosilicone Surfactants and Their Effects on Sulfonylurea Herbicide Activity," Thesis Submitted to the Faculty of the Virginia Polytechnic Institute and State University dated Apr. 5, 1996.
Sun et al., "Antisense oligodeoxynucleotide inhibition as a potent strategy in plant biology: identification of SUSIBA2 as a transcriptional activator in plant sugar signalling," The Plant Journal, 44:128-138 (2005).
Sun et al., "A Highly efficient Transformation Protocol for Micro-Tom, a Model Cultivar for Tomato Functional Genomics," Plant Cell Physiol., 47(3):426-431 (2006).
Sun et al., "Sweet delivery—sugar translocators as ports of entry for antisense oligodeoxynucleotides in plant cells," The Plant Journal, 52:1192-1198 (2007).
Sutton et al., "Activity of mesotrione on resistant weeds in maize," Pest Herewith. Manag. Sci., 58:981-984 (2002).
Supplementary European Search Report dated Jan. 17, 2018, in European Patent Application No. 15773480.7.
Supplementary Partial European Search Report dated Jan. 11, 2018 in European Appln. 15 82 6865.
Supplementary Partial European Search Report dated Oct. 16, 2017, in European Patent Application No. 15773480.7.
Swarts et al., "DNA-guided DNA interference by a prokaryotic Argonaute," Nature, 507(7491):258-61 (2014).

(56) References Cited

OTHER PUBLICATIONS

Swarts et al., "Argonaute of the archaeon Pyrococcus furiosus is a DNA-guided nuclease that targets cognate DNA," Nucleic Acid Res., 43(10):5120-5129 (2015).
Takasaki et al., "An Effective Method for Selecting siRNA Target Sequences in Mammalian Cells," Cell Cycle, 3:790-795 (2004).
Tang et al., "Efficient delivery of small interfering RNA to plant cells by a nanosecond pulsed laser-induced stress wave for post-transcriptional gene silencing," Plant Science, 171:375-381 (2006).
Tank Mixing Chemicals Applied to Peanut Crops: Are the Chemicals Compatible?, College of Agriculture & Life Sciences, NC State University, AGW-653, pp. 1-11 (2004).
Taylor, "Seed Storage, Germination and Quality," The Physiology of Vegetable Crops, pp. 1-36 (1997).
Temple et al., "Can glutamine synthetase activity levels be modulated in transgenic plants by the use of recombinant DNA technology?" Transgenic Plants and Plant Biochemistry, 22(4):915-920 (1994).
Temple et al., "Down-regulation of specific members of the glutamine synthetase gene family in Alfalfa by antisense RNA technology," Plant Molecular Biology, 37:535-547 (1998).
Templeton et al., "Improved DNA: liposome complexes for increased systemic delivery and gene expression," Nature Biotechnology, 15:647-652 (1997).
Teng et al., "Tic21 Is an Essential Translocon Component for Protein Translocation across the Chloroplast Inner Envelope Membrane," The Plant Cell, 18:2247-2257 (2006).
Tenllado et al., "Crude extracts of bacterially expressed dsRNA can be used to protect plants against virus infection," BMC Biotechnology, 3(3):1-11 (2003).
Tenllado et al., "Double-Stranded RNA-Mediated Interference with Plant Virus Infection," Journal of Virology, 75(24):12288-12297 (2001).
Tenllado et al., "RNA interference as a new biotechnological tool for the control of virus diseases in plants," Virus Research, 102:85-96 (2004).
Tepfer, "Risk assessment of virus resistant transgenic plants," Annual Review of Phytopathology, 40:467-491 (2002).
Terenius et al., RNA interference in Lepidoptera: an overview of successful and unsuccessful studies and implications for experimental design, Journal of Insect Physiology, 57(2):231-245 (2011).
The Seed Biology Place, Website Gerhard Leubner Lab Royal Holloway, University of London.
Third Office Action dated Nov. 25, 2014, in Chinese Patent Application No. 201080056585.9.
Third Party Submission filed on Nov. 29, 2012 in U.S. Appl. No. 13/042,856.
Thomas et al., "Size constraints for targeting post-transcriptional gene silencing and for RNA-directed methylation in Nicotiana benthamiana using a potato virus X vector," The Plant Journal, 25(4):417-425 (2001).
Thompson, et al., "CLUSTAL W: improving the sensitivity of progressive multiple sequence alignment through sequence weighting, position-specific gap penalties and weight matrix choice," Nucl. Acids Res., 22(22):4673-4680 (1994).
Tian et al., "Developmental Control of a Lepidopteran Pest *Spodoptera exigua* by Ingestion of Bacteria Expressing dsRNA of a Non-Midgut Gene," *PLoS ONE*, 4:e6225, pp. 1-14 (2009).
Tice, "Selecting the right compounds for screening: does Lipinski's Rule of 5 for pharmaceuticals apply to agrochemicals?" Pest Management Science, 57(1):3-16 (2001).
Timmons et al., "Specific interference by ingested dsRNA," Nature, 395:854 (1998).
Tomari et al., "Perspective: machines for RNAi," Genes & Dev., 19:517-529 (2005).
Tomlinson, "Evidence that the hexose-to-sucrose ratio does not control the switch to storage product accumulation in oilseeds: analysis of tobacco seed development and effects . . . ," Jrnl of Exper Bot, 55(406):2291-2303 (2004).

Töpfer et al., "Uptake and Transient Expression of Chimeric Genes in Seed-Derived Embryos," Plant Cell, 1:133-139 (1989).
Toriyama et al., "Transgenic Rice Plants After Direct Gene Transfer Into Protoplasts," *Bio/Technology*, 6:1072-1074 (1988).
Townsend et al., "High frequency modification of plant genes using engineered zinc finger nucleases," Nature, 459:442-445 (2009).
Tran et al., "Control of specific gene expression in mammalian cells by co-expression of long complementary RNAs," FEBS Lett.;573(1-3):127-134 (2004).
Tranel et al., "Resistance of weeds to ALS-inhibiting herbicides: what have we learned?," Weed Science, 50:700-712 (2002).
TransIT-TKO® Transfection Reagent, Frequently Asked Questions, Web. 2019.
Translation dated Jan. 15, 2015 of Office Action dated Dec. 18, 2014 From the Israel Patent Office Re. Application No. 216154.
Translation dated Jan. 20, 2015 of Office Action dated Dec. 31, 2014 From the Israel Patent Office Re. Application No. 205594.
Translation of Office Action dated Jul. 2, 2013 From the State Intellectual Property Office of the People's Republic of China Re. Application No. 201080056585.9.
Trucco et al., "Amaranthus hybridus can be pollinated frequently by A. tuberculatus under filed conditions," Heredity, 94:64-70 (2005).
Tsugawa et al., "Efficient transformation of rice protoplasts mediated by a synthetic polycationic amino polymer," Theor Appl Genet, 97:1019-1026 (1998).
Turina et al., "Tospoviruses in the Mediterranean Area," Advances in Virus Research, 84:403-437 (2012).
Turner et al., "RNA interference in the light brown apple moth, *Epiphyas postvittana* (Walker) induced by double-stranded RNA feeding," Insect Mol. Biol., 15(3):383-391 (2006).
Tuschl, "Expanding small RNA interference," Nature Biotechnol., 20: 446-448 (2002).
Tuschl, "RNA Interference and Small Interfering RNAs," ChemBiochem. 2(4):239-245 (2001).
Ui-Tei et al., "Guidelines for the selection of highly effective siRNA sequences for mammalian and chick RNA interference," Nucleic Acids Res., 32(3): 936-948 (2004).
Ullu et al., "RNA Interference in Protozoan Parasites," *Cellular Microbiology*, 6(6):509-519 (2004).
Ulrich et al., "Large scale RNAi screen in Tribolium reveals novel target genes for pest control and the proteasome as prime target," BMC genomics, 16(1):671 (2015).
Unnamalai et al., "Cationic oligopeptide-mediated delivery of dsRNA for post-transcriptional gene silencing in plant cells," FEBS Letters, 566:307-310 (2004).
Unniraman et al., "Alternate Paradigm for Intrinsic Transcription Termination in Eubacteria," The Journal of Biological Chemistry, 276(45)(9):41850-41855 (2001).
Unniraman et al., "Conserved Economics of Transcription Termination in Eubacteria," Nucleic Acids Research, 30(3):675-684 (2002).
Upadhyay et al., RNA interference for the control of whiteflies (*Bemisia tabaci*) by oral route, J. Biosci., 36(1):153-161 (2011).
Urayama et al., "Knock-down of OsDCL2 in Rice Negatively Affects Maintenance of the Endogenous dsRNA Virus, *Oryza sativa* Endornavirus," Plant and Cell Physiology, 51(1):58-67 (2010).
Van der Meer et al., "Promoted analysis of the chalcone synthase (chs A) gene of Petunia hybrid: a 67 bp promoter region directs flower-specific expression," Plant Mol. Biol., 15:95-109 (1990).
Van de Wetering et al., "Specific inhibition of gene expression using a stably integrated, inducible small-interfering-RNA vector," EMBO Rep., 4(6):609-615 (2003).
Vasil et al., "Herbicide Resistant Fertile Transgenic Wheat Plants Obtained by Microprojectile Bombardment of Regenerable Embryogenic Callus," Bio/Technology,10:667-674 (1992).
Vaucheret, "Post-transcriptional small RNA pathways in plants: mechanisms and regulations," Genes Dev., 20:759-771 (2006).
Vencill et al., "Resistance of Weeds to Herbicides," Herbicides and Environment, 29:585-594 (2011).
Verma et al., "Modified oligonucleotides: synthesis and strategy for users," Annu. Rev. Biochem., 67:99-134 (1998).
Vermeulen et al., "The contributions of dsRNA structure to Dicer specificity and efficiency," RNA, 11(5):674-682 (2005).

(56) References Cited

OTHER PUBLICATIONS

Vert et al., "An accurate and interpretable model for siRNA efficacy prediction," BMC Bioinformatics, 7:520 (2006).
Vila-Aiub et al., "Glyphosate resistance in perennial *Sorghum halepense* (Johnsongrass), endowed by reduced glyphosate translocation and leaf uptake," Pest Manag Sci, 68:430-436 (2012).
Voinnet et al., "Systemic Spread of Sequence-Specific Transgene RNA Degradation in Plants Is Initiated by Localized Introduction of Ectopic Promoterless DNA," Cell, 95:177-187 (1998).
Voinnet, "Origin, Biogenesis, and Activity of Plant MicroRNAs," Cell, 136:669-687 (2009).
Wakelin et al., "A target-site mutation is present in a glyphosate-resistant Lolium rigidum population," Weed Res. (Oxford), 46(5):432-440 (2006).
Walton et al., "Thermodynamic and Kinetic Characterization of Antisense Oligodeoxynucleotide Binding to a Structured mRNA," *Biophysical Journal*, 82:366-377 (2002).
Walton et al., "Prediction of antisense oligonucleotide binding affinity to a structured RNA target," Biotechnol Bioeng 65(1):1-9 (1999).
Wan et al., "Generation of Large Numbers of Independently Transformed Fertile Barley Plants," Plant Physiol., 104:37-48 (1994).
Wang et al. "Molecular Characterization of an Arachnid Sodium Channel Gene From the Varroa Mite (Varroa Destructor)", Insect Biochemistry and Molecular Biology, XP002621492, 33(7): 733-739, Jul. 2003. Abstract.
Wang et al. "Tracking Anonymous Peer-to-Peer VoIP Calls on the Internet", ACM, CCS'05, Alexandria, VA, USA, Nov. 7-11, 2005, 11 P., 2005.
Wang et al., "Foliar uptake of pesticides—Present status and future challenge," ScienceDirect, 87:1-8 (2007).
Wang et al., "Principle and technology of genetic engineering in plants," in Plant genetic engineering principles and techniques, Beijing:Science Press, pp. 313-315 (1998).
Wang et al. ,"Silkworm Coatomers and Their Role in Tube Expansion of Posterior Silkgland," *PLoS ONE* 5(10): E133252 (2010).
Watson et al., "RNA silencing platforms in plants," FEBS Letters, 579:5982-5987 (2005).
Wardell, "Floral Induction of Vegetative Plants Supplied a Purified Fraction of Deoxyribonucleic Acid from Stems of Flowering Plants," Plant Physiol, 60:885-891 (1977).
Wardell,"Floral Activity in Solutions of Deoxyribonucleic Acid Extracted from Tobacco Stems," Plant Physiol, 57:855-861 (1976).
Waterhouse et al., "Virus resistance and gene silencing in plants can be induced by simultaneous expression of sense and antisense RNA," Proc Natl Acad Sci USA, 95 13959-13964 (1998).
Welch et al., "Expression of ribozymes in gene transfer systems to modulate target RNA levels," Curr Opin Biotechnol. 9(5):486-496 (1998).
Whyard et al., "Ingested double-stranded RNAs can act as species-specific insecticides," *Insect Biochem. Mol. Biol.*, 39(11):824-832 (2009).
Widholm et al., "Glyphosate selection of gene amplification in suspension cultures of 3 plant species," Phyisologia Plantarum, 112:540-545 (2001).
Wiesman et al., "Novel cationic vesicle platform derived from vemonia oil for efficient delivery of DNA through plant cuticle membranes," Journal of Biotechnology, 130:85-94 (2007).
Wild Carrot, Noxious Weed Control Board (NWCB) of Washington State (2010) <www.nwcb.wa.gov/detail.asp?weed=46>.
Williams "Unique Physiology of Host-Parasite Interactions in Microsporidia Infections," *Cellular Microbiology*, 11(11):1551-1560 (2009).
Williams et al., "Genome Sequence Surveys of Brachiola Algerae and Edhazardia Aedis Reveal Micriosporidia With Low Gene Densities," *BMC Genomics*, 9(200):1-9 (2008).
Wilson, et al., "Transcription termination at intrinsic terminators: The role of the RNA hairpin," Proc. Natl. Acad. Sci. USA, 92:8793-8797 (1995).
Winkler et al., "Thiamine derivatives bind messenger RNAs directly to regulate bacterial gene expression," Nature, 419:952-956 (2002).
Written Opinion dated Apr. 7, 2016, in Singapore Patent Application No. 201206152-9.
Written Opinion dated Aug. 13, 2009, in International Application No. PCT/IL2008/001440.
Written Opinion dated Mar. 6, 2017, in Singaporean Patent Application No. 2012061529.
Written Opinion dated May 8, 2014, in International Application No. PCT/IL2013/050447.
Written Opinion dated Sep. 1, 2014, in Singapore Patent Application No. 201206152-9.
Wool et al., "Structure and evolution of mammalian ribosomal proteins," Biochem. Cell Biol., 73:933-947 (1995).
Xu et al., "Characterization and Functional Analysis of the Calmodulin-Binding Domain of Rac1 GTPase," PLoS One, 7(8):e42975 (2012).
Yadav et al., "Host-Generated Double Stranded RNA Induces RNAi in Plant-Parasitic Nematodes and Protects the Host From Infection," *Molecular & Biochemical Parasitology*, 148:219-222 (2006).
Yao et al., "Development of RNAi Methods for Peregrinus maidis, the Corn Planthopper," PLOS One, 8(8):1-11 (2013).
Yan et al., Seed Science, China Agriculture Press, pp. 101-103, Tables 2-7 (2001).
Yin et al., "Production of double-stranded RNA for interference with TMV infection utilizing a bacterial prokaryotic expression system," Appl. Microbiol. Biotechnol., 84(2):323-333 (2009).
YouTube video by General Electric Company "Silwet Surfactants," screen shot taken on Jan. 11, 2012 of video of www.youtube.com/watch?v=WBw7nXMqHk8 (uploaded Jul. 13, 2009).
Yu et al., "Glyphosate, paraquat and ACCase multiple herbicide resistance evolved in a Lolium rigidum biotype," Planta, 225:499-513 (2007).
Yu et al., "Diversity of Acetyl-Coenzyme A Carboxylase Mutations in Resistant Lolium Populations: Evaluation Using Clethodim," Plant Physiology, 145:547-558 (2007).
Zabkiewicz, "Adjuvants and herbicidal efficacy—present status and future prospects," Weed Research, 40:139-149 (2000).
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," PNAS, 98(12):6617-6622 (2001).
Zhang et al., "DEG: a database of essential genes," Nucleic Acids Res., 32:D271-D272 (2004).
Zhang et al., "Agrobacterium-mediated transformation of *Arabidopsis thaliana* using the floral dip method," Nature Protocols, 1(2):1-6 (2006).
Zhang et al., "Cationic lipids and polymers mediated vectors for delivery of siRNA," Journal of Controlled Release, 123:1-10 (2007).
Zhang et al., "Development and Validation of Endogenous Reference Genes for Expression Profiling of Medaka (Oryzias latipes) Exposed to Endocrine Disrupting Chemicals by Quantitative Real-Time RT-PCR," Toxicological Sciences, 95(2):356-368 (2007).
Zhang et al., "A novel rice gene, NRR responds to macronutrient deficiency and regulates root growth," Mol Plant, 5(1):63-72 (2012).
Zhang et al., "Progress in research of honey bee mite Varro destructor," Journal of Environmental Entomology, 34(3):345-353 (2012).
Zhang et al., "Transgenic rice plants produced by electroporation-mediated plasmid uptake into protoplasts," The Plant Cell Rep., 7:379-384 (1988).
Zhang, "Artificial trans-acting small interfering RNA: a tool for plant biology study and crop improvements," Planta, 239:1139-1146 (2014).
Zhang, Chapter 10: New Characteristics of Pesticide Research & Development, p. 209 (2010).
Zhao et al., "Phyllotreta striolata (Coleoptera: Chrysomelidae):Arginine kinase cloning and RNAi-based pest control," European Journal of Entomology, 105(5):815-822 (2008).
Zhao et al., "Vegetable Statdardized Production Technology," Hangzhou: Zhejiang Science and Technology Press, p. 19 (2008).

(56) References Cited

OTHER PUBLICATIONS

Zhao et al., "PsOr1, a potential target for RNA interference-based pest management," *Insect Molecular Biology* 20(1):97-104 (2011).
Zhu et al., "Ingested RNA interference for managing the populations of the Colorado potato beetle, *Leptinotarsa decemlineata*," Pest Manag Sci, 67:175-182 (2010).
Zhong et al., "A pea antisense gene for the chloroplast stromal processing peptidase yields seedling lethals in *Arabidopsis*: survivors show defective GFP import in vivo," The Plant Journal, 34:802-812 (2003).
Zhong et al., "A forward genetic screen to explore chloroplast protein import in vivo identifies Moco sulfurase, pivotal for ABA and IAA biosynthesis and purine turnover," The Plant Journal, 63:44-59 (2010).
Zidack et al., "Promotion of Bacterial Infection of Leaves by an Organosilicone Surfactant: Implications for Biological Weed Control," Biological Control, 2:111-117 (1992).
Zipperian et al., "Silicon Carbide Abrasive Grinding," Quality Matters Newsletter, PACE Technologies 1(2):1-3 (2002).
Zotti et al., "RNAi technology for insect management and protection of beneficial insects from diseases: lessons, challenges and risk assessments," Neotropical Entomology, 44(3):197-213 (2015).

\* cited by examiner

COMPOSITIONS AND METHODS FOR CONTROLLING INSECT PESTS

CROSS-REFERENCE TO RELATED APPLICATIONS AND INCORPORATION OF SEQUENCE LISTINGS

This application is a continuation of U.S. patent application Ser. No. 15/329,808, filed Jan. 27, 2017 (now U.S. Pat. No. 10,378,012, issued Aug. 13, 2019), which is a U.S. National Stage of International Application No. PCT/US2015/042415, filed Jul. 28, 2015, which claims the benefit of U.S. Provisional Application No. 62/030,430, filed Jul. 29, 2014, all of which are incorporated by reference in their entireties herein. A sequence listing contained in the file named "P34170US03_SL.TXT" which is 2,153,082 bytes (measured in MS-Windows®) and created on Jun. 27, 2019, is filed electronically herewith and incorporated by reference in its entirety.

FIELD

Disclosed herein are methods for controlling invertebrate pest infestations, particularly in plants, compositions and polynucleotides useful in such methods, and plants having improved resistance to the invertebrate pests. More specifically, polynucleotides and methods of use thereof for modifying the expression of genes in an insect pest, particularly through RNA interference are disclosed. Pest species of interest include flea beetles, such as *Phyllotreta* spp. and *Psylliodes* spp.

BACKGROUND

Commercial crops are often the targets of attack by invertebrate pests such as insects. Compositions for controlling insect infestations in plants have typically been in the form of chemical insecticides. However, there are several disadvantages to using chemical insecticides. For example, chemical insecticides are generally not selective, and applications of chemical insecticides intended to control insect pests in crop plants can exert their effects on non-target insects and other invertebrates as well. Chemical insecticides often persist in the environment and can be slow to degrade, thus potentially accumulating in the food chain. Furthermore the use of persistent chemical insecticides can result in the development of resistance in the target insect species. Thus there has been a long felt need for more environmentally friendly methods for controlling or eradicating insect infestation on or in plants, e. g., methods which are species-selective, environmentally inert, non-persistent, and biodegradable, and that fit well into pest resistance management schemes.

RNA interference (RNAi, RNA-mediated gene suppression) is an approach that shows promise for use in environmentally friendly pest control. In invertebrates, RNAi-based gene suppression was first demonstrated in nematodes (Fire et al., (1998) *Nature,* 391:806-811; Timmons & Fire (1998) *Nature,* 395:854). Subsequently, RNAi-based suppression of invertebrate genes using recombinant nucleic acid techniques has been reported in a number of species, including agriculturally or economically important pests from various insect and nematode taxa, such as: root-knot nematodes (*Meloidogyne* spp.), see Huang et al. (2006) *Proc. Natl. Acad. Sci. USA,* 103:14302-14306, doi:10.1073/pnas.0604698103); cotton bollworm (*Helicoverpa armigera*), see Mao et al. (2007) *Nature Biotechnol.,* 25:1307-1313, doi:10.1038/nbt1352; Western corn rootworm (*Diabrotica virgifera* LeConte), see Baum et al. (2007) *Nature Biotechnol.,* 25:1322-1326, doi:10.1038/nbt1359; sugar beet cyst nematode (*Heterodera schachtii*), see Sindhu et al. (2008) *J. Exp. Botany,* 60:315-324, doi:10.1093/jxb/ern289; mosquito (*Aedes aegypti*), see Pridgeon et al. (2008) *J. Med. Entomol.,* 45:414-420, doi: full/10.1603/0022-2585%282008%2945%5B414%3ATAADRK%5D2.0.CO%3B2; fruit flies (*Drosophila melanogaster*), flour beetles (*Tribolium castaneum*), pea aphids (*Acyrthosiphon pisum*), and tobacco hornworms (*Manduca sexta*), see Whyard et al. (2009) *Insect Biochem. Mol. Biol.,* 39:824-832, doi:10.1016/j.ibmb.2009.09.00; diamondback moth (*Plutella xylostella*), see Gong et al. (2011) *Pest Manag. Sci.,* 67: 514-520, doi:10.1002/ps.2086; green peach aphid (*Myzus persicae*), see Pitino et al. (2011) PLoS ONE, 6:e25709, doi:10.1371/journal.pone.0025709; brown planthopper (*Nilaparvata lugens*), see Li et al. (2011) *Pest Manag. Sci.,* 67:852-859, doi:10.1002/ps.2124; and whitefly (*Bemisia tabaci*), see Upadhyay et al. (2011) *J. Biosci.,* 36:153-161, doi:10.1007/s12038-011-9009-1.

SUMMARY

The present embodiments relate to control of insect species, especially flea beetle species that are economically or agriculturally important pests. The compositions and methods disclosed herein include recombinant polynucleotide molecules, such as recombinant DNA constructs for making transgenic plants resistant to infestation by insect species and polynucleotide agents, such as RNA "triggers", that are useful for controlling or preventing infestation by that insect species. Several embodiments described herein relate to a polynucleotide-containing composition (e. g., a composition containing a dsRNA trigger for suppressing a target gene) that is topically applied to an insect species or to a plant, plant part, or seed to be protected from infestation by an insect species. Other embodiments relate to methods for selecting preferred insect target genes that are more likely to be effective targets for RNAi-mediated control of an insect species.

Several embodiments relate to a method for controlling an insect infestation of a plant including contacting the insect with a dsRNA including at least one segment of 18 or more contiguous nucleotides with a sequence of about 95% to about 100% complementarity with a fragment of a target gene of the insect. In some embodiments, the dsRNA includes at least one segment of 21 contiguous nucleotides with a sequence of 100% complementarity with a fragment of a target gene of the insect. In some embodiments, the target gene is selected from the group consisting of Act5C, arginine kinase, COPI (coatomer subunit) alpha, COPI (coatomer subunit) beta, COPI (coatomer subunit) betaPrime, COPI (coatomer subunit) delta, COPI (coatomer subunit) epsilon, COPI (coatomer subunit) gamma, COPI (coatomer subunit) zeta, RpL07, RpL19, RpL3, RpL40, RpS21, RpS4, Rpn2, Rpn3, Rpt6, Rpn8, Rpn9, Rpn6-PB-like protein, Sar1, sec6, sec23, sec23A, shrb (snf7), Tubulin gamma chain, ProsAlpha2, ProsBeta5, Proteasome alpha 2, Proteasome beta 5, VATPase E, VATPase A, VATPase B, VATPase D, Vps2, Vps4, Vps16A, Vps20, Vps24, Vps27, Vps28, Vha26 (V-ATPase A), Vha68-2 (V-ATPase D/E), 40S ribosomal protein S14, and 60S ribosomal protein L13. In some embodiments, the target gene has a DNA sequence selected from the group consisting of SEQ ID NOs:1-859. In some embodiments, the dsRNA includes an RNA strand with a sequence of about 95% to about 100% identity or complementarity with a sequence selected from the group consisting of SEQ ID NOs:860-1718 and 1722-1724 or a fragment thereof. In some embodiments, the dsRNA includes an RNA strand with a sequence selected from the group consisting of SEQ ID NOs:860-1718 and 1722-1724. In various embodiments, the contacting of the insect is by oral delivery, or by non-oral contact, e. g., by absorption through the cuticle, or through a combination of oral and non-oral delivery. In some embodiments, the dsRNA trigger suppresses a target gene in the insect and stunts growth, development or reproduction by the insect, or kills the insect.

Several embodiments relate to a method of causing mortality or stunting in an insect, including providing in the diet of an insect at least one polynucleotide including at least one silencing element, wherein the at least one silencing element is essentially identical or essentially complementary to a fragment of a target gene sequence of the insect, and wherein ingestion of the polynucleotide by the insect results in mortality or stunting in the insect. In some embodiments, the target gene is selected from the group consisting of Act5C, arginine kinase, COPI (coatomer subunit) alpha, COPI (coatomer subunit) beta, COPI (coatomer subunit) betaPrime, COPI (coatomer subunit) delta, COPI (coatomer subunit) epsilon, COPI (coatomer subunit) gamma, COPI (coatomer subunit) zeta, RpL07, RpL19, RpL3, RpL40, RpS21, RpS4, Rpn2, Rpn3, Rpt6, Rpn8, Rpn9, Rpn6-PB-like protein, Sar 1, sec6, sec23, sec23A, shrb (snf7), Tubulin gamma chain, ProsAlpha2, ProsBeta5, Proteasome alpha 2, Proteasome beta 5, VATPase E, VATPase A, VATPase B, VATPase D, Vps2, Vps4, Vps16A, Vps20, Vps24, Vps27, Vps28, Vha26 (V-ATPase A), Vha68-2 (V-ATPase D/E), 40S ribosomal protein S14, and 60S ribosomal protein L13. In some embodiments, the target gene sequence is selected from the group consisting of SEQ ID NOs:1-859. In some embodiments, the silencing element includes an RNA strand with a sequence of about 95% to about 100% identity or complementarity with a sequence selected from the group consisting of SEQ ID NOs:860-1718 and 1722-1724 or a fragment thereof. In some embodiments, the silencing element includes an RNA strand with a sequence selected from the group consisting of SEQ ID NOs:860-1718 and 1722-1724. In some embodiments, the polynucleotide is provided in the diet of the insect in the form of a plant or bacterial cell containing the polynucleotide, or as a synthetic polynucleotide molecule, or as a fermentation product (e. g., a hairpin form of a dsRNA, produced in a bacterium). In some embodiments, the polynucleotide is a recombinant RNA molecule. In some embodiments, the polynucleotide is a double-stranded RNA molecule.

Several embodiments relate to an insecticidal composition including an insecticidally effective amount of a polynucleotide, wherein the polynucleotide includes 18 or more contiguous nucleotides with about 95% to about 100% complementarity with a corresponding portion of a target gene of an insect that infests a plant. In some embodiments, the polynucleotide includes 21 contiguous nucleotides with a sequence of 100% complementarity with a corresponding portion of the target gene. In some embodiments, the target gene is selected from the group consisting of Act5C, arginine kinase, COPI (coatomer subunit) alpha, COPI (coatomer subunit) beta, COPI (coatomer subunit) betaPrime, COPI (coatomer subunit) delta, COPI (coatomer subunit) epsilon, COPI (coatomer subunit) gamma, COPI (coatomer subunit) zeta, RpL07, RpL19, RpL3, RpL40, RpS21, RpS4, Rpn2, Rpn3, Rpt6, Rpn8, Rpn9, Rpn6-PB-like protein, Sar1, sec6, sec23, sec23A, shrb (snf7), Tubulin gamma chain, ProsAlpha2, ProsBeta5, Proteasome alpha 2, Proteasome beta 5, VATPase E, VATPase A, VATPase B, VATPase D, Vps2, Vps4, Vps16A, Vps20, Vps24, Vps27, Vps28, Vha26 (V-ATPase A), Vha68-2 (V-ATPase D/E), 40S ribosomal protein S14, and 60S ribosomal protein L13. In some embodiments, the polynucleotide includes 18 or more contiguous nucleotides with about 95% to about 100% complementarity with a DNA sequence selected from the group consisting of SEQ ID NOs:1-859 or a fragment thereof. In some embodiments, the polynucleotide includes 21 contiguous nucleotides with a sequence of 100% complementarity with a DNA sequence selected from the group consisting of SEQ ID NOs:1-859 or a fragment thereof. In some embodiments, the polynucleotide is recombinant RNA. In some embodiments, the polynucleotide is molecule is dsRNA. In some embodiments, the polynucleotide includes at least one segment (e. g., an RNA strand or segment of an RNA strand) with a sequence of about 95% to about 100% identity or complementarity with a sequence selected from the group consisting of SEQ ID NOs:860-1718 and 1722-1724 or a fragment thereof. In some embodiments, polynucleotide includes at least one segment (e. g., an RNA strand or segment of an RNA strand) with a sequence selected from the group consisting of SEQ ID NOs:860-1718 and 1722-1724 or a fragment thereof. In some embodiments, the insecticidal composition further includes one or more of a carrier agent, a surfactant, an organosilicone, a cationic lipid, a polynucleotide herbicidal molecule, a non-polynucleotide herbicidal molecule, a non-polynucleotide pesticide, a fungicide, a safener, an insect attractant, and an insect growth regulator. Embodiments of the insecticidal compositions include non-polynucleotide insecticides, e. g., a bacterially produced insecticidal protein.

Several embodiments relate to a method of providing a plant having improved resistance to an insect, including expressing in the plant a recombinant DNA construct, wherein the recombinant DNA construct includes DNA encoding an RNA polynucleotide having a sequence essentially identical or essentially complementary to a fragment of at least one target gene of the insect, and wherein ingestion of the polynucleotide by the insect results in mortality or stunting in the insect. In some embodiments, the target gene is selected from the group consisting of Act5C, arginine kinase, COPI (coatomer subunit) alpha, COPI (coatomer subunit) beta, COPI (coatomer subunit) betaPrime, COPI (coatomer subunit) delta, COPI (coatomer subunit) epsilon, COPI (coatomer subunit) gamma, COPI (coatomer subunit) zeta, RpL07, RpL19, RpL3, RpL40, RpS21, RpS4, Rpn2, Rpn3, Rpt6, Rpn8, Rpn9, Rpn6-PB-like protein, Sar1, sec6, sec23, sec23A, shrb (snf7), Tubulin gamma chain, ProsAlpha2, ProsBeta5, Proteasome alpha 2, Proteasome beta 5, VATPase E, VATPase A, VATPase B, VATPase D, Vps2, Vps4, Vps16A, Vps20, Vps24, Vps27, Vps28, Vha26 (V-ATPase A), Vha68-2 (V-ATPase D/E), 40S ribosomal protein S14, and 60S ribosomal protein L13. In some embodiments, the target gene has a DNA sequence selected from the group consisting of SEQ ID NOs:1-859. In some embodiments, the polynucleotide is single-stranded RNA (ssRNA). In other embodiments, the polynucleotide is double-stranded RNA (dsRNA), which may include single-stranded portions, such as a loop in a stem-loop structure. In some embodiments, the polynucleotide is RNA (e. g., an RNA strand or segment of an RNA strand) with a sequence of about 95% to about 100% identity or complementarity with a sequence selected from the group consisting of SEQ ID NOs:860-1718 and 1722-1724 or a fragment thereof. In some embodiments, the polynucleotide is RNA (e. g., an RNA strand or segment of an RNA strand) with a sequence selected from the group consisting of SEQ ID NOs:860-1718 and 1722-1724 or a fragment thereof.

Several embodiments relate to a recombinant DNA construct including a heterologous promoter operably linked to DNA encoding an RNA transcript including a sequence of about 95% to about 100% identity or complementarity with a sequence selected from the group consisting of SEQ ID NOs:860-1718 and 1722-1724 or a fragment thereof. Several embodiments relate to a commercial unit of seed, such as a bag, in which all or substantially all of the seeds include a recombinant DNA construct including a heterologous promoter operably linked to DNA encoding an RNA transcript including a sequence of about 95% to about 100% identity or complementarity with a sequence selected from the group consisting of SEQ ID NOs:860-1718 and 1722-1724 or a fragment thereof. In some embodiments, the RNA transcript is single-stranded RNA (ssRNA). In other embodiments, the RNA transcript is double-stranded RNA (dsRNA), which may include single-stranded portions, such as a loop in a stem-loop structure. In some embodiments, the RNA transcript includes RNA (e. g., an RNA strand or segment of an RNA strand) with a sequence of about 95% to about 100% identity or complementarity with a sequence selected from the group consisting of SEQ ID NOs:860-1718 and 1722-1724 or a fragment thereof. In some embodiments, the RNA transcript includes RNA (e. g., an RNA strand or segment of an RNA strand) with a sequence selected from the group consisting of SEQ ID NOs:860-1718 and 1722-1724 or a fragment thereof.

In related aspects, provided herein are man-made compositions including a polynucleotide or trigger as described herein, such as dsRNA formulations useful for topical application to a plant or substance in need of protection from an insect infestation; recombinant constructs and vectors useful for making transgenic plant cells and transgenic plants; formulations and coatings useful for treating plants (including plant seeds or propagatable parts such as tubers); plant seeds or propagatable parts such as tubers treated with or containing a polynucleotide as described herein as well as commodity products and foodstuffs produced from such plants; seeds, or propagatable parts (especially commodity products and foodstuffs having a detectable amount of a polynucleotide disclosed herein). Several embodiments relate to polyclonal or monoclonal antibodies that bind a peptide or protein encoded by a sequence or a fragment of a sequence selected from the group consisting of SEQ ID NOs:1-859. Several embodiments relate to polyclonal or monoclonal antibodies that bind a peptide or protein encoded by a sequence or a fragment of a sequence selected from the group consisting of SEQ ID NOs:860-1718 and 1722-1724 or the complement thereof. Such antibodies are made by routine methods as known to one of ordinary skill in the art.

Other aspects and specific embodiments are disclosed in the following detailed description and working Examples.

DETAILED DESCRIPTION

The present embodiments relate to methods and compositions for controlling insect pests, in particular the group of coleopteran insects commonly known as "flea beetles", of which there are several genera. Disclosed herein are target genes identified as useful for designing polynucleotide agents for preventing or treating flea beetle infestations, especially of commercially important plants. The methods and compositions are especially useful for preventing or treating flea beetle infestations of commercially important *Brassica* species including species commercially used as oilseed, food, or livestock feed (e. g., canola, rapeseed, turnips, and field mustard or turnip rape). Such *Brassica* species include *B. napus, B. juncea, B. carinata, B. rapa, B. oleracea, B. rupestris, B. septiceps, B. nigra, B. narinosa, B. perviridus, B. tournefortii,* and *B. fructiculosa*. Also disclosed are sequences for suppressing one or more flea beetle target genes. Several embodiments relate to polynucleotide agents, for example, in the form of dsRNA "triggers" that suppress flea beetle target genes. In some embodiments, polynucleotides and recombinant DNA molecules and constructs useful in methods of controlling insect pests, especially flea beetles are provided. Several embodiments relate to insecticidal compositions, as well as to transgenic plants resistant to infestation by insect pests. Several embodiments relate to methods of identifying efficacious polynucleotide agents, for example, double-stranded RNA molecules for controlling insect pests and methods for identifying target genes that are likely to represent essential functions, making these genes preferred targets for RNAi-mediated silencing and control of insect pests.

Several embodiments relate to methods and compositions for inhibiting or controlling flea beetle infestation of a plant by inhibiting in the flea beetle the expression of one or more target gene selected from the group consisting of Act5C, arginine kinase, COPI (coatomer subunit) alpha, COPI (coatomer subunit) beta, COPI (coatomer subunit) betaPrime, COPI (coatomer subunit) delta, COPI (coatomer subunit) epsilon, COPI (coatomer subunit) gamma, COPI (coatomer subunit) zeta, RpL07, RpL19, RpL3, RpL40, RpS21, RpS4, Rpn2, Rpn3, Rpt6, Rpn8, Rpn9, Rpn6-PB-like protein, Sar1, sec6, sec23, sec23A, shrb (snf7), Tubulin gamma chain, ProsAlpha2, ProsBeta5, Proteasome alpha 2, Proteasome beta 5, VATPase E, VATPase A, VATPase B, VATPase D, Vps2, Vps4, Vps16A, Vps20, Vps24, Vps27, Vps28, Vha26 (V-ATPase A), Vha68-2 (V-ATPase D/E), 40S ribosomal protein S14, and 60S ribosomal protein L13. In some embodiments, inhibiting the expression of one or more target gene in the flea beetle results in stunting or mortality.

Several embodiments relate to a polynucleotide molecule, such as a dsRNA, which includes one or more segments including 18 or more contiguous nucleotides, for example 21 or more contiguous nucleotides, having 95% to about 100% (e. g., about 95%, about 96%, about 97%, about 98%, about 99%, or about 100%) complementarity with a fragment of an insect target gene selected from the group consisting of Act5C, arginine kinase, COPI (coatomer subunit) alpha, COPI (coatomer subunit) beta, COPI (coatomer subunit) betaPrime, COPI (coatomer subunit) delta, COPI (coatomer subunit) epsilon, COPI (coatomer subunit) gamma, COPI (coatomer subunit) zeta, RpL07, RpL19, RpL3, RpL40, RpS21, RpS4, Rpn2, Rpn3, Rpt6, Rpn8, Rpn9, Rpn6-PB-like protein, Sar 1, sec6, sec23, sec23A, shrb (snf7), Tubulin gamma chain, ProsAlpha2, ProsBeta5, Proteasome alpha 2, Proteasome beta 5, VATPase E, VATPase A, VATPase B, VATPase D, Vps2, Vps4, Vps16A, Vps20, Vps24, Vps27, Vps28, Vha26 (V-ATPase A), Vha68-2 (V-ATPase D/E), 40S ribosomal protein S14, and 60S ribosomal protein L13. In some embodiments, the polynucleotide, such as dsRNA, includes multiple segments each of 18 or more contiguous nucleotides with a sequence of about 95% to about 100% (e. g., about 95%, about 96%, about 97%, about 98%, about 99%, or about 100%) complementarity with a fragment of a DNA sequence selected from the group consisting of SEQ ID NOs:1-859. In some embodiments, the polynucleotide, such as dsRNA, includes 21 contiguous nucleotides having 100% complementarity with a fragment of a DNA sequence selected from the group consisting of SEQ ID NOs:1-859. For example, the polynucleotide, such as dsRNA, includes segments corresponding to different regions of the target gene, or can include multiple copies of a segment. In other embodiments, the polynucleotide, such as dsRNA, includes multiple segments, each of 18 or more contiguous nucleotides with a sequence of about 95% to about 100% (e. g., about 95%, about 96%, about 97%, about 98%, about 99%, or about 100%) complementarity with a fragment of a different target gene; in this way multiple target genes, or multiple insect species, can be suppressed.

Several embodiments relate to a dsRNA molecule, sometimes referred to herein as a "trigger", which inhibits the expression of one or more insect target genes selected from the group consisting of Act5C, arginine kinase, COPI (coatomer subunit) alpha, COPI (coatomer subunit) beta, COPI (coatomer subunit) betaPrime, COPI (coatomer subunit) delta, COPI (coatomer subunit) epsilon, COPI (coatomer subunit) gamma, COPI (coatomer subunit) zeta, RpL07, RpL19, RpL3, RpL40, RpS21, RpS4, Rpn2, Rpn3, Rpt6, Rpn8, Rpn9, Rpn6-PB-like protein, Sar1, sec6, sec23, sec23A, shrb (snf7), Tubulin gamma chain, ProsAlpha2, ProsBeta5, Proteasome alpha 2, Proteasome beta 5, VATPase E, VATPase A, VATPase B, VATPase D, Vps2, Vps4, Vps16A, Vps20, Vps24, Vps27, Vps28, Vha26 (V-ATPase A), Vha68-2 (V-ATPase D/E), 40S ribosomal protein S14, and 60S ribosomal protein L13. Several embodiments relate to a dsRNA having a length greater than that which is typical of naturally occurring regulatory small RNAs (such as endogenously produced siRNAs and mature miRNAs), e. g, the dsRNA is at least about 30 contiguous base-pairs in length. In some embodiments, the dsRNA has a length of between about 50 to about 500 base-pairs. In some embodiments, the dsRNA is at least 50 base pairs in length. In some embodiments, the dsRNA is formed from two separate, essentially complementary strands (e. g., where each strand is separately provided, or where each strand is encoded on a separate DNA molecule, or where the two strands are encoded on separate sections of a DNA and are separately transcribed or made separate, for example, by the action of a recombinase or nuclease), wherein at least one RNA strand includes a sequence of about 95% to about 100% (e. g., about 95%, about 96%, about 97%, about 98%, about 99%, or about 100%) identity or complementarity with a sequence selected from the group consisting of SEQ ID NOs:860-1718 and 1722-1724 or a fragment thereof. In some embodiments, the dsRNA is blunt-ended, e. g., two separate, equal-length strands of RNA which form the dsRNA through intermolecular hybridisation. In some embodiments, the dsRNA has an overhang at one or both ends (termini), e. g., two separate, unequal-length strands of RNA which form the dsRNA through intermolecular hybridisation; the overhang can be a single nucleotide or 2, 3, 4, 5, 6, or more nucleotides, and can be located on the 5' end or on the 3' end of a strand. In some embodiments, the dsRNA includes at least one stem-loop, e. g., a single RNA molecule that forms a dsRNA with a "hairpin" secondary structure through intramolecular hybridization. In some embodiments, the dsRNA is formed from a single self-hybridizing hairpin transcript, wherein one "arm" of the hairpin includes a sequence of about 95% to about 100% (e. g., about 95%, about 96%, about 97%, about 98%, about 99%, or about 100%) identity or complementarity with a sequence selected from the group consisting of SEQ ID NOs:860-1718 and 1722-1724 or a fragment thereof. In embodiments, self-hybridizing transcripts which form hairpins (or partial hairpins) include dsRNA molecules that include "spacer" nucleotides or a single-stranded "loop region" between the dsRNA-forming complementary "arms" of sense sequence and anti-sense sequence. In embodiments, such spacers or loops include nucleotides having a sequence unrelated (not complementary or identical to) the target gene corresponding to the double-stranded portion of the hairpin. Examples of spacers or loops include those encoded by SEQ ID NOs:1719-1721. In embodiments, the dsRNA includes multiple stem-loops, with or without spacer nucleotides between each stem-loop. In embodiments, the dsRNA includes a modified stem-loop such as a "stabilized anti-sense" loop or a "stabilized sense" loop; see, e. g., U.S. Pat. Nos. 7,855,323 and 9,006,414, which are incorporated by reference in their entirety herein.

The dsRNA can be chemically synthesized (e. g., by in vitro transcription, such as transcription using a T7 polymerase or other polymerase), or can be produced by expression in a microorganism, by expression in a plant cell, or by microbial fermentation. The dsRNA can be chemically modified, e. g., to improve stability, ease of formulation, or efficacy. In some embodiments, the dsRNA molecule is provided in a microbial or plant cell that expresses dsRNA (such as a hairpin form of a dsRNA trigger), or in a microbial fermentation product.

A variety of methods for designing and producing a variety of forms of dsRNA are known in the art and are useful in the compositions and methods disclosed herein. See, for example, the following patents which are incorporated by reference in their entirety herein: (1) U.S. Pat. No. 8,598,332 to Waterhouse et al., which discloses recombinant DNA constructs including DNA encoding sense RNA and anti-sense RNA sequences in a single transcript that forms an artificial "hairpin" RNA structure with a double-stranded RNA stem by base-pairing between the sense and anti-sense nucleotide sequences; embodiments include hairpins with spacer nucleotides between the sense and anti-sense nucleotide sequences; (2) U.S. Pat. No. 8,158,414 to Rommens et al., which discloses recombinant DNA constructs including convergently oriented first and second promoters, which produce, e. g., an RNA duplex that is formed by annealing of two separate RNA transcripts; and (3) U.S. Pat. Nos. 7,855,323 and 9,006,414 to Huang et al., which disclose recombinant DNA constructs including DNA encoding "stabilized anti-sense" transcripts which form a loop of anti-sense-oriented RNA for suppressing one or more target genes; recombinant DNA constructs can be designed to similarly encode "stabilized sense" transcripts which form a loop of sense-oriented RNA for suppressing one or more target genes.

Embodiments of the compositions including polynucleotides such as the dsRNA triggers described herein further contain one or more additional components or adjuvants, e. g., a carrier agent, an encapsulation agent, an emulsifying agent, a surfactant, an organosilicone, a cationic lipid, a spreading agent, a photoprotective agent, a rainfastness agent, a polynucleotide herbicidal molecule, a non-polynucleotide herbicidal molecule, a non-polynucleotide pesticide, a non-polynucleotide fungicide, a safener, a bait, an insect attractant, an insect pheromone, and an insect growth regulator. In embodiments, these additional components or adjuvants are edible or digestible if ingested by a flea beetle.

In embodiments, the polynucleotides such as dsRNA triggers disclosed herein are used in combination with a non-nucleotide pesticidal agent such as a small-molecule pesticidal agent or a proteinaceous pesticidal agent, either concurrently or sequentially. Examples of non-nucleotide pesticidal agents include patatins, plant lectins, phytoecdysteroids, and bacterial insecticidal proteins (e. g., insecticidal proteins from *Bacillus thuringiensis, Xenorhabdus* sp., *Photorhabdus* sp., *Brevibacillus laterosporus* (previously *Bacillus laterosporus*), *Lysinibacillus sphaericus* (previously *Bacillus sphaericus*), *Chromobacterium* sp., *Chromobacterium subtsugae, Paenibacillus* sp., *Paenibacillus lentimorbus*, and *Paenibacillus popilliae*), a bacterium that produces an insecticidal protein, and an entomicidal bacterial species. In embodiments, the compositions including polynucleotides for flea beetle control such as the dsRNA triggers described herein can further include, or can be used concurrently or sequentially with, conventional pesticides such as Spiromesifen, Spirodiclofen, Spirotetramat, Pyridaben, Tebufenpyrad, Tolfenpyrad, Fenpyroximate, Flufenerim, Pyrimidifen, Fenazaquin, Rotenone, Cyenopyrafen, Hydramethylnon, Acequinocyl, Fluacrypyrim, Aluminium phosphide, Calcium phosphide, Phosphine, Zinc phosphide, Cyanide, Diafenthiuron, Azocyclotin, Cyhexatin, Fenbutatin oxide, Propargite, Tetradifon, Bensultap, Thiocyclam, Thiosultap-sodium, Flonicamid, Etoxazole, Clofentezine, Diflovidazin, Hexythiazox, Chlorfluazuron, Bistrifluron, Diflubenzuron, Flucycloxuron, Flufenoxuron, Hexaflumuron, Lufenuron, Novaluron, Noviflumuron, Teflubenzuron, Triflumuron, Buprofezin, Cyromazine, Hydroprene, Kinoprene, Methoprene, Fenoxycarb, Pyriproxyfen, Pymetrozine, Pyrifluquinazon, Chlorfenapyr, Tralopyril, B.t. (*Bacillus thuringiensis*) var. *aizawai*, B.t. var. *israelensis*, B.t. var. *kurstaki*, B.t. var. *sphaericus*, B.t. var. *tenebrionensis*, *Bacillus thuringiensis* crop proteins including Cry1Ab, Cry1Ac, Cry1Fa, Cry2Ab, mCry3A, Cry3Ab, Cry3Bb, Cry34/35Ab1, Methyl bromide and other alkyl halides, Chloropicrin, Sulfuryl fluoride, Benclothiaz, Chinomethionat, Cryolite, Methylneodecanamide, Benzoximate, Cymiazole, Fluensulfone, Azadirachtin, Bifenazate, Amidoflumet, Dicofol, Plifenate, Cyflumetofen, Pyridalyl, *Beauveria bassiana* GHA, Sulfoxaflor, Spinetoram, Spinosad, Spinosad, Emamectin benzoate, Lepimectin, Milbemectin, Abamectin, Methoxyfenozide, Chromafenozide, Halofenozide, Tebufenozide, Amitraz, Chlorantraniliprole, Cyantraniliprole, Flubendiamide, alpha-endosulfan, Chlordane, Endosulfan, Fipronil, Acetoprole, Ethiprole, Pyrafluprole, Pyriprole, Indoxacarb and Metaflumizone, Acrinathrin, Allethrin, Allethrin-cis-trans, Allethrin-trans, beta-Cyfluthrin, beta-Cypermethrin, Bifenthrin, Bioallethrin, Bioallethrin S-cyclopentenyl, Bioresmethrin, Cycloprothrin, Cyfluthrin, Cyhalothrin, Cypermethrin, Cyphenothrin [(1R)-trans-isomers], Dimefluthrin, Empenthrin [(EZ)-(1R)-isomers], Esfenvalerate, Etofenprox, Fenpropathrin, Fenvalerate, Flucythrinate, Flumethrin, Gamma-cyhalothryn, lambda-Cyhalothrin, Meperfluthrin, Metofluthrin, Permethrin, Phenothrin [(1R)-trans-isomer], Prallethrin, Profluthrin, Protrifenbute, Resmethrin, Silafluofen, tau-Fluvalinate, Tefluthrin, Tetramethrin, Tetramethrin [(1R)-isomers], Tetramethylfluthrin, theta-Cypermethrin, Tralomethrin, Transfluthrin, zeta-Cypermethrin, alpha-Cypermethrin, Deltamethrin, D D T, and Methoxychlor, Thiodicarb, Alanycarb, Aldicarb, Bendiocarb, Benfuracarb, Butoxycarboxim, Carbaryl, Carbofuran, Carbosulfan, Ethiofencarb, Fenobucarb, Formetanate, Furathiocarb, Isoprocarb, Methiocarb, Methomyl, Metolcarb, Oxamyl, Pirimicarb, Propoxur, Thiofanox, Triazamate, Trimethacarb, XMC, Xylylcarb, Chlorpyrifos, Malathion, Acephate, Azamethiphos, Azinphos-ethyl, Azinphos-methyl, Cadusafos, Chlorethoxyfos, Chlorfenvinphos, Chlormephos, Chlorpyrifos-methyl, Coumaphos, Cyanophos, Demeton-S-methyl, Diazinon, Dichlorvos/DDVP, Dicrotophos, Dimethoate, Dimethylvinphos, Disulfoton, EPN, Ethion, Ethoprophos, Famphur, Fenamiphos, Fenitrothion, Fenthion, Fonofos, Fosthiazate, Imicyafos, Isofenphos-methyl, Mecarbam, Methamidophos, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Pirimiphos-ethyl, Profenofos, Propaphos, Propetamphos, Prothiofos, Pyraclofos, Pyridaphenthion, Quinalphos, Sulfotep, Tebupirimfos, Temephos, Terbufos, Tetrachlorvinphos, Thiometon, Triazophos, Trichlorfon, Vamidothion Imidacloprid, Thiamethoxam, Acetamiprid, Clothianidin, Dinotefuran, Nitenpyram, Nithiozine, Nicotine, Thiacloprid, chlorantraniliprole, and cyantraniliprole. In embodiments, the compositions including polynucleotides for flea beetle control in *Brassica* species including canola further include, or are used concurrently or sequentially with, foliar sprays including one or more pesticides selected from the group consisting of Deltamethrin, Cypermethrin, Lambda-cyhalothrin, Permethrin, Carbaryl, Carbofuran, and Malathion, or seed treatments including one or more pesticides selected from the group consisting of Thiamethoxam, Imidacloprid, and Clothianidin.

In embodiments, the compositions including polynucleotides for flea beetle control such as the dsRNA triggers described herein can further include, or can be used concurrently or sequentially with, conventional fungicides such as bupirimate, dimethirimol, ethirimol, cyprodinil, pyrimethanil, mepanipyrim, fenpiclonil, fludioxonil; phenylamides, benalaxyl, furalaxyl, metalaxyl, R-metalaxyl, ofurace, oxadixyl, benomyl, carbendazim, debacarb, fuberidazole, thiabendazole, chlozolinate, dichlozoline, iprodine, myclozoline, procymidone, vinclozolin, carboxin, fenfuram, flutolanil, mepronil, oxycarboxin, thifluzamide, guazatine, dodine, iminoctadine, azoxystrobin, kresoxim-methyl, metominostrobin, or trifloxystrobin, ferbam, mancozeb, maneb, metiram, propineb, thiram, zineb, ziram, captafol, captan, dichlofluanid, fluoromide, folpet, tolyfluanid, copper hydroxide, copper oxychloride, copper sulfate, cuprous oxide, mancopper, oxine-copper, dinocap, nitrothal-isopropyl, edifenphos, iprobenphos, isoprothiolane, phosdiphen, pyrazopho, toclofos-methyl, acibenzolar-S-methyl, harpin, anilazine, blasticidin-S, chinomethionat, chloroneb, chlorothalonil, cymoxanil, dichione, diclomezine, dicloran, diethofencarb, dimethomorph, dithianon, etridiazole, famoxadone, fenamidone, fentin, fenpyrazamine, ferimzone, fluazinam, flusulfamide, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, validamycin, azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizol, triticonazole, triforine, ancymidol, fenarimol or nuarimol, dodemorph, fenpropidin, fenpropimorph, spiroxamine, tridemorph, and fenhexamid. In embodiments, the compositions including polynucleotides for flea beetle control in *Brassica* species including canola further include, or are used concurrently or sequentially with, foliar sprays including one or more fungicides selected from the group consisting of Azoxystrobin, *Bacillus subtilis* strain QST 2808, Boscalid, Fluxopyroxad, Pyraclostrobin, Metconazole, Prothioconazole, Penthiopyrad, Picoxystrobin, and Thiophanate Methyl, or seed treatments including one or more fungicides selected from the group consisting of Azoxystrobin, Metalaxyl, Trifloxystrobin, Pyraclostrobin, Sedaxane, Penflufen, Fludioxonil, and Mefenoxam.

In embodiments, the compositions including polynucleotides for flea beetle control such as the dsRNA triggers described herein can further include, or can be used concurrently or sequentially with, conventional herbicides such as glyphosate, auxin-like herbicides such as dicamba, phosphinothricin, glufosinate, 2,2-dichloropropionic acid (Dalapon), acetolactate synthase inhibitors such as sulfonylurea, imidazolinone, triazolopyrimidine, pyrimidyloxybenzoates, and phthalide, bromoxynil, cyclohexanedione (sethoxydim) and aryloxyphenoxypropionate (haloxyfop), sulfonamide herbicides, triazine herbicides, 5-methyltryptophan, aminoethyl cysteine, pyridazinone herbicides such as norflurazon, cyclopropylisoxazole herbicides such as isoxaflutole, protoporphyrinogen oxidase inhibitors, herbicidea containing an aryloxyalkanoate moiety, phenoxy auxins such as 2,4-D and dichlorprop, pyridyloxy auxins such as fluroxypyr and triclopyr, aryloxyphenoxypropionates (AOPP) acetyl-coenzyme A carboxylase (ACCase) inhibitors such as haloxyfop, quizalofop, and diclofop, and 5-substituted phenoxyacetate protoporphyrinogen oxidase IX inhibitors such as pyraflufen and flumiclorac. In embodiments, the compositions including polynucleotides for flea beetle control in *Brassica* species including canola further include, or are used concurrently or sequentially with, one or more post-emergence herbicides selected from the group consisting of Quizalofop, Sethoxydim, Clethodim, and Clopyralid. In embodiments, the compositions including polynucleotides for flea beetle control in herbicide-resistant *Brassica* species including herbicide-resistant canola further include, or are used concurrently or sequentially with, one or more herbicides selected from the group consisting of Imazamox, Glyphosate, and Glufosinate.

The compositions and methods disclosed are useful for inhibiting or controlling flea beetle infestation of a plant, such as a *Brassica* species. In embodiments, the compositions and methods are used to treat a growing plant, such as a field of *Brassica* plants. Embodiments include compositions including polynucleotides disclosed herein in a composition in the form of a solid, liquid, powder, suspension, emulsion, spray, encapsulation, microbeads, carrier particulates, film, matrix, soil drench, or seed treatment composition. In embodiments, such compositions are applied to a surface of the plant in need of protection from or treatment for flea beetle infestations, or applied directly to the flea beetles, or provided in an ingestible form to the flea beetles. In embodiments, a composition including polynucleotides disclosed herein is applied directly to ungerminated seeds (such as ungerminated *Brassica* species seeds), providing plants germinated from the treated seeds increased resistance to flea beetle infestations; examples of seed treatment methods are disclosed in U.S. patent application Ser. No. 14/143,836, which is incorporated by reference in its entirety herein. An embodiment includes a *Brassica* seed that is treated by directly contacting the seed with a polynucleotide (such as a dsRNA trigger) disclosed herein, followed by germination into a *Brassica* plant that exhibits increased resistance to flea beetle infestations.

Unless defined otherwise, all technical and scientific terms used have the same meaning as commonly understood by one of ordinary skill in the art. The terms "to comprise" or "to include" are understood to mean "to include, but not to be limited to". Generally, the nomenclature used and the manufacturing or laboratory procedures described below are well known and commonly employed in the art. Conventional methods are used for these procedures, such as those provided in the art and various general references. Where a term is provided in the singular, the inventors also contemplate aspects described by the plural of that term. Where there are discrepancies in terms and definitions used in references that are incorporated by reference, the terms used in this application shall have the definitions given. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" ($6^{th}$ edition, 2002, McGraw-Hill, New York), or the "Oxford Dictionary of Biology" ($6^{th}$ edition, 2008, Oxford University Press, Oxford and New York). The inventors do not intend to be limited to a mechanism or mode of action. Reference thereto is provided for illustrative purposes only.

Unless otherwise stated, nucleic acid sequences in the text of this specification are given, when read from left to right, in the 5' to 3' direction. One of skill in the art would be aware that a given DNA sequence is understood to define a corresponding RNA sequence which is identical to the DNA sequence except for replacement of the thymine (T) nucleotides of the DNA with uracil (U) nucleotides. Thus, providing a specific DNA sequence is understood to define the exact RNA equivalent. A given first polynucleotide sequence, whether DNA or RNA, further defines the sequence of its exact complement (which can be DNA or RNA), i. e., a second polynucleotide that hybridizes perfectly to the first polynucleotide by forming Watson-Crick base-pairs. By "essentially identical" or "essentially complementary" to a target gene or a fragment of a target gene is meant that a polynucleotide strand (or at least one strand of a double-stranded polynucleotide) is designed to hybridize (generally under physiological conditions such as those found in a living plant or animal cell) to a target gene or to a fragment of a target gene or to the transcript of the target gene or the fragment of a target gene; one of skill in the art would understand that such hybridization does not necessarily require 100% sequence identity or complementarity. A first nucleic acid sequence is "operably" connected or "linked" with a second nucleic acid sequence when the first nucleic acid sequence is placed in a functional relationship with the second nucleic acid sequence. For example, a promoter sequence is "operably linked" to DNA if the promoter provides for transcription or expression of the DNA. Generally, operably linked DNA sequences are contiguous.

The term "polynucleotide" commonly refers to a DNA or RNA molecule containing multiple nucleotides and generally refers both to "oligonucleotides" (a polynucleotide molecule of 18-25 nucleotides in length) and longer polynucleotides of 26 or more nucleotides. Polynucleotides also include molecules containing multiple nucleotides including non-canonical nucleotides or chemically modified nucleotides as commonly practiced in the art; see, e. g., chemical modifications disclosed in the technical manual "RNA Interference (RNAi) and DsiRNAs", 2011 (Integrated DNA Technologies Coralville, Iowa). Generally, polynucleotide as described herein, whether DNA or RNA or both, and whether single- or double-stranded, include at least one segment of 18 or more contiguous nucleotides (or, in the case of double-stranded polynucleotides, at least 18 contiguous base-pairs) that are essentially identical or complementary to a fragment of equivalent size of the DNA of a target gene or the target gene's RNA transcript. Throughout this disclosure, "at least 18 contiguous" means "from about 18 to about 10,000, including every whole number point in between". Thus, embodiments include compositions including oligonucleotides having a length of 18-25 nucleotides (18-mers, 19-mers, 20-mers, 21-mers, 22-mers, 23-mers, 24-mers, or 25-mers), or medium-length polynucleotides having a length of 26 or more nucleotides (polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e. g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene). Where a polynucleotide is double-stranded, such as the dsRNA triggers described in the working Examples, its length can be similarly described in terms of base pairs. Double-stranded polynucleotides, such as the dsRNA triggers described in the working examples, can further be described in terms of one or more of the single-stranded components.

The polynucleotides described herein can be single-stranded (ss) or double-stranded (ds). "Double-stranded" refers to the base-pairing that occurs between sufficiently complementary, anti-parallel nucleic acid strands to form a double-stranded nucleic acid structure, generally under physiologically relevant conditions. Embodiments include those wherein the polynucleotide is selected from the group consisting of sense single-stranded DNA (ssDNA), sense single-stranded RNA (ssRNA), double-stranded RNA (dsRNA), double-stranded DNA (dsDNA), a double-stranded DNA/RNA hybrid, anti-sense ssDNA, or anti-sense ssRNA; a mixture of polynucleotides of any of these types can be used. In some embodiments, the polynucleotide is double-stranded RNA of a length greater than that which is typical of naturally occurring regulatory small RNAs (such as endogenously produced siRNAs and mature miRNAs). In some embodiments, the polynucleotide is double-stranded RNA of at least about 30 contiguous base-pairs in length. In some embodiments, the polynucleotide is double-stranded RNA with a length of between about 50 to about 500 base-pairs. In some embodiments, the polynucleotide can include components other than standard ribonucleotides, e. g., an embodiment is an RNA that includes terminal deoxyribonucleotides.

Effective polynucleotides of any size can be used, alone or in combination, in the various methods and compositions described herein. In some embodiments, a single polynucleotide trigger is used to make a composition (e. g., a composition for topical application, or a recombinant DNA construct useful for making a transgenic plant). In other embodiments, a mixture or pool of different polynucleotide triggers is used; in such cases the polynucleotide triggers can be for a single target gene or for multiple target genes.

In various embodiments, the polynucleotide described herein includes naturally occurring nucleotides, such as those which occur in DNA and RNA. In certain embodiments, the polynucleotide is a combination of ribonucleotides and deoxyribonucleotides, for example, synthetic polynucleotides consisting mainly of ribonucleotides but with one or more terminal deoxyribonucleotides or one or more terminal dideoxyribonucleotides or synthetic polynucleotides consisting mainly of deoxyribonucleotides but with one or more terminal dideoxyribonucleotides. In certain embodiments, the polynucleotide includes non-canonical nucleotides such as inosine, thiouridine, or pseudouridine. In certain embodiments, the polynucleotide includes chemically modified nucleotides. Examples of chemically modified oligonucleotides or polynucleotides are well known in the art; see, for example, U.S. Patent Publication 2011/0171287, U.S. Patent Publication 2011/0171176, U.S. Patent Publication 2011/0152353, U.S. Patent Publication 2011/0152346, and U.S. Patent Publication 2011/0160082, which are herein incorporated by reference. Illustrative examples include, but are not limited to, the naturally occurring phosphodiester backbone of an oligonucleotide or polynucleotide which can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labeled with a fluorescent moiety (e. g., fluorescein or rhodamine) or other label (e. g., biotin).

The term "recombinant", as used to refer to a polynucleotide (such as the recombinant RNA molecules or recombinant DNA constructs described herein), means that the polynucleotide is not a naturally occurring molecule, i. e., that human intervention is required for the polynucleotide to exist. A recombinant polynucleotide is produced using recombinant nucleic acid techniques, or by chemical synthesis, and can include combinations of sequences that do not occur in nature (e. g., combinations of a heterologous promoter and a DNA encoding an RNA to be expressed, or an RNA molecule that includes concatenated segments of a target gene that do not in nature occur adjacent to one another). A recombinant polynucleotide can be biologically produced in a cell (such as a bacterial or plant or animal cell), for example, when that cell is transfected or transformed with a vector encoding the recombinant polynucleotide (e. g., a vector encoding a hairpin form of a dsRNA, produced in a bacterium). A recombinant polynucleotide can include sequences of nucleotides designed in silico using appropriate algorithms.

The polynucleotides or triggers disclosed herein are generally designed to suppress or silence one or more genes ("target genes"). The term "gene" refers to any portion of a nucleic acid that provides for expression of a transcript or encodes a transcript, or that is a hereditable nucleic acid sequence. A "gene" can include, but is not limited to, a promoter region, 5' untranslated regions, transcript encoding regions that can include intronic regions, 3' untranslated regions, or combinations of these regions. In embodiments, the target genes can include coding or non-coding sequence or both. In other embodiments, the target gene has a sequence identical to or complementary to a messenger RNA, e. g., in embodiments the target gene is a cDNA.

As used herein, the term "isolated" refers to separating a molecule from other molecules normally associated with it in its native or natural state. The term "isolated" thus may refer to a DNA molecule that has been separated from other DNA molecule(s) which normally are associated with it in its native or natural state. Such a DNA molecule may be present in a recombined state, such as a recombinant DNA molecule. Thus, DNA molecules fused to regulatory or coding sequences with which they are not normally associated, for example as the result of recombinant techniques, are considered isolated, even when integrated as a transgene into the chromosome of a cell or present with other DNA molecules.

By "insecticidally effective" is meant effective in inducing a physiological or behavioural change in an insect (e. g., adult or larval flea beetles) that infests a plant such as, but not limited to, growth stunting, increased mortality, decrease in reproductive capacity or decreased fecundity, decrease in or cessation of feeding behavior or movement, or decrease in or cessation of metamorphosis stage development. In some embodiments, application of an insecticidally effective amount of the polynucleotide, such as a dsRNA molecule, to a plant improves the plant's resistance to infestation by the insect. In some embodiments, application of an insecticidally effective amount of the polynucleotide, such as a dsRNA molecule, to a crop plant improves yield (e. g., increased biomass, increased seed or fruit production, or increased oil, starch, sugar, or protein content) of that crop plant, in comparison to a crop plant not treated with the polynucleotide. While there is no upper limit on the concentrations and dosages of a polynucleotide as described herein that can be useful in the methods and compositions provided herein, lower effective concentrations and dosages will generally be sought for efficiency and economy. Non-limiting embodiments of effective amounts of a polynucleotide include a range from about 10 nanograms per milliliter to about 100 micrograms per milliliter of a polynucleotide in a liquid form sprayed on a plant, or from about 10 milligrams per acre to about 100 grams per acre of polynucleotide applied to a field of plants, or from about 0.001 to about 0.1 microgram per milliliter of polynucleotide in an artificial diet for feeding the insect. Where compositions as described herein are topically applied to a plant, the concentrations can be adjusted in consideration of the volume of spray or treatment applied to plant leaves or other plant part surfaces, such as flower petals, stems, tubers, fruit, anthers, pollen, leaves, roots, or seeds. In one embodiment, a useful treatment for herbaceous plants using 25-mer polynucleotides as described herein is about 1 nanomole (nmol) of polynucleotides per plant, for example, from about 0.05 to 1 nmol polynucleotides per plant. Other embodiments for herbaceous plants include useful ranges of about 0.05 to about 100 nmol, or about 0.1 to about 20 nmol, or about 1 nmol to about 10 nmol of polynucleotides per plant. In certain embodiments, about 40 to about 50 nmol of a single-stranded polynucleotide as described herein are applied. In certain embodiments, about 0.5 nmol to about 2 nmol of a dsRNA as described herein is applied. In certain embodiments, a composition containing about 0.5 to about 2.0 milligrams per milliliter, or about 0.14 milligrams per milliliter of a dsRNA (or a single-stranded 21-mer) as described herein is applied. In certain embodiments, a composition of about 0.5 to about 1.5 milligrams per milliliter of a dsRNA polynucleotide as described herein of about 50 to about 200 or more nucleotides is applied. In certain embodiments, about 1 nmol to about 5 nmol of a dsRNA as described herein is applied to a plant. In certain embodiments, the polynucleotide composition as topically applied to the plant contains at least one polynucleotide as described herein at a concentration of about 0.01 to about 10 milligrams per milliliter, or about 0.05 to about 2 milligrams per milliliter, or about 0.1 to about 2 milligrams per milliliter. Very large plants, trees, or vines can require correspondingly larger amounts of polynucleotides. When using long dsRNA molecules that can be processed into multiple oligonucleotides (e. g., multiple triggers encoded by a single recombinant DNA molecule as disclosed herein, lower concentrations can be used. Non-limiting examples of effective polynucleotide treatment regimes include a treatment of between about 0.1 to about 1 nmol of polynucleotide molecule per plant, or between about 1 nmol to about 10 nmol of polynucleotide molecule per plant, or between about 10 nmol to about 100 nmol of polynucleotide molecule per plant.

Methods of Causing Insect Mortality and of Controlling Insect Infestations

Several embodiments relate to a method of causing mortality or stunting in an insect, including providing in the diet of an insect at least one recombinant RNA including at least one silencing element essentially identical or essentially complementary to a fragment of a target gene sequence of the insect, wherein the target gene sequence is selected from the group consisting of SEQ ID NOs:1-859, and wherein ingestion of the recombinant RNA by the insect results in mortality or stunting in the insect. These methods are useful for controlling insect infestations of a plant, for example for prevention or treatment of a flea beetle infestation of a crop plant, particularly commercially important *Brassica* species.

In embodiments, the at least one silencing element includes an RNA strand including a sequence of about 95% to about 100% identity or complementarity with a sequence selected from the group consisting of SEQ ID NOs:860-1718 and 1722-1724 or a fragment thereof. In embodiments, the at least one silencing element includes an RNA strand including at least one segment of 18 or more contiguous nucleotides with a sequence of 100% complementarity with a fragment of the target gene of the insect, wherein the target gene has a DNA sequence selected from the group consisting of SEQ ID NOs:1-859. In embodiments, the at least one silencing element includes an RNA strand including at least one segment of 18 or more contiguous nucleotides of an RNA sequence selected from the group consisting of SEQ ID NOs:860-1718 and 1722-1724 or a fragment thereof. In embodiments, the at least one silencing element includes an RNA strand including a sequence selected from the group consisting of SEQ ID NOs:860-1718 and 1722-1724 or a fragment thereof. In embodiments the at least one silencing element includes dsRNA including at least one RNA strand including a sequence of about 95% to about 100% identity or complementarity with a sequence selected from the group consisting of SEQ ID NOs:860-1718 and 1722-1724 or a fragment thereof.

In embodiments, the recombinant RNA is provided in a microbial or plant cell that expresses the recombinant RNA, or in a microbial fermentation product, or is chemically synthesized. In embodiments, the at least one silencing element includes dsRNA. In embodiments, the dsRNA is blunt-ended, or has an overhang at least one terminus, or includes at least one stem-loop. The dsRNA is provided by convenient techniques commonly used. In embodiments, the dsRNA is chemically synthesized, produced by expression in a microorganism, produced by expression in a plant cell, or produced by microbial fermentation. In embodiments, the dsRNA is made from naturally occurring ribonucleotides; in other embodiments the dsRNA is chemically modified.

In embodiments, the method is useful for causing mortality or stunting in insects that are pests of commercially important crop plants, such as an insect pest of a *Brassica* species. In embodiments, the insect is a flea beetle. In embodiments, the insect is a species of a genus selected from the group consisting of the genera *Altica, Anthobiodes, Aphthona, Aphthonaltica, Aphthonoides, Apteopeda, Argopistes, Argopus, Arrhenocoela, Batophila, Blepharida, Chaetocnema, Clitea, Crepidodera, Derocrepis, Dibolia, Disonycha, Epitrix, Hermipyxis, Hermaeophaga, Hespera, Hippuriphila, Horaia, Hyphasis, Lipromima, Liprus, Longitarsus, Luperomorpha, Lythraria, Manobia, Mantura, Meishania, Minota, Mniophila, Neicrepidodera, Nonartha, Novofoudrasia, Ochrosis, Oedionychis, Oglobinia, Omeisphaera, Ophrida, Orestia, Paragopus, Pentamesa, Philopona, Phygasia, Phyllotreta, Podagrica, Podagricomela, Podontia, Pseudodera, Psylliodes, Sangariola, Sinaltica, Sphaeroderma, Systena, Trachyaphthona, Xuthea,* and *Zipangia*. In embodiments, the insect is a species selected from the group consisting of *Altica ambiens* (alder flea beetle), *Altica canadensis* (prairie flea beetle), *Altica chalybaea* (grape flea beetle), *Altica prasina* (poplar flea beetle), *Altica rosae* (rose flea beetle), *Altica sylvia* (blueberry flea beetle), *Altica ulmi* (elm flea beetle), *Chaetocnema pulicaria* (corn flea beetle), *Chaetocnema conofinis* (sweet potato flea beetle), *Epitrix cucumeris* (potato flea beetle), *Systena blanda* (palestripped fleabeetle), and *Systena frontalis* (redheaded flea beetle). In embodiments, the insect is a species selected from the group consisting of *Phyllotreta armoraciae* (horseradish flea beetle), *Phyllotreta cruciferae* (canola flea beetle), *Phyllotreta pusilla* (western black flea beetle), *Phyllotreta nemorum* (striped turnip flea beetle), *Phyllotreta atra* (turnip flea beetle), *Phyllotreta robusta* (garden flea beetle), *Phyllotreta striolata* (striped flea beetle), *Phyllotreta undulata, Psylliodes chrysocephala,* and *Psylliodes punctulata* (hop flea beetle).

Embodiments of the method include those in which the recombinant RNA is designed to silence a target gene in a genus- or species-specific manner, for example, wherein (a) the insect is a *Phyllotreta* species and the target gene has a DNA sequence selected from the group consisting of SEQ ID NOs:1-551; (b) the insect is *Phyllotreta atra* (turnip flea beetle) and the target gene has a DNA sequence selected from the group consisting of SEQ ID NOs:1-296; (c) the insect is *Phyllotreta cruciferae* (canola flea beetle) and the target gene has a DNA sequence selected from the group consisting of SEQ ID NOs:297-532; (d) the insect is *Phyllotreta striolata* (striped flea beetle) and the target gene has a DNA sequence selected from the group consisting of SEQ ID NOs:533-551; (e) the insect is a *Psylliodes* species and the target gene has a DNA sequence selected from the group consisting of SEQ ID NOs:552-859; or (f) the insect is *Psylliodes chrysocephala* and the target gene has a DNA sequence selected from the group consisting of SEQ ID NOs:552-859. Embodiments of the method also include those wherein (a) the insect is a *Phyllotreta* species and the silencing element includes an RNA strand including a sequence selected from the group consisting of SEQ ID NOs:860-1410 or a fragment thereof; (b) the insect is *Phyllotreta atra* (turnip flea beetle) and the silencing element includes an RNA strand including a sequence selected from the group consisting of SEQ ID NOs:860-1155 or a fragment thereof; (c) the insect is *Phyllotreta cruciferae* (canola flea beetle) the silencing element includes an RNA strand including a sequence selected from the group consisting of SEQ ID NOs:1156-1391 or a fragment thereof; (d) the insect is *Phyllotreta striolata* (striped flea beetle) and the silencing element includes an RNA strand including a sequence selected from the group consisting of SEQ ID NOs:1392-1410 or a fragment thereof; (e) the insect is a *Psylliodes* species and the silencing element includes an RNA strand including a sequence selected from the group consisting of SEQ ID NOs:1411-1718 or a fragment thereof; or (f) the insect is *Psylliodes chrysocephala* and the silencing element includes an RNA strand including a sequence selected from the group consisting of SEQ ID NOs:1411-1718 or a fragment thereof.

Embodiments of the method include those wherein the at least one recombinant RNA is provided in a composition including the at least one recombinant RNA, wherein the composition is applied to a surface of the insect or to a surface of a seed or plant in need of protection from infestation by the insect. Embodiments of such compositions include those where the composition includes a solid, liquid, powder, suspension, emulsion, spray, encapsulation, microbeads, carrier particulates, film, matrix, soil drench, or seed treatment. In many embodiments, the composition is formulated in a form that is ingested by the insect. In embodiments, the composition further includes one or more components selected from the group consisting of a carrier agent, a surfactant, an organosilicone, a polynucleotide herbicidal molecule, a non-polynucleotide herbicidal molecule, a non-polynucleotide pesticide, a fungicide, a safener, a fertilizer, a micronutrient, an insect attractant, and an insect growth regulator. In embodiments, the composition further includes at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, a *Bacillus sphaericus* insecticidal protein, a bacterium that produces an insecticidal protein, an entomicidal bacterial species, *Lysinibacillus sphaericus* (*Bacillus sphaericus*), *Brevibacillus laterosporus* (*Bacillus laterosporus*), *Chromobacterium* species, *Chromobacterium subtsugae, Paenibacillus* species, *Paenibacillus lentimorbus,* and *Paenibacillus popilliae.*

Several embodiments relate to a method for controlling an insect infestation of a plant including contacting the plant and/or an insect that infests a plant with a double-stranded RNA (dsRNA), wherein the dsRNA includes at least one segment of 18 or more contiguous nucleotides with a sequence of about 95% to about 100% (e. g., about 95%, about 96%, about 97%, about 98%, about 99%, or about 100%) complementarity with a fragment of a target gene of the insect selected from the group consisting of Act5C, arginine kinase, COPI (coatomer subunit) alpha, COPI (coatomer subunit) beta, COPI (coatomer subunit) betaPrime, COPI (coatomer subunit) delta, COPI (coatomer subunit) epsilon, COPI (coatomer subunit) gamma, COPI (coatomer subunit) zeta, RpL07, RpL19, RpL3, RpL40, RpS21, RpS4, Rpn2, Rpn3, Rpt6, Rpn8, Rpn9, Rpn6-PB-like protein, Sar1, sec6, sec23, sec23A, shrb (snf7), Tubulin gamma chain, ProsAlpha2, ProsBeta5, Proteasome alpha 2, Proteasome beta 5, VATPase E, VATPase A, VATPase B, VATPase D, Vps2, Vps4, Vps16A, Vps20, Vps24, Vps27, Vps28, Vha26 (V-ATPase A), Vha68-2 (V-ATPase D/E), 40S ribosomal protein S14, and 60S ribosomal protein L13. In some embodiments, the dsRNA includes at least one segment of 18 or more contiguous nucleotides with a sequence of about 95% to about 100% complementarity with a fragment of a DNA sequence selected from the group consisting of SEQ ID NOs:1-859. In some embodiments, the dsRNA includes at least one segment of 21 contiguous nucleotides with a sequence of 100% complementarity with a fragment of a DNA sequence selected from the group consisting of SEQ ID NOs:1-859. In this context "controlling" includes inducement of a physiological or behavioural change in an insect (adult or larvae or nymphs) such as, but not limited to, growth stunting, increased mortality, decrease in reproductive capacity, decrease in or cessation of feeding behavior or movement, or decrease in or cessation of metamorphosis stage development. In some embodiments, the dsRNA includes a sequence selected from the group consisting of SEQ ID NOs:860-1155 or a fragment thereof, or the complement thereof.

In various embodiments, the insect is a flea beetle, e. g., a species of a genus selected from the group consisting of the genera *Altica, Anthobiodes, Aphthona, Aphthonaltica, Aphthonoides, Apteopeda, Argopistes, Argopus, Arrhenocoela, Batophila, Blepharida, Chaetocnema, Clitea, Crepidodera, Derocrepis, Dibolia, Disonycha, Epitrix, Hermipyxis, Hermaeophaga, Hespera, Hippuriphila, Horaia, Hyphasis, Lipromima, Liprus, Longitarsus, Luperomorpha, Lythraria, Manobia, Mantura, Meishania, Minota, Mniophila, Neicrepidodera, Nonarthra, Novofoudrasia, Ochrosis, Oedionychis, Oglobinia, Omeisphaera, Ophrida, Orestia, Paragopus, Pentamesa, Philopona, Phygasia, Phyllotreta, Podagrica, Podagricomela, Podontia, Pseudodera, Psylliodes, Sangariola, Sinaltica, Sphaeroderma, Systena, Trachyaphthona, Xuthea,* and *Zipangia*. In some embodiments, the insect is selected from the group consisting of *Altica ambiens* (alder flea beetle), *Altica canadensis* (prairie flea beetle), *Altica chalybaea* (grape flea beetle), *Altica prasina* (poplar flea beetle), *Altica rosae* (rose flea beetle), *Altica sylvia* (blueberry flea beetle), *Altica ulmi* (elm flea beetle), *Chaetocnema pulicaria* (corn flea beetle), *Chaetocnema conofinis* (sweet potato flea beetle), *Epitrix cucumeris* (potato flea beetle), *Systena blanda* (palestripped fleabeetle), and *Systena frontalis* (redheaded flea beetle). In some embodiments, the insect is selected from the group consisting of *Phyllotreta armoraciae* (horseradish flea beetle), *Phyllotreta cruciferae* (canola flea beetle), *Phyllotreta pusilla* (western black flea beetle), *Phyllotreta nemorum* (striped turnip flea beetle), *Phyllotreta atra* (turnip flea beetle), *Phyllotreta robusta* (garden flea beetle), *Phyllotreta striolata* (striped flea beetle), *Phyllotreta undulata, Psylliodes chrysocephala,* and *Psylliodes punctulata* (hop flea beetle).

The plant can be any plant that is subject to infestation by an insect that can be controlled by the polynucleotides disclosed herein. Plants of particular interest include commercially important plants, including row crop plants, vegetables, and fruits, and other plants of agricultural or decorative use. Examples of suitable plants are provided under the heading "Plants". The method is especially useful for controlling an insect infestation of an ornamental plant or a crop plant. Various embodiments of the method include those wherein the plant is a plant in the family Brassicaceae, including a *Brassica* species selected from the group consisting of *B. napus, B. juncea, B. carinata, B. rapa, B. oleracea, B. rupestris, B. sepficeps, B. nigra, B. narinosa, B. perviridus, B. tournefortii,* and *B. fructiculosa*. In other embodiments, the plant is selected from the group consisting of *Glycine max, Linum usitatissimum, Zea mays, Carthamus tinctorius, Helianthus annuus, Nicotiana tabacum, Arabidopsis thaliana, Betholettia excelsa, Ricinus communis, Cocus nucifera, Coriandrum sativum, Gossypium* spp., *Arachis hypogaea, Simmondsia chinensis, Solanum tuberosum, Elaeis guineensis, Olea europaea, Oryza sativa, Cucurbita maxim, Hordeum vulgare,* and *Trificum aestivum*.

Methods include those developed for specific flea beetle pests for a given plant, e. g., wherein the plant is a potato plant and the insect is *Epitrix cucumeris* (potato flea beetle). In some embodiments, specific target genes are identified as targets for RNAi-mediated control in a given insect species. Various embodiments of the method include those wherein (a) the insect is *Phyllotreta atra* (turnip flea beetle) and the target gene has a DNA sequence selected from the group consisting of SEQ ID NOs:1-296; (b) the insect is *Phyllotreta cruciferae* (canola flea beetle) and the target gene has a DNA sequence selected from the group consisting of SEQ ID NOs:297-532; (c) the insect is *Phyllotreta striolata* (striped flea beetle) and the target gene has a DNA sequence selected from the group consisting of SEQ ID NOs:533-551; or (d) the insect is *Psylliodes chrysocephala* and the target gene has a DNA sequence selected from the group consisting of SEQ ID NOs:552-859.

In some embodiments, specific dsRNA "triggers" are developed for specific target genes in a given insect species. Embodiments of the method include those wherein (a) the insect is *Phyllotreta atra* (turnip flea beetle) and the dsRNA includes at least one RNA sequence selected from the group consisting of SEQ ID NOs:860-1155 or a fragment thereof; (b) the insect is *Phyllotreta cruciferae* (canola flea beetle) and the dsRNA includes at least one RNA sequence selected from the group consisting of SEQ ID NOs:1156-1391 or a fragment thereof; (c) the insect is *Phyllotreta striolata* (striped flea beetle) and the dsRNA includes at least one RNA sequence selected from the group consisting of SEQ ID NOs:1392-1410 or a fragment thereof; or (d) the insect is *Psylliodes chrysocephala* and the dsRNA includes at least one RNA sequence selected from the group consisting of SEQ ID NOs:1411-1718 or a fragment thereof.

The method includes contacting an insect, such as a flea beetle, with a double-stranded RNA (dsRNA). Embodiments include contacting via oral delivery to the insect, or non-oral delivery to the insect, or a combination of oral and non-oral delivery to the insect. Embodiments include contacting insects in the adult stage, or in larval stages, or in the egg stage. In some embodiments, contacting results in mortality (death) or stunting (growth stunting or decrease in or cessation of metamorphosis stage development) of the insect, thereby preventing or treating infestation of the plant by the insect. In some embodiments, contacting results in inducement of a physiological or behavioural change in an insect (adult or larvae or nymphs) that results in a decreased ability of the insect to infest or damage a plant, for example, a decrease in reproductive capacity, or a decrease in or cessation of feeding behavior or movement.

In some embodiments of the method, the contacting includes application of a composition including the dsRNA to a surface of the insect or to a surface of the plant infested by the insect. The composition can include or be in the form of a solid, liquid, powder, suspension, emulsion, spray, encapsulation, microbeads, carrier particulates, film, matrix, soil drench, or seed treatment. In some embodiments, the contacting includes providing the dsRNA in a composition that further includes one or more components selected from the group consisting of a carrier agent, a surfactant, an organosilicone, a polynucleotide herbicidal molecule, a non-polynucleotide herbicidal molecule, a non-polynucleotide pesticide, a fungicide, a safener, an insect attractant, and an insect growth regulator. In some embodiments, the contacting includes providing the dsRNA in a composition that further includes at least one pesticidal agent selected from the group consisting of a patatin, a plant lectin, a phytoecdy steroid, a *Bacillus thuringiensis* insecticidal protein, a *Xenorhabdus* insecticidal protein, a *Photorhabdus* insecticidal protein, a *Bacillus laterosporous* insecticidal protein, a *Bacillus sphaericus* insecticidal protein, a bacterium that produces an insecticidal protein, an entomicidal bacterial species, *Lysinibacillus sphaericus* (*Bacillus sphaericus*), *Brevibacillus laterosporus* (*Bacillus laterosporus*), *Chromobacterium* species, *Chromobacterium subtsugae*, *Paenibacillus* species, *Paenibacillus lentimorbus*, and *Paenibacillus popilliae*.

In some embodiments of the method, the contacting includes providing the dsRNA in a composition that is ingested by the insect, such as in a liquid, emulsion, or powder applied to a plant on which the insect feeds, or in the form of bait. Such compositions can further includes one or more components selected from the group consisting of a carrier agent, a surfactant, an organosilicone, a polynucleotide herbicidal molecule, a non-polynucleotide herbicidal molecule, a non-polynucleotide pesticide, a fungicide, a safener, an insect attractant, and an insect growth regulator. Such compositions can further include at least one pesticidal agent selected from the group consisting of a patatin, a plant lectin, a phytoecdy steroid, a *Bacillus thuringiensis* insecticidal protein, a *Xenorhabdus* insecticidal protein, a *Photorhabdus* insecticidal protein, a *Bacillus laterosporous* insecticidal protein, a *Bacillus sphaericus* insecticidal protein, a bacterium that produces an insecticidal protein, an entomicidal bacterial species, *Lysinibacillus sphaericus* (*Bacillus sphaericus*), *Brevibacillus laterosporus* (*Bacillus laterosporus*), *Chromobacterium* species, *Chromobacterium subtsugae*, *Paenibacillus* species, *Paenibacillus lentimorbus*, and *Paenibacillus popilliae*. In embodiments, the combination of the dsRNA and the pesticidal agent provides a level of insect control that is greater than the sum of the effects of the dsRNA and the pesticidal agent components if tested separately.

Insecticidal Compositions

Several embodiments relate to an insecticidal composition including an insecticidally effective amount of a polynucleotide, such as a dsRNA molecule, wherein the polynucleotide includes at least 18 or more contiguous nucleotides with a sequence of about 95% to about 100% (e.g., about 95%, about 96%, about 97%, about 98%, about 99%, or about 100%) complementarity with a fragment of an insect target gene selected from the group consisting of Act5C, arginine kinase, COPI (coatomer subunit) alpha, COPI (coatomer subunit) beta, COPI (coatomer subunit) betaPrime, COPI (coatomer subunit) delta, COPI (coatomer subunit) epsilon, COPI (coatomer subunit) gamma, COPI (coatomer subunit) zeta, RpL07, RpL19, RpL3, RpL40, RpS21, RpS4, Rpn2, Rpn3, Rpt6, Rpn8, Rpn9, Rpn6-PB-like protein, Sar1, sec6, sec23, sec23A, shrb (snf7), Tubulin gamma chain, ProsAlpha2, ProsBeta5, Proteasome alpha 2, Proteasome beta 5, VATPase E, VATPase A, VATPase B, VATPase D, Vps2, Vps4, Vps16A, Vps20, Vps24, Vps27, Vps28, Vha26 (V-ATPase A), Vha68-2 (V-ATPase D/E), 40S ribosomal protein S14, and 60S ribosomal protein L13. In some embodiments the polynucleotide includes at least 18 or more contiguous nucleotides having about 95% to about 100% complementarity with a fragment of a DNA sequence selected from the group consisting of SEQ ID NOs:1-859. In some embodiments the polynucleotide includes 21 contiguous nucleotides having 100% complementarity with a fragment of a DNA sequence selected from the group consisting of SEQ ID NOs:1-859. In embodiments, the polynucleotide includes a sequence selected from the group consisting of SEQ ID NOs:860-1718 and 1722-1724 or a fragment thereof.

In various embodiments of the insecticidal composition, the insect is a flea beetle, e.g., a species of a genus selected from the group consisting of the genera *Altica, Anthobiodes, Aphthona, Aphthonaltica, Aphthonoides, Apteopeda, Argopistes, Argopus, Arrhenocoela, Batophila, Blepharida, Chaetocnema, Clitea, Crepidodera, Derocrepis, Dibolia, Disonycha, Epitrix, Hermipyxis, Hermaeophaga, Hespera, Hippuriphila, Horaia, Hyphasis, Dpromima, Liprus, Longitarsus, Luperomorpha, Lythraria, Manobia, Mantura, Meishania, Minota, Mniophila, Neicrepidodera, Nonarthra, Novofoudrasia, Ochrosis, Oedionychis, Oglobinia, Omeisphaera, Ophrida, Orestia, Paragopus, Pentamesa, Philopona, Phygasia, Phyllotreta, Podagrica, Podagricomela, Podonfia, Pseudodera, Psylliodes, Sangariola, Sinaltica, Sphaeroderma, Systena, Trachyaphthona, Xuthea,* and *Zipangia*. In some embodiments, the insect is selected from the group consisting of *Altica ambiens* (alder flea beetle), *Altica canadensis* (prairie flea beetle), *Altica chalybaea* (grape flea beetle), *Altica prasina* (poplar flea beetle), *Altica rosae* (rose flea beetle), *Altica sylvia* (blueberry flea beetle), *Altica ulmi* (elm flea beetle), *Chaetocnema pulicaria* (corn flea beetle), *Chaetocnema conofinis* (sweet potato flea beetle), *Epitrix cucumeris* (potato flea beetle), *Systena blanda* (palestripped fleabeetle), and *Systena frontalis* (red-headed flea beetle). In some embodiments, the insect is selected from the group consisting of *Phyllotreta armoraciae* (horseradish flea beetle), *Phyllotreta cruciferae* (canola flea beetle), *Phyllotreta pusilla* (western black flea beetle), *Phyllotreta nemorum* (striped turnip flea beetle), *Phyllotreta atra* (turnip flea beetle), *Phyllotreta robusta* (garden flea beetle), *Phyllotreta striolata* (striped flea beetle), *Phyllotreta undulata, Psylliodes chrysocephala*, and *Psylliodes punctulata* (hop flea beetle).

The insecticidal composition is useful for treating a plant or area in the vicinity of a plant to provide protection or treatment from insects, especially flea beetles. A related aspect is a plant treated with an insecticidal composition as described herein, or a seed of the treated plant, wherein the plant exhibits improved resistance to the insect (e.g., improved resistance to flea beetles). In some embodiments, the plant exhibiting improved resistance to the insect is characterized by improved yield, when compared to a plant not treated with the insecticidal composition. In an embodiment, yield (oilseed biomass or oil content) in canola or oilseed rape plants is improved by application of an insecticidally effective amount of a polynucleotide, such as a dsRNA molecule, forgetting one or more genes identified from *Phyllotreta cruciferae* (canola flea beetle); in particular embodiments, the target gene has a DNA sequence selected from the group consisting of SEQ ID NOs:297-532. The plant can be any plant that is subject to infestation by an insect that can be controlled by the insecticidal composition. Plants of particular interest include commercially important plants, including row crop plants, vegetables, and fruits, and other plants of agricultural or decorative use. Examples of suitable plants are provided under the heading "Plants". The method is especially useful for controlling an insect infestation of an ornamental plant or a crop plant. Various embodiments include those wherein the plant is a plant in the family Brassicaceae, including a *Brassica* species selected from the group consisting of *B. napus, B. juncea, B. carinata, B. rapa, B. oleracea, B. rupestris, B. septiceps, B. nigra, B. narinosa, B. perviridis, B. tournefortii,* and *B. fructiculosa*. In other embodiments, the plant is selected from the group consisting of *Glycine max, Linum usitatissimum, Zea mays, Carthamus tinctorius, Helianthus annuus, Nicotiana tabacum, Arabidopsis thaliana, Betholettia excelsa, Ricinus communis, Cocus nucifera, Coriandrum sativum, Gossypium* spp., *Arachis hypogaea, Simmondsia chinensis, Solanum tuberosum, Elaeis guineensis, Olea europaea, Oryza sativa, Cucurbita maxim, Hordeum vulgare*, and *Triticum aestivum*.

In some embodiments, the insecticidal composition is developed for specific flea beetle pests for a given plant, e. g., where the plant is a potato plant and the insect is *Epitrix cucumeris* (potato flea beetle). In some embodiments, the insecticidal composition is developed for specific target genes in a given insect species. Specific embodiments of the insecticidal composition include those wherein (a) the insect is *Phyllotreta atra* (turnip flea beetle) and the target gene has a DNA sequence selected from the group consisting of SEQ ID NOs:1-296; (b) the insect is *Phyllotreta cruciferae* (canola flea beetle) and the target gene has a DNA sequence selected from the group consisting of SEQ ID NOs:297-532; (c) the insect is *Phyllotreta striolata* (striped flea beetle) and the target gene has a DNA sequence selected from the group consisting of SEQ ID NOs:533-551; or (d) the insect is *Psylliodes chrysocephala* and the target gene has a DNA sequence selected from the group consisting of SEQ ID NOs:552-859.

In some embodiments the dsRNA molecule of use in this method is provided as an isolated dsRNA molecule (not part of an expression construct, e. g., lacking additional elements such as a promoter or terminator sequences). Such dsRNA molecules can be relatively short, such as single- or double-stranded RNA molecules of between about 18 to about 300 or between about 50 to about 500 nucleotides (for single-stranded polynucleotides) or between about 18 to about 300 or between about 50 to about 500 base-pairs (for double-stranded polynucleotides). In embodiments the polynucleotide is a dsRNA including a segment including a sequence selected from the group consisting of SEQ ID NOs:860-1718 and 1722-1724 or a fragment thereof.

In some embodiments, the insecticidal composition is in a form selected from the group consisting of a solid, liquid, powder, suspension, emulsion, spray, encapsulation, microbeads, carrier particulates, film, matrix, soil drench, insect diet or insect bait, and seed treatment. In some embodiments, the insecticidal composition is provided in a form that is ingested by the insect, such as in a liquid, emulsion, or powder applied to a plant on which the insect feeds, or in the form of bait. The insecticidal compositions can further include one or more components selected from the group consisting of a carrier agent, a surfactant, an organosilicone, a polynucleotide herbicidal molecule, a non-polynucleotide herbicidal molecule, a non-polynucleotide pesticide, a fungicide, a safener, an insect attractant, and an insect growth regulator. The insecticidal compositions can further include at least one pesticidal agent selected from the group consisting of a patatin, a plant lectin, a phytoecdy steroid, a *Bacillus thuringiensis* insecticidal protein, a *Xenorhabdus* insecticidal protein, a *Photorhabdus* insecticidal protein, a *Bacillus laterosporous* insecticidal protein, a *Bacillus sphaericus* insecticidal protein, a bacterium that produces an insecticidal protein, an entomicidal bacterial species, *Lysinibacillus sphaericus (Bacillus sphaericus), Brevibacillus laterosporus (Bacillus laterosporus), Chromobacterium* species, *Chromobacterium subtsugae, Paenibacillus* species, *Paenibacillus lentimorbus*, and *Paenibacillus popilliae*. In some embodiments, the combination of the recombinant RNA molecule and the pesticidal agent provides a level of insect control that is greater than the sum of the effects of the recombinant RNA molecule and the pesticidal agent components if tested separately.

Embodiments of the compositions optionally include the appropriate stickers and wetters required for efficient foliar coverage as well as UV protectants to protect polynucleotides such as dsRNAs from UV damage. Such additives are commonly used in the bioinsecticide industry and are known to those skilled in the art. Compositions for soil application can include granular formulations that serve as bait for insect larvae. Embodiments include a carrier agent, a surfactant, an organosilicone, a polynucleotide herbicidal molecule, a non-polynucleotide herbicidal molecule, a non-polynucleotide pesticide, a fungicide, a safener, an insect attractant, and an insect growth regulator.

Embodiments of compositions may include a "transfer agent", an agent that, when combined with a composition including a polynucleotide as disclosed herein that is topically applied to the surface of an organism, enables the polynucleotide to enter the cells of that organism. Such transfer agents can be incorporated as part of the composition including a polynucleotide as disclosed herein, or can be applied prior to, contemporaneously with, or following application of the composition including a polynucleotide as described herein. In some embodiments, a transfer agent is an agent that improves the uptake of a polynucleotide by an insect. In some embodiments, a transfer agent is an agent that conditions the surface of plant tissue, e. g., seeds, leaves, stems, roots, flowers, or fruits, to permeation by a polynucleotide into plant cells. In some embodiments, the transfer agent enables a pathway for a polynucleotide through cuticle wax barriers, stomata, and/or cell wall or membrane barriers into plant cells.

Suitable transfer agents include agents that increase permeability of the exterior of the organism or that increase permeability of cells of the organism to polynucleotides. Suitable transfer agents include a chemical agent, or a physical agent, or combinations thereof. Chemical agents for conditioning or transfer include (a) surfactants, (b) an organic solvent or an aqueous solution or aqueous mixtures of organic solvents, (c) oxidizing agents, (d) acids, (e) bases, (f) oils, (g) enzymes, or combinations thereof. In some embodiments, application of a polynucleotide and a transfer agent optionally includes an incubation step, a neutralization step (e. g., to neutralize an acid, base, or oxidizing agent, or to inactivate an enzyme), a rinsing step, or combinations thereof. Suitable transfer agents can be in the form of an emulsion, a reverse emulsion, a liposome, or other micellar-like composition, or can cause the polynucleotide composition to take the form of an emulsion, a reverse emulsion, a liposome, or other micellar-like composition. Embodiments of transfer agents include counter-ions or other molecules that are known to associate with nucleic acid molecules, e. g., cationic lipids, inorganic ammonium ions, alkyl ammonium ions, lithium ions, polyamines such as spermine, spermidine, or putrescine, and other cations. Embodiments of transfer agents include organic solvents such as DMSO, DMF, pyridine, N-pyrrolidine, hexamethylphosphoramide, acetonitrile, dioxane, polypropylene glycol, or other solvents miscible with water or that dissolve phosphonucleotides in non-aqueous systems (such as is used in synthetic reactions). Embodiments of transfer agents include naturally derived or synthetic oils with or without surfactants or emulsifiers, e. g., plant-sourced oils, crop oils (such as those listed in the 9th Compendium of Herbicide Adjuvants, publicly available on-line at herbicide.adjuvants.com), paraffinic oils, polyol fatty acid esters, or oils with short-chain molecules modified with amides or polyamines such as polyethyleneimine or N-pyrrolidine.

Embodiments of transfer agents include organosilicone preparations. For example, a suitable transfer agent is an organosilicone preparation that is commercially available as SILWET L-77® brand surfactant having CAS Number 27306-78-1 and EPA Number: CAL.REG.NO. 5905-50073-AA, and currently available from Momentive Performance Materials, Albany, N.Y. In embodiments where a SILWET L-77® brand surfactant organosilicone preparation is used as transfer agent in the form of a spray treatment (applied prior to, contemporaneously with, or following application of the composition including a polynucleotide as disclosed herein) of plant leaves or other plant surfaces, freshly made concentrations in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of a polynucleotide as disclosed herein into plant cells from a topical application on the surface. One embodiment includes a composition that includes a polynucleotide and a transfer agent including an organosilicone preparation such as Silwet L-77 in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent). One embodiment includes a composition that includes a polynucleotide and a transfer agent including SILWET L-77® brand surfactant in the range of about 0.3 to about 1 percent by weight (wt percent) or about 0.5 to about 1%, by weight (wt percent).

Organosilicone compounds useful as transfer agents for use in compositions and methods disclosed herein include, but are not limited to, compounds that include: (a) a trisiloxane head group that is covalently linked to, (b) an alkyl linker including, but not limited to, an n-propyl linker, that is covalently linked to, (c) a polyglycol chain, that is covalently linked to, (d) a terminal group. Trisiloxane head groups of such organosilicone compounds include, but are not limited to, heptamethyltrisiloxane. Alkyl linkers can include, but are not limited to, an n-propyl linker. Polyglycol chains include, but are not limited to, polyethylene glycol or polypropylene glycol. Polyglycol chains can include a mixture that provides an average chain length "n" of about "7.5". In certain embodiments, the average chain length "n" can vary from about 5 to about 14. Terminal groups can include, but are not limited to, alkyl groups such as a methyl group. Organosilicone compounds useful as transfer agents for use in compositions and methods disclosed herein include, but are not limited to, trisiloxane ethoxylate surfactants or polyalkylene oxide modified heptamethyl trisiloxane. An example of a transfer agent for use in compositions and methods disclosed herein is Compound I:

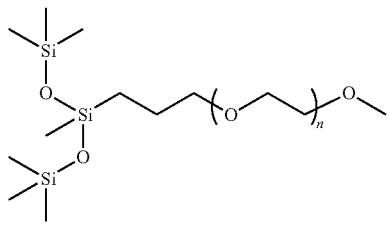

(Compound I: polyalkyleneoxide heptamethyltrisiloxane, average n=7.5).

Organosilicone compounds useful as transfer agents for use in compositions and methods disclosed herein are used, e. g., as freshly made concentrations in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent).

Embodiments of transfer agents include one or more salts such as ammonium chloride, tetrabutylphosphonium bromide, and ammonium sulfate, provided in or used with a composition including a polynucleotide disclosed herein. In some embodiments, ammonium chloride, tetrabutylphosphonium bromide, and/or ammonium sulfate are used at a concentration of about 0.5% to about 5% (w/v), or about 1% to about 3% (w/v), or about 2% (w/v). In certain embodiments, the composition including a polynucleotide includes an ammonium salt at a concentration greater or equal to 300 millimolar. In certain embodiments, the composition including a polynucleotide includes an organosilicone transfer agent in a concentration of about 0.015 to about 2 percent by weight (wt percent) as well as ammonium sulfate at concentrations from about 80 to about 1200 millimolar or about 150 millimolar to about 600 millimolar.

Embodiments of transfer agents include a phosphate salt. Phosphate salts useful in a composition including a polynucleotide include, but are not limited to, calcium, magnesium, potassium, or sodium phosphate salts. In certain embodiments, the composition including a polynucleotide includes a phosphate salt at a concentration of at least about 5 millimolar, at least about 10 millimolar, or at least about 20 millimolar. In certain embodiments, the composition including a polynucleotide includes a phosphate salt in a range of about 1 millimolar to about 25 millimolar or in a range of about 5 millimolar to about 25 millimolar. In certain embodiments, the composition including a polynucleotide includes sodium phosphate at a concentration of at least about 5 millimolar, at least about 10 millimolar, or at least about 20 millimolar. In certain embodiments, the composition including a polynucleotide includes sodium phosphate at a concentration of about 5 millimolar, about 10 millimolar, or about 20 millimolar. In certain embodiments, the composition including a polynucleotide includes a sodium phosphate salt in a range of about 1 millimolar to about 25 millimolar or in a range of about 5 millimolar to about 25 millimolar. In certain embodiments, the composition including a polynucleotide includes a sodium phosphate salt in a range of about 10 millimolar to about 160 millimolar or in a range of about 20 millimolar to about 40 millimolar. In certain embodiments, the composition including a polynucleotide includes a sodium phosphate buffer at a pH of about 6.8.

Embodiments of transfer agents include surfactants and/or effective molecules contained therein. Surfactants and/or effective molecules contained therein include, but are not limited to, sodium or lithium salts of fatty acids (such as tallow or tallowamines or phospholipids) and organosilicone surfactants. In certain embodiments, the composition including a polynucleotide is formulated with counter-ions or other molecules that are known to associate with nucleic acid molecules. Non-limiting examples include, tetraalkyl ammonium ions, trialkyl ammonium ions, sulfonium ions, lithium ions, and polyamines such as spermine, spermidine, or putrescine. In certain embodiments, the composition including a polynucleotide is formulated with a non-polynucleotide herbicide e. g., glyphosate, auxin-like benzoic acid herbicides including dicamba, chloramben, and TBA, glufosinate, auxin-like herbicides including phenoxy carboxylic acid herbicide, pyridine carboxylic acid herbicide, quinoline carboxylic acid herbicide, pyrimidine carboxylic acid herbicide, and benazolin-ethyl herbicide, sulfonylureas, imidazolinones, bromoxynil, delapon, cyclohezanedione, protoporphyrinogen oxidase inhibitors, and 4-hydroxyphenyl-pyruvate-dioxygenase inhibiting herbicides. In certain embodiments, the composition including a polynucleotide is formulated with a non-polynucleotide pesticide, e. g., a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein.

Methods of Providing Plants with Improved Insect Resistance

Several embodiments relate to a method of providing a plant having improved resistance to an insect, including expressing in the plant a recombinant DNA construct, wherein the recombinant DNA construct includes DNA encoding an RNA having a sequence essentially identical or essentially complementary to a fragment of at least one insect target gene selected from the group consisting of Act5C, arginine kinase, COPI (coatomer subunit) alpha, COPI (coatomer subunit) beta, COPI (coatomer subunit) betaPrime, COPI (coatomer subunit) delta, COPI (coatomer subunit) epsilon, COPI (coatomer subunit) gamma, COPI (coatomer subunit) zeta, RpL07, RpL19, RpL3, RpL40, RpS21, RpS4, Rpn2, Rpn3, Rpt6, Rpn8, Rpn9, Rpn6-PB-like protein, Sar1, sec6, sec23, sec23A, shrb (snf7), Tubulin gamma chain, ProsAlpha2, ProsBeta5, Proteasome alpha 2, Proteasome beta 5, VATPase E, VATPase A, VATPase B, VATPase D, Vps2, Vps4, Vps16A, Vps20, Vps24, Vps27, Vps28, Vha26 (V-ATPase A), Vha68-2 (V-ATPase D/E), 40S ribosomal protein S14, and 60S ribosomal protein L13. In some embodiments, the DNA construct includes DNA encoding an RNA including a sequence essentially identical or essentially complementary to a fragment of a DNA sequence selected from the group consisting of SEQ ID NOs:1-859. Several embodiments relate to a plant produced by such method. In some embodiments, the DNA construct includes DNA encoding an RNA having about 95% to about 100% (e. g., about 95%, about 96%, about 97%, about 98%, about 99%, or about 100%) identity or complementarity with a sequence selected from the group consisting of SEQ ID NOs:860-1718 and 1722-1724 or a fragment thereof.

In some embodiments, the recombinant DNA construct further includes a heterologous promoter operably linked to the DNA encoding an RNA, wherein the heterologous promoter is functional in a plant cell. "Heterologous" refers to nucleic acid sequences that are not usually operably linked in a native or naturally occurring genome; by "heterologous promoter" is meant that the promoter is not natively operably linked with the DNA encoding an RNA. Promoters functional in a plant cell include those listed under the heading "Promoters".

In some embodiments, the recombinant DNA construct is expressed in the plant by means of transgenic expression or transient expression. In some embodiments, the method further includes expression in the plant of at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, a *Bacillus sphaericus* insecticidal protein, a bacterium that produces an insecticidal protein, an entomicidal bacterial species, *Lysinibacillus sphaericus* (*Bacillus sphaericus*), *Brevibacillus laterosporus* (*Bacillus laterosporus*), *Chromobacterium* species, *Chromobacterium subtsugae*, *Paenibacillus* species, *Paenibacillus lentimorbus*, and *Paenibacillus popilliae*. The pesticidal agent can be expressed from the same recombinant DNA construct that includes the DNA encoding an RNA, or from a different recombinant DNA construct.

A related aspect is a plant having improved resistance to an insect (e. g., improved resistance to flea beetles), or the seed of such a plant, wherein the plant is provided by the method including expressing in the plant a recombinant DNA construct, wherein the recombinant DNA construct includes DNA encoding an RNA having a sequence essentially identical or essentially complementary to a fragment of at least one target gene of the insect, wherein the target gene is selected from the group consisting of Act5C, arginine kinase, COPI (coatomer subunit) alpha, COPI (coatomer subunit) beta, COPI (coatomer subunit) betaPrime, COPI (coatomer subunit) delta, COPI (coatomer subunit) epsilon, COPI (coatomer subunit) gamma, COPI (coatomer subunit) zeta, RpL07, RpL19, RpL3, RpL40, RpS21, RpS4, Rpn2, Rpn3, Rpt6, Rpn8, Rpn9, Rpn6-PB-like protein, Sar1, sec6, sec23, sec23A, shrb (snf7), Tubulin gamma chain, ProsAlpha2, ProsBeta5, Proteasome alpha 2, Proteasome beta 5, VATPase E, VATPase A, VATPase B, VATPase D, Vps2, Vps4, Vps16A, Vps20, Vps24, Vps27, Vps28, Vha26 (V-ATPase A), Vha68-2 (V-ATPase D/E), 40S ribosomal protein S14, and 60S ribosomal protein L13. In some embodiments, the recombinant DNA construct includes DNA encoding an RNA including a sequence essentially identical or essentially complementary to a fragment of a DNA sequence selected from the group consisting of SEQ ID NOs:1-859. In some embodiments, the plant exhibiting improved resistance to the insect is characterized by improved yield, when compared to a plant not expressing the recombinant DNA construct. In an embodiment, yield (oilseed biomass or oil content) in canola or oilseed rape plants is improved by expressing in the canola or oilseed rape plants a polynucleotide, such as a dsRNA molecule, targetting one or more genes of *Phyllotreta* cruciferae (canola flea beetle), e. g., wherein the target gene has a DNA sequence selected from the group consisting of SEQ ID NOs:297-532. Several embodiments relate to fruit, seed, or propagatable parts of the plant provided by this method and exhibiting improved resistance to the insect. The plant can be any plant that is subject to infestation by an insect that can be controlled by expressing in the plant the recombinant DNA construct according to this method. Plants of particular interest include commercially important plants, including row crop plants, vegetables, and fruits, and other plants of agricultural or decorative use. Examples of suitable plants are provided under the heading "Plants". The method is especially useful for providing an ornamental plant or a crop plant with improved resistance to flea beetles. Various embodiments of the method include those wherein the plant is a plant in the family Brassicaceae, including a *Brassica* species selected from the group consisting of *B. napus, B. juncea, B. carinata, B. rapa, B. oleracea, B. rupestris, B. sepficeps, B. nigra, B. narinosa, B. perviridus, B. tournefortii,* and *B. fructiculosa*. In other embodiments, the plant is selected from the group consisting of *Glycine max, Linum usitafissimum, Zea mays, Carthamus tinctorius, Helianthus annuus, Nicofiana tabacum, Arabidopsis thaliana, Betholettia excelsa, Ricinus communis, Cocus nucifera, Coriandrum sativum, Gossypium* spp., *Arachis hypogaea, Simmondsia chinensis, Solanum tuberosum, Elaeis guineensis, Olea europaea, Oryza sativa, Cucurbita maxim, Hordeum vul-*

*gare*, and *Triticum aestivum*. In an embodiment, the method provides a potato plant with improved resistance to *Epitrix cucumeris* (potato flea beetle).

Embodiments of the method provide a plant having improved resistance to one or more flea beetle species, e. g., a species of a genus selected from the group consisting of the genera *Altica, Anthobiodes, Aphthona, Aphthonaltica, Aphthonoides, Apteopeda, Argopistes, Argopus, Arrhenocoela, Batophila, Blepharida, Chaetocnema, Clitea, Crepidodera, Derocrepis, Dibolia, Disonycha, Epitrix, Hermipyxis, Hermaeophaga, Hespera, Hippuriphila, Horaia, Hyphasis, Lipromima, Liprus, Longitarsus, Luperomorpha, Lythraria, Manobia, Mantura, Meishania, Minota, Mniophila, Neicrepidodera, Nonarthra, Novofoudrasia, Ochrosis, Oedionychis, Oglobinia, Omeisphaera, Ophrida, Orestia, Paragopus, Pentamesa, Philopona, Phygasia, Phyllotreta, Podagrica, Podagricomela, Podontia, Pseudodera, Psylliodes, Sangariola, Sinaltica, Sphaeroderma, Systena, Trachyaphthona, Xuthea*, and *Zipangia*. In embodiments, the insect is selected from the group consisting of *Altica ambiens* (alder flea beetle), *Altica canadensis* (prairie flea beetle), *Altica chalybaea* (grape flea beetle), *Altica prasina* (poplar flea beetle), *Altica rosae* (rose flea beetle), *Altica sylvia* (blueberry flea beetle), *Altica ulmi* (elm flea beetle), *Chaetocnema pulicaria* (corn flea beetle), *Chaetocnema conofinis* (sweet potato flea beetle), *Epitrix cucumeris* (potato flea beetle), *Systena blanda* (palestripped fleabeetle), and *Systena frontalis* (redheaded flea beetle). In embodiments, the method provides a plant having improved resistance to an insect selected from the group consisting of *Phyllotreta armoraciae* (horseradish flea beetle), *Phyllotreta cruciferae* (canola flea beetle), *Phyllotreta pusilla* (western black flea beetle), *Phyllotreta nemorum* (striped turnip flea beetle), *Phyllotreta atra* (turnip flea beetle), *Phyllotreta robusta* (garden flea beetle), *Phyllotreta striolata* (striped flea beetle), *Phyllotreta undulata, Psylliodes chrysocephala*, and *Psylliodes punctulata* (hop flea beetle).

In some embodiments, the method is developed for specific target genes in a given insect species. In some embodiments, a plant having improved resistance to *Phyllotreta atra* (turnip flea beetle), wherein the target gene has a DNA sequence selected from the group consisting of SEQ ID NOs:1-296, is provided. In some embodiments, a plant having improved resistance to *Phyllotreta cruciferae* (canola flea beetle), wherein the target gene has a DNA sequence selected from the group consisting of SEQ ID NOs:297-532, is provided. In some embodiments, a plant having improved resistance to *Phyllotreta striolata* (striped flea beetle), wherein the target gene has a DNA sequence selected from the group consisting of SEQ ID NOs:533-551, is provided. In some embodiments, a plant having improved resistance to *Psylliodes chrysocephala*, wherein the target gene has a DNA sequence selected from the group consisting of SEQ ID NOs:552-859, is provided. In some embodiments, a plant having improved resistance to *Phyllotreta atra* (turnip flea beetle) that expresses from a recombinant DNA construct a dsRNA strand including a sequence of about 95% to about 100% identity with a sequence selected from the group consisting of SEQ ID NOs:860-1155 or a fragment thereof is provided. In some embodiments, a plant having improved resistance to *Phyllotreta cruciferae* (canola flea beetle) that expresses from a recombinant DNA construct a dsRNA including a strand including a sequence of about 95% to about 100% identity with a sequence selected from the group consisting of SEQ ID NOs:1156-1391 or a fragment thereof is provided. In some embodiments, a plant having improved resistance to *Phyllotreta striolata* (striped flea beetle) that expresses from a recombinant DNA construct a dsRNA including a strand including a sequence of about 95% to about 100% identity with a sequence selected from the group consisting of SEQ ID NOs:1392-1410 or a fragment thereof is provided. In some embodiments, a plant having improved resistance to *Psylliodes chrysocephala* that expresses from a recombinant DNA construct a dsRNA including a strand including a sequence of about 95% to about 100% identity with a sequence selected from the group consisting of SEQ ID NOs:1411-1718 or a fragment thereof is provided.

Recombinant DNA Constructs Encoding RNA for Insect Control

Several embodiments relate to a recombinant DNA construct including a heterologous promoter operably linked to DNA encoding an RNA transcript including a sequence of about 95% to about 100% (e. g., about 95%, about 96%, about 97%, about 98%, about 99%, or about 100%) identity or complementarity with a sequence selected from the group consisting of SEQ ID NOs:860-1718 and 1722-1724 or a fragment thereof.

In some embodiments of the recombinant DNA construct, the RNA transcript includes at least one RNA strand including a sequence of about 95% to about 100% (e. g., about 95%, about 96%, about 97%, about 98%, about 99%, or about 100%) identity or complementarity with a sequence selected from the group consisting of SEQ ID NOs:860-1718 and 1722-1724 or a fragment thereof. In some embodiments, the RNA transcript forms dsRNA. In some embodiments, the RNA transcript is a dsRNA including an RNA strand including at least one segment of 18 or more contiguous nucleotides of an RNA sequence selected from the group consisting of SEQ ID NOs:860-1718 and 1722-1724 or a fragment thereof. In some embodiments, the RNA transcript is a dsRNA including an RNA strand including at least one segment of 21 contiguous nucleotides of an RNA sequence selected from the group consisting of SEQ ID NOs:860-1718 and 1722-1724 or a fragment thereof. In some embodiments, the RNA transcript is a dsRNA including at least one RNA strand including a sequence of about 95% to about 100% identity or complementarity with a sequence selected from the group consisting of SEQ ID NOs:860-1718 and 1722-1724 or a fragment thereof. In some embodiments, the RNA transcript is a dsRNA including an RNA strand including a sequence selected from the group consisting of SEQ ID NOs:860-1718 and 1722-1724 or a fragment thereof.

In some embodiments of the recombinant DNA construct, the heterologous promoter is functional for expression of the RNA transcript in a bacterium. In some embodiments where the recombinant DNA construct is to be expressed in a bacterium, the bacterium is selected from the group consisting of *Escherichia coli, Bacillus* species, *Pseudomonas* species, *Xenorhabdus* species, or *Photorhabdus* species. In other embodiments, the recombinant DNA construct includes a heterologous promoter that is functional in a plant cell.

In some embodiments, the recombinant DNA construct is contained in a recombinant vector, such as a recombinant plant virus vector or a recombinant baculovirus vector. In embodiments, the recombinant DNA construct is integrated into a plant chromosome or plastid, e. g., by stable transformation.

Related aspects include a transgenic plant cell including in its genome the recombinant DNA construct, and a transgenic plant including such a transgenic plant cell. Transgenic plant cells and plants are made by methods known in the art, such as those described under the heading "Making and Using Transgenic Plant Cells and Transgenic Plants". Further aspects include a commodity product produced from such a transgenic plant, and transgenic progeny seed or propagatable plant part of the transgenic plant.

Related Information and Techniques

Plants

The methods and compositions described herein for treating and protecting plants from insect infestations are useful across a broad range of plants. Suitable plants in which the methods and compositions disclosed herein can be used include, but are not limited to, cereals and forage grasses (rice, maize, wheat, barley, oat, sorghum, pearl millet, finger millet, cool-season forage grasses, and bahiagrass), oilseed crops (soybean, oilseed brassicas including canola and oilseed rape, sunflower, peanut, flax, sesame, and safflower), legume grains and forages (common bean, cowpea, pea, fava bean, lentil, tepary bean, Asiatic beans, pigeonpea, vetch, chickpea, lupine, alfalfa, and clovers), temperate fruits and nuts (apple, pear, peach, plums, berry crops, cherries, grapes, olive, almond, and Persian walnut), tropical and subtropical fruits and nuts (citrus including limes, oranges, and grapefruit; banana and plantain, pineapple, papaya, mango, avocado, kiwifruit, passionfruit, and persimmon), vegetable crops (solanaceous plants including tomato, eggplant, and peppers; vegetable brassicas; radish, carrot, cucurbits, alliums, asparagus, and leafy vegetables), sugar, tuber, and fiber crops (sugarcane, sugar beet, stevia, potato, sweet potato, cassava, and cotton), plantation crops, ornamentals, and turf grasses (tobacco, coffee, cocoa, tea, rubber tree, medicinal plants, ornamentals, and turf grasses), and forest tree species. Specific plant species of interest are plants in the family Brassicaceae, including the *Brassica* species *B. napus, B. juncea, B. carinata, B. rapa, B. oleracea, B. rupestris, B. sepficeps, B. nigra, B. narinosa, B. perviridus, B. tournefortii,* and *B. frucficulosa*. Additional plant species of interest are *Glycine max, Linum usitatissimum, Zea mays, Carthamus tinctorius, Helianthus annuus, Nicotiana tabacum, Arabidopsis thaliana, Betholettia excelsa, Ricinus communis, Cocos nucifera, Coriandrum sativum, Gossypium* spp., *Arachis hypogaea, Simmondsia chinensis, Solanum tuberosum, Elaeis guineensis, Olea europaea, Oryza sativa, Cucurbita maxim, Hordeum vulgare,* and *Triticum aestivum*.

Additional Construct Elements

Embodiments of the polynucleotides and nucleic acid molecules disclosed herein can include additional elements, such as promoters, small RNA recognition sites, aptamers or ribozymes, additional and additional expression cassettes for expressing coding sequences (e. g., to express a transgene such as an insecticidal protein or selectable marker) or non-coding sequences (e. g., to express additional suppression elements). For example, an aspect provides a recombinant DNA construct including a heterologous promoter operably linked to DNA encoding an RNA transcript including a sequence of about 95% to about 100% identity or complementarity with a sequence selected from the group consisting of SEQ ID NOs:860-1718 and 1722-1724 or a fragment thereof. In another embodiment, a recombinant DNA construct including a promoter operably linked to DNA encoding: (a) an RNA transcript including a sequence of about 95% to about 100% identity or complementarity with a sequence selected from the group consisting of SEQ ID NOs:860-1718 and 1722-1724 or a fragment thereof, and (b) an aptamer, is stably integrated into the plant's genome from where RNA transcripts including the RNA aptamer and the RNA silencing element are expressed in cells of the plant; the aptamer serves to guide the RNA silencing element to a desired location in the cell. In another embodiment, inclusion of one or more recognition sites for binding and cleavage by a small RNA (e. g., by a miRNA or an siRNA that is expressed only in a particular cell or tissue) allows for more precise expression patterns in a plant, wherein the expression of the recombinant DNA construct is suppressed where the small RNA is expressed. Such additional elements are described below.

Promoters

Promoters of use in the compositions and methods disclosed herein are functional in the cell in which the construct is intended to be transcribed. Generally these promoters are heterologous promoters, as used in recombinant constructs, i. e., they are not in nature found to be operably linked to the other nucleic elements used in the constructs. In various embodiments, the promoter is selected from the group consisting of a constitutive promoter, a spatially specific promoter, a temporally specific promoter, a developmentally specific promoter, and an inducible promoter. In many embodiments the promoter is a promoter functional in a plant, for example, a pol II promoter, a pol III promoter, a pol IV promoter, or a pol V promoter.

Non-constitutive promoters suitable for use with the recombinant DNA constructs disclosed herein include spatially specific promoters, temporally specific promoters, and inducible promoters. Spatially specific promoters can include organelle-, cell-, tissue-, or organ-specific promoters (e. g., a plastid-specific, a root-specific, a pollen-specific, or a seed-specific promoter for expression in plastids, roots, pollen, or seeds, respectively). In many cases a seed-specific, embryo-specific, aleurone-specific, or endosperm-specific promoter is especially useful. Temporally specific promoters can include promoters that tend to promote expression during certain developmental stages in a plant's growth cycle, or during different times of day or night, or at different seasons in a year. Inducible promoters include promoters induced by chemicals or by environmental conditions such as, but not limited to, biotic or abiotic stress (e. g., water deficit or drought, heat, cold, high or low nutrient or salt levels, high or low light levels, or pest or pathogen infection). MicroRNA promoters are useful, especially those having a temporally specific, spatially specific, or inducible expression pattern; examples of miRNA promoters, as well as methods for identifying miRNA promoters having specific expression patterns, are provided in U. S. Patent Application Publications 2006/0200878, 2007/0199095, and 2007/0300329, which are specifically incorporated herein by reference. An expression-specific promoter can also include promoters that are generally constitutively expressed but at differing degrees or "strengths" of expression, including promoters commonly regarded as "strong promoters" or as "weak promoters".

Promoters of particular interest include the following examples: an opaline synthase promoter isolated from T-DNA of *Agrobacterium*; a cauliflower mosaic virus 35S promoter; enhanced promoter elements or chimeric promoter elements such as an enhanced cauliflower mosaic virus (CaMV) 35S promoter linked to an enhancer element (an intron from heat shock protein 70 of *Zea mays*); root specific promoters such as those disclosed in U.S. Pat. Nos. 5,837,848; 6,437,217 and 6,426,446; a maize L3 oleosin promoter disclosed in U.S. Pat. No. 6,433,252; a promoter for a plant nuclear gene encoding a plastid-localized aldolase disclosed in U. S. Patent Application Publication 2004/0216189; cold-inducible promoters disclosed in U.S. Pat. No. 6,084,089; salt-inducible promoters disclosed in U.S.

Pat. No. 6,140,078; light-inducible promoters disclosed in U.S. Pat. No. 6,294,714; pathogen-inducible promoters disclosed in U.S. Pat. No. 6,252,138; and water deficit-inducible promoters disclosed in U.S. Patent Application Publication 2004/0123347 A1. All of the above-described patents and patent publications disclosing promoters and their use, especially in recombinant DNA constructs functional in plants are incorporated herein by reference.

Plant vascular- or phloem-specific promoters of interest include a rolC or rolA promoter of *Agrobacterium rhizogenes*, a promoter of a *Agrobacterium tumefaciens* T-DNA gene 5, the rice sucrose synthase RSsl gene promoter, a *Commelina* yellow mottle badnavirus promoter, a coconut foliar decay virus promoter, a rice tungro baciliform virus promoter, the promoter of a pea glutamine synthase GS3A gene, a invCD111 and invCD141 promoters of a potato invertase genes, a promoter isolated from *Arabidopsis* shown to have phloem-specific expression in tobacco by Kertbundit et al. (1991) *Proc. Natl. Acad. Sci. USA.,* 88:5212-5216, a VAHOX1 promoter region, a pea cell wall invertase gene promoter, an acid invertase gene promoter from carrot, a promoter of a sulfate transporter gene Sultr1; 3, a promoter of a plant sucrose synthase gene, and a promoter of a plant sucrose transporter gene.

Promoters suitable for use with a recombinant DNA construct or polynucleotide disclosed herein include polymerase II ("pol II") promoters and polymerase III ("pol III") promoters. RNA polymerase II transcribes structural or catalytic RNAs that are usually shorter than 400 nucleotides in length, and recognizes a simple run of T residues as a termination signal; it has been used to transcribe siRNA duplexes (see, e. g., Lu et al. (2004) *Nucleic Acids Res.,* 32:e171). Pol II promoters are therefore preferred in certain embodiments where a short RNA transcript is to be produced from a recombinant DNA construct. In one embodiment, the recombinant DNA construct includes a pol II promoter to express an RNA transcript flanked by self-cleaving ribozyme sequences (e. g., self-cleaving hammerhead ribozymes), resulting in a processed RNA, such as a single-stranded RNA that binds to the transcript of the flea beetle target gene, with defined 5' and 3' ends, free of potentially interfering flanking sequences. An alternative approach uses pol III promoters to generate transcripts with relatively defined 5' and 3' ends, i. e., to transcribe an RNA with minimal 5' and 3' flanking sequences. In some embodiments, Pol III promoters (e. g., U6 or H1 promoters) are preferred for adding a short AT-rich transcription termination site that results in 2 base-pair overhangs (UU) in the transcribed RNA; this is useful, e. g., for expression of siRNA-type constructs. Use of pol III promoters for driving expression of siRNA constructs has been reported; see van de Wetering et al. (2003) *EMBO Rep.,* 4: 609-615, and Tuschl (2002) *Nature Biotechnol.,* 20: 446-448. Baculovirus promoters such as baculovirus polyhedrin and p10 promoters are known in the art and commercially available; see, e. g., Invitrogen's "Guide to Baculovirus Expression Vector Systems (BEVS) and Insect Cell Culture Techniques", 2002 (Life Technologies, Carlsbad, Calif.) and F. J. Haines et al. "Baculovirus Expression Vectors", undated (Oxford Expression Technologies, Oxford, UK).

The promoter element can include nucleic acid sequences that are not naturally occurring promoters or promoter elements or homologues thereof but that can regulate expression of a gene. Examples of such "gene independent" regulatory sequences include naturally occurring or artificially designed RNA sequences that include a ligand-binding region or aptamer (see "Aptamers", below) and a regulatory region (which can be cis-acting). See, for example, Isaacs et al. (2004) *Nat. Biotechnol.,* 22:841-847, Bayer and Smolke (2005) *Nature Biotechnol.,* 23:337-343, Mandal and Breaker (2004) *Nature Rev. Mol. Cell Biol.,* 5:451-463, Davidson and Ellington (2005) *Trends Biotechnol.,* 23:109-112, Winkler et al. (2002) *Nature,* 419:952-956, Sudarsan et al. (2003) *RNA,* 9:644-647, and Mandal and Breaker (2004) *Nature Struct. Mol. Biol.,* 11:29-35. Such "riboregulators" could be selected or designed for specific spatial or temporal specificity, for example, to regulate translation of DNA that encodes a silencing element for suppressing a target gene only in the presence (or absence) of a given concentration of the appropriate ligand. One example is a riboregulator that is responsive to an endogenous ligand (e. g., jasmonic acid or salicylic acid) produced by the plant when under stress (e. g., abiotic stress such as water, temperature, or nutrient stress, or biotic stress such as attach by pests or pathogens); under stress, the level of endogenous ligand increases to a level sufficient for the riboregulator to begin transcription of the DNA that encodes a silencing element for suppressing a target gene.

Recombinase Sites

In some embodiments, the recombinant DNA construct or polynucleotide includes DNA encoding one or more site-specific recombinase recognition sites. In one embodiment, the recombinant DNA construct includes at least a pair of loxP sites, wherein site-specific recombination of DNA between the loxP sites is mediated by a Cre recombinase. The position and relative orientation of the loxP sites is selected to achieve the desired recombination; for example, when the loxP sites are in the same orientation, the DNA between the loxP sites is excised in circular form. In another embodiment, the recombinant DNA construct includes DNA encoding one loxP site; in the presence of Cre recombinase and another DNA with a loxP site, the two DNAs are recombined.

Aptamers

In some embodiments, the recombinant DNA construct or polynucleotide includes DNA that is processed to an RNA aptamer, that is, an RNA that binds to a ligand through binding mechanism that is not primarily based on Watson-Crick base-pairing (in contrast, for example, to the base-pairing that occurs between complementary, anti-parallel nucleic acid strands to form a double-stranded nucleic acid structure). See, for example, Ellington and Szostak (1990) *Nature,* 346:818-822. Examples of aptamers can be found, for example, in the public Aptamer Database, available on line at aptamer.icmb.utexas.edu (Lee et al. (2004) *Nucleic Acids Res.,* 32(1):D95-100). Aptamers can, however, be monovalent (binding a single ligand) or multivalent (binding more than one individual ligand, e. g., binding one unit of two or more different ligands).

Ligands include any molecule (or part of a molecule) that can be recognized and be bound by a nucleic acid secondary structure by a mechanism not primarily based on Watson-Crick base pairing. In this way, the recognition and binding of ligand and aptamer is analogous to that of antigen and antibody, or of biological effector and receptor. Ligands can include single molecules (or part of a molecule), or a combination of two or more molecules (or parts of a molecule), and can include one or more macromolecular complexes (e. g., polymers, lipid bilayers, liposomes, cellular membranes or other cellular structures, or cell surfaces). Examples of specific ligands include vitamins such as coenzyme $B_{12}$ and thiamine pyrophosphate, flavin mononucleotide, guanine, adenosine, S-adenosylmethionine, S-adenosylhomocysteine, coenzyme A, lysine, tyrosine, dopamine, glucosamine-6-phosphate, caffeine, theophylline, antibiotics such as chloramphenicol and neomycin, herbicides such as glyphosate and dicamba, proteins including viral or phage coat proteins and invertebrate epidermal or digestive tract surface proteins, and RNAs including viral RNA, transfer-RNAs (t-RNAs), ribosomal RNA (rRNA), and RNA polymerases such as RNA-dependent RNA polymerase (RdRP). One class of RNA aptamers are "thermo-switches" that do not bind a ligand but are thermally responsive, that is to say, the aptamer's conformation is determined by temperature; see, for example, Box 3 in Mandal and Breaker (2004) *Nature Rev. Mol. Cell Biol.*, 5:451-463.

Transgene Transcription Units

In some embodiments, the recombinant DNA construct or polynucleotide disclosed herein includes a transgene transcription unit. A transgene transcription unit includes DNA sequence encoding a gene of interest, e. g., a natural protein or a heterologous protein. A gene of interest can be any coding or non-coding sequence from any species (including, but not limited to, non-eukaryotes such as bacteria, and viruses; fungi, protists, plants, invertebrates, and vertebrates. Particular genes of interest are genes encoding one or more proteins conferring resistance to an herbicide and genes encoding at least one pesticidal agent selected from the group consisting of a patatin, a plant lectin, a phytoecdy steroid, a *Bacillus thuringiensis* insecticidal protein, a *Xenorhabdus* insecticidal protein, a *Photorhabdus* insecticidal protein, a *Bacillus* laterosporous insecticidal protein, a *Bacillus sphaericus* insecticidal protein, and an insecticidal protein produced by any of Lysinibacillus *sphaericus* (*Bacillus sphaericus*), *Brevibacillus laterosporus* (*Bacillus laterosporus*), *Chromobacterium* species, *Chromobacterium* subtsugae, *Paenibacillus* species, *Paenibacillus lentimorbus*, and *Paenibacillus popilliae*. The transgene transcription unit can further include 5' or 3' sequence or both as required for transcription of the transgene.

Introns

In some embodiments, the recombinant DNA construct or polynucleotide includes DNA encoding a spliceable intron. By "intron" is generally meant a segment of DNA (or the RNA transcribed from such a segment) that is located between exons (protein-encoding segments of the DNA or corresponding transcribed RNA), wherein, during maturation of the messenger RNA, the intron present is enzymatically "spliced out" or removed from the RNA strand by a cleavage/ligation process that occurs in the nucleus in eukaryotes. The term "intron" is also applied to non-coding DNA sequences that are transcribed to RNA segments that can be spliced out of a maturing RNA transcript, but are not introns found between protein-coding exons. One example of these are spliceable sequences that that have the ability to enhance expression in plants (in some cases, especially in monocots) of a downstream coding sequence; these spliceable sequences are naturally located in the 5' untranslated region of some plant genes, as well as in some viral genes (e. g., the tobacco mosaic virus 5' leader sequence or "omega" leader described as enhancing expression in plant genes by Gallie and Walbot (1992) *Nucleic Acids Res.*, 20:4631-4638). These spliceable sequences or "expression-enhancing introns" can be artificially inserted in the 5' untranslated region of a plant gene between the promoter but before any protein-coding exons. Examples of such expression-enhancing introns include, but are not limited to, a maize alcohol dehydrogenase (Zm-Adh1), a maize Bronze-1 expression-enhancing intron, a rice actin 1 (Os-Act1) intron, a Shrunken-1 (Sh-1) intron, a maize sucrose synthase intron, a heat shock protein 18 (hsp18) intron, and an 82 kilodalton heat shock protein (hsp82) intron. U.S. Pat. Nos. 5,593,874 and 5,859,347, specifically incorporated by reference herein, describe methods of improving recombinant DNA constructs for use in plants by inclusion of an expression-enhancing intron derived from the 70 kilodalton maize heat shock protein (hsp70) in the non-translated leader positioned 3' from the gene promoter and 5' from the first protein-coding exon.

Ribozymes

In some embodiments, the recombinant DNA construct or polynucleotide includes DNA encoding one or more ribozymes. Ribozymes of particular interest include a self-cleaving ribozyme, a hammerhead ribozyme, or a hairpin ribozyme. In one embodiment, the recombinant DNA construct includes DNA encoding one or more ribozymes that serve to cleave the transcribed RNA to provide defined segments of RNA, such as separate sense or anti-sense single-stranded RNA segments (which in embodiments hybridise to form dsRNA), or an RNA segment having self-complementary nucleotide sequences that form at least partially dsRNA (e. g., in a stem-loop structure) for suppressing a flea beetle target gene.

Gene Suppression Elements

In some embodiments, the recombinant DNA construct or polynucleotide includes DNA encoding additional gene suppression element for suppressing a target gene other than a flea beetle target gene. The target gene to be suppressed can include coding or non-coding sequence or both.

Suitable gene suppression elements are described in detail in U. S. Patent Application Publication 2006/0200878, which disclosure is specifically incorporated herein by reference, and include one or more of:

(a) DNA that includes at least one anti-sense DNA segment that is anti-sense to at least one segment of the gene to be suppressed;

(b) DNA that includes multiple copies of at least one anti-sense DNA segment that is anti-sense to at least one segment of the gene to be suppressed;

(c) DNA that includes at least one sense DNA segment that is at least one segment of the gene to be suppressed;

(d) DNA that includes multiple copies of at least one sense DNA segment that is at least one segment of the gene to be suppressed;

(e) DNA that transcribes to RNA for suppressing the gene to be suppressed by forming double-stranded RNA and includes at least one anti-sense DNA segment that is anti-sense to at least one segment of the gene to be suppressed and at least one sense DNA segment that is at least one segment of the gene to be suppressed;

(f) DNA that transcribes to RNA for suppressing the gene to be suppressed by forming a single double-stranded RNA and includes multiple serial anti-sense DNA segments that are anti-sense to at least one segment of the gene to be suppressed and multiple serial sense DNA segments that are at least one segment of the gene to be suppressed;

(g) DNA that transcribes to RNA for suppressing the gene to be suppressed by forming multiple double strands of RNA and includes multiple anti-sense DNA segments that are anti-sense to at least one segment of the gene to be suppressed and multiple sense DNA segments that are at least one segment of the gene to be suppressed, and wherein the multiple anti-sense DNA segments and the multiple sense DNA segments are arranged in a series of inverted repeats;

(h) DNA that includes nucleotides derived from a plant miRNA;
(i) DNA that includes nucleotides of a siRNA;
(j) DNA that transcribes to an RNA aptamer capable of binding to a ligand; and
(k) DNA that transcribes to an RNA aptamer capable of binding to a ligand, and DNA that transcribes to regulatory RNA capable of regulating expression of the gene to be suppressed, wherein the regulation is dependent on the conformation of the regulatory RNA, and the conformation of the regulatory RNA is allosterically affected by the binding state of the RNA aptamer.

In some embodiments, an intron is used to deliver a gene suppression element in the absence of any protein-coding exons (coding sequence). In one example, an intron, such as an expression-enhancing intron (preferred in certain embodiments), is interrupted by embedding within the intron a gene suppression element, wherein, upon transcription, the gene suppression element is excised from the intron. Thus, protein-coding exons are not required to provide the gene suppressing function of the recombinant DNA constructs disclosed herein.

Transcription Regulatory Elements

In some embodiments, the recombinant DNA construct or polynucleotide includes DNA encoding a transcription regulatory element. Transcription regulatory elements include elements that regulate the expression level of the recombinant DNA construct (relative to its expression in the absence of such regulatory elements). Examples of suitable transcription regulatory elements include riboswitches (cis- or trans-acting), transcript stabilizing sequences, and miRNA recognition sites, as described in detail in U. S. Patent Application Publication 2006/0200878, specifically incorporated herein by reference.

Transgenic Plant Cells and Transgenic Plants

The recombinant DNA constructs disclosed herein can be stacked with other recombinant DNA for imparting additional traits (e. g., in the case of transformed plants, traits including herbicide resistance, pest resistance, cold germination tolerance, water deficit tolerance, and the like) for example, by expressing or suppressing other genes. Constructs for coordinated decrease and increase of gene expression are disclosed in U.S. Patent Application Publication 2004/0126845 A1, specifically incorporated by reference.

In certain transgenic plant cells and transgenic plants, it is sometimes desirable to concurrently express a gene of interest while also modulating expression of a flea beetle target gene. Thus, in some embodiments, the transgenic plant contains recombinant DNA further including a gene expression element for expressing at least one gene of interest, and transcription of the recombinant DNA construct for flea beetle control is preferably effected with concurrent transcription of the gene expression element. In embodiments, the transgenic plant expresses DNA encoding a recombinant RNA transcript as disclosed herein for suppression of a flea beetle target gene, and also expresses DNA encoding a non-nucleotide pesticidal agent such as a small-molecule pesticidal agent or a proteinaceous pesticidal agent; such DNAs can be stacked in a single recombinant construct or expression cassette, or alternatively can be expressed from discrete recombinant constructs or expression cassettes. Examples of non-nucleotide pesticidal agents include patatins, plant lectins, phytoecdysteroids, and bacterial insecticidal proteins (e. g., insecticidal proteins from *Bacillus thuringiensis*, *Xenorhabdus* sp., *Photorhabdus* sp., *Brevibacillus laterosporus* (*Bacillus laterosporus*), *Lysinibacillus sphaericus* (*Bacillus sphaericus*), *Chromobacterium* sp., *Chromobacterium subtsugae*, *Paenibacillus* sp., *Paenibacillus lentimorbus*, and *Paenibacillus popilliae*). In embodiments, the transgenic plant expresses DNA encoding a recombinant RNA transcript as disclosed herein for suppression of a flea beetle target gene, and also expresses DNA encoding one or more proteins conferring tolerance to an herbicide. Examples of proteins conferring tolerance to an herbicide include 5-enolpyruvylshikimate-3-phosphate synthases (EPSPS; see, e. g., U.S. Pat. Nos. 5,627,061, 5,633, 435 RE39247, 6,040,497, and 5,094,945, and PCT International Application Publications WO04074443 and WO04009761), glyphosate oxidoreductase (GOX; U.S. Pat. No. 5,463,175), glyphosate decarboxylase (PCT International Application Publication WO05003362, U.S. Pat. No. 7,405,347, and U. S. Patent Application Publication 2004/0177399), glyphosate-N-acetyl transferase (GAT; U.S. Pat. No. 7,714,188) conferring tolerance to glyphosate; dicamba monooxygenase conferring tolerance to auxin-like herbicides such as dicamba (U.S. Pat. No. 7,105,724); phosphinothricin acetyltransferase (pat or bar) conferring tolerance to phosphinothricin or glufosinate (U.S. Pat. No. 5,646,024); 2,2-dichloropropionic acid dehalogenase conferring tolerance to 2,2-dichloropropionic acid (Dalapon) (PCT International Application Publication WO9927116); acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. No. 6,225,105); haloarylnitrilase (Bxn) for conferring tolerance to bromoxynil (U.S. Pat. No. 4,810,648); modified acetyl-coenzyme A carboxylase for conferring tolerance to cyclohexanedione (sethoxydim) and aryloxyphenoxypropionate (haloxyfop) (U.S. Pat. No. 6,414,222); dihydropteroate synthase (sul I) for conferring tolerance to sulfonamide herbicides (U.S. Pat. No. 5,719, 046); 32 kDa photosystem II polypeptide (psbA) for conferring tolerance to triazine herbicides (Hirschberg et al., 1983, Science, 222:1346-1349); anthranilate synthase for conferring tolerance to 5-methyltryptophan (U.S. Pat. No. 4,581,847); dihydrodipicolinic acid synthase (dap A) for conferring to tolerance to aminoethyl cysteine (PCT International Application Publication WO8911789); phytoene desaturase (crtl) for conferring tolerance to pyridazinone herbicides such as norflurazon (Japan Patent JP06343473); hydroxyphenylpyruvate dioxygenase, a 4-hydroxyphenylacetic acid oxidase and a 4-hydroxyphenylacetic 1-hydrolase (U.S. Pat. No. 7,304,209) for conferring tolerance to cyclopropylisoxazole herbicides such as isoxaflutole (U.S. Pat. No. 6,268,549); modified protoporphyrinogen oxidase I (protox) for conferring tolerance to protoporphyrinogen oxidase inhibitors (U.S. Pat. No. 5,939,602); aryloxyalkanoate dioxygenase (AAD-1) for conferring tolerance to an herbicide containing an aryloxyalkanoate moiety (WO05107437); a serine hydroxymethyltransferase (US Patent Application Publication 2008/0155716), a glufosinate-tolerant glutamine synthase (US Patent Application Publication 2009/0018016). Examples of such herbicides include phenoxy auxins (such as 2,4-D and dichlorprop), pyridyloxy auxins (such as fluroxypyr and triclopyr), aryloxyphenoxypropionates (AOPP) acetylcoenzyme A carboxylase (ACCase) inhibitors (such as haloxyfop, quizalofop, and diclofop), and 5-substituted phenoxyacetate protoporphyrinogen oxidase IX inhibitors (such as pyraflufen and flumiclorac). The nucleotide sequences of the nucleic acids encoding herbicide-tolerance proteins and the sequences of the herbicide-tolerance proteins, as disclosed in the U. S. patent and patent application publications cited in this paragraph are incorporated herein by reference.

In some embodiments, the recombinant DNA constructs disclosed herein can be transcribed in any plant cell or tissue or in a whole plant of any developmental stage. Transgenic plants can be derived from any monocot or dicot plant, such as, but not limited to, plants of commercial or agricultural interest, such as crop plants (especially crop plants used for human food or animal feed), wood- or pulp-producing trees, vegetable plants, fruit plants, and ornamental plants. Examples of plants of interest include grain crop plants (such as wheat, oat, barley, maize, rye, triticale, rice, millet, sorghum, quinoa, amaranth, and buckwheat); forage crop plants (such as forage grasses and forage dicots including alfalfa, vetch, clover, and the like); oilseed crop plants (such as cotton, safflower, sunflower, soybean, canola, rapeseed, flax, peanuts, and oil palm); tree nuts (such as walnut, cashew, hazelnut, pecan, almond, and the like); sugarcane, coconut, date palm, olive, sugarbeet, tea, and coffee; wood- or pulp-producing trees; vegetable crop plants such as legumes (for example, beans, peas, lentils, alfalfa, peanut), lettuce, asparagus, artichoke, celery, carrot, radish, the brassicas (for example, cabbages, kales, mustards, and other leafy brassicas, broccoli, cauliflower, Brussels sprouts, turnip, kohlrabi), edible cucurbits (for example, cucumbers, melons, summer squashes, winter squashes), edible alliums (for example, onions, garlic, leeks, shallots, chives), edible members of the Solanaceae (for example, tomatoes, eggplants, potatoes, peppers, groundcherries), and edible members of the Chenopodiaceae (for example, beet, chard, spinach, quinoa, amaranth); fruit crop plants such as apple, pear, citrus fruits (for example, orange, lime, lemon, grapefruit, and others), stone fruits (for example, apricot, peach, plum, nectarine), banana, pineapple, grape, kiwifruit, papaya, avocado, and berries; plants grown for biomass or biofuel (for example, *Miscanthus* grasses, switchgrass, jatropha, oil palm, eukaryotic microalgae such as *Botryococcus braunii*, *Chlorella* spp., and *Dunaliella* spp., and eukaryotic macroalgae such as *Gracilaria* spp., and *Sargassum* spp.); and ornamental plants including ornamental flowering plants, ornamental trees and shrubs, ornamental groundcovers, and ornamental grasses. Specific plant species of interest in which a recombinant DNA construct is transcribed to provide resistance to flea beetles are plants in the family Brassicaceae, including the *Brassica* species *B. napus, B. juncea, B. carinata, B. rapa, B. oleracea, B. rupestris, B. septiceps, B. nigra, B. narinosa, B. perviridus, B. tournefortii*, and *B. fructiculosa*. Additional plant species of interest in which a recombinant DNA construct is transcribed to provide resistance to flea beetles are *Glycine max, Linum usitatissimum, Zea mays, Carthamus tinctorius, Helianthus annuus, Nicotiana tabacum, Arabidopsis thaliana, Bethoettia excelsa, Ricinus communis, Cocos nucifera, Coriandrum sativum, Gossypium* spp., *Arachis hypogaea, Simmondsia chinensis, Solanum tuberosum, Elaeis guineensis, Olea europaea, Oryza sativa, Cucurbita maxim, Hordeum vulgare*, and *Triticum aestivum*.

Also disclosed herein are commodity products produced from a transgenic plant cell, plant, or seed expressing a recombinant DNA construct imparting improved resistance to flea beetles as disclosed herein, including, but not limited to, harvested leaves, roots, shoots, tubers, stems, fruits, seeds, or other parts of a plant, meals, oils, extracts, fermentation or digestion products, crushed or whole grains or seeds of a plant, or any food or non-food product including such commodity products produced from a transgenic plant cell, plant, or seed as disclosed herein. The detection of one or more of nucleic acid sequences of the recombinant DNA constructs for flea beetle control as disclosed herein in one or more commodity or commodity products contemplated herein is de facto evidence that the commodity or commodity product contains or is derived from a transgenic plant cell, plant, or seed expressing such a recombinant DNA construct.

Generally a transgenic plant having in its genome a recombinant DNA construct as disclosed herein exhibits increased resistance to an insect infestation, specifically increased resistance to a flea beetle infestation. In various embodiments, for example, where the transgenic plant expresses a recombinant DNA construct for flea beetle control that is stacked with other recombinant DNA for imparting additional traits, the transgenic plant has at least one additional altered trait, relative to a plant lacking the recombinant DNA construct, selected from the group of traits consisting of:

(a) improved abiotic stress tolerance;
(b) improved biotic stress tolerance;
(c) modified primary metabolite composition;
(d) modified secondary metabolite composition;
(e) modified trace element, carotenoid, or vitamin composition;
(f) improved yield;
(g) improved ability to use nitrogen, phosphate, or other nutrients;
(h) modified agronomic characteristics;
(i) modified growth or reproductive characteristics; and
(j) improved harvest, storage, or processing quality.

In some embodiments, the transgenic plant is characterized by: improved tolerance of abiotic stress (e. g., tolerance of water deficit or drought, heat, cold, non-optimal nutrient or salt levels, non-optimal light levels) or of biotic stress (e. g., crowding, allelopathy, or wounding); by a modified primary metabolite (e. g., fatty acid, oil, amino acid, protein, sugar, or carbohydrate) composition; a modified secondary metabolite (e. g., alkaloids, terpenoids, polyketides, non-ribosomal peptides, and secondary metabolites of mixed biosynthetic origin) composition; a modified trace element (e. g., iron, zinc), carotenoid (e. g., beta-carotene, lycopene, lutein, zeaxanthin, or other carotenoids and xanthophylls), or vitamin (e. g., tocopherols) composition; improved yield (e. g., improved yield under non-stress conditions or improved yield under biotic or abiotic stress); improved ability to use nitrogen, phosphate, or other nutrients; modified agronomic characteristics (e. g., delayed ripening; delayed senescence; earlier or later maturity; improved shade tolerance; improved resistance to root or stalk lodging; improved resistance to "green snap" of stems; modified photoperiod response); modified growth or reproductive characteristics (e. g., intentional dwarfing; intentional male sterility, useful, e. g., in improved hybridization procedures; improved vegetative growth rate; improved germination; improved male or female fertility); improved harvest, storage, or processing quality (e. g., improved resistance to pests during storage, improved resistance to breakage, improved appeal to consumers); or any combination of these traits.

In another embodiment, transgenic seed, or seed produced by the transgenic plant, has modified primary metabolite (e. g., fatty acid, oil, amino acid, protein, sugar, or carbohydrate) composition, a modified secondary metabolite composition, a modified trace element, carotenoid, or vitamin composition, an improved harvest, storage, or processing quality, or a combination of these. In another embodiment, it can be desirable to change levels of native components of the transgenic plant or seed of a transgenic plant, for example, to decrease levels of an allergenic protein or glycoprotein or of a toxic metabolite.

EXAMPLES

Example 1

This example illustrates non-limiting embodiments of coding DNA sequences useful as target genes for controlling insect species and for making compositions for controlling insects and insect-resistant transgenic plants, and identifies dsRNA trigger sequences useful for controlling insect species. More specifically, embodiments of target genes identified by name (annotation) and sequence identifier (SEQ ID NO.) for controlling flea beetles are provided in SEQ ID NOs:1-859, and embodiments of dsRNA trigger sequences ranging in size from 135 to 352 base pairs and designed to suppress these target genes are provided in SEQ ID NOs.: 860-1718.

TABLE 1

| Target Gene SEQ ID NO. | Trigger SEQ ID NO.* |
|---|---|
| 1 | 860 |
| 2 | 861 |
| 3 | 862 |
| 4 | 863 |
| 5 | 864 |
| 6 | 865 |
| 7 | 866 |
| 8 | 867 |
| 9 | 868 |
| 10 | 869 |
| 11 | 870 |
| 12 | 871 |
| 13 | 872 |
| 14 | 873 |
| 15 | 874 |
| 16 | 875 |
| 17 | 876 |
| 18 | 877 |
| 19 | 878 |
| 20 | 879 |
| 21 | 880 |
| 22 | 881 |
| 23 | 882 |
| 24 | 883 |
| 25 | 884 |
| 26 | 885 |
| 27 | 886 |
| 28 | 887 |
| 29 | 888 |
| 30 | 889 |
| 31 | 890 |
| 32 | 891 |
| 33 | 892 |
| 34 | 893 |
| 35 | 894 |
| 36 | 895 |
| 37 | 896 |
| 38 | 897 |
| 39 | 898 |
| 40 | 899 |
| 41 | 900 |
| 42 | 901 |
| 43 | 902 |
| 44 | 903 |
| 45 | 904 |
| 46 | 905 |
| 47 | 906 |
| 48 | 907 |
| 49 | 908 |
| 50 | 909 |
| 51 | 910 |
| 52 | 911 |
| 53 | 912 |
| 54 | 913 |
| 55 | 914 |
| 56 | 915 |
| 57 | 916 |
| 58 | 917 |
| 59 | 918 |
| 60 | 919 |
| 61 | 920 |
| 62 | 921 |
| 63 | 922 |
| 64 | 923 |
| 65 | 924 |
| 66 | 925 |
| 67 | 926 |
| 68 | 927 |
| 69 | 928 |
| 70 | 929 |
| 71 | 930 |
| 72 | 931 |
| 73 | 932 |
| 74 | 933 |
| 75 | 934 |
| 76 | 935 |
| 77 | 936 |
| 78 | 937 |
| 79 | 938 |
| 80 | 939 |
| 81 | 940 |
| 82 | 941 |
| 83 | 942 |
| 84 | 943 |
| 85 | 944 |
| 86 | 945 |
| 87 | 946 |
| 88 | 947 |
| 89 | 948 |
| 90 | 949 |
| 91 | 950 |
| 92 | 951 |
| 93 | 952 |
| 94 | 953 |
| 95 | 954 |
| 96 | 955 |
| 97 | 956 |
| 98 | 957 |
| 99 | 958 |
| 100 | 959 |
| 101 | 960 |
| 102 | 961 |
| 103 | 962 |
| 104 | 963 |
| 105 | 964 |
| 106 | 965 |
| 107 | 966 |
| 108 | 967 |
| 109 | 968 |
| 110 | 969 |
| 111 | 970 |
| 112 | 971 |
| 113 | 972 |
| 114 | 973 |
| 115 | 974 |
| 116 | 975 |
| 117 | 976 |
| 118 | 977 |
| 119 | 978 |
| 120 | 979 |
| 121 | 980 |
| 122 | 981 |
| 123 | 982 |
| 124 | 983 |
| 125 | 984 |
| 126 | 985 |
| 127 | 986 |
| 128 | 987 |
| 129 | 988 |
| 130 | 989 |
| 131 | 990 |
| 132 | 991 |
| 133 | 992 |

TABLE 1-continued

| Target Gene SEQ ID NO. | Trigger SEQ ID NO.* |
|---|---|
| 134 | 993 |
| 135 | 994 |
| 136 | 995 |
| 137 | 996 |
| 138 | 997 |
| 139 | 998 |
| 140 | 999 |
| 141 | 1000 |
| 142 | 1001 |
| 143 | 1002 |
| 144 | 1003 |
| 145 | 1004 |
| 146 | 1005 |
| 147 | 1006 |
| 148 | 1007 |
| 149 | 1008 |
| 150 | 1009 |
| 151 | 1010 |
| 152 | 1011 |
| 153 | 1012 |
| 154 | 1013 |
| 155 | 1014 |
| 156 | 1015 |
| 157 | 1016 |
| 158 | 1017 |
| 159 | 1018 |
| 160 | 1019 |
| 161 | 1020 |
| 162 | 1021 |
| 163 | 1022 |
| 164 | 1023 |
| 165 | 1024 |
| 166 | 1025 |
| 167 | 1026 |
| 168 | 1027 |
| 169 | 1028 |
| 170 | 1029 |
| 171 | 1030 |
| 172 | 1031 |
| 173 | 1032 |
| 174 | 1033 |
| 175 | 1034 |
| 176 | 1035 |
| 177 | 1036 |
| 178 | 1037 |
| 179 | 1038 |
| 180 | 1039 |
| 181 | 1040 |
| 182 | 1041 |
| 183 | 1042 |
| 184 | 1043 |
| 185 | 1044 |
| 186 | 1045 |
| 187 | 1046 |
| 188 | 1047 |
| 189 | 1048 |
| 190 | 1049 |
| 191 | 1050 |
| 192 | 1051 |
| 193 | 1052 |
| 194 | 1053 |
| 195 | 1054 |
| 196 | 1055 |
| 197 | 1056 |
| 198 | 1057 |
| 199 | 1058 |
| 200 | 1059 |
| 201 | 1060 |
| 202 | 1061 |
| 203 | 1062 |
| 204 | 1063 |
| 205 | 1064 |
| 206 | 1065 |
| 207 | 1066 |
| 208 | 1067 |
| 209 | 1068 |
| 210 | 1069 |

TABLE 1-continued

| Target Gene SEQ ID NO. | Trigger SEQ ID NO.* |
|---|---|
| 211 | 1070 |
| 212 | 1071 |
| 213 | 1072 |
| 214 | 1073 |
| 215 | 1074 |
| 216 | 1075 |
| 217 | 1076 |
| 218 | 1077 |
| 219 | 1078 |
| 220 | 1079 |
| 221 | 1080 |
| 222 | 1081 |
| 223 | 1082 |
| 224 | 1083 |
| 225 | 1084 |
| 226 | 1085 |
| 227 | 1086 |
| 228 | 1087 |
| 229 | 1088 |
| 230 | 1089 |
| 231 | 1090 |
| 232 | 1091 |
| 233 | 1092 |
| 234 | 1093 |
| 235 | 1094 |
| 236 | 1095 |
| 237 | 1096 |
| 238 | 1097 |
| 239 | 1098 |
| 240 | 1099 |
| 241 | 1100 |
| 242 | 1101 |
| 243 | 1102 |
| 244 | 1103 |
| 245 | 1104 |
| 246 | 1105 |
| 247 | 1106 |
| 248 | 1107 |
| 249 | 1108 |
| 250 | 1109 |
| 251 | 1110 |
| 252 | 1111 |
| 253 | 1112 |
| 254 | 1113 |
| 255 | 1114 |
| 256 | 1115 |
| 257 | 1116 |
| 258 | 1117 |
| 259 | 1118 |
| 260 | 1119 |
| 261 | 1120 |
| 262 | 1121 |
| 263 | 1122 |
| 264 | 1123 |
| 265 | 1124 |
| 266 | 1125 |
| 267 | 1126 |
| 268 | 1127 |
| 269 | 1128 |
| 270 | 1129 |
| 271 | 1130 |
| 272 | 1131 |
| 273 | 1132 |
| 274 | 1133 |
| 275 | 1134 |
| 276 | 1135 |
| 277 | 1136 |
| 278 | 1137 |
| 279 | 1138 |
| 280 | 1139 |
| 281 | 1140 |
| 282 | 1141 |
| 283 | 1142 |
| 284 | 1143 |
| 285 | 1144 |
| 286 | 1145 |
| 287 | 1146 |

TABLE 1-continued

| Target Gene SEQ ID NO. | Trigger SEQ ID NO.* |
|---|---|
| 288 | 1147 |
| 289 | 1148 |
| 290 | 1149 |
| 291 | 1150 |
| 292 | 1151 |
| 293 | 1152 |
| 294 | 1153 |
| 295 | 1154 |
| 296 | 1155 |
| 297 | 1156 |
| 298 | 1157 |
| 299 | 1158 |
| 300 | 1159 |
| 301 | 1160 |
| 302 | 1161 |
| 303 | 1162 |
| 304 | 1163 |
| 305 | 1164 |
| 306 | 1165 |
| 307 | 1166 |
| 308 | 1167 |
| 309 | 1168 |
| 310 | 1169 |
| 311 | 1170 |
| 312 | 1171 |
| 313 | 1172 |
| 314 | 1173 |
| 315 | 1174 |
| 316 | 1175 |
| 317 | 1176 |
| 318 | 1177 |
| 319 | 1178 |
| 320 | 1179 |
| 321 | 1180 |
| 322 | 1181 |
| 323 | 1182 |
| 324 | 1183 |
| 325 | 1184 |
| 326 | 1185 |
| 327 | 1186 |
| 328 | 1187 |
| 329 | 1188 |
| 330 | 1189 |
| 331 | 1190 |
| 332 | 1191 |
| 333 | 1192 |
| 334 | 1193 |
| 335 | 1194 |
| 336 | 1195 |
| 337 | 1196 |
| 338 | 1197 |
| 339 | 1198 |
| 340 | 1199 |
| 341 | 1200 |
| 342 | 1201 |
| 343 | 1202 |
| 344 | 1203 |
| 345 | 1204 |
| 346 | 1205 |
| 347 | 1206 |
| 348 | 1207 |
| 349 | 1208 |
| 350 | 1209 |
| 351 | 1210 |
| 352 | 1211 |
| 353 | 1212 |
| 354 | 1213 |
| 355 | 1214 |
| 356 | 1215 |
| 357 | 1216 |
| 358 | 1217 |
| 359 | 1218 |
| 360 | 1219 |
| 361 | 1220 |
| 362 | 1221 |
| 363 | 1222 |
| 364 | 1223 |
| 365 | 1224 |
| 366 | 1225 |
| 367 | 1226 |
| 368 | 1227 |
| 369 | 1228 |
| 370 | 1229 |
| 371 | 1230 |
| 372 | 1231 |
| 373 | 1232 |
| 374 | 1233 |
| 375 | 1234 |
| 376 | 1235 |
| 377 | 1236 |
| 378 | 1237 |
| 379 | 1238 |
| 380 | 1239 |
| 381 | 1240 |
| 382 | 1241 |
| 383 | 1242 |
| 384 | 1243 |
| 385 | 1244 |
| 386 | 1245 |
| 387 | 1246 |
| 388 | 1247 |
| 389 | 1248 |
| 390 | 1249 |
| 391 | 1250 |
| 392 | 1251 |
| 393 | 1252 |
| 394 | 1253 |
| 395 | 1254 |
| 396 | 1255 |
| 397 | 1256 |
| 398 | 1257 |
| 399 | 1258 |
| 400 | 1259 |
| 401 | 1260 |
| 402 | 1261 |
| 403 | 1262 |
| 404 | 1263 |
| 405 | 1264 |
| 406 | 1265 |
| 407 | 1266 |
| 408 | 1267 |
| 409 | 1268 |
| 410 | 1269 |
| 411 | 1270 |
| 412 | 1271 |
| 413 | 1272 |
| 414 | 1273 |
| 415 | 1274 |
| 416 | 1275 |
| 417 | 1276 |
| 418 | 1277 |
| 419 | 1278 |
| 420 | 1279 |
| 421 | 1280 |
| 422 | 1281 |
| 423 | 1282 |
| 424 | 1283 |
| 425 | 1284 |
| 426 | 1285 |
| 427 | 1286 |
| 428 | 1287 |
| 429 | 1288 |
| 430 | 1289 |
| 431 | 1290 |
| 432 | 1291 |
| 433 | 1292 |
| 434 | 1293 |
| 435 | 1294 |
| 436 | 1295 |
| 437 | 1296 |
| 438 | 1297 |
| 439 | 1298 |
| 440 | 1299 |
| 441 | 1300 |

TABLE 1-continued

| Target Gene SEQ ID NO. | Trigger SEQ ID NO.* |
|---|---|
| 442 | 1301 |
| 443 | 1302 |
| 444 | 1303 |
| 445 | 1304 |
| 446 | 1305 |
| 447 | 1306 |
| 448 | 1307 |
| 449 | 1308 |
| 450 | 1309 |
| 451 | 1310 |
| 452 | 1311 |
| 453 | 1312 |
| 454 | 1313 |
| 455 | 1314 |
| 456 | 1315 |
| 457 | 1316 |
| 458 | 1317 |
| 459 | 1318 |
| 460 | 1319 |
| 461 | 1320 |
| 462 | 1321 |
| 463 | 1322 |
| 464 | 1323 |
| 465 | 1324 |
| 466 | 1325 |
| 467 | 1326 |
| 468 | 1327 |
| 469 | 1328 |
| 470 | 1329 |
| 471 | 1330 |
| 472 | 1331 |
| 473 | 1332 |
| 474 | 1333 |
| 475 | 1334 |
| 476 | 1335 |
| 477 | 1336 |
| 478 | 1337 |
| 479 | 1338 |
| 480 | 1339 |
| 481 | 1340 |
| 482 | 1341 |
| 483 | 1342 |
| 484 | 1343 |
| 485 | 1344 |
| 486 | 1345 |
| 487 | 1346 |
| 488 | 1347 |
| 489 | 1348 |
| 490 | 1349 |
| 491 | 1350 |
| 492 | 1351 |
| 493 | 1352 |
| 494 | 1353 |
| 495 | 1354 |
| 496 | 1355 |
| 497 | 1356 |
| 498 | 1357 |
| 499 | 1358 |
| 500 | 1359 |
| 501 | 1360 |
| 502 | 1361 |
| 503 | 1362 |
| 504 | 1363 |
| 505 | 1364 |
| 506 | 1365 |
| 507 | 1366 |
| 508 | 1367 |
| 509 | 1368 |
| 510 | 1369 |
| 511 | 1370 |
| 512 | 1371 |
| 513 | 1372 |
| 514 | 1373 |
| 515 | 1374 |
| 516 | 1375 |
| 517 | 1376 |
| 518 | 1377 |
| 519 | 1378 |
| 520 | 1379 |
| 521 | 1380 |
| 522 | 1381 |
| 523 | 1382 |
| 524 | 1383 |
| 525 | 1384 |
| 526 | 1385 |
| 527 | 1386 |
| 528 | 1387 |
| 529 | 1388 |
| 530 | 1389 |
| 531 | 1390 |
| 532 | 1391 |
| 533 | 1392 |
| 534 | 1393 |
| 535 | 1394 |
| 536 | 1395 |
| 537 | 1396 |
| 538 | 1397 |
| 539 | 1398 |
| 540 | 1399 |
| 541 | 1400 |
| 542 | 1401 |
| 543 | 1402 |
| 544 | 1403 |
| 545 | 1404 |
| 546 | 1405 |
| 547 | 1406 |
| 548 | 1407 |
| 549 | 1408 |
| 550 | 1409 |
| 551 | 1410 |
| 552 | 1411 |
| 553 | 1412 |
| 554 | 1413 |
| 555 | 1414 |
| 556 | 1415 |
| 557 | 1416 |
| 558 | 1417 |
| 559 | 1418 |
| 560 | 1419 |
| 561 | 1420 |
| 562 | 1421 |
| 563 | 1422 |
| 564 | 1423 |
| 565 | 1424 |
| 566 | 1425 |
| 567 | 1426 |
| 568 | 1427 |
| 569 | 1428 |
| 570 | 1429 |
| 571 | 1430 |
| 572 | 1431 |
| 573 | 1432 |
| 574 | 1433 |
| 575 | 1434 |
| 576 | 1435 |
| 577 | 1436 |
| 578 | 1437 |
| 579 | 1438 |
| 580 | 1439 |
| 581 | 1440 |
| 582 | 1441 |
| 583 | 1442 |
| 584 | 1443 |
| 585 | 1444 |
| 586 | 1445 |
| 587 | 1446 |
| 588 | 1447 |
| 589 | 1448 |
| 590 | 1449 |
| 591 | 1450 |
| 592 | 1451 |
| 593 | 1452 |
| 594 | 1453 |
| 595 | 1454 |

TABLE 1-continued

| Target Gene SEQ ID NO. | Trigger SEQ ID NO.* |
|---|---|
| 596 | 1455 |
| 597 | 1456 |
| 598 | 1457 |
| 599 | 1458 |
| 600 | 1459 |
| 601 | 1460 |
| 602 | 1461 |
| 603 | 1462 |
| 604 | 1463 |
| 605 | 1464 |
| 606 | 1465 |
| 607 | 1466 |
| 608 | 1467 |
| 609 | 1468 |
| 610 | 1469 |
| 611 | 1470 |
| 612 | 1471 |
| 613 | 1472 |
| 614 | 1473 |
| 615 | 1474 |
| 616 | 1475 |
| 617 | 1476 |
| 618 | 1477 |
| 619 | 1478 |
| 620 | 1479 |
| 621 | 1480 |
| 622 | 1481 |
| 623 | 1482 |
| 624 | 1483 |
| 625 | 1484 |
| 626 | 1485 |
| 627 | 1486 |
| 628 | 1487 |
| 629 | 1488 |
| 630 | 1489 |
| 631 | 1490 |
| 632 | 1491 |
| 633 | 1492 |
| 634 | 1493 |
| 635 | 1494 |
| 636 | 1495 |
| 637 | 1496 |
| 638 | 1497 |
| 639 | 1498 |
| 640 | 1499 |
| 641 | 1500 |
| 642 | 1501 |
| 643 | 1502 |
| 644 | 1503 |
| 645 | 1504 |
| 646 | 1505 |
| 647 | 1506 |
| 648 | 1507 |
| 649 | 1508 |
| 650 | 1509 |
| 651 | 1510 |
| 652 | 1511 |
| 653 | 1512 |
| 654 | 1513 |
| 655 | 1514 |
| 656 | 1515 |
| 657 | 1516 |
| 658 | 1517 |
| 659 | 1518 |
| 660 | 1519 |
| 661 | 1520 |
| 662 | 1521 |
| 663 | 1522 |
| 664 | 1523 |
| 665 | 1524 |
| 666 | 1525 |
| 667 | 1526 |
| 668 | 1527 |
| 669 | 1528 |
| 670 | 1529 |
| 671 | 1530 |
| 672 | 1531 |
| 673 | 1532 |
| 674 | 1533 |
| 675 | 1534 |
| 676 | 1535 |
| 677 | 1536 |
| 678 | 1537 |
| 679 | 1538 |
| 680 | 1539 |
| 681 | 1540 |
| 682 | 1541 |
| 683 | 1542 |
| 684 | 1543 |
| 685 | 1544 |
| 686 | 1545 |
| 687 | 1546 |
| 688 | 1547 |
| 689 | 1548 |
| 690 | 1549 |
| 691 | 1550 |
| 692 | 1551 |
| 693 | 1552 |
| 694 | 1553 |
| 695 | 1554 |
| 696 | 1555 |
| 697 | 1556 |
| 698 | 1557 |
| 699 | 1558 |
| 700 | 1559 |
| 701 | 1560 |
| 702 | 1561 |
| 703 | 1562 |
| 704 | 1563 |
| 705 | 1564 |
| 706 | 1565 |
| 707 | 1566 |
| 708 | 1567 |
| 709 | 1568 |
| 710 | 1569 |
| 711 | 1570 |
| 712 | 1571 |
| 713 | 1572 |
| 714 | 1573 |
| 715 | 1574 |
| 716 | 1575 |
| 717 | 1576 |
| 718 | 1577 |
| 719 | 1578 |
| 720 | 1579 |
| 721 | 1580 |
| 722 | 1581 |
| 723 | 1582 |
| 724 | 1583 |
| 725 | 1584 |
| 726 | 1585 |
| 727 | 1586 |
| 728 | 1587 |
| 729 | 1588 |
| 730 | 1589 |
| 731 | 1590 |
| 732 | 1591 |
| 733 | 1592 |
| 734 | 1593 |
| 735 | 1594 |
| 736 | 1595 |
| 737 | 1596 |
| 738 | 1597 |
| 739 | 1598 |
| 740 | 1599 |
| 741 | 1600 |
| 742 | 1601 |
| 743 | 1602 |
| 744 | 1603 |
| 745 | 1604 |
| 746 | 1605 |
| 747 | 1606 |
| 748 | 1607 |
| 749 | 1608 |

TABLE 1-continued

| Target Gene SEQ ID NO. | Trigger SEQ ID NO.* |
|---|---|
| 750 | 1609 |
| 751 | 1610 |
| 752 | 1611 |
| 753 | 1612 |
| 754 | 1613 |
| 755 | 1614 |
| 756 | 1615 |
| 757 | 1616 |
| 758 | 1617 |
| 759 | 1618 |
| 760 | 1619 |
| 761 | 1620 |
| 762 | 1621 |
| 763 | 1622 |
| 764 | 1623 |
| 765 | 1624 |
| 766 | 1625 |
| 767 | 1626 |
| 768 | 1627 |
| 769 | 1628 |
| 770 | 1629 |
| 771 | 1630 |
| 772 | 1631 |
| 773 | 1632 |
| 774 | 1633 |
| 775 | 1634 |
| 776 | 1635 |
| 777 | 1636 |
| 778 | 1637 |
| 779 | 1638 |
| 780 | 1639 |
| 781 | 1640 |
| 782 | 1641 |
| 783 | 1642 |
| 784 | 1643 |
| 785 | 1644 |
| 786 | 1645 |
| 787 | 1646 |
| 788 | 1647 |
| 789 | 1648 |
| 790 | 1649 |
| 791 | 1650 |
| 792 | 1651 |
| 793 | 1652 |
| 794 | 1653 |
| 795 | 1654 |
| 796 | 1655 |
| 797 | 1656 |
| 798 | 1657 |
| 799 | 1658 |
| 800 | 1659 |
| 801 | 1660 |
| 802 | 1661 |
| 803 | 1662 |
| 804 | 1663 |
| 805 | 1664 |
| 806 | 1665 |
| 807 | 1666 |
| 808 | 1667 |
| 809 | 1668 |
| 810 | 1669 |
| 811 | 1670 |
| 812 | 1671 |
| 813 | 1672 |
| 814 | 1673 |
| 815 | 1674 |
| 816 | 1675 |
| 817 | 1676 |
| 818 | 1677 |
| 819 | 1678 |
| 820 | 1679 |
| 821 | 1680 |
| 822 | 1681 |
| 823 | 1682 |
| 824 | 1683 |
| 825 | 1684 |
| 826 | 1685 |
| 827 | 1686 |
| 828 | 1687 |
| 829 | 1688 |
| 830 | 1689 |
| 831 | 1690 |
| 832 | 1691 |
| 833 | 1692 |
| 834 | 1693 |
| 835 | 1694 |
| 836 | 1695 |
| 837 | 1696 |
| 838 | 1697 |
| 839 | 1698 |
| 840 | 1699 |
| 841 | 1700 |
| 842 | 1701 |
| 843 | 1702 |
| 844 | 1703 |
| 845 | 1704 |
| 846 | 1705 |
| 847 | 1706 |
| 848 | 1707 |
| 849 | 1708 |
| 850 | 1709 |
| 851 | 1710 |
| 852 | 1711 |
| 853 | 1712 |
| 854 | 1713 |
| 855 | 1714 |
| 856 | 1715 |
| 857 | 1716 |
| 858 | 1717 |
| 859 | 1718 |

*Trigger sequences are provided for the anti-sense strand of the dsRNA trigger in 5' to 3' direction.
** T44966 and T44967 are positive controls based on a *Phyllotreta striolata* arginine kinase mRNA disclosed in Zhao et al. (2008), *Eur. J. Entomol.*, 5: 815.

The embodiments of dsRNA trigger sequences provided in Table 1 are generally useful for RNA-mediated suppression of the corresponding target gene identified in Table 1. These dsRNA triggers are useful for controlling insects, especially flea beetles, including the source species from which the target genes in Table 1 were identified. RNA-mediated suppression of one or more of the target genes provided in Table 1, or use of one or more of the dsRNA triggers provided in Table 1, is useful for causing mortality or stunting, or otherwise controlling, target insect species in the following genera: *Altica, Anthobiodes, Aphthona, Aphthonaltica, Aphthonoides, Apteopeda, Argopistes, Argopus, Arrhenocoela, Batophila, Blepharida, Chaetocnema, Clitea, Crepidodera, Derocrepis, Dibolia, Disonycha, Epitrix, Hermipyxis, Hermaeophaga, Hespera, Hippuriphila, Horaia, Hyphasis, Lipromima, Liprus, Longitarsus, Luperomorpha, Lythraria, Manobia, Mantura, Meishania, Minota, Mniophila, Neicrepidodera, Nonarthra, Novofoudrasia, Ochrosis, Oedionychis, Oglobinia, Omeisphaera, Ophrida, Orestia, Paragopus, Pentamesa, Philopona, Phygasia, Phyllotreta, Podagrica, Podagricomela, Podontia, Pseudodera, Psylliodes, Sangariola, Sinaltica, Sphaeroderma, Systena, Trachyaphthona, Xuthea,* and *Zipangia*. In embodiments, compositions including a dsRNA trigger for suppression of one or more of the target genes provided in Table 1 (e.g., a composition including an effective amount of one or more of the dsRNA triggers provided in Table 1) are useful for controlling at least one of *Altica ambiens* (alder flea beetle), *Altica canadensis* (prairie flea beetle), *Altica chalybaea* (grape flea beetle), *Altica prasina* (poplar flea beetle), *Altica rosae* (rose flea beetle), *Altica sylvia* (blueberry flea beetle), *Altica ulmi* (elm flea beetle),

*Chaetocnema pulicaria* (corn flea beetle), *Chaetocnema conofinis* (sweet potato flea beetle), *Epitrix cucumeris* (potato flea beetle), *Systena blanda* (palestripped fleabeetle), and *Systena frontalis* (redheaded flea beetle), thus preventing or treating plant infestation by these species. For example, a composition including an effective amount of one or more of the dsRNA triggers provided in Table 1 is useful for preventing or treating infestation of potato plants by *Epitrix cucumeris* (potato flea beetle).

In embodiments, RNA-mediated suppression of one or more of the target genes provided in Table 1, or use of one or more of the dsRNA triggers provided in Table 1, is useful for causing mortality or stunting in flea beetle species in the genera *Phyllotreta* and *Psylliodes*, thus preventing or treating plant infestation by these species. In specific embodiments, RNA-mediated suppression of one or more of the target genes provided in Table 1, or use of one or more of the dsRNA triggers provided in Table 1, is useful for causing mortality or stunting in at least one flea beetle species selected from the group consisting of *Phyllotreta armoraciae* (horseradish flea beetle), *Phyllotreta cruciferae* (canola flea beetle), *Phyllotreta pusilla* (western black flea beetle), *Phyllotreta nemorum* (striped turnip flea beetle), *Phyllotreta atra* (turnip flea beetle), *Phyllotreta robusta* (garden flea beetle), *Phyllotreta striolata* (striped flea beetle), *Phyllotreta undulata, Psylliodes chrysocephala,* and *Psylliodes punctulata* (hop flea beetle). In embodiments, RNA-mediated suppression of one or more of the target genes having a sequence selected from the group consisting of SEQ ID NOs:1-296 is used to cause mortality or stunting in *Phyllotreta atra* (turnip flea beetle) adults or larvae, for example, by contacting *Phyllotreta atra* adults, larvae, or eggs with an effective amount of a dsRNA trigger including a sequence selected from the group consisting of SEQ ID NOs:860-1155. In embodiments, RNA-mediated suppression of one or more of the target genes having a sequence selected from the group consisting of SEQ ID NOs:297-532 is used to cause mortality or stunting in *Phyllotreta cruciferae* (canola flea beetle) adults or larvae, for example, by contacting *Phyllotreta cruciferae* adults, larvae, or eggs with an effective amount of a dsRNA trigger including a sequence selected from the group consisting of SEQ ID NOs:1156-1391. In embodiments, RNA-mediated suppression of one or more of the target genes having a sequence selected from the group consisting of SEQ ID NOs:533-551 is used to cause mortality or stunting in *Phyllotreta striolata* (striped flea beetle) adults or larvae, for example, by contacting *Phyllotreta striolata* adults, larvae, or eggs with an effective amount of a dsRNA trigger including a sequence selected from the group consisting of SEQ ID NOs:1392-1410. In embodiments, RNA-mediated suppression of one or more of the target genes having a sequence selected from the group consisting of SEQ ID NOs:552-859 is used to cause mortality or stunting in *Psylliodes chrysocephala* adults or larvae, for example, by contacting *Psylliodes chrysocephala* adults, larvae, or eggs with an effective amount of a dsRNA trigger including a sequence selected from the group consisting of SEQ ID NOs:1411-1718.

Plants which can be protected by such infestation by transgenic expression or topical application of one or more of the dsRNA triggers provided in Table 1 include any plant species or variety that is subject to infestation by flea beetles, especially plants of economic importance, including ornamental plants and crop plants. Embodiments of such plants include plants in the family Brassicaceae (mustard family), such as a plant in the genus *Brassica* including, for example, one of the following: *B. napus* (rapeseed, including cultivars such as canola and rutabaga), *B. juncea* (Indian mustard), *B. carinata* (Abyssinian mustard), *B. rapa* (turnip), *B. oleracea* (wild cabbage, including domesticated cultivars such as, kale, cabbage, broccoli, cauliflower, brussels sprouts, etc.) *B. rupestris* (brown mustard), *B. septiceps* (seventop mustard), *B. nigra* (black mustard), *B. narinosa* (broadbeaked mustard), *B. perviridus* (mustard spinach), *B. tournefortii* (asian mustard), and *B. fructiculosa* (Mediterranean cabbage). In additional embodiments, the target plants may include, but not limited to, one of the following: *Glycine max* (soybean), *Linum usitatissimum* (linseed/flax), *Zea mays* (maize), *Carthamus tinctorius* (safflower), *Helianthus annuus* (sunflower), *Nicodana tabacum* (tobacco), *Arabidopsis thaliana, Betholettia excelsa* (Brazil nut), *Ricinus communis* (castor bean), *Cocos nucifera* (coconut), *Coriandrum sativum* (coriander), *Gossypium* spp. (cotton), *Arachis hypogaea* (groundnut or peanut), *Simmondsia chinensis* (jojoba), *Solanum tuberosum* (potato) *Elaeis guineensis* (oil palm), *Olea europaea* (olive), *Oryza sativa* (rice), *Cucurbita maxima* (squash), *Hordeum vulgare* (barley), and *Triticum aestivum* (wheat).

An aspect includes compositions including an effective amount of one or more of the dsRNA triggers provided in Table 1 for topical treatment of a plant to be treated for, or be protected from, flea beetle infestation. Another aspect includes a recombinant DNA construct encoding at least one strand of at least one the dsRNA triggers provided in Table 1 for transgenic expression in a plant that has improved resistance to flea beetle infestation, in comparison to a plant not expressing such a construct.

Example 2

This example illustrates non-limiting embodiments of testing the efficacy of dsRNA trigger sequences and validating the triggers' utility for suppressing coding DNA sequences useful as target genes for controlling insect species. More specifically this example illustrates a method including contacting an insect, such as a flea beetle adult or larva, with one or more dsRNA triggers designed to cause stunting or mortality in the insect. Other embodiments include methods where the dsRNA trigger is delivered to the insect by oral delivery (e. g., on or in a food material ingested by the insect), or through non-oral delivery (e. g., delivery through the insect's cuticle, or delivery by contacting an egg of the insect).

In one embodiment, a feeding assay is used to determine efficacy of a dsRNA trigger in causing stunting or mortality in insects, such as flea beetles. To test the efficacy of the dsRNA triggers to kill or stunt flea beetles, a single discriminating dose (for example, 100 nanograms/milliliter) is used to identify dsRNA triggers with measureable ability to kill or stunt flea beetles at that dose. A negative control dsRNA trigger, such as a dsRNA targetting green fluorescent protein (GFP), is also included in the assay. Each dsRNA trigger is coated evenly onto 1.0 centimeter diameter canola leaf discs and placed in multiwell trays, with 2 male and 2 female adult flea beetles or 4 flea beetle larvae per well. Every 24 hours for a set period (e. g., 2 weeks), new, freshly-coated leaves are provided. Stunting and mortality are scored periodically (e. g., daily, or every 2 or 3 days).

The dsRNA triggers that show efficacy in this single-dose assay are tested further. Using a similar protocol, varying doses of dsRNA triggers are tested, as described above, to determine the LC50 dose for each of the active dsRNAs. Bioassays include 12-24 insects per dose, performed in triplicate. Stunting and mortality is assessed over a 2 week period, scored on every third day.

The dsRNA trigger sequences that are confirmed to be effective in suppressing a target gene in a sequence-specific manner are useful for identifying efficacious RNA delivery agents and formulations. The insecticidal activity of formulations containing the dsRNA triggers can be optimized by various techniques, such as modifying the chemical entities in the formulation or modifying the ratio of the chemical components in the formulation. Non-limiting examples of delivery agents and formulations are provided in Example 5.

Example 3

This example illustrates non-limiting embodiments of methods for validating dsRNA trigger efficacy for suppressing or silencing a target gene in an insect cell or causing stunting or mortality in an insect. More specifically this example illustrates methods for testing dsRNA triggers for efficacy in preventing or treating flea beetle infestations in whole plants.

Polynucleotides (such as the dsRNA trigger sequences described in Examples 1 and 2) that have been confirmed to be effective in suppressing a target gene in a sequence-specific manner are further evaluated in whole plant assays. In one method, the polynucleotides (e. g., dsRNA triggers) are applied directly to the insect surface (e. g. by spraying or dusting). In another method, the polynucleotides are provided to the insect in an insect diet (e. g., in a bacterial or plant cell expressing a dsRNA trigger such as a hairpin form of a dsRNA trigger, or in an artificial bait containing RNA). Stunting and mortality are scored periodically, as described in Example 2.

In various methods that are also appropriate for large-scale application (e. g., to fields of crop plants), the polynucleotide is applied in a foliar application through aerial or terrestrial spraying or dusting or chemigation on the leaf surface to control early season damage from the adult stage of the life cycle, or applied as a seed treatment to control larval or adult stages of the insect life cycle, or applied as a soil in-furrow or drench application to control larval or adult stages of the insect life cycle. An example of a foliar testing regime includes treating the plant immediately after emergence from the ground and evaluating foliar damage caused by adult flea beetles 1-2 weeks after plant emergence. For in-furrow or seed treatment similar timing for damage evaluation is followed.

Example 4

The polynucleotides are generally designed to modulate expression by inducing regulation or suppression of an insect target gene and are designed to have a nucleotide sequence essentially identical or essentially complementary to the nucleotide sequence an insect target gene or cDNA (e. g., SEQ ID NOs:1-859) or to the sequence of RNA transcribed from an insect target gene, which can be coding sequence or non-coding sequence. These effective polynucleotide molecules that modulate expression are referred to herein as a "trigger", or "triggers". This example describes non-limiting techniques useful in the design and selection of polynucleotides as "triggers" to modulate expression of an insect target gene.

Selection of Polynucleotide Triggers by "Tiling"

Polynucleotides of use in the compositions and methods disclosed herein need not be of the full length of a target gene, and in many embodiments are of much shorter length in comparison to the target gene. An example of a technique that is useful for selecting effective triggers is "tiling", or evaluation of polynucleotides corresponding to adjacent or partially overlapping segments of a target gene.

Effective polynucleotide "triggers" can be identified by "tiling" gene targets in selected length fragments, e. g., fragments of 200-300 nucleotides in length, with partially overlapping regions, e. g., of about 25 nucleotides, along the length of the target gene. To suppress a single gene, trigger sequences are designed to correspond to (have a nucleotide identity or complementarity with) regions that are unique to the target gene; the selected region of the target gene can include coding sequence or non-coding sequence (e. g., promoter regions, 3' untranslated regions, introns and the like) or a combination of both.

Where it is of interest to design a target effective in suppressing multiple target genes, the multiple target gene sequences are aligned and polynucleotide triggers designed to correspond to regions with high sequence homology in common among the multiple targets. Conversely, where it is of interest to design a target effective in selectively suppressing one among multiple target sequences, the multiple target gene sequences are aligned and polynucleotide triggers designed to correspond to regions with no or low sequence homology in common among the multiple targets.

In a non-limiting example, anti-sense single-stranded RNA triggers are designed for each of the target genes listed in Table 1 as follows. Multiple anti-sense single-stranded RNA triggers, each of 200-300 nucleotides in length and with a sequence corresponding to (e. g., for anti-sense triggers, complementary to) a fragment of a target gene having a sequence selected from SEQ ID NOs:1-859 are designed so that each trigger's sequence overlaps about 25 nucleotides of the next adjacent trigger's sequence, in such a way that the multiple triggers in combination cover the full length of the target gene. (Sense triggers are designed in an analogous fashion, where the trigger sequence is identical to a fragment of the target gene. Similarly, double-stranded triggers can be designed by providing pairs of sense and anti-sense triggers, each pair of triggers overlapping the next adjacent pair of triggers.)

The polynucleotide triggers are tested by any convenient means for efficacy in silencing the insect target gene. Examples of a suitable test include the bioassays described herein in the working Examples. Another test involves the topical application of the polynucleotide triggers either directly to individual insects or to the surface of a plant to be protected from an insect infestation. One desired result of treatment with a polynucleotide as disclosed herein is prevention or control of an insect infestation, e. g., by inducing in an insect a physiological or behavioural change such as, but not limited to, growth stunting, increased mortality, decrease in reproductive capacity, decrease in or cessation of feeding behavior or movement, or decrease in or cessation of metamorphosis stage development. Another desired result of treatment with a polynucleotide as disclosed herein is provision of a plant that exhibits improved resistance to an insect infestation.

The tiling procedure can be repeated, if desired. A polynucleotide trigger found to provide desired activity can itself be subjected to a tiling procedure. For example, multiple overlapping anti-sense single-stranded RNA triggers are designed, each of 50-60 nucleotides in length and with a sequence corresponding to (e. g., for anti-sense triggers, complementary to) the fragment of a target gene having a sequence selected from SEQ ID NOs:1-859 for which a single polynucleotide trigger of 300 nucleotides was found to be effective. Additional rounds of tiling analysis can be carried out, where triggers as short as 18, 19, 20, or 21 nucleotides are tested.

Effective polynucleotide triggers of any size can be used, alone or in combination, in the various methods disclosed herein. In some embodiments, a single polynucleotide trigger is used to make a composition (e. g., a composition for topical application, or a recombinant DNA construct useful for making a transgenic plant). In other embodiments, a mixture or pool of different polynucleotide triggers is used; in such cases the polynucleotide triggers can be for a single target gene or for multiple target genes. In some embodiments, a polynucleotide trigger is designed to target different regions of the target gene, e. g., a trigger can include multiple segments that correspond to different exon regions of the target gene, and "spacer" nucleotides which do not correspond to a target gene can optionally be used in between or adjacent to the segments.

Thermodynamic Considerations in Selecting Polynucleotide Triggers

Polynucleotide triggers can be designed or their sequence optimised using thermodynamic considerations. For example, polynucleotide triggers can be selected based on the thermodynamics controlling hybridization between one nucleic acid strand (e. g., a polynucleotide trigger or an individual siRNA) and another (e. g., a target gene transcript)

Methods and algorithms to predict nucleotide sequences that are likely to be effective at RNAi-mediated silencing of a target gene are known in the art. Non-limiting examples of such methods and algorithms include "i-score", described by Ichihara et al. (2007) *Nucleic Acids Res.,* 35(18): 123e; "Oligowalk", publicly available at rna.urmc.rochester.edu/servers/oligowalk and described by Lu et al. (2008) *Nucleic Acids Res.,* 36:W104-108; and "Reynolds score", described by Khovorova et al. (2004) *Nature Biotechnol.,* 22:326-330.

Permitted Mismatches

By "essentially identical" or "essentially complementary" is meant that the trigger polynucleotide (or at least one strand of a double-stranded polynucleotide) has sufficient identity or complementarity to the target gene or to the RNA transcribed from a target gene (e. g., the transcript) to suppress expression of a target gene (e. g., to effect a reduction in levels or activity of the target gene transcript and/or encoded protein). Polynucleotides need not have 100 percent identity or complementarity to a target gene or to the RNA transcribed from a target gene to suppress expression of the target gene (e. g., to effect a reduction in levels or activity of the target gene transcript or encoded protein, or to provide control of an insect species). In some embodiments, the polynucleotide or a portion thereof is designed to be essentially identical to, or essentially complementary to, a sequence of at least 18 or 19 contiguous nucleotides in either the target gene or the RNA transcribed from the target gene. In some embodiments, the polynucleotide or a portion thereof is designed to be exactly identical to, or exactly complementary to, a sequence of 21 contiguous nucleotides in either the target gene or the RNA transcribed from the target gene. In certain embodiments, an "essentially identical" polynucleotide has 100 percent sequence identity or at least about 83, 84, 85, 86, 87, 88, 89, 90, 91, 92, 93, 94, 95, 96, 97, 98, or 99 percent sequence identity when compared to the sequence of 18 or more contiguous nucleotides in either the endogenous target gene or to an RNA transcribed from the target gene. In certain embodiments, an "essentially complementary" polynucleotide has 100 percent sequence complementarity or at least about 83, 84, 85, 86, 87, 88, 89, 90, 91, 92, 93, 94, 95, 96, 97, 98, or 99 percent sequence complementarity when compared to the sequence of 18 or more contiguous nucleotides in either the target gene or RNA transcribed from the target gene.

Polynucleotides containing mismatches to the target gene or transcript can be used in certain embodiments of the compositions and methods disclosed herein. In some embodiments, the polynucleotide includes at least 18 or at least 19 contiguous nucleotides that are essentially identical or essentially complementary to a segment of equivalent length in the target gene or target gene's transcript. In certain embodiments, a polynucleotide of 19 contiguous nucleotides that is essentially identical or essentially complementary to a segment of equivalent length in the target gene or target gene's transcript can have 1 or 2 mismatches to the target gene or transcript (i. e., 1 or 2 mismatches between the polynucleotide's 19 contiguous nucleotides and the segment of equivalent length in the target gene or target gene's transcript). In certain embodiments, a polynucleotide of 20 or more nucleotides that contains a contiguous 19 nucleotide span of identity or complementarity to a segment of equivalent length in the target gene or target gene's transcript can have 1 or 2 mismatches to the target gene or transcript. In certain embodiments, a polynucleotide of 21 continuous nucleotides that is essentially identical or essentially complementary to a segment of equivalent length in the target gene or target gene's transcript can have 1, 2, or 3 mismatches to the target gene or transcript. In certain embodiments, a polynucleotide of 22 or more nucleotides that contains a contiguous 21 nucleotide span of identity or complementarity to a segment of equivalent length in the target gene or target gene's transcript can have 1, 2, or 3 mismatches to the target gene or transcript.

In designing polynucleotides with mismatches to an endogenous target gene or to an RNA transcribed from the target gene, mismatches of certain types and at certain positions that are more likely to be tolerated can be used. In certain exemplary embodiments, mismatches formed between adenine and cytosine or guanosine and uracil residues are used as described by Du et al. (2005) *Nucleic Acids Res.,* 33:1671-1677. In some embodiments, mismatches in 19 base-pair overlap regions are located at the low tolerance positions 5, 7, 8 or 11 (from the 5' end of a 19-nucleotide target), at medium tolerance positions 3, 4, and 12-17 (from the 5' end of a 19-nucleotide target), and/or at the high tolerance positions at either end of the region of complementarity, e. g., positions 1, 2, 18, and 19 (from the 5' end of a 19-nucleotide target) as described by Du et al. (2005) *Nucleic Acids Res.,* 33:1671-1677. Tolerated mismatches can be empirically determined in routine assays such as those described herein in the working Examples.

In some embodiments, the polynucleotides include additional nucleotides for reasons of stability or for convenience in cloning or synthesis. In one embodiment, the polynucleotide is a dsRNA including an RNA strand with a segment of at least 21 contiguous nucleotides of a sequence selected from the group consisting of SEQ ID NOs:860-1718 and 1722-1724 and further including an additional 5' G or an additional 3' C or both, adjacent to the segment. In another embodiment, the polynucleotide is a double-stranded RNA including additional nucleotides to form an overhang, for example, a dsRNA including 2 deoxyribonucleotides to form a 3' overhang.

Embedding Active Triggers in Neutral Sequence

In an embodiment, a bioactive trigger (i. e., a polynucleotide with a sequence corresponding to the target gene and which is responsible for an observed suppression of the target gene) is embedded in "neutral" sequence, e. g., inserted into additional nucleotides that have no sequence identity or complementarity to the target gene. Neutral sequence can be desirable, e. g., to increase the overall length of a polynucleotide. For example, it can be desirable for a polynucleotide to be of a particular size for reasons of stability, cost-effectiveness in manufacturing, or biological activity.

It has been reported that in another coleopteran species, *Diabrotica virgifera*, dsRNAs greater than or equal to approximately 60 base-pairs (bp) are required for biological activity in artificial diet bioassays; see Bolognesi et al. (2012) PLoS ONE 7(10): e47534. doi:10.1371/journal.pone.0047534. Thus, in one embodiment, a 21-base-pair dsRNA trigger corresponding to a target gene in Table 1 and found to provide control of an insect infestation is embedded in neutral sequence of an additional 39 base pairs, thus forming a polynucleotide of about 60 base pairs. In another embodiment, a single 21-base-pair trigger is found to be efficacious when embedded in larger sections of neutral sequence, e. g., where the total polynucleotide length is from about 60 to about 300 base pairs. In another embodiment, at least one segment of at least 21 contiguous nucleotides of a sequence selected from the group consisting of SEQ ID NOs:860-1718 and 1722-1724 is embedded in larger sections of neutral sequence to provide an efficacious trigger. In another embodiment, segments from multiple sequences selected from the group consisting of SEQ ID NOs:860-1718 and 1722-1724 are embedded in larger sections of neutral sequence to provide an efficacious trigger.

It is anticipated that the combination of certain recombinant RNAs disclosed herein (e. g., the dsRNA triggers including a sequence selected from the group consisting of SEQ ID NOs:860-1718 and 1722-1724, or active fragments of these triggers) with one or more non-polynucleotide pesticidal agents will result in a synergetic improvement in prevention or control of insect infestations, when compared to the effect obtained with the recombinant RNA alone or the non-polynucleotide pesticidal agent alone. Routine insect bioassays such as the bioassays described herein in the working Examples are useful for defining dose-responses for larval mortality or growth inhibition using combinations of the polynucleotides disclosed herein and one or more non-polynucleotide pesticidal agents (e. g., a patatin, a plant lectin, a phytoecdy steroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein). One of skill in the art can test combinations of polynucleotides and non-polynucleotide pesticidal agents in routine bioassays to identify combinations of bioactives that are synergistic and desirable for use in protecting plants from insect infestations.

Example 5

This example illustrates non-limiting embodiments of methods of testing the efficacy of dsRNA triggers in flea beetles. More specifically this example illustrates a method including oral delivery of dsRNAs to flea beetles, resulting in stunting or mortality in the flea beetles.

*P. cruciferae* were collected from a canola field where no pesticides had been applied in the previous 3 months. Three dsRNAs (SEQ ID NOs:1169, 1193, and 1392) targeting *Phyllotreta* genes and one negative control dsRNA targeting GFP were tested on groups of 30 *P. cruciferae*. The dsRNAs were resuspended in water and applied to 6 millimeter leaf discs (55±6 milligrams each) at a discriminating dose of 50 nanograms dsRNA/milligram leaf tissue, which were fed to groups of 5 flea beetles. Leaf discs with freshly applied dsRNA were replaced every other day, and the number of surviving individuals was recorded over a 2-week period. A low non-specific mortality rate was observed in the negative-control insect groups (3 out of 30 insects dying over 2 weeks, or 10% non-specific mortality). Mortality was observed beginning at day 4 and continuing through the 2 week period. Specific mortality was observed for all dsRNA treatments (Table 2). Correcting for non-specific mortality (subtracting non-specific mortality rate of 3 insects per group for corrected N=27), the percent mortality observed at the end of the 2-week period was 85% (SEQ ID NO:1169), 0.70% (SEQ ID NO:1193), and 0.63% (SEQ ID NO:1392). These results demonstrated the efficacy of the dsRNA triggers in causing mortality in flea beetles when provided in the flea beetles' diet.

TABLE 2

Cumulative number of dead *P. cruciferae* (N = 30)

| Day | Negative control | SEQ ID NO: 1169 | SEQ ID NO: 1193 | SEQ ID NO: 1392 |
|---|---|---|---|---|
| 0 | 0 | 0 | 0 | 0 |
| 2 | 1 | 2 | 1 | 1 |
| 4 | 2 | 6 | 2 | 2 |
| 6 | 2 | 9 | 3 | 3 |
| 8 | 2 | 13 | 8 | 9 |
| 10 | 3 | 18 | 16 | 15 |
| 12 | 3 | 23 | 19 | 18 |
| 14 | 3 | 26 | 22 | 20 |

In a second series of experiments carried out in a similar manner, several dsRNA triggers were tested at a discriminating dose of 50 nanograms dsRNA/milligram leaf tissue on *P. cruciferae*; two lower doses (15 nanograms dsRNA/milligram leaf tissue and 2 nanograms dsRNA/milligram leaf tissue) were also tested. Ten beetles were tested at each dose. The negative control (five replicates) used was a dsRNA trigger targetting the bacterial gene uidA encoding beta-glucuronidase (NCBI accession number NC_000913.3). Leaf discs with freshly applied dsRNA were replaced every other day, and mortality was recorded over a 12 day period. The overall mortality rate for the negative controls was ~4% (likely due to handling injuries) over the 12-day observation period. The observed cumulative mortality (N=10) following 12 days exposure to the dsRNAs are provided in Table 3; the negative control mortality values are given as an average (N=5). Eight of the dsRNA triggers (indicated by a mortality rating of +++) caused 90-100% mortality at the highest dose and were still highly effective (80% or higher mortality) at the lowest dose tested. Some dsRNA triggers (indicated by a mortality rating of ++) induced mortality in a proportion of the insects at the highest dose, but were less effective at lower doses (<20% mortality).

TABLE 3 cumulative mortality (N = 10)

| Trigger SEQ ID NO: | 50 ng/mg | 15 ng/mg | 2 ng/mg | Mortality Rating* |
|---|---|---|---|---|
| 870 | 3 | 1 | 0 | – |
| 876 | 3 | 1 | 0 | – |
| 1156 | 2 | 0 | 0 | – |
| 1157 | 10 | 3 | 0 | – |
| 1158 | 2 | 0 | 0 | – |
| 1159 | 5 | 2 | 0 | – |
| 1160 | 2 | 0 | 0 | – |
| 1161 | 10 | 3 | 1 | – |
| 1163 | 4 | 4 | 2 | – |

TABLE 3-continued

| Trigger SEQ ID NO: | cumulative mortality (N = 10) | | | Mortality Rating* |
|---|---|---|---|---|
| | 50 ng/mg | 15 ng/mg | 2 ng/mg | |
| 1164 | 10 | 8 | 4 | ++ |
| 1165 | 8 | 7 | 5 | ++ |
| 1166 | 5 | 2 | 2 | − |
| 1167 | 6 | 2 | 0 | − |
| 1168 | 8 | 5 | 0 | − |
| 1169 | 10 | 10 | 8 | +++ |
| 1170 | 9 | 5 | 3 | − |
| 1171 | 10 | 10 | 6 | ++ |
| 1392 | 3 | 2 | 0 | − |
| 1393 | 6 | 1 | 0 | − |
| 1186 | 9 | 7 | 5 | − |
| 1394 | 9 | 9 | 5 | − |
| 1187 | 9 | 9 | 8 | +++ |
| 1193 | 10 | 10 | 9 | +++ |
| 1210 | 6 | 3 | 1 | − |
| 1219 | 8 | 3 | 2 | − |
| 1224 | 10 | 9 | 8 | +++ |
| 1234 | 10 | 7 | 6 | ++ |
| 1243 | 5 | 2 | 0 | − |
| 1258 | 9 | 4 | 2 | − |
| 1396 | 9 | 6 | 5 | ++ |
| 1397 | 6 | 3 | 0 | − |
| 1398 | 8 | 7 | 7 | ++ |
| 1399 | 10 | 10 | 8 | +++ |
| 1400 | 2 | 1 | 1 | − |
| 1403 | 9 | 6 | 6 | − |
| 1404 | 10 | 7 | 4 | − |
| 1405 | 6 | 6 | 2 | − |
| 1406 | 9 | 9 | 7 | +++ |
| 1407 | 10 | 9 | 8 | +++ |
| 1408 | 9 | 9 | 9 | +++ |
| negative control (GFP) | 0.6 | 0.6 | 0.4 | − |
| negative control (beta-glucuronidase) | 0.4 | 0.6 | 0.2 | − |
| negative control (water only) | 0.2 | 0.4 | 0.6 | − |

*+++ rating indicates high (>80%) mortalities for all three doses; ++ rating indicates high mortalities for the highest dose, and within 40 to 70% mortality with the lower two doses.

Other techniques for delivering these or similar dsRNA triggers are contemplated and include applying the dsRNA triggers directly to the insect surface (e. g. by spraying or dusting), or providing the dsRNA triggers to the insect in a diet or bait (e. g., in a bacterial or plant cell expressing a dsRNA trigger such as a hairpin form of a dsRNA trigger, or in an artificial bait containing the dsRNA). In an embodiment, a hairpin version of the *Phyllotreta* trigger with the sequence SEQ ID NO: 1169 is designed; this hairpin version is encoded by the DNA sequence SEQ ID NO:1722, which contains, in 5' to 3' order, anti-sense sequence (nucleotide positions 1-267), loop sequence (nucleotide positions 268-373) which does not contain matches to *Phyllotreta* sequences, and sense sequence (nucleotide positions 374-640). This DNA sequence is expressed as a single-stranded RNA transcript, wherein the anti-sense and sense regions anneal to form the double-stranded "stem" region of the hairpin. The construct is expressed in a bacterium, such as *E. coli*; the resulting dsRNA hairpin produced in the bacterium is provided to flea beetles as a crude or purified fermentation product, or in the form of the bacterial cells Similar constructs are designed encoding dsRNAs having modified stem-loops, such as "stabilized anti-sense" or "stabilized sense" versions, which contain stabilized loops formed by an extended anti-sense or sense sequence, respectively, of trigger sequence corresponding to the intended target gene.

Example 6

This example discloses embodiments related to polynucleotide molecules having a nucleotide sequence containing specific modifications such as nucleotide substitutions. Embodiments of such modifications include modified dsRNA triggers that provide improved sequence discrimination between the intended target gene of the insect pest of interest, and genetic sequences of other, non-target species.

Selected dsRNA triggers identified in Table 1 were screened for unintended sequence matches to a sequence of at least 19 contiguous nucleotides identified in a non-target gene or a non-target organism (NTO, e. g., *Apis mellifera, Bombus impatiens* and *B. terrestris; Coleomegilla* spp.; *Danaus plexippus; Homo sapiens; Megachile rotundata; Mus musculus*; and *Brassica rapa*). Nucleotide changes are made in an original trigger sequence to eliminate undesirable sequence matches to a non-target gene or non-target organism. Examples of such modified trigger sequences are provided by SEQ ID NO:1723, which corresponds to SEQ ID NO:1393 (which targets the same flea beetle gene as does the trigger SEQ ID NO:1392), and SEQ ID NO:1724, which corresponds to SEQ ID NO:1169. These modified trigger sequences provide improved discrimination between the intended target species and non-target organisms.

Example 7

This example discloses embodiments related to polynucleotide molecules having a nucleotide sequence for silencing a target gene in more than one species. Embodiments include dsRNA sequences of at least 21 contiguous nucleotides identified as having 100% complementarity or identity to more than one species-specific target gene.

Table 4 provides a list of sequences, each at least 21 contiguous nucleotides in length and identified by the sequence's coordinates in a dsRNA trigger for one flea beetle species, wherein the identical sequence is also found in a dsRNA trigger for a different flea beetle species. These sequences are useful as triggers in the multiple species in which the sequence co-occurs. For example, the trigger having the sequence of SEQ ID NO:1186 (targetting a *Phyllotreta cruciferae* COPI alpha target gene, SEQ ID NO:327) contains five sequences of at least 21 contiguous nucleotides at positions 1-71, 88-116, 136-209, 238-266, and 274-296, all of which match a sequence in the triggers having the sequences of SEQ ID NOs:882 and 888 (targetting a *Phyllotreta atra* COPI alpha target genes, SEQ ID NOs:23 and 29, respectively); these five sequences are therefore useful in targeting a gene in the two *Phyllotreta* species.

TABLE 4

| QUERY Trigger | | | | QUERY Trigger | | | |
|---|---|---|---|---|---|---|---|
| SEQ ID NO: | start | end | SUBJECT Trigger SEQ ID NO: | SEQ ID NO: | start | end | SUBJECT Trigger Trigger SEQ ID NO: |
| 1186 | 1 | 71 | 882, 888 | 1333 | 329 | 351 | 1039-1043, 1045, 1594, 1597, 1598 |
| 1186 | 88 | 116 | 882, 888 | 1334 | 42 | 98 | 1039-1043, 1045, 1594, 1597, 1598 |

TABLE 4-continued

| QUERY Trigger | | | | QUERY Trigger | | | |
|---|---|---|---|---|---|---|---|
| SEQ ID NO: | start | end | SUBJECT Trigger SEQ ID NO: | SEQ ID NO: | start | end | SUBJECT Trigger Trigger SEQ ID NO: |
| 1186 | 136 | 209 | 882, 888 | 1334 | 109 | 185 | 1039-1043, 1045, 1594, 1597, 1598 |
| 1186 | 238 | 266 | 882, 888 | 1334 | 187 | 254 | 1039-1043, 1045, 1594, 1597, 1598 |
| 1186 | 274 | 296 | 882, 888 | 1334 | 271 | 302 | 1039-1043, 1045, 1594, 1597, 1598 |
| 1191 | 51 | 96 | 900-908, 910 | 1335 | 2 | 47 | 1039-1043, 1045, 1594, 1597, 1598 |
| 1191 | 137 | 177 | 900-908, 910 | 1335 | 49 | 116 | 1039-1043, 1045, 1594, 1597, 1598 |
| 1191 | 179 | 216 | 900-908, 910 | 1335 | 133 | 164 | 1039-1043, 1045, 1594, 1597, 1598 |
| 1191 | 218 | 255 | 900-908, 910 | 1335 | 229 | 251 | 1039-1043, 1045, 1594, 1597, 1598 |
| 1191 | 257 | 342 | 900-908, 910 | 1336 | 34 | 90 | 1039-1043, 1045, 1594, 1597, 1598 |
| 1192 | 2 | 25 | 900-908, 910 | 1336 | 101 | 177 | 1039-1043, 1045, 1594, 1597, 1598 |
| 1192 | 66 | 106 | 900-908, 910 | 1336 | 179 | 246 | 1039-1043, 1045, 1594, 1597, 1598 |
| 1192 | 108 | 145 | 900-908, 910 | 1336 | 263 | 294 | 1039-1043, 1045, 1594, 1597, 1598 |
| 1192 | 147 | 184 | 900-908, 910 | 1338 | 40 | 96 | 1039-1043, 1045, 1594, 1597, 1598 |
| 1192 | 186 | 271 | 900-908, 910 | 1338 | 107 | 183 | 1039-1043, 1045, 1594, 1597, 1598 |
| 1192 | 273 | 298 | 900-908, 910 | 1338 | 185 | 252 | 1039-1043, 1045, 1594, 1597, 1598 |
| 1192 | 300 | 330 | 900-908, 910 | 1338 | 269 | 300 | 1039-1043, 1045, 1594, 1597, 1598 |
| 1191 | 58 | 96 | 900-908, 910 | 1328 | 35 | 59 | 1039-1043, 1045, 1594, 1597, 1598 |
| 1192 | 300 | 336 | 900-908, 910 | 1331 | 60 | 84 | 1039-1043, 1045, 1594, 1597, 1598 |
| 1191 | 44 | 96 | 900-908, 910 | 1332 | 1 | 26 | 1039-1043, 1045, 1594, 1597, 1598 |
| 1191 | 179 | 200 | 900-908, 910 | 1333 | 36 | 60 | 1039-1043, 1045, 1594, 1597, 1598 |
| 1192 | 108 | 129 | 900-908, 910 | 1334 | 74 | 98 | 1039-1043, 1045, 1594, 1597, 1598 |
| 1191 | 218 | 242 | 900-908, 910 | 1336 | 66 | 90 | 1039-1043, 1045, 1594, 1597, 1598 |
| 1192 | 147 | 171 | 900-908, 910 | 1338 | 72 | 96 | 1039-1043, 1045, 1594, 1597, 1598 |
| 1191 | 257 | 277 | 900-908, 910 | 1331 | 1 | 26 | 1039-1043, 1045, 1594, 1597, 1598 |
| 1192 | 186 | 206 | 900-908, 910 | 1334 | 2 | 40 | 1039-1043, 1045, 1594, 1597, 1598 |
| 1191 | 257 | 334 | 900-908, 910 | 1336 | 2 | 32 | 1039-1043, 1045, 1594, 1597, 1598 |
| 1192 | 186 | 263 | 900-908, 910 | 1338 | 2 | 38 | 1039-1043, 1045, 1594, 1597, 1598 |
| 1191 | 257 | 320 | 900-908, 910 | 1328 | 36 | 59 | 1039-1043, 1045, 1594, 1597, 1598 |
| 1192 | 186 | 249 | 900-908, 910 | 1331 | 61 | 84 | 1039-1043, 1045, 1594, 1597, 1598 |
| 1193 | 15 | 101 | 911, 915, 916, 919 | 1332 | 3 | 26 | 1039-1043, 1045, 1594, 1597, 1598 |
| 1194 | 6 | 92 | 911, 915, 916, 919 | 1333 | 37 | 60 | 1039-1043, 1045, 1594, 1597, 1598 |
| 1195 | 2 | 107 | 911, 915, 916, 919 | 1334 | 75 | 98 | 1039-1043, 1045, 1594, 1597, 1598 |
| 1195 | 121 | 207 | 911, 915, 916, 919 | 1336 | 67 | 90 | 1039-1043, 1045, 1594, 1597, 1598 |
| 1196 | 2 | 122 | 911, 915, 916, 919 | 1338 | 73 | 96 | 1039-1043, 1045, 1594, 1597, 1598 |
| 1196 | 136 | 222 | 911, 915, 916, 919 | 1329 | 172 | 191 | 1039-1043 1045 |
| 1197 | 2 | 20 | 911, 915, 916, 919 | 1329 | 265 | 296 | 1039-1043 1045 |
| 1197 | 22 | 42 | 911, 915, 916, 919 | 1329 | 298 | 317 | 1039-1043 1045 |
| 1197 | 44 | 180 | 911, 915, 916, 919 | 1329 | 319 | 343 | 1039-1043 1045 |
| 1197 | 194 | 280 | 911, 915, 916, 919 | 1330 | 181 | 200 | 1039-1043 1045 |
| 1198 | 18 | 38 | 911, 915, 916, 919 | 1330 | 274 | 305 | 1039-1043 1045 |
| 1198 | 40 | 176 | 911, 915, 916, 919 | 1330 | 307 | 326 | 1039-1043 1045 |
| 1198 | 190 | 276 | 911, 915, 916, 919 | 1330 | 328 | 352 | 1039-1043 1045 |

TABLE 4-continued

| QUERY Trigger | | | | QUERY Trigger | | | |
|---|---|---|---|---|---|---|---|
| SEQ ID NO: | start | end | SUBJECT Trigger SEQ ID NO: | SEQ ID NO: | start | end | SUBJECT Trigger Trigger SEQ ID NO: |
| 1199 | 5 | 25 | 911, 915, 916, 919 | 1335 | 283 | 302 | 1039-1043, 1045, 1594, 1597, 1598 |
| 1199 | 27 | 163 | 911, 915, 916, 919 | 1337 | 1 | 19 | 1043, 1045 |
| 1199 | 177 | 263 | 911, 915, 916, 919 | 1337 | 93 | 124 | 1043, 1045 |
| 1200 | 16 | 152 | 911, 915, 916, 919 | 1337 | 126 | 145 | 1043, 1045 |
| 1200 | 166 | 252 | 911, 915, 916, 919 | 1337 | 147 | 171 | 1043, 1045 |
| 1201 | 19 | 105 | 911, 915, 916, 919 | 1329 | 319 | 352 | 1039-1043 1045 |
| 1202 | 2 | 119 | 911, 915, 916, 919 | 1337 | 147 | 180 | 1043, 1045 |
| 1202 | 133 | 219 | 911, 915, 916, 919 | 1386 | 2 | 38 | 1054-1057, 1060, 1496, 1498 |
| 1203 | 14 | 100 | 911, 915, 916, 919 | 1386 | 40 | 59 | 1054-1057, 1060, 1496, 1498 |
| 1193 | 123 | 189 | 911, 915, 916, 919 | 1386 | 70 | 95 | 1054-1057, 1060, 1496, 1498 |
| 1194 | 114 | 180 | 911, 915, 916, 919 | 1386 | 103 | 161 | 1054-1057, 1060, 1496, 1498 |
| 1195 | 229 | 295 | 911, 915, 916, 919 | 1386 | 196 | 262 | 1054-1057, 1060, 1496, 1498 |
| 1196 | 244 | 310 | 911, 915, 916, 919 | 1388 | 2 | 51 | 1054-1057, 1060, 1496, 1498 |
| 1197 | 302 | 350 | 911, 915, 916, 919 | 1388 | 53 | 72 | 1054-1057, 1060, 1496, 1498 |
| 1198 | 298 | 350 | 911, 915, 916, 919 | 1388 | 83 | 108 | 1054-1057, 1060, 1496, 1498 |
| 1199 | 285 | 352 | 911, 915, 916, 919 | 1388 | 116 | 174 | 1054-1057, 1060, 1496, 1498 |
| 1200 | 274 | 340 | 911, 915, 916, 919 | 1388 | 209 | 275 | 1054-1057, 1060, 1496, 1498 |
| 1201 | 127 | 193 | 911, 915, 916, 919 | 1390 | 88 | 119 | 1054-1057, 1060, 1492, 1496-1498 |
| 1202 | 241 | 307 | 911, 915, 916, 919 | 1390 | 145 | 194 | 1054-1057, 1060, 1492, 1496-1498 |
| 1203 | 122 | 188 | 911, 915, 916, 919 | 1390 | 196 | 215 | 1054-1057, 1060, 1492, 1496-1498 |
| 1193 | 123 | 196 | 911, 915, 916, 919 | 1390 | 226 | 251 | 1054-1057, 1060, 1492, 1496-1498 |
| 1193 | 198 | 230 | 911, 915, 916, 919 | 1390 | 259 | 317 | 1054-1057, 1060, 1492, 1496-1498 |
| 1194 | 114 | 187 | 911, 915, 916, 919 | 1391 | 19 | 50 | 1054-1057, 1060, 1492, 1496-1498 |
| 1194 | 189 | 221 | 911, 915, 916, 919 | 1391 | 76 | 125 | 1054-1057, 1060, 1492, 1496-1498 |
| 1195 | 229 | 302 | 911, 915, 916, 919 | 1391 | 127 | 146 | 1054-1057, 1060, 1492, 1496-1498 |
| 1195 | 304 | 336 | 911, 915, 916, 919 | 1391 | 157 | 182 | 1054-1057, 1060, 1492, 1496-1498 |
| 1196 | 1 | 122 | 911, 915, 916, 919 | 1391 | 190 | 248 | 1054-1057, 1060, 1492, 1496-1498 |
| 1196 | 244 | 317 | 911, 915, 916, 919 | 1391 | 283 | 349 | 1054-1057, 1060, 1492, 1496-1498 |
| 1196 | 319 | 351 | 911, 915, 916, 919 | 1384 | 20 | 39 | 1055, 1058, 1059, 1061-1063, 1500 |
| 1197 | 60 | 180 | 911, 915, 916, 919 | 1384 | 62 | 84 | 1055, 1058, 1059, 1061-1063, 1500 |
| 1198 | 56 | 176 | 911, 915, 916, 919 | 1384 | 134 | 204 | 1055, 1058, 1059, 1061-1063, 1500 |
| 1199 | 43 | 163 | 911, 915, 916, 919 | 1384 | 206 | 249 | 1055, 1058, 1059, 1061-1063, 1500 |
| 1199 | 285 | 351 | 911, 915, 916, 919 | 1384 | 251 | 270 | 1055, 1058, 1059, 1061-1063, 1500 |
| 1200 | 32 | 152 | 911, 915, 916, 919 | 1384 | 284 | 305 | 1055, 1058, 1059, 1061-1063, 1500 |
| 1200 | 274 | 347 | 911, 915, 916, 919 | 1385 | 21 | 40 | 1055, 1058, 1059, 1061-1063, 1500 |
| 1201 | 127 | 200 | 911, 915, 916, 919 | 1385 | 63 | 85 | 1055, 1058, 1059, 1061-1063, 1500 |
| 1201 | 202 | 234 | 911, 915, 916, 919 | 1385 | 135 | 205 | 1055, 1058, 1059, 1061-1063, 1500 |
| 1202 | 241 | 314 | 911, 915, 916, 919 | 1385 | 207 | 250 | 1055, 1058, 1059, 1061-1063, 1500 |
| 1202 | 316 | 348 | 911, 915, 916, 919 | 1385 | 252 | 271 | 1055, 1058, 1059, 1061-1063, 1500 |
| 1203 | 122 | 195 | 911, 915, 916, 919 | 1385 | 285 | 306 | 1055, 1058, 1059, 1061-1063, 1500 |
| 1203 | 197 | 229 | 911, 915, 916, 919 | 1387 | 2 | 21 | 1055, 1058, 1059, 1061-1063, 1500, 1057 |
| 1204 | 6 | 25 | 920, 921, 922, 923, 924 | 1387 | 23 | 42 | 1055, 1058, 1059, 1061-1063, 1500, 1057 |
| 1204 | 27 | 49 | 920, 921, 922, 923, 924 | 1387 | 56 | 77 | 1055, 1058, 1059, 1061-1063, 1500, 1057 |
| 1204 | 51 | 118 | 920, 921, 922, 923, 924 | 1389 | 1 | 55 | 1055, 1058, 1059, 1061-1063, 1500 |
| 1204 | 186 | 214 | 920, 921, 922, 923, 924 | 1389 | 57 | 100 | 1055, 1058, 1059, 1061-1063, 1500 |

TABLE 4-continued

| QUERY Trigger | | | | QUERY Trigger | | | |
|---|---|---|---|---|---|---|---|
| SEQ ID NO: | start | end | SUBJECT Trigger SEQ ID NO: | SEQ ID NO: | start | end | SUBJECT Trigger Trigger SEQ ID NO: |
| 1204 | 219 | 268 | 920, 921, 922, 923, 924 | 1389 | 102 | 121 | 1055, 1058, 1059, 1061-1063, 1500 |
| 1204 | 270 | 295 | 920, 921, 922, 923, 924 | 1389 | 135 | 156 | 1055, 1058, 1059, 1061-1063, 1500 |
| 1204 | 306 | 351 | 920, 921, 922, 923, 924 | 1386 | 196 | 255 | 1054-1057, 1060, 1496, 1498 |
| 1205 | 180 | 199 | 920, 921, 922, 923, 924 | 1388 | 209 | 268 | 1054-1057, 1060, 1496, 1498 |
| 1205 | 201 | 223 | 920, 921, 922, 923, 924 | 1391 | 283 | 342 | 1054-1057, 1060, 1492, 1496-1498 |
| 1205 | 225 | 292 | 920, 921, 922, 923, 924 | 1387 | 257 | 321 | 1055, 1058, 1059, 1061-1063, 1500, 1057 |
| 1206 | 10 | 29 | 920, 921, 922, 923, 924 | 1387 | 332 | 351 | 1055, 1058, 1059, 1061-1063, 1500, 1057 |
| 1206 | 31 | 53 | 920, 921, 922, 923, 924 | 1390 | 25 | 56 | 1054-1057, 1060, 1492, 1496-1498 |
| 1206 | 55 | 122 | 920, 921, 922, 923, 924 | 1384 | 284 | 321 | 1055, 1058, 1059, 1061-1063, 1500 |
| 1206 | 190 | 218 | 920, 921, 922, 923, 924 | 1385 | 285 | 322 | 1055, 1058, 1059, 1061-1063, 1500 |
| 1206 | 223 | 272 | 920, 921, 922, 923, 924 | 1387 | 56 | 93 | 1055, 1058, 1059, 1061-1063, 1500, 1057 |
| 1206 | 274 | 299 | 920, 921, 922, 923, 924 | 1389 | 135 | 172 | 1055, 1058, 1059, 1061-1063, 1500 |
| 1206 | 310 | 351 | 920, 921, 922, 923, 924 | 1386 | 196 | 332 | 1054-1057, 1060, 1496, 1498 |
| 1207 | 11 | 33 | 920, 921, 922, 923, 924 | 1388 | 209 | 345 | 1054-1057, 1060, 1496, 1498 |
| 1207 | 35 | 102 | 920, 921, 922, 923, 924 | 1391 | 283 | 352 | 1054-1057, 1060, 1492, 1496-1498 |
| 1207 | 170 | 198 | 920, 921, 922, 923, 924 | 1384 | 323 | 348 | 1055, 1058, 1059, 1061-1063, 1500 |
| 1207 | 203 | 252 | 920, 921, 922, 923, 924 | 1385 | 324 | 349 | 1055, 1058, 1059, 1061-1063, 1500 |
| 1207 | 254 | 279 | 920, 921, 922, 923, 924 | 1387 | 95 | 120 | 1055, 1058, 1059, 1061-1063, 1500, 1057 |
| 1207 | 290 | 335 | 920, 921, 922, 923, 924 | 1387 | 128 | 153 | 1055, 1058, 1059, 1061-1063, 1500, 1057 |
| 1208 | 18 | 40 | 920, 921, 922, 923, 924 | 1387 | 161 | 186 | 1055, 1058, 1059, 1061-1063, 1500, 1057 |
| 1208 | 42 | 109 | 920, 921, 922, 923, 924 | 1387 | 191 | 210 | 1055, 1058, 1059, 1061-1063, 1500, 1057 |
| 1208 | 177 | 205 | 920, 921, 922, 923, 924 | 1389 | 174 | 199 | 1055, 1058, 1059, 1061-1063, 1500 |
| 1208 | 210 | 259 | 920, 921, 922, 923, 924 | 1389 | 207 | 232 | 1055, 1058, 1059, 1061-1063, 1500 |
| 1208 | 261 | 286 | 920, 921, 922, 923, 924 | 1389 | 240 | 265 | 1055, 1058, 1059, 1061-1063, 1500 |
| 1208 | 297 | 342 | 920, 921, 922, 923, 924 | 1389 | 270 | 289 | 1055, 1058, 1059, 1061-1063, 1500 |
| 1209 | 101 | 120 | 920, 921, 922, 923, 924 | 1283 | 177 | 208 | 1064-1070 |
| 1209 | 122 | 144 | 920, 921, 922, 923, 924 | 1284 | 130 | 161 | 1064-1070 |
| 1209 | 146 | 213 | 920, 921, 922, 923, 924 | 1284 | 301 | 351 | 1064-1070 |
| 1209 | 281 | 309 | 920, 921, 922, 923, 924 | 1286 | 210 | 241 | 1064-1070 |
| 1209 | 314 | 351 | 920, 921, 922, 923, 924 | 1287 | 126 | 157 | 1064-1070 |
| 1205 | 2 | 91 | 920, 921, 922, 923, 924 | 1287 | 297 | 351 | 1064-1070 |
| 1205 | 114 | 142 | 920, 921, 922, 923, 924 | 1288 | 326 | 351 | 1064-1070, 1071 |
| 1205 | 144 | 178 | 920, 921, 922, 923, 924 | 1289 | 41 | 72 | 1064-1070 |
| 1209 | 35 | 63 | 920, 921, 922, 923, 924 | 1289 | 212 | 288 | 1064-1070 |
| 1209 | 65 | 99 | 920, 921, 922, 923, 924 | 1289 | 320 | 351 | 1064-1070 |
| 1204 | 306 | 347 | 920, 921, 922, 923, 924 | 1290 | 178 | 209 | 1064-1070 |
| 1207 | 290 | 331 | 920, 921, 922, 923, 924 | 1291 | 228 | 259 | 1064-1070, 1071 |
| 1208 | 297 | 338 | 920, 921, 922, 923, 924 | 1292 | 43 | 74 | 1064-1070 |
| 1207 | 290 | 352 | 920, 921, 922, 923, 924 | 1292 | 214 | 290 | 1064-1070 |
| 1208 | 297 | 351 | 920, 921, 922, 923, 924 | 1292 | 322 | 351 | 1064-1070 |
| 1205 | 18 | 91 | 920, 921, 922, 923, 924 | 1293 | 330 | 351 | 1064-1070, 1071 |
| 1224 | 1 | 43 | 947-949, 951-956 | 1377 | 37 | 68 | 1064-1070 |
| 1224 | 57 | 95 | 947-949, 951-956 | 1377 | 208 | 284 | 1064-1070 |
| 1224 | 97 | 145 | 947-949, 951-956 | 1377 | 316 | 348 | 1064-1070 |
| 1224 | 147 | 175 | 947-949, 951-956 | 1289 | 212 | 274 | 1064-1070 |
| 1224 | 177 | 208 | 947-949, 951-956 | 1292 | 214 | 276 | 1064-1070 |
| 1224 | 210 | 262 | 947-949, 951-956 | 1377 | 208 | 270 | 1064-1070 |
| 1224 | 285 | 350 | 947-949, 951-956 | 1285 | 123 | 148 | 1067, 1069, 1071 |
| 1225 | 150 | 192 | 947, 949, 951-956 | 1288 | 107 | 132 | 1064-1070, 1071 |
| 1225 | 206 | 244 | 947, 949, 951-956 | 1291 | 9 | 34 | 1064-1070, 1071 |
| 1225 | 246 | 294 | 947, 949, 951-956 | 1293 | 111 | 136 | 1064-1070, 1071 |
| 1225 | 296 | 324 | 947, 949, 951-956 | 1287 | 297 | 347 | 1064-1070 |
| 1225 | 326 | 351 | 947, 949, 951-956 | 1289 | 212 | 262 | 1064-1070 |
| 1226 | 258 | 300 | 947, 949, 951-955 | 1292 | 214 | 264 | 1064-1070 |

TABLE 4-continued

| QUERY Trigger SEQ ID NO: | start | end | SUBJECT Trigger SEQ ID NO: | QUERY Trigger SEQ ID NO: | start | end | SUBJECT Trigger SEQ ID NO: |
|---|---|---|---|---|---|---|---|
| 1226 | 314 | 351 | 947, 949, 951-955 | 1377 | 208 | 258 | 1064-1070 |
| 1227 | 253 | 295 | 947, 949, 951-955 | 1287 | 297 | 352 | 1064-1070 |
| 1227 | 309 | 347 | 947, 949, 951-955 | 1289 | 212 | 266 | 1064-1070 |
| 1228 | 206 | 248 | 947, 949, 951-956 | 1292 | 214 | 268 | 1064-1070 |
| 1228 | 262 | 300 | 947, 949, 951-956 | 1377 | 208 | 262 | 1064-1070 |
| 1228 | 302 | 350 | 947, 949, 951-956 | 1285 | 18 | 61 | 1067, 1069, 1071 |
| 1229 | 171 | 213 | 947, 949, 951-956 | 1288 | 2 | 45 | 1064-1070, 1071 |
| 1229 | 227 | 265 | 947, 949, 951-956 | 1293 | 6 | 49 | 1064-1070, 1071 |
| 1229 | 267 | 315 | 947, 949, 951-956 | 1357 | 1 | 40 | 1079-1082, 1152-1154, 1455, 1457, 1458 |
| 1229 | 317 | 345 | 947, 949, 951-956 | 1357 | 63 | 85 | 1079-1082, 1152-1154, 1455, 1457, 1458 |
| 1230 | 252 | 294 | 947, 949, 951-955 | 1357 | 102 | 157 | 1079-1082, 1152-1154, 1455, 1457, 1458 |
| 1230 | 308 | 346 | 947, 949, 951-955 | 1357 | 159 | 189 | 1079-1082, 1152-1154, 1455, 1457, 1458 |
| 1231 | 191 | 233 | 947, 949, 951-956 | 1357 | 191 | 322 | 1079-1082, 1152-1154, 1455, 1457, 1458 |
| 1231 | 247 | 285 | 947, 949, 951-956 | 1358 | 25 | 47 | 1079-1082, 1152-1154, 1455, 1457, 1458 |
| 1231 | 287 | 335 | 947, 949, 951-956 | 1358 | 64 | 119 | 1079-1082, 1152-1154, 1455, 1457, 1458 |
| 1232 | 196 | 238 | 947, 949, 951-956 | 1358 | 121 | 151 | 1079-1082, 1152-1154, 1455, 1457, 1458 |
| 1232 | 252 | 290 | 947, 949, 951-956 | 1358 | 153 | 284 | 1079-1082, 1152-1154, 1455, 1457, 1458 |
| 1232 | 292 | 340 | 947, 949, 951-956 | 1359 | 31 | 53 | 1079-1082, 1152-1154, 1455, 1457, 1458 |
| 1233 | 209 | 251 | 947, 949, 951-956 | 1359 | 70 | 125 | 1079-1082, 1152-1154, 1455, 1457, 1458 |
| 1233 | 265 | 303 | 947, 949, 951-956 | 1359 | 127 | 157 | 1079-1082, 1152-1154, 1455, 1457, 1458 |
| 1233 | 305 | 351 | 947, 949, 951-956 | 1359 | 159 | 290 | 1079-1082, 1152-1154, 1455, 1457, 1458 |
| 1224 | 177 | 202 | 947-949, 951-956 | 1360 | 38 | 60 | 1079-1082, 1152-1154, 1455, 1457, 1458 |
| 1225 | 1 | 72 | 947, 949, 951-956 | 1360 | 77 | 132 | 1079-1082, 1152-1154, 1455, 1457, 1458 |
| 1225 | 74 | 135 | 947, 949, 951-956 | 1360 | 134 | 164 | 1079-1082, 1152-1154, 1455, 1457, 1458 |
| 1225 | 137 | 192 | 947, 949, 951-956 | 1360 | 166 | 297 | 1079-1082, 1152-1154, 1455, 1457, 1458 |
| 1226 | 110 | 180 | 947, 949, 951-955 | 1361 | 1 | 41 | 1079-1082, 1152-1154, 1455, 1457, 1458 |
| 1226 | 182 | 243 | 947, 949, 951-955 | 1361 | 64 | 86 | 1079-1082, 1152-1154, 1455, 1457, 1458 |
| 1226 | 245 | 300 | 947, 949, 951-955 | 1361 | 103 | 158 | 1079-1082, 1152-1154, 1455, 1457, 1458 |
| 1227 | 105 | 175 | 947, 949, 951-955 | 1361 | 160 | 190 | 1079-1082, 1152-1154, 1455, 1457, 1458 |
| 1227 | 177 | 238 | 947, 949, 951-955 | 1361 | 192 | 323 | 1079-1082, 1152-1154, 1455, 1457, 1458 |
| 1227 | 240 | 295 | 947, 949, 951-955 | 1362 | 31 | 53 | 1079-1082, 1152-1154, 1455, 1457, 1458 |
| 1228 | 58 | 128 | 947, 949, 951-956 | 1362 | 70 | 125 | 1079-1082, 1152-1154, 1455, 1457, 1458 |
| 1228 | 130 | 191 | 947, 949, 951-956 | 1362 | 127 | 157 | 1079-1082, 1152-1154, 1455, 1457, 1458 |
| 1228 | 193 | 248 | 947, 949, 951-956 | 1362 | 159 | 290 | 1079-1082, 1152-1154, 1455, 1457, 1458 |
| 1229 | 23 | 93 | 947, 949, 951-956 | 1363 | 33 | 55 | 1079-1082, 1152-1154, 1455, 1457, 1458 |
| 1229 | 95 | 156 | 947, 949, 951-956 | 1363 | 72 | 127 | 1079-1082, 1152-1154, 1455, 1457, 1458 |
| 1229 | 158 | 213 | 947, 949, 951-956 | 1363 | 129 | 159 | 1079-1082, 1152-1154, 1455, 1457, 1458 |
| 1230 | 104 | 174 | 947, 949, 951-955 | 1363 | 161 | 292 | 1079-1082, 1152-1154, 1455, 1457, 1458 |
| 1230 | 176 | 237 | 947, 949, 951-955 | 1364 | 4 | 59 | 1079-1082, 1152-1154, 1455, 1457, 1458 |
| 1230 | 239 | 294 | 947, 949, 951-955 | 1364 | 61 | 91 | 1079-1082, 1152-1154, 1455, 1457, 1458 |
| 1231 | 43 | 113 | 947, 949, 951-956 | 1364 | 93 | 224 | 1079-1082, 1152-1154, 1455, 1457, 1458 |

TABLE 4-continued

| QUERY Trigger | | | | QUERY Trigger | | | |
|---|---|---|---|---|---|---|---|
| SEQ ID NO: | start | end | SUBJECT Trigger SEQ ID NO: | SEQ ID NO: | start | end | SUBJECT Trigger Trigger SEQ ID NO: |
| 1231 | 115 | 176 | 947, 949, 951-956 | 1365 | 35 | 57 | 1079-1082, 1152-1154, 1455, 1457, 1458 |
| 1231 | 178 | 233 | 947, 949, 951-956 | 1365 | 74 | 129 | 1079-1082, 1152-1154, 1455, 1457, 1458 |
| 1232 | 48 | 118 | 947, 949, 951-956 | 1365 | 131 | 161 | 1079-1082, 1152-1154, 1455, 1457, 1458 |
| 1232 | 120 | 181 | 947, 949, 951-956 | 1365 | 163 | 294 | 1079-1082, 1152-1154, 1455, 1457, 1458 |
| 1232 | 183 | 238 | 947, 949, 951-956 | 1366 | 2 | 26 | 1079-1082, 1152-1154, 1455, 1457, 1458 |
| 1233 | 61 | 131 | 947, 949, 951-956 | 1366 | 28 | 58 | 1079-1082, 1152-1154, 1455, 1457, 1458 |
| 1233 | 133 | 194 | 947, 949, 951-956 | 1366 | 60 | 191 | 1079-1082, 1152-1154, 1455, 1457, 1458 |
| 1233 | 196 | 251 | 947, 949, 951-956 | 1367 | 2 | 116 | 1079, 1080, 1081, 1082, 1152, 1153, 1154 |
| 1224 | 227 | 262 | 947-949, 951-956 | 1358 | 322 | 345 | 1079-1082, 1152-1154, 1455, 1457, 1458 |
| 1224 | 57 | 94 | 947-949, 951-956 | 1359 | 328 | 350 | 1079-1082, 1152-1154, 1455, 1457, 1458 |
| 1225 | 2 | 72 | 947, 949, 951-956 | 1362 | 328 | 351 | 1079-1082, 1152-1154, 1455, 1457, 1458 |
| 1225 | 206 | 243 | 947, 949, 951-956 | 1363 | 330 | 352 | 1079-1082, 1152-1154, 1455, 1457, 1458 |
| 1226 | 1 | 96 | 947, 949, 951-955 | 1364 | 262 | 285 | 1079-1082, 1152-1154, 1455, 1457, 1458 |
| 1226 | 98 | 180 | 947, 949, 951-955 | 1365 | 332 | 351 | 1079-1082, 1152-1154, 1455, 1457, 1458 |
| 1227 | 2 | 91 | 947, 949, 951-955 | 1366 | 229 | 252 | 1079-1082, 1152-1154, 1455, 1457, 1458 |
| 1227 | 93 | 175 | 947, 949, 951-955 | 1367 | 154 | 177 | 1079-1082, 1152-1154 |
| 1227 | 309 | 346 | 947, 949, 951-955 | 1358 | 322 | 344 | 1079-1082, 1152-1154, 1455, 1457, 1458 |
| 1228 | 2 | 44 | 947, 949, 951-956 | 1362 | 328 | 350 | 1079-1082, 1152-1154, 1455, 1457, 1458 |
| 1228 | 46 | 128 | 947, 949, 951-956 | 1364 | 262 | 284 | 1079-1082, 1152-1154, 1455, 1457, 1458 |
| 1228 | 262 | 299 | 947, 949, 951-956 | 1366 | 229 | 251 | 1079-1082, 1152-1154, 1455, 1457, 1458 |
| 1229 | 11 | 93 | 947, 949, 951-956 | 1367 | 154 | 176 | 1079-1082, 1152-1154 |
| 1229 | 227 | 264 | 947, 949, 951-956 | 1368 | 126 | 145 | 1083, 1087 |
| 1230 | 2 | 90 | 947, 949, 951-955 | 1368 | 153 | 177 | 1083, 1087 |
| 1230 | 92 | 174 | 947, 949, 951-955 | 1368 | 186 | 208 | 1083, 1087 |
| 1230 | 308 | 345 | 947, 949, 951-955 | 1368 | 224 | 253 | 1083, 1087 |
| 1231 | 2 | 29 | 949, 951-956 | 1369 | 161 | 180 | 1083, 1084, 1089 |
| 1231 | 31 | 113 | 947, 949, 951-956 | 1370 | 124 | 143 | 1083, 1087 |
| 1231 | 247 | 284 | 947, 949, 951-956 | 1370 | 151 | 175 | 1083, 1087 |
| 1232 | 2 | 34 | 947, 949, 951-956 | 1370 | 184 | 206 | 1083, 1087 |
| 1232 | 36 | 118 | 947, 949, 951-956 | 1370 | 222 | 251 | 1083, 1087 |
| 1232 | 252 | 289 | 947, 949, 951-956 | 1369 | 278 | 303 | 1083, 1084, 1089 |
| 1233 | 2 | 47 | 947, 949, 951-956 | 1369 | 182 | 201 | 1083, 1084, 1089 |
| 1233 | 49 | 131 | 947, 949, 951-956 | 1371 | 1 | 71 | 1093-1095, 1098, 1100-1103 |
| 1233 | 265 | 302 | 947, 949, 951-956 | 1371 | 82 | 122 | 1093-1095, 1098, 1100-1103 |
| 1226 | 7 | 96 | 947, 949, 951-955 | 1371 | 124 | 180 | 1093-1095, 1098, 1100-1103 |
| 1227 | 1 | 91 | 947, 949, 951-955 | 1371 | 182 | 244 | 1093-1095, 1098, 1100-1103 |
| 1226 | 8 | 96 | 947, 949, 951-955 | 1372 | 16 | 56 | 1093-1095, 1098, 1100-1103 |
| 1227 | 3 | 91 | 947, 949, 951-955 | 1372 | 58 | 114 | 1093-1095, 1098, 1100-1103 |
| 1230 | 1 | 90 | 947, 949, 951-955 | 1372 | 116 | 178 | 1093-1095, 1098, 1100-1103 |
| 1226 | 54 | 96 | 947, 949, 951-955 | 1373 | 2 | 61 | 1093-1095, 1098, 1100-1103 |
| 1227 | 49 | 91 | 947, 949, 951-955 | 1373 | 72 | 112 | 1093-1095, 1098, 1100-1103 |
| 1228 | 1 | 44 | 947, 949, 951-956 | 1373 | 114 | 170 | 1093-1095, 1098, 1100-1103 |
| 1230 | 48 | 90 | 947, 949, 951-955 | 1373 | 172 | 234 | 1093-1095, 1098, 1100-1103 |
| 1233 | 5 | 47 | 947, 949, 951-956 | 1374 | 1 | 68 | 1093-1095, 1098, 1100-1103 |
| 1224 | 125 | 145 | 947-949, 951-956 | 1374 | 79 | 119 | 1093-1095, 1098, 1100-1103 |
| 1225 | 274 | 294 | 947, 949, 951-956 | 1374 | 121 | 177 | 1093-1095, 1098, 1100-1103 |
| 1228 | 330 | 350 | 947, 949, 951-956 | 1374 | 179 | 241 | 1093-1095, 1098, 1100-1103 |
| 1229 | 295 | 315 | 947, 949, 951-956 | 1375 | 2 | 41 | 1093-1095, 1098, 1100-1103 |
| 1231 | 315 | 335 | 947, 949, 951-956 | 1375 | 52 | 92 | 1093-1095, 1098, 1100-1103 |
| 1232 | 320 | 340 | 947, 949, 951-956 | 1375 | 94 | 150 | 1093-1095, 1098, 1100-1103 |
| 1233 | 333 | 351 | 947, 949, 951-956 | 1375 | 152 | 214 | 1093-1095, 1098, 1100-1103 |
| 1234 | 50 | 135 | 960, 964 | 1376 | 7 | 47 | 1093-1095, 1098, 1100-1103 |
| 1234 | 149 | 168 | 960, 964 | 1376 | 49 | 105 | 1093-1095, 1098, 1100-1103 |
| 1234 | 170 | 350 | 960, 964 | 1376 | 107 | 169 | 1093-1095, 1098, 1100-1103 |
| 1235 | 175 | 260 | 960, 963, 964 | 1371 | 124 | 148 | 1093-1095, 1098, 1100-1103 |
| 1235 | 274 | 293 | 960, 963, 964 | 1372 | 58 | 82 | 1093-1095, 1098, 1100-1103 |

TABLE 4-continued

| QUERY Trigger SEQ ID NO: | start | end | SUBJECT Trigger SEQ ID NO: | QUERY Trigger SEQ ID NO: | start | end | SUBJECT Trigger Trigger SEQ ID NO: |
|---|---|---|---|---|---|---|---|
| 1235 | 295 | 351 | 960, 963, 964 | 1373 | 114 | 138 | 1093-1095, 1098, 1100-1103 |
| 1236 | 190 | 275 | 960, 963, 964 | 1374 | 121 | 145 | 1093-1095, 1098, 1100-1103 |
| 1236 | 289 | 308 | 960, 963, 964 | 1375 | 94 | 118 | 1093-1095, 1098, 1100-1103 |
| 1236 | 310 | 351 | 960, 963, 964 | 1376 | 49 | 73 | 1093-1095, 1098, 1100-1103 |
| 1237 | 269 | 350 | 960, 963, 964 | 1371 | 182 | 276 | 1093-1095, 1098, 1100-1103 |
| 1238 | 51 | 136 | 960, 964 | 1371 | 278 | 333 | 1093-1095, 1098, 1100-1103 |
| 1238 | 150 | 169 | 960, 964 | 1372 | 116 | 210 | 1093-1095, 1098, 1100-1103 |
| 1238 | 171 | 350 | 960, 964 | 1372 | 212 | 267 | 1093-1095, 1098, 1100-1103 |
| 1239 | 50 | 135 | 960, 964 | 1372 | 269 | 309 | 1093-1095, 1098, 1100-1103 |
| 1239 | 149 | 168 | 960, 964 | 1372 | 311 | 352 | 1093-1095, 1098, 1100-1103 |
| 1239 | 170 | 351 | 960, 964 | 1373 | 172 | 266 | 1093-1095, 1098, 1100-1103 |
| 1240 | 103 | 188 | 960, 963, 964 | 1373 | 268 | 323 | 1093-1095, 1098, 1100-1103 |
| 1240 | 202 | 221 | 960, 963, 964 | 1373 | 325 | 351 | 1093-1095, 1098, 1100-1103 |
| 1240 | 223 | 351 | 960, 963, 964 | 1374 | 179 | 273 | 1093-1095, 1098, 1100-1103 |
| 1241 | 269 | 351 | 960, 963, 964 | 1374 | 275 | 330 | 1093-1095, 1098, 1100-1103 |
| 1242 | 87 | 172 | 960, 963, 964 | 1374 | 332 | 351 | 1093-1095, 1098, 1100-1103 |
| 1242 | 186 | 205 | 960, 963, 964 | 1375 | 152 | 246 | 1093-1095, 1098, 1100-1103 |
| 1242 | 207 | 351 | 960, 963, 964 | 1375 | 248 | 303 | 1093-1095, 1098, 1100-1103 |
| 1235 | 2 | 23 | 960, 963, 964 | 1375 | 305 | 345 | 1093-1095, 1098, 1100-1103 |
| 1235 | 25 | 114 | 960, 963, 964 | 1376 | 107 | 201 | 1093-1095, 1098, 1100-1103 |
| 1236 | 2 | 38 | 960, 963, 964 | 1376 | 203 | 258 | 1093-1095, 1098, 1100-1103 |
| 1236 | 40 | 129 | 960, 963, 964 | 1376 | 260 | 300 | 1093-1095, 1098, 1100-1103 |
| 1237 | 2 | 39 | 960, 963, 964 | 1376 | 302 | 342 | 1093-1095, 1098, 1100-1103 |
| 1237 | 41 | 117 | 960, 963, 964 | 1371 | 278 | 303 | 1093-1095, 1098, 1100-1103 |
| 1237 | 119 | 208 | 960, 963, 964 | 1372 | 212 | 237 | 1093-1095, 1098, 1100-1103 |
| 1240 | 2 | 42 | 960, 963, 964 | 1373 | 268 | 293 | 1093-1095, 1098, 1100-1103 |
| 1241 | 2 | 39 | 960, 963, 964 | 1374 | 275 | 300 | 1093-1095, 1098, 1100-1103 |
| 1241 | 41 | 117 | 960, 963, 964 | 1375 | 248 | 273 | 1093-1095, 1098, 1100-1103 |
| 1241 | 119 | 208 | 960, 963, 964 | 1376 | 203 | 228 | 1093-1095, 1098, 1100-1103 |
| 1242 | 2 | 26 | 960, 963, 964 | 1371 | 124 | 155 | 1093-1095, 1098, 1100-1103 |
| 1234 | 38 | 135 | 960, 964 | 1372 | 58 | 89 | 1093-1095, 1098, 1100-1103 |
| 1234 | 170 | 211 | 960, 964 | 1373 | 114 | 145 | 1093-1095, 1098, 1100-1103 |
| 1235 | 25 | 136 | 960, 963, 964 | 1374 | 121 | 152 | 1093-1095, 1098, 1100-1103 |
| 1235 | 163 | 260 | 960, 963, 964 | 1375 | 94 | 125 | 1093-1095, 1098, 1100-1103 |
| 1235 | 295 | 336 | 960, 963, 964 | 1376 | 49 | 80 | 1093-1095, 1098, 1100-1103 |
| 1236 | 1 | 38 | 960, 963, 964 | 1371 | 182 | 241 | 1093-1095, 1098, 1100-1103 |
| 1236 | 40 | 151 | 960, 963, 964 | 1372 | 116 | 175 | 1093-1095, 1098, 1100-1103 |
| 1236 | 178 | 275 | 960, 963, 964 | 1373 | 172 | 231 | 1093-1095, 1098, 1100-1103 |
| 1237 | 81 | 117 | 960, 963, 964 | 1374 | 179 | 238 | 1093-1095, 1098, 1100-1103 |
| 1237 | 119 | 230 | 960, 963, 964 | 1375 | 152 | 211 | 1093-1095, 1098, 1100-1103 |
| 1237 | 257 | 350 | 960, 963, 964 | 1376 | 107 | 166 | 1093-1095, 1098, 1100-1103 |
| 1238 | 39 | 136 | 960, 964 | 1371 | 278 | 325 | 1093-1095, 1098, 1100-1103 |
| 1238 | 171 | 212 | 960, 964 | 1372 | 212 | 259 | 1093-1095, 1098, 1100-1103 |
| 1239 | 38 | 135 | 960, 964 | 1373 | 268 | 315 | 1093-1095, 1098, 1100-1103 |
| 1239 | 170 | 211 | 960, 964 | 1374 | 275 | 322 | 1093-1095, 1098, 1100-1103 |
| 1240 | 2 | 64 | 960, 963, 964 | 1375 | 248 | 295 | 1093-1095, 1098, 1100-1103 |
| 1240 | 91 | 188 | 960, 963, 964 | 1376 | 203 | 250 | 1093-1095, 1098, 1100-1103 |
| 1240 | 223 | 264 | 960, 963, 964 | 1309 | 1 | 69 | 1114, 1115 |
| 1241 | 81 | 117 | 960, 963, 964 | 1309 | 71 | 96 | 1114, 1115 |
| 1241 | 119 | 230 | 960, 963, 964 | 1309 | 98 | 144 | 1114, 1115 |
| 1241 | 257 | 351 | 960, 963, 964 | 1309 | 152 | 195 | 1114, 1115 |
| 1242 | 2 | 48 | 960, 963, 964 | 1309 | 197 | 237 | 1114, 1115 |
| 1242 | 75 | 172 | 960, 963, 964 | 1309 | 254 | 352 | 1114, 1115 |
| 1242 | 207 | 248 | 960, 963, 964 | 1310 | 25 | 92 | 1114, 1115 |
| 1243 | 118 | 158 | 965, 966, 968, 969 | 1310 | 94 | 119 | 1114, 1115 |
| 1243 | 283 | 304 | 965, 966, 968, 969 | 1310 | 121 | 167 | 1114, 1115 |
| 1243 | 310 | 348 | 965, 966, 968, 969 | 1310 | 175 | 218 | 1114, 1115 |
| 1244 | 165 | 205 | 965, 966, 968, 969 | 1310 | 220 | 260 | 1114, 1115 |
| 1244 | 330 | 351 | 965, 966, 968, 969 | 1310 | 277 | 351 | 1114, 1115 |
| 1246 | 205 | 245 | 965, 966, 967, 968, 969 | 1311 | 7 | 74 | 1114, 1115 |
| 1247 | 206 | 246 | 965, 966, 967, 968, 969 | 1311 | 76 | 101 | 1114, 1115 |
| 1248 | 163 | 203 | 965, 966, 968, 969 | 1311 | 103 | 149 | 1114, 1115 |
| 1248 | 328 | 349 | 965, 966, 968, 969 | 1311 | 157 | 200 | 1114, 1115 |
| 1245 | 1 | 20 | 967 | 1311 | 202 | 242 | 1114, 1115 |
| 1245 | 22 | 42 | 967 | 1311 | 259 | 351 | 1114, 1115 |
| 1245 | 104 | 135 | 967 | 1312 | 9 | 76 | 1114, 1115 |
| 1245 | 137 | 155 | 967 | 1312 | 78 | 103 | 1114, 1115 |
| 1245 | 187 | 209 | 967 | 1312 | 105 | 151 | 1114, 1115 |
| 1246 | 36 | 58 | 965, 966, 967, 968, 969 | 1312 | 159 | 202 | 1114, 1115 |
| 1247 | 37 | 59 | 965, 966, 967, 968, 969 | 1312 | 204 | 244 | 1114, 1115 |
| 1244 | 330 | 352 | 965, 966, 968, 969 | 1312 | 261 | 352 | 1114, 1115 |
| 1249 | 2 | 20 | 970, 973, 974, 978, 979 | 1309 | 2 | 69 | 1114, 1115 |
| 1250 | 5 | 84 | 969-971, 973-979 | 1309 | 254 | 327 | 1114, 1115 |
| 1250 | 86 | 270 | 969-971, 973-979 | 1310 | 22 | 92 | 1114, 1115 |
| 1250 | 278 | 306 | 969-971, 973-979 | 1310 | 277 | 350 | 1114, 1115 |

TABLE 4-continued

| QUERY Trigger SEQ ID NO: | start | end | SUBJECT Trigger SEQ ID NO: | QUERY Trigger SEQ ID NO: | start | end | SUBJECT Trigger SEQ ID NO: |
|---|---|---|---|---|---|---|---|
| 1250 | 326 | 351 | 969-971, 973-979 | 1311 | 4 | 74 | 1114, 1115 |
| 1251 | 2 | 52 | 969-971, 973-979 | 1311 | 259 | 332 | 1114, 1115 |
| 1251 | 54 | 238 | 969-971, 973-979 | 1312 | 6 | 76 | 1114, 1115 |
| 1251 | 246 | 274 | 969-971, 973-979 | 1312 | 261 | 334 | 1114, 1115 |
| 1251 | 294 | 322 | 969-971, 973-979 | 1315 | 56 | 87 | 1117, 1119-1125 |
| 1253 | 115 | 194 | 969-971, 973-979 | 1315 | 91 | 114 | 1117, 1119-1125 |
| 1253 | 196 | 351 | 969-971, 973-979 | 1315 | 116 | 144 | 1117, 1119-1125 |
| 1254 | 3 | 31 | 970, 971, 973, 974, 977-979 | 1315 | 146 | 171 | 1117, 1119-1125 |
| 1254 | 51 | 79 | 970, 971, 973, 974, 977-979 | 1315 | 185 | 225 | 1117, 1119-1125 |
| 1255 | 282 | 352 | 970, 971, 973-978, 1626, 1629 | 1315 | 275 | 294 | 1117, 1119-1125 |
| 1256 | 1 | 53 | 970, 971, 973-978 | 1315 | 317 | 342 | 1117, 1119-1125 |
| 1256 | 55 | 239 | 970, 971, 973-978 | 1316 | 22 | 45 | 1117, 1119-1125 |
| 1256 | 247 | 275 | 970, 971, 973-978 | 1316 | 47 | 75 | 1117, 1119-1125 |
| 1256 | 295 | 323 | 970, 971, 973-978 | 1316 | 77 | 102 | 1117, 1119-1125 |
| 1257 | 6 | 85 | 970, 971, 973-978 | 1316 | 116 | 156 | 1117, 1119-1125 |
| 1257 | 87 | 271 | 970, 971, 973-978 | 1316 | 206 | 225 | 1117, 1119-1125 |
| 1257 | 279 | 307 | 970, 971, 973-978 | 1316 | 248 | 273 | 1117, 1119-1125 |
| 1257 | 327 | 351 | 970, 971, 973-978 | 1316 | 275 | 317 | 1117, 1119-1125 |
| 1250 | 1 | 84 | 969-971, 973-979 | 1318 | 144 | 175 | 1117, 1119-1125 |
| 1250 | 326 | 352 | 969-971, 973-979 | 1318 | 179 | 202 | 1117, 1119-1125 |
| 1251 | 294 | 319 | 969-971, 973-979 | 1318 | 204 | 232 | 1117, 1119-1125 |
| 1253 | 112 | 194 | 969-971, 973-979 | 1318 | 234 | 259 | 1117, 1119-1125 |
| 1254 | 51 | 76 | 970, 971, 973, 974, 977-979 | 1318 | 273 | 313 | 1117, 1119-1125 |
| 1255 | 279 | 352 | 970, 971, 973-978, 1626, 1629 | 1319 | 2 | 20 | 1117, 1119-1125 |
| 1256 | 295 | 320 | 970, 971, 973-978 | 1319 | 24 | 47 | 1117, 1119-1125 |
| 1257 | 3 | 85 | 970, 971, 973-978 | 1319 | 49 | 77 | 1117, 1119-1125 |
| 1252 | 31 | 89 | 972 | 1319 | 79 | 104 | 1117, 1119-1125 |
| 1252 | 91 | 236 | 972 | 1319 | 118 | 158 | 1117, 1119-1125 |
| 1252 | 238 | 266 | 972 | 1319 | 208 | 227 | 1117, 1119-1125 |
| 1252 | 277 | 337 | 972 | 1319 | 250 | 275 | 1117, 1119-1125 |
| 1249 | 2 | 23 | 970, 973, 974, 978, 979 | 1319 | 277 | 319 | 1117, 1119-1125 |
| 1249 | 25 | 44 | 970, 973, 974, 978, 979 | 1313 | 17 | 81 | 1118, 1125 |
| 1250 | 34 | 84 | 969-971, 973-979 | 1313 | 92 | 117 | 1118, 1125 |
| 1251 | 1 | 52 | 969-971, 973-979 | 1313 | 137 | 204 | 1118, 1125 |
| 1251 | 294 | 325 | 969-971, 973-979 | 1313 | 215 | 240 | 1118, 1125 |
| 1251 | 327 | 346 | 969-971, 973-979 | 1313 | 242 | 291 | 1118, 1125 |
| 1253 | 144 | 194 | 969-971, 973-979 | 1313 | 293 | 329 | 1118, 1125 |
| 1254 | 51 | 82 | 970, 971, 973, 974, 977-979 | 1314 | 22 | 89 | 1118-1125 |
| 1254 | 84 | 103 | 970, 971, 973, 974, 977-979 | 1314 | 100 | 125 | 1118-1125 |
| 1255 | 311 | 352 | 970, 971, 973-978, 1626, 1629 | 1314 | 127 | 176 | 1118-1125 |
| 1256 | 3 | 53 | 970, 971, 973-978 | 1314 | 178 | 214 | 1118-1125 |
| 1256 | 295 | 326 | 970, 971, 973-978 | 1317 | 25 | 92 | 1118, 1120-1122, 1124, 1125 |
| 1256 | 328 | 347 | 970, 971, 973-978 | 1317 | 103 | 128 | 1118, 1120-1122, 1124, 1125 |
| 1257 | 35 | 85 | 970, 971, 973-978 | 1317 | 130 | 179 | 1118, 1120-1122, 1124, 1125 |
| 1250 | 47 | 84 | 969-971, 973-979 | 1317 | 181 | 217 | 1118, 1120-1122, 1124, 1125 |
| 1251 | 15 | 52 | 969-971, 973-979 | 1314 | 332 | 351 | 1118-1125 |
| 1253 | 157 | 194 | 969-971, 973-979 | 1315 | 27 | 51 | 1117, 1119-1125 |
| 1255 | 324 | 352 | 970, 971, 973-978, 1626, 1629 | 1316 | 275 | 306 | 1117, 1119-1125 |
| 1256 | 16 | 53 | 970, 971, 973-978 | 1318 | 115 | 139 | 1117, 1119-1125 |
| 1257 | 48 | 85 | 970, 971, 973-978 | 1319 | 277 | 308 | 1117, 1119-1125 |
| 1250 | 2 | 84 | 969-971, 973-979 | 1314 | 330 | 351 | 1118-1125 |
| 1250 | 86 | 241 | 969-971, 973-979 | 1315 | 25 | 51 | 1117, 1119-1125 |
| 1251 | 54 | 209 | 969-971, 973-979 | 1316 | 275 | 303 | 1117, 1119-1125 |
| 1253 | 1 | 68 | 969-971, 973-979 | 1317 | 333 | 351 | 1118, 1120-1122, 1124, 1125 |
| 1253 | 91 | 194 | 969-971, 973-979 | 1318 | 113 | 139 | 1117, 1119-1125 |
| 1253 | 196 | 352 | 969-971, 973-979 | 1319 | 277 | 305 | 1117, 1119-1125 |
| 1255 | 169 | 235 | 970, 971, 973-978, 1626, 1629 | 1314 | 262 | 293 | 1118-1125 |
| 1255 | 258 | 352 | 970, 971, 973-978, 1626, 1629 | 1314 | 295 | 314 | 1118-1125 |
| 1256 | 55 | 210 | 970, 971, 973-978 | 1314 | 316 | 351 | 1118-1125 |
| 1257 | 1 | 85 | 970, 971, 973-978 | 1315 | 11 | 51 | 1117, 1119-1125 |
| 1257 | 87 | 242 | 970, 971, 973-978 | 1317 | 265 | 296 | 1118, 1120-1122, 1124, 1125 |
| 1250 | 86 | 110 | 969-971, 973-979 | 1317 | 298 | 317 | 1118, 1120-1122, 1124, 1125 |
| 1251 | 54 | 78 | 969-971, 973-979 | 1317 | 319 | 351 | 1118, 1120-1122, 1124, 1125 |
| 1253 | 2 | 76 | 969-971, 973-979 | 1318 | 45 | 76 | 1117, 1119-1125 |
| 1253 | 196 | 220 | 969-971, 973-979 | 1318 | 78 | 97 | 1117, 1119-1125 |
| 1255 | 39 | 130 | 970, 971, 973-978, 1626, 1629 | 1318 | 99 | 139 | 1117, 1119-1125 |
| 1255 | 132 | 235 | 970, 971, 973-978, 1626, 1629 | 1316 | 275 | 324 | 1117, 1119-1125 |

TABLE 4-continued

| QUERY Trigger SEQ ID NO: | start | end | SUBJECT Trigger SEQ ID NO: | QUERY Trigger SEQ ID NO: | start | end | SUBJECT Trigger SEQ ID NO: |
|---|---|---|---|---|---|---|---|
| 1256 | 55 | 79 | 970, 971, 973-978 | 1319 | 277 | 326 | 1117, 1119-1125 |
| 1257 | 87 | 111 | 970, 971, 973-978 | 1299 | 50 | 96 | 1126-1131, 1651-1653 |
| 1250 | 326 | 350 | 969-971, 973-979 | 1300 | 2 | 43 | 1126-1131, 1651-1653 |
| 1251 | 294 | 318 | 969-971, 973-979 | 1300 | 66 | 112 | 1126-1131, 1651-1653 |
| 1253 | 110 | 194 | 969-971, 973-979 | 1300 | 123 | 154 | 1126-1131, 1651-1653 |
| 1254 | 51 | 75 | 970, 971, 973, 974, 977-979 | 1300 | 183 | 211 | 1126-1131, 1651-1653 |
| 1255 | 277 | 352 | 970, 971, 973-978, 1626, 1629 | 1300 | 213 | 232 | 1126-1131, 1651-1653 |
| 1256 | 295 | 319 | 970, 971, 973-978 | 1300 | 264 | 310 | 1126-1131, 1651-1653 |
| 1257 | 327 | 352 | 970, 971, 973-978 | 1301 | 1 | 35 | 1126-1131 |
| 1250 | 32 | 84 | 969-971, 973-979 | 1301 | 37 | 84 | 1126-1131 |
| 1253 | 142 | 194 | 969-971, 973-979 | 1301 | 107 | 153 | 1126-1131 |
| 1255 | 309 | 352 | 970, 971, 973-978, 1626, 1629 | 1301 | 164 | 195 | 1126-1131 |
| 1257 | 33 | 85 | 970, 971, 973-978 | 1301 | 224 | 252 | 1126-1131 |
| 1249 | 46 | 68 | 970, 973, 974, 978, 979 | 1301 | 254 | 273 | 1126-1131 |
| 1250 | 61 | 84 | 969-971, 973-979 | 1301 | 305 | 351 | 1126-1131 |
| 1251 | 29 | 52 | 969-971, 973-979 | 1302 | 26 | 54 | 1126-1131, 1651-1653 |
| 1253 | 171 | 194 | 969-971, 973-979 | 1302 | 56 | 75 | 1126-1131, 1651-1653 |
| 1254 | 105 | 127 | 970, 971, 973, 974, 977-979 | 1302 | 107 | 153 | 1126-1131, 1651-1653 |
| 1256 | 30 | 53 | 970, 971, 973-978 | 1303 | 11 | 39 | 1126-1131, 1651-1653 |
| 1257 | 62 | 85 | 970, 971, 973-978 | 1303 | 41 | 60 | 1126-1131, 1651-1653 |
| 1259 | 192 | 226 | 999-1004 | 1303 | 92 | 138 | 1126-1131, 1651-1653 |
| 1259 | 249 | 298 | 999-1004 | 1299 | 50 | 114 | 1126-1131, 1651-1653 |
| 1259 | 321 | 352 | 999-1004 | 1299 | 131 | 162 | 1126-1131, 1651-1653 |
| 1260 | 190 | 224 | 999-1004 | 1299 | 215 | 236 | 1126-1131, 1651-1653 |
| 1260 | 247 | 296 | 999-1004 | 1299 | 248 | 270 | 1126-1131, 1651-1653 |
| 1260 | 319 | 351 | 999-1004 | 1299 | 272 | 309 | 1126-1131, 1651-1653 |
| 1261 | 99 | 133 | 999-1004 | 1300 | 264 | 328 | 1126-1131, 1651-1653 |
| 1261 | 156 | 205 | 999-1004 | 1302 | 107 | 171 | 1126-1131, 1651-1653 |
| 1261 | 228 | 289 | 999-1004 | 1302 | 188 | 219 | 1126-1131, 1651-1653 |
| 1261 | 300 | 334 | 999-1004 | 1302 | 272 | 293 | 1126-1131, 1651-1653 |
| 1262 | 82 | 116 | 999-1004 | 1302 | 305 | 327 | 1126-1131, 1651-1653 |
| 1262 | 139 | 188 | 999-1004 | 1302 | 329 | 351 | 1126-1131, 1651-1653 |
| 1262 | 211 | 272 | 999-1004 | 1303 | 92 | 156 | 1126-1131, 1651-1653 |
| 1262 | 283 | 317 | 999-1004 | 1303 | 173 | 204 | 1126-1131, 1651-1653 |
| 1262 | 319 | 350 | 999-1004 | 1303 | 257 | 278 | 1126-1131, 1651-1653 |
| 1263 | 324 | 351 | 999-1004 | 1303 | 290 | 312 | 1126-1131, 1651-1653 |
| 1264 | 191 | 225 | 999-1004 | 1303 | 314 | 351 | 1126-1131, 1651-1653 |
| 1264 | 248 | 297 | 999-1004 | 1299 | 272 | 352 | 1126-1131, 1651-1653 |
| 1264 | 320 | 351 | 999-1004 | 1299 | 272 | 344 | 1126-1131, 1651-1653 |
| 1265 | 98 | 132 | 999-1004 | 1299 | 272 | 318 | 1126-1131, 1651-1653 |
| 1265 | 155 | 204 | 999-1004 | 1299 | 272 | 310 | 1126-1131, 1651-1653 |
| 1265 | 227 | 288 | 999-1004 | 1304 | 2 | 25 | 1132, 1134, 1135, 1136 |
| 1265 | 299 | 333 | 999-1004 | 1304 | 36 | 169 | 1132, 1134, 1135, 1136 |
| 1259 | 95 | 145 | 999-1004 | 1304 | 186 | 214 | 1132, 1134, 1135, 1136 |
| 1259 | 165 | 226 | 999-1004 | 1304 | 231 | 250 | 1132, 1134, 1135, 1136 |
| 1260 | 93 | 143 | 999-1004 | 1304 | 264 | 307 | 1132, 1134, 1135, 1136 |
| 1260 | 163 | 224 | 999-1004 | 1306 | 2 | 70 | 1132, 1134, 1135, 1136 |
| 1261 | 1 | 52 | 999-1004 | 1306 | 87 | 115 | 1132, 1134, 1135, 1136 |
| 1261 | 72 | 133 | 999-1004 | 1306 | 132 | 151 | 1132, 1134, 1135, 1136 |
| 1262 | 1 | 35 | 999-1004 | 1306 | 165 | 208 | 1132, 1134, 1135, 1136 |
| 1262 | 55 | 116 | 999-1004 | 1307 | 1 | 27 | 1132, 1134, 1135, 1136 |
| 1263 | 227 | 277 | 999-1004 | 1307 | 29 | 69 | 1132, 1134, 1135, 1136 |
| 1263 | 297 | 351 | 999-1004 | 1307 | 80 | 213 | 1132, 1134, 1135, 1136 |
| 1264 | 94 | 144 | 999-1004 | 1307 | 230 | 258 | 1132, 1134, 1135, 1136 |
| 1264 | 164 | 225 | 999-1004 | 1307 | 275 | 294 | 1132, 1134, 1135, 1136 |
| 1265 | 2 | 51 | 999-1004 | 1307 | 308 | 351 | 1132, 1134, 1135, 1136 |
| 1265 | 71 | 132 | 999-1004 | 1308 | 2 | 33 | 1132, 1134, 1135, 1136 |
| 1259 | 15 | 40 | 999-1004 | 1308 | 44 | 177 | 1132, 1134, 1135, 1136 |
| 1259 | 42 | 64 | 999-1004 | 1308 | 194 | 222 | 1132, 1134, 1135, 1136 |
| 1259 | 66 | 88 | 999-1004 | 1308 | 239 | 258 | 1132, 1134, 1135, 1136 |
| 1259 | 90 | 145 | 999-1004 | 1308 | 272 | 315 | 1132, 1134, 1135, 1136 |
| 1259 | 165 | 219 | 999-1004 | 1347 | 2 | 28 | 1132, 1134, 1135, 1136 |
| 1260 | 13 | 38 | 999-1004 | 1347 | 39 | 172 | 1132, 1134, 1135, 1136 |
| 1260 | 40 | 62 | 999-1004 | 1347 | 189 | 217 | 1132, 1134, 1135, 1136 |
| 1260 | 64 | 86 | 999-1004 | 1347 | 234 | 253 | 1132, 1134, 1135, 1136 |
| 1260 | 88 | 143 | 999-1004 | 1347 | 267 | 310 | 1132, 1134, 1135, 1136 |
| 1260 | 163 | 217 | 999-1004 | 1305 | 1 | 133 | 1133, 1137, 1138, 1580, 1581, 1583 |
| 1261 | 2 | 52 | 999-1004 | 1305 | 135 | 154 | 1133, 1137, 1138, 1580, 1581, 1583 |
| 1261 | 72 | 126 | 999-1004 | 1305 | 156 | 178 | 1133, 1137, 1138, 1580, 1581, 1583 |

TABLE 4-continued

| QUERY Trigger SEQ ID NO: | start | end | SUBJECT Trigger SEQ ID NO: | QUERY Trigger SEQ ID NO: | start | end | SUBJECT Trigger Trigger SEQ ID NO: |
|---|---|---|---|---|---|---|---|
| 1262 | 55 | 109 | 999-1004 | 1305 | 195 | 280 | 1133, 1137, 1138, 1580, 1581, 1583 |
| 1263 | 1 | 60 | 999-1004 | 1305 | 330 | 351 | 1133, 1137, 1138, 1580, 1581, 1583 |
| 1263 | 105 | 127 | 999-1004 | 1344 | 13 | 35 | 1133, 1137, 1138, 1580, 1581, 1583 |
| 1263 | 147 | 172 | 999-1004 | 1344 | 52 | 137 | 1133, 1137, 1138, 1580, 1581, 1583 |
| 1263 | 174 | 196 | 999-1004 | 1344 | 187 | 208 | 1133, 1137, 1138, 1580, 1581, 1583 |
| 1263 | 198 | 220 | 999-1004 | 1345 | 50 | 181 | 1133, 1137, 1138, 1580, 1581, 1583 |
| 1263 | 222 | 277 | 999-1004 | 1345 | 183 | 202 | 1133, 1137, 1138, 1580, 1581, 1583 |
| 1263 | 297 | 352 | 999-1004 | 1345 | 204 | 226 | 1133, 1137, 1138, 1580, 1581, 1583 |
| 1264 | 14 | 39 | 999-1004 | 1345 | 243 | 328 | 1133, 1137, 1138, 1580, 1581, 1583 |
| 1264 | 41 | 63 | 999-1004 | 1346 | 2 | 81 | 1133, 1137, 1138 |
| 1264 | 65 | 87 | 999-1004 | 1346 | 131 | 152 | 1133, 1137, 1138 |
| 1264 | 89 | 144 | 999-1004 | 1304 | 1 | 25 | 1132, 1134, 1135, 1136 |
| 1264 | 164 | 218 | 999-1004 | 1304 | 264 | 334 | 1132, 1134, 1135, 1136 |
| 1265 | 71 | 125 | 999-1004 | 1306 | 165 | 235 | 1132, 1134, 1135, 1136 |
| 1259 | 190 | 226 | 999-1004 | 1307 | 46 | 69 | 1132, 1134, 1135, 1136 |
| 1260 | 188 | 224 | 999-1004 | 1308 | 10 | 33 | 1132, 1134, 1135, 1136 |
| 1261 | 97 | 133 | 999-1004 | 1308 | 272 | 342 | 1132, 1134, 1135, 1136 |
| 1262 | 80 | 116 | 999-1004 | 1347 | 5 | 28 | 1132, 1134, 1135, 1136 |
| 1263 | 322 | 351 | 999-1004 | 1347 | 267 | 337 | 1132, 1134, 1135, 1136 |
| 1264 | 189 | 225 | 999-1004 | 1304 | 101 | 169 | 1132, 1134, 1135, 1136 |
| 1265 | 96 | 132 | 999-1004 | 1306 | 1 | 70 | 1132, 1134, 1135, 1136 |
| 1259 | 96 | 145 | 999-1004 | 1306 | 237 | 310 | 1132, 1134, 1135, 1136 |
| 1260 | 94 | 143 | 999-1004 | 1306 | 312 | 352 | 1132, 1134, 1135, 1136 |
| 1261 | 3 | 52 | 999-1004 | 1307 | 145 | 213 | 1132, 1134, 1135, 1136 |
| 1263 | 228 | 277 | 999-1004 | 1308 | 109 | 177 | 1132, 1134, 1135, 1136 |
| 1264 | 95 | 144 | 999-1004 | 1347 | 104 | 172 | 1132, 1134, 1135, 1136 |
| 1265 | 1 | 51 | 999-1004 | 1307 | 38 | 69 | 1132, 1134, 1135, 1136 |
| 1259 | 165 | 218 | 999-1004 | 1308 | 1 | 33 | 1132, 1134, 1135, 1136 |
| 1260 | 163 | 216 | 999-1004 | 1344 | 187 | 239 | 1133, 1137, 1138, 1580, 1581, 1583 |
| 1261 | 72 | 125 | 999-1004 | 1344 | 241 | 272 | 1133, 1137, 1138, 1580, 1581, 1583 |
| 1262 | 55 | 108 | 999-1004 | 1344 | 286 | 308 | 1133, 1137, 1138, 1580, 1581, 1583 |
| 1263 | 2 | 60 | 999-1004 | 1344 | 310 | 329 | 1133, 1137, 1138, 1580, 1581, 1583 |
| 1263 | 297 | 350 | 999-1004 | 1346 | 131 | 183 | 1133, 1137, 1138 |
| 1264 | 164 | 217 | 999-1004 | 1346 | 185 | 216 | 1133, 1137, 1138 |
| 1265 | 71 | 124 | 999-1004 | 1346 | 230 | 252 | 1133, 1137, 1138 |
| 1266 | 2 | 39 | 1016-1023 | 1346 | 254 | 273 | 1133, 1137, 1138 |
| 1266 | 41 | 87 | 1016-1023 | 1305 | 227 | 280 | 1133, 1137, 1138, 1580, 1581, 1583 |
| 1266 | 89 | 129 | 1016-1023 | 1344 | 84 | 137 | 1133, 1137, 1138, 1580, 1581, 1583 |
| 1267 | 2 | 74 | 1016-1023 | 1345 | 275 | 328 | 1133, 1137, 1138, 1580, 1581, 1583 |
| 1267 | 76 | 122 | 1016-1023 | 1346 | 28 | 81 | 1133, 1137, 1138 |
| 1267 | 124 | 164 | 1016-1023 | 1346 | 290 | 351 | 1133, 1137, 1138 |
| 1268 | 2 | 53 | 1016-1023 | 1348 | 44 | 66 | 1139, 1140, 1141, 1142 |
| 1268 | 55 | 101 | 1016-1023 | 1348 | 104 | 129 | 1139, 1140, 1141, 1142 |
| 1268 | 103 | 143 | 1016-1023 | 1348 | 131 | 156 | 1139, 1140, 1141, 1142 |
| 1269 | 2 | 72 | 1016-1023 | 1348 | 158 | 195 | 1139, 1140, 1141, 1142 |
| 1269 | 74 | 120 | 1016-1023 | 1348 | 167 | 189 | 1139, 1140, 1141, 1142 |
| 1269 | 122 | 162 | 1016-1023 | 1348 | 197 | 237 | 1139, 1140, 1141, 1142 |
| 1270 | 2 | 107 | 1016-1023 | 1348 | 215 | 234 | 1139, 1140, 1141, 1142 |
| 1270 | 109 | 155 | 1016-1023 | 1348 | 4 | 49 | 1139, 1140, 1141, 1142 |
| 1270 | 157 | 197 | 1016-1023 | 1348 | 4 | 74 | 1139, 1140, 1141, 1142 |
| 1271 | 2 | 62 | 1016-1023 | 1348 | 4 | 85 | 1139, 1140, 1141, 1142 |
| 1271 | 64 | 110 | 1016-1023 | 1349 | 19 | 90 | 1143 |
| 1271 | 112 | 152 | 1016-1023 | 1349 | 146 | 207 | 1143 |
| 1266 | 131 | 177 | 1016-1023 | 1349 | 209 | 256 | 1143 |
| 1266 | 179 | 207 | 1016-1023 | 1350 | 32 | 51 | 1144-1151, 1703 |
| 1266 | 209 | 243 | 1016-1023 | 1350 | 71 | 90 | 1144-1151, 1703 |
| 1267 | 166 | 212 | 1016-1023 | 1351 | 118 | 137 | 1144-1151 |
| 1267 | 214 | 242 | 1016-1023 | 1351 | 157 | 176 | 1144-1151 |
| 1267 | 244 | 278 | 1016-1023 | 1353 | 81 | 100 | 1144-1151 |

TABLE 4-continued

| QUERY Trigger | | | | QUERY Trigger | | | |
|---|---|---|---|---|---|---|---|
| SEQ ID NO: | start | end | SUBJECT Trigger SEQ ID NO: | SEQ ID NO: | start | end | SUBJECT Trigger SEQ ID NO: |
| 1268 | 145 | 191 | 1016-1023 | 1353 | 120 | 139 | 1144-1151 |
| 1268 | 193 | 221 | 1016-1023 | 1354 | 1 | 42 | 1144-1151 |
| 1268 | 223 | 257 | 1016-1023 | 1354 | 218 | 237 | 1144-1151 |
| 1269 | 164 | 210 | 1016-1023 | 1354 | 257 | 276 | 1144-1151 |
| 1269 | 212 | 240 | 1016-1023 | 1356 | 43 | 62 | 1144-1151 |
| 1269 | 242 | 276 | 1016-1023 | 1356 | 82 | 101 | 1144-1151 |
| 1270 | 199 | 245 | 1016-1023 | 1350 | 176 | 201 | 1144-1151, 1703 |
| 1270 | 247 | 275 | 1016-1023 | 1350 | 209 | 231 | 1144-1151, 1703 |
| 1270 | 277 | 311 | 1016-1023 | 1350 | 236 | 267 | 1144-1151, 1703 |
| 1271 | 154 | 200 | 1016-1023 | 1351 | 262 | 287 | 1144-1151 |
| 1271 | 202 | 230 | 1016-1023 | 1351 | 295 | 317 | 1144-1151 |
| 1271 | 232 | 266 | 1016-1023 | 1351 | 322 | 351 | 1144-1151 |
| 1266 | 209 | 294 | 1016-1023 | 1353 | 225 | 250 | 1144-1151 |
| 1266 | 296 | 316 | 1016-1023 | 1353 | 258 | 280 | 1144-1151 |
| 1267 | 1 | 74 | 1016-1023 | 1353 | 285 | 316 | 1144-1151 |
| 1267 | 244 | 329 | 1016-1023 | 1356 | 187 | 212 | 1144-1151 |
| 1267 | 331 | 351 | 1016-1023 | 1356 | 220 | 242 | 1144-1151 |
| 1268 | 223 | 308 | 1016-1023 | 1356 | 247 | 278 | 1144-1151 |
| 1268 | 310 | 330 | 1016-1023 | 1350 | 236 | 265 | 1144-1151, 1703 |
| 1269 | 242 | 327 | 1016-1023 | 1351 | 322 | 352 | 1144-1151 |
| 1269 | 329 | 349 | 1016-1023 | 1353 | 285 | 314 | 1144-1151 |
| 1270 | 35 | 107 | 1016-1023 | 1356 | 247 | 276 | 1144-1151 |
| 1270 | 277 | 351 | 1016-1023 | 1350 | 287 | 306 | 1144-1151, 1703 |
| 1271 | 232 | 317 | 1016-1023 | 1350 | 323 | 348 | 1144-1151, 1703 |
| 1271 | 319 | 339 | 1016-1023 | 1352 | 2 | 21 | 1147, 1150, 1151, 1703 |
| 1266 | 296 | 318 | 1016-1023 | 1352 | 38 | 63 | 1147, 1150, 1151, 1703 |
| 1267 | 4 | 74 | 1016-1023 | 1355 | 5 | 24 | 1147, 1150, 1151, 1703 |
| 1268 | 310 | 332 | 1016-1023 | 1355 | 41 | 66 | 1147, 1150, 1151, 1703 |
| 1269 | 1 | 72 | 1016-1023 | 1356 | 298 | 317 | 1144-1151 |
| 1269 | 329 | 351 | 1016-1023 | 1358 | 322 | 351 | 1079-1082, 1152-1154, 1455, 1457, 1458 |
| 1270 | 37 | 107 | 1016-1023 | 1364 | 262 | 291 | 1079-1082, 1152-1154, 1455, 1457, 1458 |
| 1271 | 319 | 341 | 1016-1023 | 1366 | 229 | 258 | 1079-1082, 1152-1154, 1455, 1457, 1458 |
| 1266 | 131 | 157 | 1016-1023 | 1367 | 154 | 183 | 1079-1082, 1152-1154 |
| 1267 | 166 | 192 | 1016-1023 | 1361 | 2 | 41 | 1079-1082, 1152-1154, 1455, 1457, 1458 |
| 1268 | 145 | 171 | 1016-1023 | 1210 | 1 | 35 | 1431 |
| 1269 | 164 | 190 | 1016-1023 | 1211 | 30 | 63 | 1431 |
| 1270 | 199 | 225 | 1016-1023 | 1213 | 15 | 48 | 1431 |
| 1271 | 154 | 180 | 1016-1023 | 1217 | 19 | 52 | 1431 |
| 1295 | 113 | 168 | 1026, 1027, 1024 | 1357 | 162 | 200 | 1079-1082, 1152-1154, 1455, 1457, 1458 |
| 1295 | 170 | 201 | 1026, 1027, 1024 | 1358 | 124 | 162 | 1079-1082, 1152-1154, 1455, 1457, 1458 |
| 1295 | 203 | 233 | 1026, 1027, 1024 | 1359 | 130 | 168 | 1079-1082, 1152-1154, 1455, 1457, 1458 |
| 1295 | 236 | 258 | 1026, 1027, 1024 | 1360 | 137 | 175 | 1079-1082, 1152-1154, 1455, 1457, 1458 |
| 1297 | 128 | 183 | 1026, 1027, 1024 | 1361 | 163 | 201 | 1079-1082, 1152-1154, 1455, 1457, 1458 |
| 1297 | 185 | 216 | 1026, 1027, 1024 | 1362 | 130 | 168 | 1079-1082, 1152-1154, 1455, 1457, 1458 |
| 1297 | 218 | 248 | 1026, 1027, 1024 | 1363 | 132 | 170 | 1079-1082, 1152-1154, 1455, 1457, 1458 |
| 1296 | 1 | 44 | 1025, 1028, 1029, 1515-1518, 1520 | 1364 | 64 | 102 | 1079-1082, 1152-1154, 1455, 1457, 1458 |
| 1298 | 7 | 57 | 1025, 1028, 1029 | 1365 | 134 | 172 | 1079-1082, 1152-1154, 1455, 1457, 1458 |
| 1298 | 59 | 96 | 1025, 1028, 1029 | 1366 | 31 | 69 | 1079-1082, 1152-1154, 1455, 1457, 1458 |
| 1298 | 110 | 132 | 1025, 1028, 1029 | 1054 | 198 | 244 | 1492, 1496, 1497, 1498 |
| 1298 | 143 | 210 | 1025, 1028, 1029 | 1054 | 285 | 319 | 1492, 1496, 1497, 1498 |
| 1295 | 17 | 87 | 1026, 1027, 1024 | 1056 | 191 | 237 | 1492, 1496, 1497, 1498 |
| 1297 | 32 | 102 | 1026, 1027, 1024 | 1056 | 278 | 312 | 1492, 1496, 1497, 1498 |
| 1294 | 127 | 153 | 1027 | 1057 | 14 | 60 | 1492, 1496, 1497, 1498 |
| 1295 | 17 | 46 | 1026, 1027, 1024 | 1057 | 101 | 135 | 1492, 1496, 1497, 1498 |
| 1297 | 32 | 61 | 1026, 1027, 1024 | 1057 | 233 | 264 | 1492, 1496, 1497, 1498 |
| 1298 | 5 | 57 | 1025, 1028, 1029 | 1060 | 269 | 315 | 1492, 1496, 1497, 1498 |
| 1320 | 249 | 268 | 1033, 1035, 1076 | 1390 | 10 | 50 | 1054-1057, 1060, 1492, 1496-1498 |
| 1324 | 2 | 23 | 1036, 1037, 1038 | 1390 | 142 | 173 | 1054-1057, 1060, 1492, 1496-1498 |

TABLE 4-continued

| QUERY Trigger SEQ ID NO: | start | end | SUBJECT Trigger SEQ ID NO: | QUERY Trigger SEQ ID NO: | start | end | SUBJECT Trigger SEQ ID NO: |
|---|---|---|---|---|---|---|---|
| 1326 | 14 | 38 | 1036, 1037, 1038 | 1391 | 73 | 104 | 1054-1057, 1060, 1492, 1496-1498 |
| 1326 | 95 | 117 | 1036, 1037, 1038 | 1055 | 85 | 131 | 1493, 1494, 1495, 1499, 1500 |
| 1326 | 152 | 174 | 1036, 1037, 1038 | 1058 | 117 | 163 | 1493, 1494, 1495, 1499, 1500 |
| 1326 | 227 | 248 | 1036, 1037, 1038 | 1059 | 118 | 164 | 1493, 1494, 1495, 1499, 1500 |
| 1327 | 44 | 65 | 1036, 1037, 1038 | 1061 | 109 | 155 | 1493, 1494, 1495, 1499, 1500 |
| 1321 | 65 | 86 | 1037 | 1062 | 222 | 268 | 1493, 1494, 1495, 1499, 1500 |
| 1321 | 88 | 132 | 1037 | 1063 | 262 | 308 | 1493, 1494, 1495, 1499, 1500 |
| 1322 | 2 | 34 | 1037 | 1054 | 15 | 64 | 1492, 1496, 1497, 1498 |
| 1322 | 36 | 67 | 1037 | 1054 | 165 | 196 | 1492, 1496, 1497, 1498 |
| 1322 | 135 | 156 | 1037 | 1056 | 8 | 57 | 1492, 1496, 1497, 1498 |
| 1322 | 158 | 202 | 1037 | 1056 | 158 | 189 | 1492, 1496, 1497, 1498 |
| 1323 | 1 | 35 | 1037 | 1060 | 86 | 135 | 1492, 1496, 1497, 1498 |
| 1323 | 37 | 68 | 1037 | 1060 | 236 | 267 | 1492, 1496, 1497, 1498 |
| 1323 | 136 | 157 | 1037 | 1386 | 199 | 248 | 1054-1057, 1060, 1496, 1498 |
| 1323 | 159 | 203 | 1037 | 1388 | 212 | 261 | 1054-1057, 1060, 1496, 1498 |
| 1324 | 2 | 51 | 1036, 1037, 1038 | 1391 | 286 | 335 | 1054-1057, 1060, 1492, 1496-1498 |
| 1324 | 56 | 93 | 1036, 1037, 1038 | 1384 | 311 | 351 | 1055, 1058, 1059, 1061-1063, 1500 |
| 1324 | 95 | 126 | 1036, 1037, 1038 | 1385 | 312 | 351 | 1055, 1058, 1059, 1061-1063, 1500 |
| 1324 | 194 | 215 | 1036, 1037, 1038 | 1387 | 83 | 123 | 1055, 1058, 1059, 1061-1063, 1500, 1057 |
| 1324 | 217 | 261 | 1036, 1037, 1038 | 1389 | 162 | 202 | 1055, 1058, 1059, 1061-1063, 1500 |
| 1325 | 2 | 31 | 1037 | 1296 | 69 | 101 | 1025, 1028, 1029, 1515, 1516, 1517, 1518, 1520 |
| 1325 | 33 | 64 | 1037 | 909 | 305 | 340 | 1531 |
| 1325 | 132 | 153 | 1037 | 960 | 70 | 101 | 1543, 1551 |
| 1325 | 155 | 199 | 1037 | 964 | 259 | 290 | 1543, 1551 |
| 1326 | 227 | 276 | 1036, 1037, 1038 | 1305 | 180 | 226 | 1133, 1137, 1138, 1580, 1581, 1583 |
| 1326 | 281 | 318 | 1036, 1037, 1038 | 1133 | 195 | 226 | 1580, 1581 |
| 1326 | 320 | 350 | 1036, 1037, 1038 | 1137 | 52 | 83 | 1580, 1581 |
| 1327 | 44 | 93 | 1036, 1037, 1038 | 1344 | 37 | 83 | 1133, 1137, 1138, 1580, 1581, 1583 |
| 1327 | 98 | 135 | 1036, 1037, 1038 | 1345 | 228 | 274 | 1133, 1137, 1138, 1580, 1581, 1583 |
| 1327 | 137 | 168 | 1036, 1037, 1038 | 1305 | 180 | 217 | 1133, 1137, 1138, 1580, 1581, 1583 |
| 1327 | 236 | 257 | 1036, 1037, 1038 | 1344 | 37 | 74 | 1133, 1137, 1138, 1580, 1581, 1583 |
| 1327 | 259 | 303 | 1036, 1037, 1038 | 1345 | 228 | 265 | 1133, 1137, 1138, 1580, 1581, 1583 |
| 1324 | 2 | 24 | 1036, 1037, 1038 | 1039 | 176 | 210 | 1590, 1594, 1597, 1598 |
| 1326 | 227 | 249 | 1036, 1037, 1038 | 1040 | 142 | 176 | 1590, 1594, 1597, 1598 |
| 1327 | 44 | 66 | 1036, 1037, 1038 | 1041 | 248 | 282 | 1590, 1594, 1597, 1598 |
| 1328 | 3 | 59 | 1039-1043, 1045, 1594, 1597, 1598 | 1042 | 141 | 175 | 1590, 1594, 1597, 1598 |
| 1328 | 70 | 146 | 1039-1043, 1045, 1594, 1597, 1598 | 1328 | 175 | 209 | 1039-1043, 1045, 1594, 1597, 1598 |
| 1328 | 148 | 215 | 1039-1043, 1045, 1594, 1597, 1598 | 1331 | 2 | 54 | 1039-1043, 1045, 1594, 1597, 1598 |
| 1328 | 232 | 263 | 1039-1043, 1045, 1594, 1597, 1598 | 1331 | 200 | 234 | 1039-1043, 1045, 1594, 1597, 1598 |
| 1328 | 328 | 350 | 1039-1043, 1045, 1594, 1597, 1598 | 1332 | 142 | 176 | 1039-1043, 1045, 1594, 1597, 1598 |
| 1329 | 22 | 53 | 1039-1043 1045 | 1333 | 176 | 210 | 1039-1043, 1045, 1594, 1597, 1598 |
| 1329 | 118 | 140 | 1039-1043 1045 | 1334 | 16 | 68 | 1039-1043, 1045, 1594, 1597, 1598 |
| 1330 | 31 | 62 | 1039-1043 1045 | 1334 | 214 | 248 | 1039-1043, 1045, 1594, 1597, 1598 |
| 1330 | 127 | 149 | 1039-1043 1045 | 1335 | 76 | 110 | 1039-1043, 1045, 1594, 1597, 1598 |
| 1331 | 28 | 84 | 1039-1043, 1045, 1594, 1597, 1598 | 1336 | 8 | 60 | 1039-1043, 1045, 1594, 1597, 1598 |
| 1331 | 95 | 171 | 1039-1043, 1045, 1594, 1597, 1598 | 1336 | 206 | 240 | 1039-1043, 1045, 1594, 1597, 1598 |
| 1331 | 173 | 240 | 1039-1043, 1045, 1594, 1597, 1598 | 1338 | 14 | 66 | 1039-1043, 1045, 1594, 1597, 1598 |
| 1331 | 257 | 288 | 1039-1043, 1045, 1594, 1597, 1598 | 1338 | 212 | 246 | 1039-1043, 1045, 1594, 1597, 1598 |

TABLE 4-continued

| QUERY Trigger | | | | QUERY Trigger | | | |
|---|---|---|---|---|---|---|---|
| SEQ ID NO: | start | end | SUBJECT Trigger SEQ ID NO: | SEQ ID NO: | start | end | SUBJECT Trigger Trigger SEQ ID NO: |
| 1332 | 2 | 26 | 1039-1043, 1045, 1594, 1597, 1598 | 1255 | 165 | 199 | 970, 971, 973-978, 1626, 1629 |
| 1332 | 37 | 113 | 1039-1043, 1045, 1594, 1597, 1598 | 976 | 129 | 163 | 1626, 1629 |
| 1332 | 115 | 182 | 1039-1043, 1045, 1594, 1597, 1598 | 1299 | 98 | 129 | 1126-1131, 1651-1653 |
| 1332 | 199 | 230 | 1039-1043, 1045, 1594, 1597, 1598 | 1300 | 312 | 343 | 1126-1131, 1651-1653 |
| 1332 | 295 | 317 | 1039-1043, 1045, 1594, 1597, 1598 | 1302 | 155 | 186 | 1126-1131, 1651-1653 |
| 1333 | 4 | 60 | 1039-1043, 1045, 1594, 1597, 1598 | 1303 | 140 | 171 | 1126-1131, 1651-1653 |
| 1333 | 71 | 147 | 1039-1043, 1045, 1594, 1597, 1598 | 1350 | 314 | 345 | 1144-1151, 1703 |
| 1333 | 149 | 216 | 1039-1043, 1045, 1594, 1597, 1598 | 1352 | 29 | 60 | 1147, 1150, 1151, 1703 |
| 1333 | 233 | 264 | 1039-1043, 1045, 1594, 1597, 1598 | 1355 | 32 | 63 | 1147, 1150, 1151, 1703 |

All of the materials and methods disclosed and claimed herein can be made and used without undue experimentation as instructed by the above disclosure. Although the materials and methods disclosed herein have been described in terms of preferred embodiments and illustrative examples, it will be apparent to those of skill in the art that variations can be applied to the materials and methods described herein without departing from the concept, spirit and scope of this invention. All such similar substitutes and modifications apparent to those skilled in the art are deemed to be within the spirit, scope and concept of this invention as defined by the appended claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11124792B2). An electronic copy of the "Sequence Listing" will also be available from the USPTO upon request and payment of the fee set forth in 37 CFR 1.19(b)(3).

What is claimed is:

1. A method of causing mortality or stunting in an insect, comprising contacting an insect with at least one recombinant double-stranded RNA (dsRNA) comprising at least one silencing element comprising an RNA strand identical or complementary to 21 or more contiguous nucleotides of an insect target gene sequence that has a DNA sequence of SEQ ID NO: 335 and the complement thereof, wherein said insect is *Phyllotreta* spp., and wherein ingestion of said recombinant dsRNA by said insect results in mortality or stunting in said insect.

2. The method of claim 1, wherein said at least one silencing element comprises an RNA strand having a sequence identical or complementary to 21 or more contiguous nucleotides of SEQ ID NO: 1193.

3. The method of claim 1, wherein said insect is *Phyllotreta cruciferae* (canola flea beetle).

4. The method of claim 1, wherein said silencing element comprises an RNA strand having a sequence of SEQ ID NO: 1193.

5. The method of claim 1, wherein said recombinant dsRNA is provided in a microbial or plant cell that expresses said recombinant RNA, or in a microbial fermentation product, or is chemically synthesized.

6. The method of claim 1, wherein said at least one recombinant dsRNA is provided in a composition comprising said at least one recombinant dsRNA, wherein said composition is applied to a surface of said insect or to a surface of a seed or a plant in need of protection from infestation by said insect.

7. The method of claim 6, wherein said plant is:

(a) selected from an ornamental plant or a crop plant;

(b) a plant in the family Brassicaceae;

(c) a *Brassica* species selected from the group consisting of *B. napus, B. juncea, B. carinata, B. rapa, B. oleracea, B. rupestris, B. septiceps, B. nigra, B. narinosa, B. perviridus, B. tournefortii*, and *B. fructiculosa;*

(d) a *Brassica* plant selected from the group consisting canola, rapeseed, turnips, and field mustard or turnip rape;

(e) selected from the group consisting of *Glycine max, Linum usitatissimum, Zea mays, Carthamus tinctorius, Helianthus annuus, Nicotiana tabacum, Arabidopsis thaliana, Betholettia excelsa, Ricinus communis, Cocos nucifera, Coriandrum sativum, Gossypium* spp., *Arachis hypogaea, Simmondsia chinensis, Solanum*

*tuberosum, Elaeis guineensis, Olea europaea, Oryza sativa, Cucurbita maxim, Hordeum vulgare*, and *Triticum aestivum*; or (f) a potato plant and said insect is *Epitrix cucumeris* (potato flea beetle).

8. The method of claim 6, wherein said contacting comprises:

(a) oral delivery to said insect, non-oral delivery to said insect, or a combination of oral and non-oral delivery to said insect;

(b) application of a composition comprising said recombinant RNA to a surface of said insect or to a surface of said plant infested by said insect;

(c) providing said recombinant RNA in a composition that further comprises one or more components selected from the group consisting of a carrier agent, a surfactant, an organosilicone, a polynucleotide herbicidal molecule, a non-polynucleotide herbicidal molecule, a non-polynucleotide pesticide, a fungicide, a safener, a fertilizer, a micronutrient, an insect attractant, and an insect growth regulator;

(d) providing said recombinant RNA in a composition that further comprises at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, a *Bacillus sphaericus* insecticidal protein, a bacterium that produces an insecticidal protein, an entomicidal bacterial species, *Lysinibacillus sphaericus* (*Bacillus sphaericus*), *Brevibacillus laterosporus* (*Bacillus laterosporus*), *Chromobacterium* species, *Chromobacterium subtsugae*, *Paenibacillus* species, *Paenibacillus lentimorbus*, and *Paenibacillus popilliae*; or (e) providing said recombinant RNA in a composition that is ingested by said insect.

* * * * *